US011021721B2

(12) United States Patent
Beckham et al.

(10) Patent No.: US 11,021,721 B2
(45) Date of Patent: Jun. 1, 2021

(54) **GENETICALLY ENGINEERED *PSEUDOMONAS* STRAINS CAPABLE OF METABOLIZING ETHYLENE GLYCOL AND ITS METABOLIC INTERMEDIATES**

(71) Applicants: Alliance for Sustainable Energy, LLC, Golden, CO (US); Rheinisch-Westfaelische Technische Hochschule (RWTH) Aachen, Aachen (DE); University of Stuttgart, Stuttgart (DE)

(72) Inventors: Gregg Tyler Beckham, Golden, CO (US); Mary Ann Franden, Centennial, CO (US); Lahiru N. Jayakody, Wheat Ridge, CO (US); Nick Johannes Petrus Wierckx, Bemelen (NL); Janosch Alexander Klebensberger, Stuttgart (DE); Lars Mathias Blank, Dortmund (DE); Wing-Jin Li, Cologne (DE); Bernhard Hauer, Stuttgart (DE); Nicholas S. Cleveland, Golden, CO (US); William E. Michener, Golden, CO (US); Jason Michael Whitham, Raleigh, NC (US)

(73) Assignees: Alliance for Sustainable Energy, LLC, Golden, CO (US); University of Stuttgart, Stuttgart (DE); UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 16/041,371

(22) Filed: Jul. 20, 2018

(65) Prior Publication Data
US 2019/0024126 A1 Jan. 24, 2019

Related U.S. Application Data

(60) Provisional application No. 62/650,925, filed on Mar. 30, 2018, provisional application No. 62/535,074, filed on Jul. 20, 2017.

(51) Int. Cl.
| | |
|---|---|
| *C12P 7/62* | (2006.01) |
| *C12N 1/20* | (2006.01) |
| *C12N 9/04* | (2006.01) |
| *C12N 9/10* | (2006.01) |
| *C12N 15/52* | (2006.01) |

(52) U.S. Cl.
CPC .............. *C12P 7/625* (2013.01); *C12N 1/20* (2013.01); *C12N 9/0006* (2013.01); *C12N 9/1022* (2013.01); *C12N 15/52* (2013.01); *C12N 2500/50* (2013.01); *C12Y 101/03015* (2013.01); *C12Y 202/01005* (2013.01)

(58) Field of Classification Search
None
See application file for complete search history.

(56) References Cited

PUBLICATIONS

Ashiuchi et al., "Biochemical Evidence that *Escherichia coli* hyi (orf b0508, gip) Gene Encodes Hydroxypyruvate Isomerase", Biochimica et Biophysica Acta (BBA)—Protein Structure and Molecular Enzymology, 1999, vol. 1435, No. 1-2, pp. 153-159.

Boronat et al., "Experimental Evolution of a Metabolic Pathway for Ethylene Glycol Utilization by *Escherichia coli*", Journal of Bacteriology, Jan. 1983, vol. 153, No. 1, pp. 134-139.

Black et al., "Aqueous Stream Characterization from Biomass Fast Pyrolysis and Catalytic Fast Pyrolysis", ACS Sustainable Chemistry & Engineering, 2016, vol. 4, No. 12, pp. 6815-6827.

Borujeni et al., "Translation Initiation is Controlled by RNA Folding Kinetics via a Ribosome Drafting Mechanism", Journal of the American Chemical Society, 2016, vol. 138, No. 22, pp. 7016-7023.

Caspi et al., "The MetaCyc Database of Metabolic Pathways and Enzymes and the BioCyc Collection of Pathway/Genome Databases", 2016, Nucleic Acids Research, 2016, vol. 44, Database Issue, pp. D471-D480.

Choi et al., "A 10-min Method for Preparation of Highly Electrocompetent *Pseudomonas aeruginosa* cells: Application for DNA Fragment Transfer Between Chromosomes and Plasmid Transformation", Journal of Microbiological Methods, Mar. 2006, vol. 64, No. 3, pp. 391-397.

Choi et al., "Improvement of Squalene Production from CO2 in *Synechococcus elongatus* PCC 7942 by Metabolic Engineering and Scalable Production in a Photobioreactor", ACS Synthetic Biology, 2017, vol. 6, No. 7, pp. 1289-1295.

Czernik et al., "Overview of Applications of Biomass Fast Pyrolysis Oil", Energy Fuels, 2004, vol. 18, No. 2, pp. 590-598.

Dam et al., "Operon Prediction Using both Genome-Specific and General Genomic Information", Nucleic Acids Research, 2007, vol. 35, No. 1, pp. 288-298.

Dvořák et al., "Bioremediation 3.0: Engineering Pollutant-Removing Bacteria in the Times of Systemic Biology", Biotechnology Advances, 2017, vol. 35, No. 7, pp. 845-866.

Harris, Poly (Ethylene Glycol) Chemistry: Biotechnical and Biomedical Applications, Springer Science & Business Media, 2013, pp. 1-12.

Hasegawa et al., "The Transcription Regulator AllR Senses Both Allantoin and Glyoxylate and Controls a Set of Genes for Degradation and Reutilization of Purines", Microbiology, Dec. 2008, vol. 154, No. 11, pp. 3366-3378.

Jambeck et al., "Plastic Waste Inputs from Land into the Ocean", Science, 2015, vol. 347, No. 6223, pp. 768-771.

(Continued)

*Primary Examiner* — Iqbal H Chowdhury
(74) *Attorney, Agent, or Firm* — Sam J. Barkley

(57) ABSTRACT

Presented herein are genetically engineered *Pseudomonas* strains capable of metabolizing ethylene glycol and producing polyhydroxyalkanoates.

19 Claims, 25 Drawing Sheets

Specification includes a Sequence Listing.

(56) References Cited

PUBLICATIONS

Jayakody et al., "SUMO Expression Shortens the Lag Phase of *Saccharomyces cerevisiae* Yeast Growth Caused by Complex Interactive Effects of Major Mixed Fermentation Inhibitors Found in Hot-Compressed Water-Treated Lignocellulosic Hydrolysate", Applied Microbiology and Biotechnology, 2015, vol. 99, No. 1, pp. 501-515.

Jayakody et al., "Identification and Detoxification of Glycolaldehyde, an Unattended Bioethanol Fermentation Inhibitor", Critical Reviews in Biotechnology, 2017, vol. 37, No. 2, pp. 177-189.

Johnson et al., "Aromatic Catabolic Pathway Selection for Optimal Production of Pyruvate and Lactate from Lignin", Metabolic Engineering, 2015, vol. 28, pp. 240-247.

Johnson et al., "Enhancing Muconic Acid Production from Glucose and Lignin-Derived Aromatic Compounds via Increased Protocatechuate Decarboxylase Activity", Metabolic Engineering Communications, 2016, vol. 3, pp. 111-119.

Kohn, "Tartaric Acid Metabolism", The Journal of Biological Chemistry, Sep. 1968, vol. 243, No. 17, pp. 4426-4433.

Kawai et al., "Bacterial Oxidation of Polyethylene Glycol", Applied and Environmental Microbiology, Apr. 1978, pp. 679-684.

Kumar et al., "Hydrolysis of Microcrystalline Cellulose in Subcritical and Supercritical Water in a Continuous Flow Reactor", Industrial & Engineering Chemistry Research, 2008, vol. 47, No. 23, pp. 9321-9329.

Law et al., "Plastic Accumulation in the North Atlantic Subtropical Gyre", Science, 2010, vol. 329, No. 5996, pp. 1185-1188.

Livak et al., "Analysis of Relative Gene Expression Data Using Real-Time Quantitative PCR and the 2-ΔΔ CT Method", Methods, Dec. 2001, vol. 25, No. 4, pp. 402-408.

Lu et al., "Two-Step Hydrolysis of Japanese Beech as Treated by Semi-Flow Hot-Compressed Water", Journal of Wood Science, 2009, vol. 55, No. 5, pp. 367-375.

Lynch et al., "Broad Host Range Vectors for Stable Genomic Library Construction", Biotechnology and Bioengineering, Feb. 2006, vol. 94, No. 1, pp. 151-158.

Mao et al., "DOOR: A Database for Prokaryotic Operons", Nucleic Acids Research, 2009, vol. 37, Database Issue, pp. D459-D463.

Mückschel et al., "Ethylene Glycol Metabolism by *Pseuomanas putida*", Applied and Environmental Microbiology, Dec. 2012, vol. 78, No. 24, pp. 8531-8539.

Narancic et al., "Microbial Biotechnology Addressing the Plastic Waste Disaster", Microbial Biotechnology, 2017, vol. 10, No. 5, pp. 1232-1235.

Novichkov et al., "RegPrecise 3.0—A Resource for Genome-scale Exploration of Transcriptional Regulation in Bacteria", BMC Genomics, 2013, vol. 14, No. 745, pp. 1471-2164.

Salvachúa et al., "Towards Lignin Consolidated Bioprocessing: Simultaneous Lignin Depolymerization and Product Generation by Bacteria", Green Chemistry, 2015, vol. 17, No. 11, pp. 4951-4967.

Solovyev et al., "Automatic Annotation of Eukaryotic Genes, Pseudogenes and Promoters", Genome Biology, 2006, vol. 7, Supplement 1, Article S10, pp. S10-S10.12.

Staples et al., "Fate, Effects and Potential Environmental Risks of Ethylene Glycol: A Review", Chemosphere, vol. 43, No. 3, pp. 377-383.

Tai et al., "Engineering the Push and Pull of Lipid Biosynthesis in Oleaginous Yeast *Yarrowia lipolytica* for Biofuel Production", Metabolic Engineering, vol. 15, pp. 1-9.

Thornalley et al., "The Autoxidation of Glyceraldehyde and Other Simple Monosaccharides Under Physiological Conditions Catalysed by Buffer Ions", Biochimica et Biophysica Acta (BBA)—General Subjects, 1984, vol. 797, No. 2, pp. 276-287.

Thornalley, "Monosaccharide Autoxidation in Health and Disease", Environmental Health Perspectives, 1985, vol. 64, pp. 297-307.

Trifunović et al., "Ethylene Glycol Metabolism in the Acetogen *Acetobacterium woodii*", Journal of Bacteriology, Apr. 2016, vol. 198, No. 7, pp. 1058-1065.

Van Heerden et al., "Fatal Attraction in Glycolysis: How *Saccharomyces cerevisiae* Manages Sudden Transitions to High Glucose", Microbial Cell, 2014, vol. 1, No. 3, pp. 103-106.

Van Heerden et al., "Lost in Transition: Start-Up of Glycolysis Yields Subpopulations of Nongrowing Cells", Science, 2014, vol. 343, No. 6174, pp. 1245114-1-1245114-9.

Vispute et al., "Renewable Chemical Commodity Feedstocks from Integrated Catalytic Processing of Pyrolysis Oils", Science, 2010, vol. 330, No. 6008, pp. 1222-1227.

Wang et al., "Monitoring Differences in Gene Expression Levels and Polyhydroxyalkanoate (PHA) Production in *Pseudomonas putida* KT2440 Grown on Different Carbon Sources", Journal of Bioscience and Bioengineering, Dec. 2010, vol. 110, No. 6, pp. 653-659.

Wehrmann et al., "Functional Role of Lanthanides in Enzymatic Activity and Transcriptional Regulation of Pyrroloquinoline Quinone-Dependent Alcohol Dehydrogenases in Pseudomonas putida KT2440", mBio, 2017, vol. 8, No. 3, pp. 1-14.

Wei, et al., "Biocatalysis as a Green Route for Recycling the Recalcitrant Plastic Polyethylene Terephthalate", Microbial Biotechnology, 2017, vol. 10, No. 6, pp. 1302-1307.

Wierckx et al., "Microbial Degradation of Furanic Compounds: Biochemistry, Genetics, and Impact", 2011, vol. 92, No. 6, pp. 1095-1105.

Wierckx et al., "Plastic Waste as a Novel Substrate for Industrial Biotechnology", Microbial Biotechnology, 2015, vol. 8, No. 6, pp. 900-903.

Winsor et al., "Enhanced Annotations and Features for Comparing Thousands of Pseudomonas Genomes in the Pseudomonas genome database", Nucleic Acids Research, 2016, vol. 44, No. D1, pp. D646-D653.

Yu et al., "Some Recent Advances in Hydrolysis of Biomass in Hot-Compressed Water and Its Comparisons with Other Hydrolysis Methods", 2008, Energy & Fuels, vol. 22, No. 1, pp. 46-60.

Yue et al., "Ethylene Glycol: Properties, Synthesis, and Applications", Chemical Society Reviews, 2012, vol. 41, No. 11, pp. 4218-4244.

Zar, J.H., 1979. Biostatistical Analysis, Englewood Cliffs, NJ, 1974. Prentice-Hall, Inc., Wackers F.J., Berger H.J., Johnstone D.E.: "Multiple Gated Cardiac Blood Pool Imaging for Left Ventricular Ejection Fraction: Validation of the Technique and Assessment of Variability, The American Journal of Cardiology", 1979, vol. 43, No. 6, pp. 1159-1166.

Zobel, "Engineering Redox Metabolism of *Pseudomonas putida* KT2440", Applied Microbiology, Apprimus Verlag, Aachen, Dec. 2016, vol. 4, pp. 1-118.

SEQUENCE LISTING

```
<160> NUMBER OF SEQ ID NOS: 48

<210> SEQ ID NO 1
<211> LENGTH: 9568
<212> TYPE: DNA
<213> ORGANISM: Artificial Sequence
<220> FEATURE:
<223> OTHER INFORMATION: engineered plasmid pLJ030

<400> SEQUENCE: 1
ttcgcggcgg ttcgacgcga gagggccgat acaaggccgc ttcaccccca gccatccata      60
cgcatggtcg ccctgaccag gcgctgctct tcctgctcga tctcccgcaa actgtcgcgt     120
atgccgttga tatgctcacg cgccgcccgc tgcgcctgct cgggcagttg ttccatgact     180
gcgcggtaca accgcgcatg ctgccgatca atctggcgtt tctgcgctgg ccggcagtac     240
aagttgttga ccgacgcaaa caccgtgctc aacgtcaggt cactgagcga ttgcaggta     300 tgcaccagca ctgggttatg cgacgcctac tgatggcccg gtgaaaggca tggtcacggc     360
```

```
gggcatgctc acgggcatcg agcgcctgcg cagcctcgtg cgcagccagc atttcttcgt    420
agcgccggcg gattagcagg cggtcgacgt cggtagcccg caacgccgcc agccgcgccg    480
actcagcctc cagcaacgcc cggacctcca gcaggtcgaa cagagtgcgc ggttgcgaac    540
gaacaggtgc atcaaaggcg tagcacccgc ctgcccggtg agatcggcga cgaacgaacc    600
ccgcccctgt tcggtgtcga tgatgccgcg cccacgcaga acgcgcaggc cctcgcgcaa    660
ggccgaacgt gaacagccaa gcttttccac cagccgccgc tccgacggca gtgcctggcc    720
caccttgagc acgccttcga cgataagccg ctcaacccgt tcggccacct ggtcggcgac    780
cttggccttg ccttcagtac ccactgcgca cactcctgct ggtaggacca ctttgactta    840
tatcgccaat ctagccagac agaaccgtga atagacagta ctgcccgaag aaactggtag    900
gaccagtcaa catctcactc gaccccaaac actagcacgc gcacgctgca tcggtgaccg    960
cttcgccaac acaacaaaaa ccgttgcgag tgagccgcgc aaaaaaccgc acccaggtgc   1020
ggttttttga attcgagctg ttgacaatta atcatcggct cgtataatgt gtcagactca   1080
ataataataa taaggaggta tcgaatgaat atcctgtacg acgaacgcgt cgatggcgcg   1140
ctgcccaacg tggacctggc cgccctgttg caggcgctgc gcgatgccct gccggatctt   1200
gaaatcctgc accgcgatga agacctcaaa ccgtacgaat gcgacggcct gtcggcctac   1260
cgcaccgtgc cactgctggt ggcgctgccc gagcgcctgg caggtgcaga cgctgttgaa   1320
gctttgccac cagcgcggcg taccggtggt tgcgcgtggc gccggtaccg gcctgtctgg   1380
tggtgccctg ccgctggcca agggcatcct gctggtgatg gcgcgcttca accgtatcct   1440
cgaggtcaac ccgcaggggc gttacgcccg cgtgcaaccg ggcgtacgca acctggccat   1500
ctcccaggcc gccgcacccc atggtatgta ctacgcaccc gacccttcct cgcaaattgc   1560
ctgctcgatc ggtggcaacg tcgccgaaaa cgccggtggc gtgcactgcc tcaagtacgg   1620
cctgaccgta cacaatgtgc tcaaggtgga catccttacg gtcgagggcg aacgcctgag   1680
cctgggcagc gatgccctgg acagcccggg cttcgacctg ctggcattgt tcacggctcc   1740
gaaggcatgc tcggtatcgt caccgaagtc accgtcaagc tgctgcccaa gccccaggtg   1800
gcgcgggtga tactggccag tttcgacagc gtcgaggacg ccggccgggc agtcgccgac   1860
atcatcgctg ccggcatcat tccggcggc ctggagatga tggacaacct ggcgatccgc   1920
gccgctgaag acttcatcca tgccggctac ccggtggacg cggcggcgat cctgctgtgc   1980
gaactggatg gcgtggaagc cgatgtttac gacgactgcg agcgcgtcgc cgccgtgctg   2040
acgcaagccg gggcccgcga ggtgcaccta ctagtagtca aaagcctccg accggaggct   2100
tttgactcat ggatgcctga aaggctccct tacagatgct gctgcagtgc ctcgaccacc   2160
atcgccaggc cttcatcggc ctcctcgatg atcgaaccca tacgcatgaa gtcatgggtc   2220
actcccggga tcaccgcaag ctgcaccgcc accccggctt gctccaagtg ccgtgcataa   2280
gcgacaccct ggtcatgcag cgggtcgcac tcggcaatca gcatcagtgc aggtgcactg   2340
ttgctggcga cgctgcccag caacggtgaa aaacgcggat cgtgacggtc tgccggcacc   2400
gtggcgtatt gctggtagaa ccactccagg gtctgcgctt caagcaggta accgctgcca   2460
tagcgctgca ccgaaggccg ccggcaactg gcatcggtca cgggtagat cattacctgc   2520
aggcgcggtg ccggcagctc gcgctgcgca gccaactggt tggccagaat ggtagccagg   2580
ctaccaccga cactgtcgcc caccaccgcc agtcgctgcg catcgatgcc cagcgcctcg   2640
gcctgctcga ccaaccagcg ccaggcatcc agggcatcgt cactggctgt cgggaaacgc   2700
cactgcggcg ccagccggta gcccacggca atcaccggca cccggcatc ctgcgccagg   2760
```

```
ttccagcaca gcgtgtcatg cgaatcgagg ctgcccacca cgtagccgcc gccatgcagg   2820
tacagcagcg ccgcgccggc cagtgcaggg tcggcctgcg gcgggcggta caagcgcacc   2880
ggcaaggtat ggccatcgcg ggtggtcaac gaaaggtcgc tgatgcagtc cggctcgtcg   2940
gccttgcccg caatcagcgc cgaggactct tcgaactggc ggcgcgcctc gtccgccgcc   3000
agggcatgca tgggcagcac cttgccggcg ctgcgtccgg cctccaccag ttgcaggtag   3060
gccgccaggt cagggttcag ggacatcgtt cgattctcca gaggggccta gcttcacgct   3120
gccgaagcac tcagggcgca agggctgcta aggaagcgg aacacgtaga aagccagtcc   3180
gcagaaacgt tgctgacccc ggatgaatgt cagctactgg gctatctgga caagggaaaa   3240
cgcaagcgca aagagaaagc aggtagcttg cagtgggctt acatggcgat agctagactg   3300
ggcggtttta tggacagcaa gcgaaccgga attgccagct ggggcgccct ctggtaaggt   3360
tgggaagccc tgcaaagtaa actggatggc tttcttgccg ccaaggatct gatggcgcag   3420
gggatcaaga tctgatcaag agacaggatg aggatcgttt cgcatgattg aacaagatgg   3480
attgcacgca ggttctccgg ccgcttgggt ggagaggcta ttcggctatg actgggcaca   3540
acagacaatc ggctgctctg atgccgccgt gttccggctg tcagcgcagg gcgcccggt    3600 tcttttgtc aagaccgacc tgtccggtgc cctgaatgaa ctccaagacg aggcagcgcg   3660
gctatcgtgg ctggccacga cgggcgttcc ttgcgcagct gtgctcgacg ttgtcactga   3720
agcgggaagg gactggctgc tattgggcga agtgccgggg caggatctcc tgtcatctca   3780
ccttgctcct gccgagaaag tatccatcat ggctgatgca atgcggcggc tgcatacgct   3840
tgatccggct acctgcccat tcgaccacca agcgaaacat cgcatcgagc gagcacgtac   3900
tcggatggaa gccggtcttg tcgatcagga tgatctggac gaagagcatc aggggctcgc   3960
gccagccgaa ctgttcgcca ggctcaaggc gcggatgccc gacggcgagg atctcgtcgt   4020
gacccatggc gatgcctgct tgccgaatat catggtggaa aatggccgct tttctggatt   4080
catcgactgt ggccggctgg gtgtggcgga ccgctatcag gacatagcgt tggctacccg   4140
tgatattgct gaagagcttg gcggcgaatg ggctgaccgc ttcctcgtgc tttacggtat   4200
cgccgctccc gattcgcagc gcatcgcctt ctatcgcctt cttgacgagt tcttctgagc   4260
gggactctgg ggttcgctag aggatcgatc cttttttaacc catcacatat acctgccgtt   4320
cactattatt tagtgaaatg agatattatg atattttctg aattgtgatt aaaaaggcaa   4380
ctttatgccc atgcaacaga aactataaaa aatacagaga atgaaaagaa acagatagat   4440 ttttagttc tttaggcccg tagtctgcaa atccttttat gattttctat caaacaaaag   4500
aggaaaatag accagttgca atccaaacga gagtctaata gaatgaggtc gaaaagtaaa   4560
tcgcgcgggt ttgttactga taaagcaggc aagacctaaa atgtgtaaag gcaaagtgt    4620 atactttggc gtcacccctt acatatttta ggtctttttt tattgtgcgt aactaacttg   4680
ccatcttcaa acaggagggc tggaagaagc agaccgctaa cacagtacat aaaaaaggag   4740
acatgaacga tgaacatcaa aaagtttgca aaacaagcaa cagtattaac ctttactacc   4800
gcactgctgg caggaggcgc aactcaagcg tttgcgaaag aaacgaacca aaagccatat   4860
aaggaaacat acggcatttc ccatattaca cgccatgata tgctgcaaat ccctgaacag   4920
caaaaaaatg aaaatatca gttttctgaa tttgattcgt ccacaattaa aaatatctct   4980
tctgcaaaag gcctggacgt ttgggacagc tggccattac aaaacgctga cggcactgtc   5040
gcaaactatc acggctacca catcgtcttt gcattagccg gagatcctaa aaatgcggat   5100
```

```
gacacatcga tttacatgtt ctatcaaaaa gtcggcgaaa cttctattga cagctggaaa    5160
aacgctggcc gcgtctttaa agacagcgac aaattcgatg caaatgattc tatcctaaaa    5220
gaccaaacac aagaatggtc aggttcagcc acatttacat ctgacggaaa aatccgttta    5280
ttctacactg atttctccgg taaacattac ggcaaacaaa cactgacaac tgcacaagtt    5340
aacgtatcag catcagacag ctctttgaac atcaacggtg tagaggatta taaatcaatc    5400
tttgacggtg acggaaaaac gtatcaaaat gtacagcagt tcatcgatga aggcaactac    5460
agctcaggcg acaaccatac gctgagagat cctcactacg tagaagataa aggccacaaa    5520
tacttagtat ttgaagcaaa cactggaact gaagatggct accaaggcga agaatcttta    5580
tttaacaaag catactatgg caaaagcaca tcattcttcc gtcaagaaag tcaaaaactt    5640
ctgcaaagcg ataaaaaacg cacggctgag ttagcaaacg cgctctcgg tatgattgag     5700 ctaaacgatg attacacact gaaaaaagtg atgaaaccgc tgattgcatc taacacagta    5760
acagatgaaa ttgaacgcgc gaacgtcttt aaaatgaacg gcaaatggta cctgttcact    5820
gactcccgcg gatcaaaaat gacgattgac ggcattacgt ctaacgatat ttacatgctt    5880
ggttatgttt ctaattcttt aactggccca tacaagccgc tgaacaaaac tggccttgtg    5940
ttaaaaatgg atcttgatcc taacgatgta acctttactt actcacactt cgctgtacct    6000
caagcgaaag gaaacaatgt cgtgattaca agctatatga caaacagagg attctacgca    6060
gacaaacaat caacgtttgc gccgagcttc ctgctgaaca tcaaaggcaa gaaaacatct    6120
gttgtcaaag acagcatcct tgaacaagga caattaacag ttaacaaata aaaacgcaaa    6180
agaaaatgcc gatgggtacc gagcgaaatg accgaccaag cgacgcccaa cctgccatca    6240
cgagatttcg attccaccgc cgccttctat gaaaggttgg gcttcggaat cgttttccgg    6300
gacgccctcg cggacgtgct catagtccac gacgcccgtg attttgtagc cctggccgac    6360
ggccagcagg taggccgaca ggctcatgcc ggccgccgcc gccttttcct caatcgctct    6420
tcgttcgtct ggaaggcagt acaccttgat aggtgggctg cccttcctgg ttggcttggt    6480
ttcatcagcc atccgcttgc cctcatctgt tacgccggcg gtagccggcc agcctcgcag    6540
agcaggattc ccgttgagca ccgccaggtg cgaataaggg acagtgaaga aggaacaccc    6600
gctcgcgggt gggcctactt cacctatcct gcccggctga cgccgttgga tacaccaagg    6660
aaagtctaca cgaaccctt tggcaaaatcc tgtatatcgt gcgaaaaagg atggatatac    6720
cgaaaaaatc gctataatga ccccgaagca gggttatgca gcggaaaagc gctgcttccc    6780
tgctgttttg tggaatatct accgactgga aacaggcaaa tgcaggaaat tactgaactg    6840
aggggacagg cgagagacga tgccaaagag ctcctgaaaa tctcgataac tcaaaaaata    6900
cgcccggtag tgatcttatt tcattatggt gaaagttgga acctcttacg tgccgatcaa    6960
cgtctcattt tcgccaaaag ttggcccagg cttcccggt atcaacaggg acaccaggat     7020
ttatttattc tgcgaagtga tcttccgtca caggtattta ttcggcgcaa agtgcgtcgg    7080
gtgatgctgc caacttactg atttagtgta tgatggtgtt tttgaggtgc tccagtggct    7140
tctgtttcta tcagctcctg aaaatctcga taactcaaaa aatacgcccg gtagtgatct    7200
tatttcatta tggtgaaagt tggaacctct tacgtgccga tcaacgtctc attttcgcca    7260
aaagttggcc cagggcttcc cggtatcaac agggacacca ggatttattt attctgcgaa    7320
gtgatcttcc gtcacaggta tttattcggc gcaaagtgcg tcgggtgatg ctgccaactt    7380
actgatttag tgtatgatgg tgttttttgag gtgctccagt ggcttctgtt tctatcaggg    7440
ctggatgatc ctccagcgcg gggatccatg ctggagttct tcgcccaccc caaaaggatc    7500
```

```
taggtgaaga tccttttga taatctcatg accaaaatcc cttaacgtga gttttcgttc    7560
cactgagcgt cagaccccgt agaaaagatc aaaggatctt cttgagatcc ttttttctg   7620
cgcgtaatct gctgcttgca acaaaaaaaa ccaccgctac cagcggtggt ttgtttgccg   7680
gatcaagagc taccaactct ttttccgaag gtaactggct tcagcagagc gcagatacca   7740
aatactgttc ttctagtgta gccgtagtta ggccaccact tcaagaactc tgtagcaccg   7800
cctacatacc tcgctctgct aatcctgtta ccagtggctg ctgccagtgg cgataagtcg   7860
tgtcttaccg ggttggactc aagacgatag ttaccggata aggcgcagcg gtcgggctga   7920
acggggggtt cgtgcacaca gcccagcttg gagcgaacga cctacaccga actgagatac   7980
ctacagcgtg agctatgaga aagcgccacg cttcccgaag ggagaaaggc ggacaggtat   8040
ccggtaagcg gcagggtcgg aacaggagag cgcacgaggg agcttccagg gggaaacgcc   8100
tggtatcttt atagtcctgt cgggtttcgc cacctctgac ttgagcgtcg attttgtga   8160
tgctcgtcag ggggggggag cctatggaaa aacgccagca acgcggcctt tttacggttc   8220
ctggccttt gctggccttt tgctcacatg ttctttcctg cgttatcccc tgattctgtg   8280
gataaccgta ttaccgcctt tgagtgagct gataccgctc gccgcagccg aacgaccgag   8340
cgcagcgagt cagtgagcga ggaagcggaa gagcgcccaa tacgcaaacc gcctctcccc   8400
gcgcgttggc cgattcatta atgcagctgg cacgacaggt ttcccgactg gaaagcgggc   8460
agtgagcgca acgcaattaa tgtgagttag aagccgaatg tcgatgatat ctacaacctg   8520
agcgagcacg tcgagcagga aggggcgtac gtcaccaccc gcctgaacat cgccgacccg   8580
ctgaaggtca tcctgggtgc acgcctggac tggtacgaca acaagtcggt gtacagcgaa   8640
atcaacgacg gctactacac caacagcgat tacaaggtca cccgcaacgt caccgctac   8700
gccggagtga tctacgacct ggacgaccac cactcggtct acgccagcta caccgatatc   8760
ttcatgccgc aatcggaact ggcgcgtgac cgctccatca tccgcccaat cgaaggcaag   8820
aactacgaga tcggcatcaa gggcgagtac ttcgacggcg cactcaacgc cagcgcggcg   8880
atcttccaga tcgaccagga aaaccgcgcc gcagaagctt ctaaccagga aggttgcgtc   8940
gacatcacct gctacgaagc ctcgggcaag gtacgcaccc acggtatcga cctggagttg   9000
atgggcgcac tgacccccaa ctggcaagtc ggcgcaggct acacctactc gcaaaccaag   9060
taccgcaagg atgccgacaa gaacaaggaa ggcaccaagt cgacaccga cctgccagaa   9120
cacctgttca agctgagcac cacctacacc ttgccgggcg agctgaacca gtggcgcgtg   9180
ggcggtaacg tgtatggcca gagcagcatc ttcaacaaag gcagcaacag cttcggcaac   9240
taccacatcg atcaaggtgc atacgcggta gtgggcctga tggtcggcta caaggtcaac   9300
aagaacctcg acactcgcct gaacctcaac aacgtattcg acaagaagta ctaccagggc   9360
attgccagca caaactcctg gagcccgtac gacgtgtatg gtgacccacg caacttcacc   9420
atcaccgcca atcagcttc tgatcgcctg acgttgaacg caaaaaaccg cacccaggtg   9480
cggtttttg aattcgagct gttgacaatt aatcatcggc tcgtataatg tgtggaattg   9540
tgagcggata caatttcac actctaga                                      9568
```

<210> SEQ ID NO 2
<211> LENGTH: 10224
<212> TYPE: DNA
<213> ORGANISM: Artificial Sequence
<220> FEATURE:
<223> OTHER INFORMATION: engineered plasmid pLJ032

<400> SEQUENCE: 2

```
tagtcaaaag cctccgaccg gaggcttttg actcatggat gcctgaaagg ctcccttaca      60
gatgctgctg cagtgcctcg accaccatcg ccaggccttc atcggcctcc tcgatgatcg     120
aacccatacg catgaagtca tgggtcactc ccgggatcac cgcaagctgc accgccaccc     180
cggcttgctc caagtgccgt gcataagcga caccctggtc atgcagcggg tcgcactcgg     240
caatcagcat cagtgcaggt gcactgttgc tggcgacgct gcccagcaac ggtgaaaaac     300
gcggatcgtg acggtctgcc ggcaccgtgg cgtattgctg gtagaaccac tccagggtct     360
gcgcttcaag caggtaaccg ctgccatagc gctgcaccga aggccgccgg caactggcat     420
cggtcaccgg gtagatcatt acctgcaggc gcggtgccgg cagctcgcgc tgcgcagcca     480
actggttggc cagaatggta gccaggctac caccgacact gtcgcccacc accgccagtc     540
gctgcgcatc gatgcccagc gcctcggcct gctcgaccaa ccagcgccag catccagggg    600
catcgtcact ggctgtcggg aaacgccact gcggcgccag ccgtagccc acggcaatca     660
ccggcacccc ggcatcctgc gccaggttcc agcacagcgt gtcatgcgaa tcgaggctgc     720
ccaccacgta ccgccgcca tgcaggtaca gcagcgccgc gccggccagt gcagggtcgg      780
cctgcggcgg gcggtacaag cgcaccggca aggtatggcc atcgcgggtg gtcaacgaaa     840
ggtcgctgat gcagtccggc tcgtcggcct tgcccgcaat cagcgccgag gactcttcga     900
actggcggcg cgcctcgtcc gccgccaggg catgcatggg cagcaccttg ccggcgctgc     960
gtccggcctc caccagttgc aggtaggccg ccaggtcagg gttcagggac atcgttcgat    1020
tctccagagg ggcctagctt cacgctgccg caagcactca gggcgcaagg gctgctaaag    1080
gaagcggaac acgtagaaag ccagtccgca gaaacggtgc tgaccccgga tgaatgtcag    1140
ctactgggct atctggacaa gggaaaacgc aagcgcaaag agaaagcagg tagcttgcag    1200
tgggcttaca tggcgatagc tagactgggc ggttttatgg acagcaagcg aaccggaatt    1260
gccagctggg gcgccctctg gtaaggttgg gaagccctgc aaagtaaact ggatggcttt    1320
cttgccgcca aggatctgat ggcgcagggg atcaagatct gatcaagaga caggatgagg    1380
atcgtttcgc atgattgaac aagatggatt gcacgcaggt tctccggccg cttgggtgga    1440
gaggctattc ggctatgact gggcacaaca gacaatcggc tgctctgatg ccgccgtgtt    1500
ccggctgtca gcgcagggggc gcccggttct ttttgtcaag accgacctgt ccggtgccct    1560
gaatgaactc caagacgagg cagcgcggct atcgtggctg gccacgacgg gcgttccttg    1620
cgcagctgtg ctcgacgttg tcactgaagc gggaagggac tggctgctat tgggcgaagt    1680
gccggggcag gatctcctgt catctcacct tgctcctgcc gagaaagtat ccatcatggc    1740
tgatgcaatg cggcggctgc atacgcttga tccggctacc tgcccattcg accaccaagc    1800
gaaacatcgc atcgagcgag cacgtactcg gatggaagcc ggtcttgtcg atcaggatga    1860
tctggacgaa gagcatcagg ggctcgcgcc agccgaactg ttcgccaggc tcaaggcgcg    1920
gatgcccgac ggcgaggatc tcgtcgtgac ccatggcgat gcctgcttgc cgaatatcat    1980
ggtggaaaat ggccgctttt ctggattcat cgactgtggc cggctgggtg tggcggaccg    2040
ctatcaggac atagcgttgg ctacccgtga tattgctgaa gagcttggcg gcgaatgggc    2100
tgaccgcttc ctcgtgcttt acggtatcgc cgctcccgat tcgcagcgca tcgccttcta    2160
tcgccttctt gacgagttct tctgagcggg actctggggt tcgctagagg atcgatcctt    2220
tttaacccat cacatatacc tgccgttcac tattatttag tgaaatgaga tattatgata    2280
ttttctgaat tgtgattaaa aaggcaactt tatgcccatg caacagaaac tataaaaaat    2340
```

```
acagagaatg aaaagaaaca gatagatttt ttagttcttt aggcccgtag tctgcaaatc    2400 ctttatgat tttctatcaa acaaaagagg aaaatagacc agttgcaatc caaacgagag     2460
tctaatagaa tgaggtcgaa aagtaaatcg cgcgggtttg ttactgataa agcaggcaag    2520
acctaaaatg tgtaaagggc aaagtgtata ctttggcgtc accccttaca tattttaggt    2580
ctttttttat tgtgcgtaac taacttgcca tcttcaaaca ggagggctgg aagaagcaga    2640
ccgctaacac agtacataaa aaggagaca tgaacgatga acatcaaaaa gtttgcaaaa     2700
caagcaacag tattaacctt tactaccgca ctgctggcag gaggcgcaac tcaagcgttt    2760
gcgaaagaaa cgaaccaaaa gccatataag gaaacatacg gcatttccca tattacacgc    2820
catgatatgc tgcaaatccc tgaacagcaa aaaaatgaaa aatatcaagt ttctgaattt    2880
gattcgtcca caattaaaaa tatctcttct gcaaaaggcc tggacgtttg ggacagctgg    2940
ccattacaaa acgctgacgg cactgtcgca aactatcacg gctaccacat cgtctttgca    3000
ttagccggag atcctaaaaa tgcggatgac acatcgattt acatgttcta tcaaaaagtc    3060
ggcgaaactt ctattgacag ctggaaaaac gctggccgcg tctttaaaga cagcgacaaa    3120
ttcgatgcaa atgattctat cctaaaagac caaacacaag aatggtcagg ttcagccaca    3180
tttacatctg acggaaaaat ccgtttattc tacactgatt tctccggtaa acattacggc    3240
aaacaaacac tgacaactgc acaagttaac gtatcagcat cagacagctc tttgaacatc    3300
aacggtgtag aggattataa atcaatcttt gacggtgacg aaaaacgta tcaaaatgta     3360 cagcagttca tcgatgaagg caactacagc tcaggcgaca accatacgct gagagatcct    3420
cactacgtag aagataaagg ccacaaatac ttagtatttg aagcaaacac tggaactgaa    3480
gatggctacc aaggcgaaga atctttattt aacaaagcat actatggcaa aagcacatca    3540
ttcttccgtc aagaaagtca aaaacttctg caaagcgata aaaaacgcac ggctgagtta    3600
gcaaacggcg ctctcggtat gattgagcta acgatgatt acacactgaa aaaagtgatg     3660
aaaccgctga ttgcatctaa cacagtaaca gatgaaattg aacgcgcgaa cgtctttaaa    3720
atgaacggca atggtacct gttcactgac tcccgcggat caaaaatgac gattgacggc     3780
attacgtcta acgatattta catgcttggt tatgtttcta attctttaac tggcccatac    3840
aagccgctga acaaaactgg ccttgtgtta aaaatggatc ttgatcctaa cgatgtaacc    3900
tttacttact cacacttcgc tgtacctcaa gcgaaaggaa acaatgtcgt gattacaagc    3960
tatatgacaa acagaggatt ctacgcagac aaacaatcaa cgtttgcgcc gagcttcctg    4020
ctgaacatca aaggcaagaa acatctgtt gtcaaagaca gcatccttga caaggacaa      4080 ttaacagtta caaataaaa acgcaaaaga aatgccgat gggtaccgag cgaaatgacc      4140
gaccaagcga cgcccaacct gccatcacga gatttcgatt ccaccgccgc cttctatgaa    4200
aggttgggct tcggaatcgt tttccgggac gccctcgcgg acgtgctcat agtccacgac    4260
gcccgtgatt ttgtagccct ggccgacggc cagcaggtag gccgacaggc tcatgccggc    4320
cgccgccgcc ttttcctcaa tcgctcttcg ttcgtctgga aggcagtaca ccttgatagg    4380
tgggctgccc ttcctggttg gcttggttc atcagccatc cgcttgccct catctgttac     4440
gccggcggta gccggccagc ctcgcagagc aggattcccg ttgagcaccg ccaggtgcga    4500
ataagggaca gtgaagaagg aacacccgct cgcgggtggg cctacttcac ctatcctgcc    4560
cggctgacgc cgttggatac accaaggaaa gtctacacga acctttggc aaaatcctgt     4620 atatcgtgcg aaaaaggatg gatataccga aaaaatcgct ataatgaccc cgaagcaggg    4680
```

```
ttatgcagcg gaaaagcgct gcttccctgc tgttttgtgg aatatctacc gactggaaac    4740
aggcaaatgc aggaaattac tgaactgagg ggacaggcga gagacgatgc caaagagctc    4800
ctgaaaatct cgataactca aaaaatacgc ccggtagtga tcttatttca ttatggtgaa    4860
agttggaacc tcttacgtgc cgatcaacgt ctcattttcg ccaaaagttg gcccagggct    4920
tcccggtatc aacagggaca ccaggattta tttattctgc gaagtgatct tccgtcacag    4980
gtatttattc ggcgcaaagt gcgtcgggtg atgctgccaa cttactgatt tagtgtatga    5040
tggtgttttt gaggtgctcc agtggcttct gtttctatca gctcctgaaa atctcgataa    5100
ctcaaaaaat acgccggta gtgatcttat ttcattatgg tgaaagttgg aacctcttac    5160
gtgccgatca acgtctcatt tcgccaaaa gttgggcccag gcttcccgg tatcaacagg    5220
gacaccagga tttatttatt ctgcgaagtg atcttccgtc acaggtattt attcggcgca    5280
aagtgcgtcg ggtgatgctg ccaacttact gatttagtgt atgatggtgt ttttgaggtg    5340
ctccagtggc ttctgtttct atcagggctg gatgatcctc cagcgcgggg atctcatgct    5400
ggagttcttc gcccaccca aaaggatcta ggtgaagatc cttttttgata atctcatgac    5460
caaaatccct taacgtgagt tttcgttcca ctgagcgtca gaccccgtag aaaagatcaa    5520
aggatcttct tgagatcctt ttttttctgcg cgtaatctgc tgcttgcaaa caaaaaaacc    5580
accgctacca gcggtggttt gtttgccgga tcaagagcta ccaactcttt ttccgaaggt    5640
aactggcttc agcagagcgc agataccaaa tactgttctt ctagtgtagc cgtagttagg    5700
ccaccacttc aagaactctg tagcaccgcc tacatacctc gctctgctaa tcctgttacc    5760
agtggctgct gccagtggcg ataagtcgtg tcttaccggg ttggactcaa gacgatagtt    5820
accggataag gcgcagcggt cgggctgaac ggggggttcg tgcacacagc ccagcttgga    5880
gcgaacgacc tacaccgaac tgagatacct acagcgtgag ctatgagaaa gcgccacgct    5940
tcccgaaggg agaaaggcgg acaggtatcc ggtaagcggc agggtcggaa caggagagcg    6000
cacgagggag cttccagggg gaaacgcctg gtatctttat agtcctgtcg ggtttcgcca    6060
cctctgactt gagcgtcgat ttttgtgatg ctcgtcaggg gggcggagcc tatggaaaaa    6120
cgccagcaac gcggcctttt tacggttcct ggccttttgc tggccttttg ctcacatgtt    6180
ctttcctgcg ttatcccctg attctgtgga taaccgtatt accgcctttg agtgagctga    6240
taccgctcgc cgcagccgaa cgaccgagcg cagcgagtca gtgagcgagg aagcggaaga    6300
gcgcccaata cgcaaaccgc ctctccccgc gcgttggccg attcattaat gcagctggca    6360
cgacaggttt cccgactgga aagcgggcag tgagcgcaac gcaattaatg tgagttagaa    6420
gccgaatgtc gatgatatct acaacctgag cgagcacgtc gagcaggaag ggcgtacgt    6480
caccacccgc ctgaacatcg ccgacccgct gaaggtcatc ctgggtgcac gcctggactg    6540
gtacgacaac aagtcggtgt acagcgaaat caacgacggc tactacacca acagcgatta    6600
caaggtcacc cgcaacgtca cccgctacgc cggagtgatc tacgacctgg acgaccacca    6660
ctcggtctac gccagctaca ccgatatctt catgccgcaa tcggaactgg cgcgtgaccg    6720
ctccatcatc cgcccaatcg aaggcaagaa ctacgagatc ggcatcaagg gcgagtactt    6780
cgacggcgca ctcaacgcca gcggccgat cttccagatc gaccaggaaa accgcgccgc    6840
agaagcttct aaccaggaag gttgcgtcga catcacctgc tacgaagcct cgggcaaggt    6900
acgcaccccac ggtatcgacc tggagttgat gggcgcactg accccaact ggcaagtcgg    6960
cgcaggctac acctactcgc aaaccaagta ccgcaaggat gccgacaaga acaaggaagg    7020
caccaagttc gacaccgacc tgccagaaca cctgttcaag ctgagcacca cctacacctt    7080
```

```
gccgggcgag ctgaaccagt ggcgcgtggg cggtaacgtg tatggccaga gcagcatctt    7140
caacaaaggc agcaacagct tcggcaacta ccacatcgat caaggtgcat acgcggtagt    7200
gggcctgatg gtcggctaca aggtcaacaa gaacctcgac actcgcctga acctcaacaa    7260
cgtattcgac aagaagtact accagggcat tgccagcaac aactcctgga gcccgtacga    7320
cgtgtatggt gacccacgca acttcaccat caccgccaag tacagcttct gatcgcctga    7380
cgttgaacgc aaaaaaccgc acccaggtgc ggttttttga attcgagctg ttgacaatta    7440
atcatcggct cgtataatgt gtggaattgt gagcggataa caatttcaca ctaaagttaa    7500
tattaaggag gtaaacatga gcaaaatgag agcaatcgat gcagccgttc tggtcatgcg    7560
ccgtgaaggt gtagataccg cgttcggcat cccgggggct gccatcaacc cgttgtattc    7620
ggccctgaaa aaagtcggtg catcgatca cgtcctcgct cgtcacgtcg aaggtgcctc    7680
gcacatggcc gagggctaca cccgcgccaa cccgggcaac atcggtgtgt gcatcggcac    7740
ttccggccct gccggcaccg acatggtcac cggcctgtac agtgcctcgg ccgactccat    7800
cccgattctg tgcatcactg gccaggcgcc acgtgcccgt ctgcacaagg aagacttcca    7860
ggctgtcgac atcaccaaca tcgtcaagcc agtgaccaag tgggcgacca ccgttctgga    7920
gccaggccag gtgccttacg ccttccagaa ggccttctat gaaatgcgta ccggccgccc    7980
aggcccggtg ctgatcgacc tgccgttcga cgtgcagatg gccgaaatcg aattcgacat    8040
cgacgcctac gaaccgctgc ccgtgcacaa accgtccgcc acacgcgtac aggccgaaaa    8100
agccctggcc ctgctcaatg acgccgagcg cccactgctg gtagccggtg gcggcatcat    8160
caacgccgac gccagtgaca agctggtcga attcgccgaa ctgaccggcg tacccgtgat    8220
cccgaccctg atgggctggg gcaccatccc ggacgaccac gcacagatgg tcggcatggt    8280
cggcctgcag acctcgcacc gctatggcaa cgcaaccctg ctgaaatccg acctggtgtt    8340
cggtatcggt aaccgctggg ccaaccgcca caccggttcc gtcgatgtct acaccgaagg    8400
ccgcaagttc gtgcacgtcg acatcgaacc gacccagatc ggccgcgtgt tcaccccgga    8460
cctgggcatc gtttccgatg ctggtaaggc actggacgtg ttcctggaag tggcccgcga    8520
gtggaaagcc gccggcaagc tcaaatgccg caaggcctgg ctggaagagt gccaggagcg    8580
caagtcgagc ctgcagcgca agacccactt cgacaacgtg ccggtcaagc cgcagcgcgt    8640
ctacgaagaa atgaaccaag tgttcggcaa ggacacctgc tacgtcagca ccatcggcct    8700
gtcgcagatt gccggcgcgc agttcctgca tgtgtacaag cctcgccact ggatcaactg    8760
cggccaggcc ggcccgctgg gctggaccat ccctgctgcg ctgggcgtgg tcaaagccga    8820
tccgaagcgc aaggttgtgg cgctgtcggg tgactacgac ttccagttca tgatcgaaga    8880
actggcggta ggcgcccagt tcaacctgcc gtacgtccac gtactggtga caacgcctca    8940
cctgggcctg atccgccagg cgcagcgtgg cttcgacatg gattactgtg tacaactggc    9000
gttcgagaac atcaactcga ccgacgctgc cacctacggt gtcgaccacg tcgctgtggt    9060
cgaaggcctg ggttgcaagg ccatccgtgt gttcgagcca gcagaaatcg cccctgccct    9120
gatcaaggca cagaagatgg ccgaagagtt ccgcgtgccg gtggtggttg aagtgattct    9180
cgagcgtgtg accaacattt ccatgggcac cgagatcaac gcggtcaacg aattcgaaga    9240
cctggccctg gtcggcaacg acgcgccaac cgccatctcg ctgctggact gatatcaaaa    9300
cgacaactaa ctaaggaggt acactatggc taaaatcggt ttcatcggca ccggcatcat    9360
gggcaagccc atggctcaga acctgcaaaa ggcaggtcac agcctgttca tttccacccca    9420
```

-continued

| | |
|---|---|
| ccacgacgcc gcgccagccg acctgatcgc tgccggtgcc gtggccctgg ccaacccgaa | 9480 |
| agaggttgcc caggaagccg aattcatcat cgtcatggtc cccgacaccc cgcaggtcga | 9540 |
| aagcgtcctg ttcggtgaaa acggcgtggc cgagggcgtt ggcccgaaca aggtggtgat | 9600 |
| cgacatgagc tcgatctcgc caaccgccac caaagccttc gccgagaaga tcaaggctac | 9660 |
| cggtgccgcc tacctggacg ccccggtgtc cggtggtgaa gtcggcgcca aggcggcgac | 9720 |
| cctgagcatc atggttggtg gctgcccgaa cgccttcgag cgcaccctgc cgctgttcga | 9780 |
| agccatgggc aagaacatca cccgcgtcgg tggcaacggt gacggccaga ccgccaaggt | 9840 |
| cgccaaccag atcattgtcg ccctgaacat ccaggccgtg gccgaagccc tgctgttcgc | 9900 |
| cgccaagaac ggcgccgacc ctgccaaggt gcgcgaagca ctgatgggcg ctttgcttc | 9960 |
| gtcgaaaatc ctcgaagtgc acgccgagcg catgatcaag gcaccttcg acccaggctt | 10020 |
| ccgcatcaac ctgcaccaga aggacctgaa cctggccctg caaggcgcca aggaactggg | 10080 |
| catcaacctg cccaacacct ccaatgccca gcaagtgttc aacacctgcc aggccctggg | 10140 |
| cggcggcaac tgggaccact cggcgctgat caaaggcctg gagcacatgg ccaacttctc | 10200 |
| gatccgcgac gacaaataac tagt | 10224 |

<210> SEQ ID NO 3
<211> LENGTH: 11170
<212> TYPE: DNA
<213> ORGANISM: Artificial Sequence
<220> FEATURE:
<223> OTHER INFORMATION: engineered plasmid pMFL160

<400> SEQUENCE: 3

| | |
|---|---|
| agtcaaaagc ctccgaccgg aggcttttga ctcatggatg cctgaaaggc tcccttacag | 60 |
| atgctgctgc agtgcctcga ccaccatcgc caggccttca tcggcctcct cgatgatcga | 120 |
| acccatacgc atgaagtcat gggtcactcc cgggatcacc gcaagctgca ccgccacccc | 180 |
| ggcttgctcc aagtgccgtg cataagcgac accctggtca tgcagcgggt cgcactcggc | 240 |
| aatcagcatc agtgcaggtg cactgttgct ggcgacgctg cccagcaacg gtgaaaaacg | 300 |
| cggatcgtga cggtctgccg gcaccgtggc gtattgctgg tagaaccact ccagggtctg | 360 |
| cgcttcaagc aggtaaccgc tgccatagcg ctgcaccgaa ggccgccggc aactggcatc | 420 |
| ggtcaccggg tagatcatta cctgcaggcg cggtgccggc agctcgcgct cgcagccaa | 480 |
| ctggttggcc agaatggtag ccaggctacc accgacactg tcgcccacca ccgccagtcg | 540 |
| ctgcgcatcg atgcccagcg cctcggcctg ctcgaccaac cagcgccagg catccagggc | 600 |
| atcgtcactg gctgtcggga acgccactg cggcgccagc cggtagccca cggcaatcac | 660 |
| cggcaccccg gcatcctgcg ccaggttcca gcacagcgtg tcatgcgaat cgaggctgcc | 720 |
| caccacgtag ccgccgccat gcaggtacag cagcgccgcg ccggccagtg cagggtcggc | 780 |
| ctgcggcggg cggtacaagc gcaccggcaa ggtatggcca tcgcgggtgg tcaacgaaag | 840 |
| gtcgctgatg cagtccggct cgtcggcctt gcccgcaatc agcgccgagg actcttcgaa | 900 |
| ctggcggcgc gcctcgtccg ccgccagggc atgcatgggc agcaccttgc ggcgctgcg | 960 |
| tccggcctcc accagttgca ggtaggccgc caggtcaggg ttcagggaca tcgttcgatt | 1020 |
| ctccagaggg gcctagcttc acgctgccgc aagcactcag ggcgcaaggg ctgctaaagg | 1080 |
| aagcggaaca cgtagaaagc cagtccgcag aaacggtgct gaccccggat gaatgtcagc | 1140 |
| tactgggcta tctggacaag ggaaaacgca agcgcaaaga gaaagcaggt agcttgcagt | 1200 |
| gggcttacat ggcgatagct agactgggcg gttttatgga cagcaagcga accggaattg | 1260 |

```
ccagctgggg cgccctctgg taaggttggg aagccctgca aagtaaactg gatggctttc    1320
ttgccgccaa ggatctgatg gcgcagggga tcaagatctg atcaagagac aggatgagga    1380
tcgtttcgca tgattgaaca agatggattg cacgcaggtt ctccggccgc ttgggtggag    1440
aggctattcg gctatgactg ggcacaacag acaatcggct gctctgatgc cgccgtgttc    1500
cggctgtcag cgcaggggcg cccggttctt tttgtcaaga ccgacctgtc cggtgccctg    1560
aatgaactcc aagacgaggc agcgcggcta tcgtggctgg ccacgacggg cgttccttgc    1620
gcagctgtgc tcgacgttgt cactgaagcg ggaagggact ggctgctatt gggcgaagtg    1680
ccggggcagg atctcctgtc atctcacctt gctcctgccg agaaagtatc catcatggct    1740
gatgcaatgc ggcggctgca tacgcttgat ccggctacct gcccattcga ccaccaagcg    1800
aaacatcgca tcgagcgagc acgtactcgg atggaagccg gtcttgtcga tcaggatgat    1860
ctggacgaag agcatcaggg gctcgcgcca gccgaactgt tcgccaggct caaggcgcgg    1920
atgcccgacg gcgaggatct cgtcgtgacc catggcgatg cctgcttgcc gaatatcatg    1980
gtggaaaatg gccgcttttc tggattcatc gactgtggcc ggctgggtgt ggcggaccgc    2040
tatcaggaca tagcgttggc tacccgtgat attgctgaag agcttggcgg cgaatgggct    2100
gaccgcttcc tcgtgcttta cggtatcgcc gctcccgatt cgcagcgcat cgccttctat    2160
cgccttcttg acgagttctt ctgagcggga ctctggggtt cgctagagga tcatcctttt    2220
ttaacccatc acatatacct gccgttcact attatttagt gaaatgagat attatgatat    2280
tttctgaatt gtgattaaaa aggcaacttt atgcccatgc aacagaaact ataaaaaata    2340
cagagaatga aagaaacag atagattttt tagttcttta ggcccgtagt ctgcaaatcc    2400
ttttatgatt ttctatcaaa caaaagagga aaatagacca gttgcaatcc aaacgagagt    2460
ctaatagaat gaggtcgaaa agtaaatcgc gcgggtttgt tactgataaa gcaggcaaga    2520
cctaaaatgt gtaaagggca aagtgtatac tttggcgtca ccccttacat attttaggtc    2580 ttttttttatt gtgcgtaact aacttgccat cttcaaacag gagggctgga agaagcagac    2640
cgctaacaca gtacataaaa aaggagacat gaacgatgaa catcaaaaag tttgcaaaac    2700
aagcaacagt attaaccttt actaccgcac tgctggcagg aggcgcaact caagcgtttg    2760
cgaaagaaac gaaccaaaag ccatataagg aaacatacgg catttcccat attacacgcc    2820
atgatatgct gcaaatccct gaacagcaaa aaaatgaaaa atatcaagtt tctgaatttg    2880
attcgtccac aattaaaaat atctcttctg caaaaggcct ggacgtttgg gacagctggc    2940
cattacaaaa cgctgacggc actgtcgcaa actatcacgg ctaccacatc gtctttgcat    3000
tagccggaga tcctaaaaat gcggatgaca catcgattta catgttctat caaaaagtcg    3060
gcgaaacttc tattgacagc tggaaaaacg ctggccgcgt ctttaaagac agcgacaaat    3120
tcgatgcaaa tgattctatc ctaaaagacc aaacacaaga atggtcaggt tcagccacat    3180
ttacatctga cggaaaaatc cgtttattct acactgattt ctccggtaaa cattacggca    3240
aacaaacact gacaactgca caagttaacg tatcagcatc agacagctct tgaacatcaa    3300
cggtgtagag gattataaat caatctttga cggtgacgga aaaacgtatc aaaatgtaca    3360
gcagttcatc gatgaaggca actacagctc aggcgacaac catacgctga gagatcctca    3420
ctacgtagaa gataaaggcc acaaatactt agtatttgaa gcaaacactg gaactgaaga    3480
tggctaccaa ggcgaagaat ctttatttaa caaagcatac tatggcaaaa gcacatcatt    3540
cttccgtcaa gaaagtcaaa aacttctgca aagcgataaa aaacgcacgg ctgagttagc    3600
```

```
aaacggcgct ctcggtatga ttgagctaaa cgatgattac acactgaaaa aagtgatgaa    3660
accgctgatt gcatctaaca cagtaacaga tgaaattgaa cgcgcgaacg tctttaaaat    3720
gaacggcaaa tggtacctgt tcactgactc ccgcggatca aaaatgacga ttgacggcat    3780
tacgtctaac gatatttaca tgcttggtta tgtttctaat tctttaactg cccatacaa     3840 gccgctgaac aaaactggcc ttgtgttaaa aatggatctt gatcctaacg atgtaacctt    3900
tacttactca cacttcgctg tacctcaagc gaaggaaac aatgtcgtga ttacaagcta     3960
tatgacaaac agaggattct acgcagacaa acaatcaacg tttgcgccga gcttcctgct    4020
gaacatcaaa ggcaagaaaa catctgttgt caaagacagc atccttgaac aaggacaatt    4080
aacagttaac aaataaaaac gcaaagaaaa atgccgatgg gtaccgagcg aaatgaccga    4140
ccaagcgacg cccaacctgc catcacgaga tttcgattcc accgccgcct tctatgaaag    4200
gttgggcttc ggaatcgttt tccgggacgc cctcgcggac gtgctcatag tccacgacgc    4260
ccgtgatttt gtagccctgg ccgacggcca gcaggtaggc cgacaggctc atgccggccg    4320
ccgccgcctt ttcctcaatc gctcttcgtt cgtctgaaag gcagtacacc ttgataggtg    4380
ggctgccctt cctggttggc ttggtttcat cagccatccg cttgccctca tctgttacgc    4440
cggcggtagc cggccagcct cgcagagcag gattcccgtt gagcaccgcc aggtgcgaat    4500
aagggacagt gaagaaggaa cacccgctcg cgggtgggcc tacttcacct atcctgcccg    4560
gctgacgccg ttgatacac caaggaaagt ctacacgaac cctttggcaa aatcctgtat     4620
atcgtgcgaa aaaggatgga tataccgaaa aaatcgctat aatgaccccg aagcagggtt    4680
atgcagcgga aaagcgctgc ttccctgctg ttttgtggaa tatctaccga ctggaaacag    4740
gcaaatgcag gaaattactg aactgagggg acaggcgaga gacgatgcca aagagctcct    4800
gaaaatctcg ataactcaaa aaatacgccc ggtagtgatc ttatttcatt atggtgaaag    4860
ttggaacctc ttacgtgccg atcaacgtct cattttcgcc aaaagttggc ccagggcttc    4920
ccggtatcaa cagggacacc aggatttatt tattctgcga agtgatcttc cgtcacaggt    4980
atttattcgg cgcaaagtgc gtcgggtgat gctgccaact tactgattta gtgtatgatg    5040 gtgttttga ggtgctccag tggcttctgt ttctatcagc tcctgaaaat ctcgataact     5100
caaaaaatac gcccggtagt gatcttattt cattatggtg aaagttggaa cctcttacgt    5160
gccgatcaac gtctcatttt cgccaaaagt tgcccaggg cttcccggta tcaacaggga    5220
caccaggatt tatttattct gcgaagtgat cttccgtcac aggtatttat tcggcgcaaa    5280
gtgcgtcggg tgatgctgcc aacttactga tttagtgtat gatggtgttt ttgaggtgct    5340
ccagtggctt ctgtttctat cagggctgga tgatcctcca gcgcggggat ctcatgctgg    5400
agttcttcgc ccaccccaaa aggatctagg tgaagatcct ttttgataat ctcatgacca    5460 aaatcccta acgtgagttt tcgttccact gagcgtcaga ccccgtagaa aagatcaaag     5520
gatcttcttg agatcctttt tttctgcgcg taatctgctg cttgcaaaca aaaaaaccac    5580
cgctaccagc ggtggtttgt ttgccggatc aagagctacc aactctttt ccgaaggtaa     5640 ctggcttcag cagagcgcag ataccaaata ctgttcttct agtgtagccg tagttaggcc    5700
accacttcaa gaactctgta gcaccgccta catacctcgc tctgctaatc ctgttacagt    5760
ggctgctgcc agtggcgata agtcgtgtct taccggttg gactcaagac gatagttacc      5820
ggataaggcg cagcggtcgg gctgaacggg gggttcgtgc acacagccca gcttggagcg    5880
aacgacctac accgaactga gatacctaca gcgtgagcta tgagaaagcg ccacgcttcc    5940
cgaagggaga aaggcggaca ggtatccggt aagcggcagg gtcggaacag gagagcgcac    6000
```

```
gagggagctt ccaggggaa  acgcctggta  tctttatagt  cctgtcgggt  ttcgccacct  6060
ctgacttgag cgtcgatttt tgtgatgctc  gtcagggggg  cggagcctat  ggaaaaacgc  6120
cagcaacgcg gccttttac  ggttcctggc  cttttgctgg  cctttttgctc acatgttctt  6180
tcctgcgtta tccctgatt  ctgtggataa  ccgtattacc  gcctttgagt  gagctgatac  6240
cgctcgccgc agccgaacga ccgagcgcag  cgagtcagtg  agcgaggaag  cggaagagcg  6300
cccaatacgc aaaccgcctc tccccgcgcg  ttggccgatt  cattaatgca  gctggcacga  6360
caggtttccc gactggaaag cgggcagtga  gcgcaacgca  attaatgtga  gttagaagcc  6420
gaatgtcgat gatatctaca acctgagcga  gcacgtcgag  caggaagggg  cgtacgtcac  6480
cacccgcctg aacatcgccg acccgctgaa  ggtcatcctg  ggtgcacgcc  tggactggta  6540
cgacaacaag tcggtgtaca gcgaaatcaa  cgacggctac  tacaccaaca  gcgattacaa  6600
ggtcacccgc aacgtcaccc gctacgccgg  agtgatctac  gacctggacg  accaccactc  6660
ggtctacgcc agctacaccg atatcttcat  gccgcaatcg  gaactggcgc  gtgaccgctc  6720
catcatccgc ccaatcgaag gcaagaacta  cgagatcggc  atcaagggcg  agtacttcga  6780
cggcgcactc aacgccagcg cggcgatctt  ccagatcgac  caggaaaacc  gcgccgcaga  6840
agcttctaac caggaaggtt gcgtcgacat  cacctgctac  gaagcctcgg  gcaaggtacg  6900
cacccacggt atcgacctgg agttgatggg  cgcactgacc  cccaactggc  aagtcggcgc  6960
aggctacacc tactcgcaaa ccaagtaccg  caaggatgcc  gacaagaaca  aggaaggcac  7020
caagttcgac accgacctgc cagaacacct  gttcaagctg  agcaccacct  acaccttgcc  7080
gggcgagctg aaccagtggc gcgtgggcgg  taacgtgtat  ggccagagca  gcatcttcaa  7140
caaaggcagc aacagcttcg gcaactacca  catcgatcaa  ggtgcatacg  cggtagtggg  7200
cctgatggtc ggctacaagg tcaacaagaa  cctcgacact  cgcctgaacc  tcaacaacgt  7260
attcgacaag aagtactacc agggcattgc  cagcaacaac  tcctggagcc  cgtacgacgt  7320
gtatggtgac ccacgcaact tcaccatcac  cgccaagtac  agcttctgat  cgcctgacgt  7380
tgaacgcaaa aaaccgcacc caggtgcggt  tttttgaatt  cgagctgttg  acaattaatc  7440
atcggctcgt ataatgtgtg gaattgtgag  cggataacaa  tttcacactc  tagagaggag  7500
gacagctatg agcaaaatga gagcaatcga  tgcagccgtt  ctggtcatgc  gccgtgaagg  7560
tgtagatacc gcgttcggca tcccgggggc  tgccatcaac  ccgttgtatt  cggccctgaa  7620
aaaagtcggt ggcatcgatc acgtcctcgc  tcgtcacgtc  gaaggtgcct  cgcacatggc  7680
cgagggctac acccgcgcca acccgggcaa  catcggtgtg  tgcatcggca  cttccggccc  7740
tgccggcacc gacatggtca ccggcctgta  cagtgcctcg  gccgactcca  tcccgattct  7800
gtgcatcact ggccaggcgc acgtgcccg   tctgcacaag  gaagacttcc  aggctgtcga  7860
catcaccaac atcgtcaagc cagtgaccaa  gtgggcgacc  accgttctgg  agccaggcca  7920
ggtgccttac gccttccaga aggccttcta  tgaaatgcgt  accggccgcc  caggccggt   7980
gctgatcgac ctgccgttcg acgtgcagat  ggccgaaatc  gaattcgaca  tcgacgccta  8040
cgaaccgctg cccgtgcaca aaccgtccgc  cacacgcgta  caggccgaaa  aagccctggc  8100
cctgctcaat gacgccgagc gcccactgct  ggtagccggt  ggcggcatca  tcaacgccga  8160
cgccagtgac aagctggtcg aattcgccga  actgaccggc  gtacccgtga  tcccgaccct  8220
gatgggctgg ggcaccatcc cggacgacca  cgcacagatg  gtcggcatgg  tcggcctgca  8280
gacctcgcac cgctatggca acgcaaccct  gctgaaatcc  gacctggtgt  tcggtatcgg  8340
```

```
taaccgctgg gccaaccgcc acaccggttc cgtcgatgtc tacaccgaag gccgcaagtt    8400
cgtgcacgtc gacatcgaac cgacccagat cggccgcgtg ttcacccegg acctgggcat    8460 cgtttccgat gctggtaagg cactggacgt gttcctggaa gtggcccgcg agtggaaagc    8520
cgccggcaag ctcaaatgcc gcaaggcctg gctggaagag tgccaggagc gcaagtcgag    8580
cctgcagcgc aagacccact cgacaacgt gccggtcaag ccgcagcgcg tctacgaaga    8640
aatgaaccaa gtgttcggca aggacacctg ctacgtcagc accatcggcc tgtcgcagat    8700
tgccggcgcg cagttcctgc atgtgtacaa gcctcgccac tggatcaact gcggccaggc    8760
cggcccgctg gctggacca tccctgctgc gctgggcgtg gtcaaagccg atccgaagcg    8820
caaggttgtg gcgctgtcgg gtgactacga cttccagttc atgatcgaag aactggcggt    8880
aggcgcccag ttcaacctgc cgtacgtcca cgtactggtg aacaacgcct acctgggcct    8940
gatccgccag gcgcagcgtg gcttcgacat ggattactgt gtacaactgg cgttcgagaa    9000
catcaactcg accgacgctg ccacctacgg tgtcgaccac gtcgctgtgg tcgaaggcct    9060
gggttgcaag gccatccgtg tgttcgagcc agcagaaatc gccccctgccc tgatcaaggc    9120 acagaagatg gccgaagagt ccgcgtgcc ggtggtggtt gaagtgattc tcgagcgtgt    9180
gaccaacatt tccatgggca ccgagatcaa cgcggtcaac gaattcgaag acctggccct    9240
ggtcggcaac gacgcgccaa ccgccatctc gctgctggac tgatcgcctg acgcccccag    9300
gcacgccctg ggggccttca tcgcaaggag acaactcatg cctcgcttcg ctgccaacct    9360
gtccatgctg ttcaccgaac aggacttcct ggcccgcttc aaggctgccg ccgatgctgg    9420
tttcagcggc gtcgaatacc tgttcccgta cgacttcagc gctgccgaca tcaagcagca    9480
gctggaggcc aacggcctga cccaggtgct gttcaacctg ccggccggcg actgggccaa    9540
aggtgagcgc ggtatcacct gccaccccga ccgcatcgaa gagttccgtg ccggtgtcga    9600
caaggccatc gagtacgcca aggtgctggg caatactcag gtcaacgccc tggccggcat    9660
ccgcccacaa ggcccggact gcgccaccgt gcgtaagacc ttcgtcgaga acctgcgcta    9720
cgccgctgac aagctcaagg gcgccgggat ccgcctggtc atggaaatga tcaacacccg    9780
cgacatcccc ggcttctacc tgaacaccac ccagcaggcc ctggaaatcc aggccgaagt    9840
gggcagcgac aacctgttcc tgcaatacga catctaccac atgcagatca tggaaggtga    9900
cctggctcgc accatggaag ccaacctgaa gctgatcaac cacatccagc tggccgacaa    9960
cccaggccgc aatgaaccag gcaccggcga gatcaactac cgcttcctgt cgaacaccct   10020
ggaccgcatt ggctaccagg ctgggtgggg cgcggagtac aagccgctga ccaccaccgg   10080
cgggcctggg ctggctgaaa acccacaacg caatctgagg aacaactcgg gaccctgtgg   10140
gagcgggctc gcccgcgaac accggcaaag ccggtgccat ccaccgagtt gtctgcttcg   10200
cgggcgagcc cgctcccaca gggggccaaa gcttgcttga gatatcacaa ttacaaagag   10260
gtaatttctc atggctaaaa tcggtttcat cggcaccggc atcatgggca agcccatggc   10320
tcagaacctg caaaaggcag gtcacagcct gttcattccc acccaccacg acgccgcgcc   10380
agccgacctg atcgctgccg gtgccgtggc cctggccaac ccgaaagagg ttgcccagga   10440
agccgaattc atcatcgtca tggtcccgga caccccgcag gtcgaaagcg tcctgttcgg   10500
tgaaaacggc gtggccgagg gcgttggccc gaacaaggtg gtgatcgaca tgagctcgat   10560
ctcgccaacc gccaccaaag ccttcgccga gaagatcaag gctaccggtg ccgcctacct   10620
ggacgccccg gtgtccggtg gtgaagtcgg cgccaaggcg gcgaccctga gcatcatggt   10680
tggtggctgc ccgaacgcct tcgagcgcac cctgccgctg ttcgaagcca tgggcaagaa   10740
```

```
catcacccgc gtcggtggca acggtgacgg ccagaccgcc aaggtcgcca accagatcat   10800
tgtcgccctg aacatccagg ccgtggccga agccctgctg ttcgccgcca agaacggcgc   10860
cgaccctgcc aaggtgcgcg aagcactgat gggcggcttt gcttcgtcga aaatcctcga   10920
agtgcacgcc gagcgcatga tcaagggcac cttcgaccca ggcttccgca tcaacctgca   10980
ccagaaggac ctgaacctgg ccctgcaagg cgccaaggaa ctgggcatca acctgcccaa   11040
cacctccaat gcccagcaag tgttcaacac ctgccaggcc ctgggcggcg caactggga   11100 ccactcggcg ctgatcaaag gcctggagca catggccaac ttctcgatcc gcgacgacaa   11160
ataaactagt                                                         11170
```

<210> SEQ ID NO 4
<211> LENGTH: 14099
<212> TYPE: DNA
<213> ORGANISM: Artificial Sequence
<220> FEATURE:
<223> OTHER INFORMATION: engineered plasmid pMFL161

<400> SEQUENCE: 4

```
agtcaaaagc ctccgaccgg aggcttttga ctcatggatg cctgaaaggc tcccttacag     60
atgctgctgc agtgcctcga ccaccatcgc caggccttca tcggcctcct cgatgatcga    120
acccatacgc atgaagtcat gggtcactcc cgggatcacc gcaagctgca ccgccacccc    180
ggcttgctcc aagtgccgtg cataagcgac accctggtca tgcagcgggt cgcactcggc    240
aatcagcatc agtgcaggtg cactgttgct ggcgacgctg cccagcaacg gtgaaaaacg    300
cggatcgtga cggtctgccg gcaccgtggc gtattgctgg tagaaccact ccagggtctg    360
cgcttcaagc aggtaaccgc tgccatagcg ctgcaccgaa ggccgccggc aactggcatc    420
ggtcaccggg tagatcatta cctgcaggcg cggtgccggc agctcgcgct gcgcagccaa    480
ctggttggcc agaatggtag ccaggctacc accgacactg tcgccaccca ccgccagtcg    540
ctgcgcatcg atgcccagcg cctcggcctg ctcgaccaac cagcgccagg catccagggc    600
atcgtcactg gctgtcggga aacgccactg cggcgccagc cggtagccca cggcaatcac    660
cggcaccccg gcatcctgcg ccaggttcca gcacagcgtg tcatgcgaat cgaggctgcc    720
caccacgtag ccgccgccat gcaggtacag cagcgccgcg ccggccagtg cagggtcggc    780
ctgcggcggg cggtacaagc gcaccggcaa ggtatggcca tcgcgggtgg tcaacgaaag    840
gtcgctgatg cagtccggct cgtcggcctt gcccgcaatc agcgccgagg actcttcgaa    900
ctggcggcgc gcctcgtccg ccgccagggc atgcatgggc agcaccttgc cggcgctgcg    960
tccggcctcc accagttgca ggtaggccgc caggtcaggg ttcagggaca tcgttcgatt   1020
ctccagaggg gcctagcttc acgctgccgc aagcactcag ggcgcaaggg ctgctaaagg   1080
aagcggaaca cgtagaaagc cagtccgcag aaacggtgct gaccccggat gaatgtcagc   1140
tactgggcta tctggacaag ggaaaacgca agcgcaaaga gaaagcaggt agcttgcagt   1200
gggcttacat ggcgatagct agactgggcg gttttatgga cagcaagcga accggaattg   1260
ccagctgggg cgccctctgg taaggttggg aagccctgca agtaaactg gatggctttc   1320 ttgccgccaa ggatctgatg gcgcagggga tcaagatctg atcaagagac aggatgagga   1380
tcgtttcgca tgattgaaca agatggattg cacgcaggtt ctccggccgc ttgggtggag   1440
aggctattcg gctatgactg ggcacaacag acaatcggct gctctgatgc cgccgtgttc   1500
cggctgtcag cgcaggggcg cccggttctt tttgtcaaga ccgacctgtc cggtgccctg   1560
```

```
aatgaactcc aagacgaggc agcgcggcta tcgtggctgg ccacgacggg cgttccttgc    1620
gcagctgtgc tcgacgttgt cactgaagcg ggaagggact ggctgctatt gggcgaagtg    1680
ccggggcagg atctcctgtc atctcacctt gctcctgccg agaaagtatc catcatggct    1740
gatgcaatgc ggcggctgca tacgcttgat ccggctacct gcccattcga ccaccaagcg    1800
aaacatcgca tcgagcgagc acgtactcgg atggaagccg gtcttgtcga tcaggatgat    1860
ctggacgaag agcatcaggg gctcgcgcca gccgaactgt tcgccaggct caaggcgcgg    1920
atgcccgacg gcgaggatct cgtcgtgacc catggcgatg cctgcttgcc gaatatcatg    1980
gtggaaaatg gccgcttttc tggattcatc gactgtggcc ggctgggtgt ggcggaccgc    2040
tatcaggaca tagcgttggc tacccgtgat attgctgaag agcttggcgg cgaatgggct    2100
gaccgcttcc tcgtgcttta cggtatcgcc gctcccgatt cgcagcgcat cgccttctat    2160
cgccttcttg acgagttctt ctgagcggga ctctggggtt cgctagagga tcgatccttt    2220
ttaacccatc acatatacct gccgttcact attatttagt gaaatgagat attatgatat    2280
tttctgaatt gtgattaaaa aggcaacttt atgcccatgc aacagaaact ataaaaaata    2340
cagagaatga aaagaaacag atagatttt tagttcttta ggcccgtagt ctgcaaatcc    2400
ttttatgatt ttctatcaaa caaaagagga aaatagacca gttgcaatcc aaacgagagt    2460
ctaatagaat gaggtcgaaa agtaaatcgc gcgggtttgt tactgataaa gcaggcaaga    2520
cctaaaatgt gtaaagggca aagtgtatac tttggcgtca cccttacat attttaggtc     2580 tttttttatt gtgcgtaact aacttgccat cttcaaacag gagggctgga agaagcagac    2640
cgctaacaca gtacataaaa aaggagacat gaacgatgaa catcaaaaag tttgcaaaac    2700
aagcaacagt attaaccttt actaccgcac tgctggcagg aggcgcaact caagcgtttg    2760
cgaaagaaac gaaccaaaag ccatataagg aaacatacgg catttcccat attacacgcc    2820
atgatatgct gcaaatccct gaacagcaaa aaatgaaaa atatcaagtt tctgaatttg    2880
attcgtccac aattaaaaat atctcttctg caaaaggcct ggacgtttgg acagctggc    2940 cattacaaaa cgctgacggc actgtcgcaa actatcacgg ctaccacatc gtctttgcat    3000
tagccggaga tcctaaaaat gcggatgaca catcgattta catgttctat caaaaagtcg    3060
gcgaaacttc tattgacagc tggaaaaacg ctggccgcgt ctttaaagac agcgacaaat    3120
tcgatgcaaa tgattctatc ctaaaagacc aaacacaaga atggtcaggt tcagccacat    3180
ttacatctga cggaaaaatc cgtttattct acactgattt ctccggtaaa cattacggca    3240
aacaaacact gacaactgca caagttaacg tatcagcatc agacagctct ttgaacatca    3300
acggtgtaga ggattataaa tcaatctttg acggtgacgg aaaaacgtat caaaatgtac    3360
agcagttcat cgatgaaggc aactacagct caggcgacaa ccatacgctg agagatcctc    3420
actacgtaga agataaaggc cacaaatact tagtatttga agcaaacact ggaactgaag    3480
atggctacca aggcgaagaa tctttattta caaagcata ctatggcaaa agcacatcat    3540
tcttccgtca agaaagtcaa aaacttctgc aaagcgataa aaaacgcacg gctgagttag    3600
caaacggcgc tctcggtatg attgagctaa cgatgatta cacactgaaa aaagtgatga    3660
aaccgctgat tgcatctaac acagtaacag atgaaattga acgcgcgaac gtcttaaaa    3720 tgaacggcaa atggtacctg ttcactgact cccgcggatc aaaaatgacg attgacggca    3780
ttacgtctaa cgatatttac atgcttggtt atgtttctaa ttctttaact ggcccataca    3840
agccgctgaa caaaactggc cttgtgttaa aaatggatct tgatcctaac gatgtaacct    3900
ttacttactc acacttcgct gtacctcaag cgaaaggaaa caatgtcgtg attacaagct    3960
```

```
atatgacaaa cagaggattc tacgcagaca aacaatcaac gtttgcgccg agcttcctgc   4020
tgaacatcaa aggcaagaaa acatctgttg tcaaagacag catccttgaa caaggacaat   4080
taacagttaa caaataaaaa cgcaaaagaa aatgccgatg ggtaccgagc gaaatgaccg   4140
accaagcgac gcccaacctg ccatcacgag atttcgattc caccgccgcc ttctatgaaa   4200
ggttgggctt cggaatcgtt ttccgggacg ccctcgcgga cgtgctcata gtccacgacg   4260
cccgtgattt tgtagccctg gccgacggcc agcaggtagg ccgacaggct catgccggcc   4320
gccgccgcct tttcctcaat cgctcttcgt tcgtctggaa ggcagtacac cttgataggt   4380
gggctgccct tcctggttgg cttggtttca tcagccatcc gcttgccctc atctgttacg   4440
ccggcggtag ccggccagcc tcgcagagca ggattcccgt tgagcaccgc caggtgcgaa   4500
taagggacag tgaagaagga acacccgctc gcgggtgggc ctacttcacc tatcctgccc   4560
ggctgacgcc gttggataca ccaaggaaag tctacacgaa ccctttggca aaatcctgta   4620
tatcgtgcga aaaaggatgg atataccgaa aaatcgcta taatgacccc gaagcagggt   4680
tatgcagcgg aaaagcgctg cttccctgct gttttgtgga atatctaccg actggaaaca   4740
ggcaaatgca ggaaattact gaactgaggg gacaggcgag agacgatgcc aaagagctcc   4800
tgaaaatctc gataactcaa aaaatacgcc cggtagtgat cttatttcat tatggtgaaa   4860
gttgaacct cttacgtgcc gatcaacgtc tcattttcgc caaaagttgg cccagggctt   4920
cccggtatca acagggacac caggatttat ttattctgcg aagtgatctt ccgtcacagg   4980
tatttattcg gcgcaaagtg cgtcgggtga tgctgccaac ttactgattt agtgtatgat   5040
ggtgttttg aggtgctcca gtggcttctg tttctatcag ctcctgaaaa tctcgataac   5100
tcaaaaaata cgcccggtag tgatcttatt tcattatggt gaaagttgga acctcttacg   5160
tgccgatcaa cgtctcattt tcgccaaaag ttggcccagg gcttcccggt atcaacaggg   5220
acaccaggat ttatttattc tgcgaagtga tcttccgtca caggtatttta ttcggcgcaa   5280
agtgcgtcgg gtgatgctgc caacttactg atttagtgta tgatggtgtt tttgaggtgc   5340
tccagtggct tctgtttcta tcagggctgg atgatcctcc agcgcgggga tctcatgctg   5400
gagttcttcg cccacccaa aaggatctag gtgaagatcc ttttttgataa tctcatgacc   5460
aaaatccctt aacgtgagtt ttcgttccac tgagcgtcag accccgtaga aaagatcaaa   5520
ggatcttctt gagatccttt ttttctgcgc gtaatctgct gcttgcaaac aaaaaaacca   5580
ccgctaccag cggtggtttg tttgccggat caagagctac caactctttt tccgaaggta   5640
actggcttca gcagagcgca gataccaaat actgttcttc tagtgtagcc gtagttaggc   5700
caccacttca agaactctgt agcaccgcct acatacctcg ctctgctaat cctgttacca   5760
gtggctgctg ccagtggcga taagtcgtgt cttaccgggt tggactcaag acgatagtta   5820
ccggataagg cgcagcggtc gggctgaacg gggggttcgt gcacacagcc cagcttggag   5880
cgaacgacct acaccgaact gagataccta cagcgtgagc tatgagaaag cgccacgctt   5940
cccgaaggga gaaaggcgga caggtatccg gtaagcggca gggtcggaac aggagagcgc   6000
acgagggagc ttccagggg aaacgcctgg tatctttata gtcctgtcgg gtttcgccac   6060
ctctgacttg agcgtcgatt tttgtgatgc tcgtcagggg ggcggagcct atggaaaaac   6120
gccagcaacg cggccttttt acggttcctg gccttttgct ggccttttgc tcacatgttc   6180
tttcctgcgt tatcccctga ttctgtggat aaccgtatta ccgcctttga gtgagctgat   6240
accgctcgcc gcagccgaac gaccgagcgc agcgagtcag tgagcgagga agcggaagag   6300
```

```
cgcccaatac gcaaaccgcc tctccccgcg cgttggccga ttcattaatg cagctggcac    6360
gacaggtttc ccgactggaa agcgggcagt gagcgcaacg caattaatgt gagttagaag    6420
ccgaatgtcg atgatatcta caacctgagc gagcacgtcg agcaggaagg ggcgtacgtc    6480
accacccgcc tgaacatcgc cgacccgctg aaggtcatcc tgggtgcacg cctggactgg    6540
tacgacaaca agtcggtgta cagcgaaatc aacgacggct actacaccaa cagcgattac    6600
aaggtcaccc gcaacgtcac ccgctacgcc ggagtgatct acgacctgga cgaccaccac    6660
tcggtctacg ccagctacac cgatatcttc atgccgcaat cggaactggc gcgtgaccgc    6720
tccatcatcc gcccaatcga aggcaagaac tacgagatcg gcatcaaggg cgagtacttc    6780
gacggcgcac tcaacgccag cgcggcgatc ttccagatcg accaggaaaa ccgcgccgca    6840
gaagcttcta accaggaagg ttgcgtcgac atcacctgct acgaagcctc gggcaaggta    6900
cgcacccacg gtatcgacct ggagttgatg ggcgcactga cccccaactg gcaagtcggc    6960
gcaggctaca cctactcgca aaccaagtac cgcaaggatg ccgacaagaa caaggaaggc    7020
accaagttcg acaccgacct gccagaacac ctgttcaagc tgagcaccac ctacaccttg    7080
ccgggcgagc tgaaccagtg gcgcgtgggc ggtaacgtgt atggccagag cagcatcttc    7140
aacaaaggca gcaacagctt cggcaactac cacatcgatc aaggtgcata cgcggtagtg    7200
ggcctgatgg tcggctacaa ggtcaacaag aacctcgaca ctcgcctgaa cctcaacaac    7260
gtattcgaca agaagtacta ccagggcatt gccagcaaca actcctggag cccgtacgac    7320
gtgtatggtg acccacgcaa cttcaccatc accgccaagt acagcttctg atcgcctgac    7380
gttgaacgca aaaaaccgca cccaggtgcg gttttttgaa ttcgagctgt tgacaattaa    7440
tcatcggctc gtataatgtg tggaattgtg agcggataac aatttcacac tctagagagg    7500
aggacagcta tgagcaaaat gagagcaatc gatgcagccg ttctggtcat cgccgtgaa    7560 ggtgtagata ccgcgttcgg catcccgggg gctgccatca cccgttgta ttcggccctg    7620 aaaaaagtcg gtggcatcga tcacgtcctc gctcgtcacg tcgaaggtgc ctcgcacatg    7680
gccgagggct acacccgcgc caacccgggc aacatcggtg tgtgcatcgg cacttccggc    7740
cctgccggca ccgacatggt caccggcctg tacagtgcct cggccgactc catcccgatt    7800
ctgtgcatca ctggccaggc gccacgtgcc cgtctgcaca aggaagactt ccaggctgtc    7860
gacatcacca acatcgtcaa gccagtgacc aagtgggcga ccaccgttct ggagccaggc    7920
caggtgcctt acgccttcca gaaggccttc tatgaaatgc gtaccggccg cccaggcccg    7980
gtgctgatcg acctgccgtt cgacgtgcag atggccgaaa tcgaattcga catcgacgcc    8040
tacgaaccgc tgcccgtgca caaaccgtcc gccacacgcg tacaggccga aaaagccctg    8100
gccctgctca atgacgccga gcgcccactg ctggtagccg gtggcggcat catcaacgcc    8160
gacgccagtg acaagctggt cgaattcgcc gaactgaccg gcgtacccgt gatcccgacc    8220
ctgatgggct ggggcaccat cccggacgac cacgcacaga tggtcggcat ggtcggcctg    8280
cagacctcgc accgctatgg caacgcaacc ctgctgaaat ccgacctggt gttcggtatc    8340
ggtaaccgct gggccaaccg ccacaccggt tccgtcgatg tctacaccga aggccgcaag    8400
ttcgtgcacg tcgacatcga accgaccag atcggccgcg tgttcacccc ggacctgggc    8460
atcgtttccg atgctggtaa ggcactggac gtgttcctgg aagtggcccg cgagtggaaa    8520
gccgccggca agctcaaatg ccgcaaggcc tggctggaag agtgccagga gcgcaagtcg    8580
agcctgcagc gcaagaccca cttcgacaac gtgccggtca gccgcagcg cgtctacgaa    8640 gaaatgaacc aagtgttcgg caaggacacc tgctacgtca gcaccatcgg cctgtcgcag    8700
```

-continued

```
attgccggcg cgcagttcct gcatgtgtac aagcctcgcc actggatcaa ctgcggccag    8760
gccggcccgc tgggctggac catccctgct gcgctgggcg tggtcaaagc cgatccgaag    8820
cgcaaggttg tggcgctgtc gggtgactac gacttccagt tcatgatcga agaactggcg    8880
gtaggcgccc agttcaacct gccgtacgtc cacgtactgg tgaacaacgc ctacctgggc    8940
ctgatccgcc aggcgcagcg tggcttcgac atggattact gtgtacaact ggcgttcgag    9000
aacatcaact cgaccgacgc tgccacctac ggtgtcgacc acgtcgctgt ggtcgaaggc    9060
ctgggttgca aggccatccg tgtgttcgag ccagcagaaa tcgcccctgc cctgatcaag    9120
gcacagaaga tggccgaaga gttccgcgtg ccggtggtgg ttgaagtgat tctcgagcgt    9180
gtgaccaaca tttccatggg caccgagatc aacgcggtca cgaattcga agacctggcc    9240
ctggtcggca acgacgcgcc aaccgccatc tcgctgctgg actgatcgcc tgacgccccc    9300
aggcacgccc tgggggcctt catcgcaagg agacaactca tgcctcgctt cgctgccaac    9360
ctgtccatgc tgttcaccga acaggacttc ctggcccgct tcaaggctgc cgccgatgct    9420
ggtttcagcg gcgtcgaata cctgttcccg tacgacttca gcgctgccga catcaagcag    9480
cagctggagg ccaacggcct gacccaggtg ctgttcaacc tgccggccgg cgactgggcc    9540
aaaggtgagc gcggtatcac ctgccacccc gaccgcatcg aagagttccg tgccggtgtc    9600
gacaaggcca tcgagtacgc caaggtgctg gcaatactc aggtcaacgc cctgccggc     9660
atccgcccac aaggcccgga ctgcgccacc gtgcgtaaga ccttcgtcga aacctgcgc    9720
tacgccgctg acaagctcaa gggcgccggg atccgcctgg tcatggaaat gatcaacacc    9780
cgcgacatcc ccggcttcta cctgaacacc acccagcagg ccctggaaat ccaggccgaa    9840
gtgggcagcg acaacctgtt cctgcaatac gacatctacc acatgcagat catgaaggt    9900
gacctggctc gcaccatgga agccaacctg aagctgatca ccacatcca gctggccgac    9960
aacccaggcc gcaatgaacc aggcaccggc gagatcaact accgcttcct gttcgaacac   10020
ctggaccgca ttggctacca gggctgggtg ggcgcggagt acaagccgct gaccaccacc   10080
gaagcgggcc tgggctggct gaaaacccac aacgcaatct gaggaacaac tcggaccct    10140
gtgggagcgg gctcgcccgc gaacaccggc aaagccggtg ccatccaccg agttgtctgc   10200
ttcgcgggcg agcccgctcc cacagggggc caaagcttgc ttgagatatc acaattacaa   10260
agaggtaatt tctcatggct aaaatcggtt tcatcggcac cggcatcatg gcaagccca    10320
tggctcagaa cctgcaaaag gcaggtcaca gcctgttcat ttccaccac cacgacgccg   10380
cgccagccga cctgatcgct gccggtgccg tggcctggc caacccgaaa gaggttgccc   10440
aggaagccga attcatcatc gtcatggtcc ccgacacccc gcaggtcgaa agcgtcctgt   10500
tcggtgaaaa cggcgtggcc gagggcgttg cccgaacaa ggtggtgatc gacatgagct   10560
cgatctcgcc aaccgccacc aaagccttcg ccgagaagat caaggctacc ggtgccgcct   10620
acctggacgc cccggtgtcc ggtggtgaag tcggcgccaa ggcggcgacc ctgagcatca   10680
tggttggtgg ctgcccgaac gccttcgagc gcaccctgcc gctgttcgaa gccatgggca   10740
agaacatcac ccgcgtcggt ggcaacggtg acggccagac cgccaaggtc gccaaccaga   10800
tcattgtcgc cctgaacatc caggccgtgg ccgaagccct gctgttcgcc gccaagaacg   10860
gcgccgaccc tgccaaggtg cgcgaagcac tgatgggcgg ctttgcttcg tcgaaaatcc   10920
tcgaagtgca cgccgagcgc atgatcaagg gcacttcga cccaggcttc cgcatcaacc   10980
tgcaccagaa ggacctgaac ctggccctgc aaggcgccaa ggaactgggc atcaacctgc   11040
```

```
ccaacacctc caatgcccag caagtgttca acacctgcca ggccctgggc ggcggcaact    11100
gggaccactc ggcgctgatc aaaggcctgg agcacatggc caacttctcg atccgcgacg    11160
acaaataaat cgttttagc ctcactggcc tcttcgcggg taaacccgct cctaccaaag     11220
accgcacaat cgctcagagc tgtgcatgta ggagcgggct tgcccgcgaa gaagccaacg    11280
ccgttgaacc tgcgaccaca ggcccaatgg tggcatcgag caacacccgc cctggttcg    11340
gcctgcacgg aggcagttcc aggggcgttt ttgattctgc agaacaacaa taattgggag    11400
cctgccatgt cggtcgatcc gcaaaaactt ctccgcgaac tgttcgacac agccatcgcc    11460
gccgcccacc cccgtcaagt cctcgaaccc tacctgcccg ccgatcgcag cggccgggtt    11520
atcgtcatcg gcgccggcaa ggccgcagct gccatggccg aagtggtcga gaaaagctgg    11580
cagggtgaag tctccggcct ggtcgtgacc cgttacggcc acggcgccaa ctgccagaag    11640
atcgaggtgg tcgaagccgc ccacccggtc ccggacgctg ccggcctggc tgtggccaag    11700
cgcgtgctgg aactggtcag caacctcaac gaagaagacc gcgtcatctt cctgctgtct    11760
ggcggtggct cggcgttgct ggccctgcct gccgaaggcc tgaccctggc cgacaagcag    11820
cagatcaaca aggcgctgct gaaatccggc gccaccatcg gcgagatgaa ctgcgtgcgc    11880
aagcacctct cggcgatcaa gggcgggcgc ctggccaagg cctgctggcc ggccacggtc    11940
tacacctatg ccatttccga tgtaccgggc gacctcgcca cggtaatcgc ctccggcccc    12000
accgtggccg acccgagcac ctcggccgac gccctggcca tcctcaaacg ctacaacatc    12060
gaagcgccca aagcggtcat cgactggctg aacaacccgg cctcggaaac cgtcaaggcc    12120
gatgacccgg ccctggcccg cagccacttc cagttgatcg ccaaaccca gcagtcgctg    12180
gaggctgccg cggtcaaagc ccgtcaggcc ggtttcagcc cgctgattct cggcgacctg    12240
gaaggtgaat cgcgcgaagt ggccaaggtg catgccggta tcgcccggca aatcgttcaa    12300
cacggccagc cgctcaaagc gccctgcgtg atcctgtcgg gtggcgaaac caccgtgacc    12360
gtgcgcggca atgccgtgg cgggcgtaac gccgagttcc tgctcagcct caccgaaagc    12420
ctgaaaggcc tgccgggcgt gtacgccctg ccggtgaca ccgacggcat cgatggctcg    12480
gaagaaaacg ccggtgcctt catgaccccg ccagctacg ccagcgccga agccttgggc    12540
ctgtcggcca gcgacgagct ggacaacaac aacggctacg gctacttcgc cgcgctggat    12600
gcgctgatcg tcaccgaacc gaccgcacc aacgtcaacg acttccgcgc catcctgatc    12660
cttgagactg cccaatcatg acgcctgata aaaagttaa gatccttgcc acccttggcc    12720
ctgcgatcaa cggcatcgac gatatccgcc agctggtcga agccggggtg aacatcttcc    12780
gcctcaactt cagccacggc gaacatgccg accacgccct gcgctaccag tggatccgcg    12840
aagtcgagca acagctgaac tacccgctgg gcatcctcat ggacctgcaa gggccgaagc    12900
tgcgcgttgg ccgcttcgcc gaaggcaagg tgcagttgca acgcgggcag gccctgcgcc    12960
tggatctgga caagaccccg ggcgacagcc gccgggtcaa cctgccgcac cccgaaatca    13020
tcgccgccct cgaacccggc atggacctgc tgctggacga cggcaagctg cgcctgcgcg    13080
tgaccgccaa gcacagcgac gccatcgaca ccgaggtgct gaatggtggc gagctttccg    13140
accgcaaggg cgtcaacgta ccgcaagcgg tgctcgacct ctccccgctc accgaaaaag    13200
accgccgcga cctggccttt ggcctggagc tgggtgtgga ctgggtcgcc ctgtcgttcg    13260
tgcagcgccc tgaggacatc gtcgaagcgc gccagctgat tggcgaccgc gcctacctga    13320
tggccaaaat cgagaaacca tcggcagtcg agcaactgca agccatcgcc gagctggcag    13380
acgcgatcat ggtggcccgt ggtgacctgg gcgtggaagt accggccgag agcgtgccgc    13440
```

```
agatccagaa gcgcatcatc ggcacctgcc gccagctagg caaacccgtg gtggtggcca    13500
cgcagatgct cgagtcgatg cgtttctcgc cagcgccaac ccgcgccgaa gtcacggacg    13560
tggccaacgc ggtggccgaa ggtgccgatg cagtgatgct gtcggccgaa accgcctcgg    13620
gtgattaccc gctggaagcc gtgcagatga tgagcaagat catccgccag gttgagaacg    13680
gcccggacta ccaggcccag ctcgacgtcg gccggccaaa ggccgaagcc accgtgtcgg    13740
atgccatcag ctgcgccatc cgccgcatca gcggcatcct gccagtggcg gtgctggtca    13800
actacagcga gtcgggtgcc tcgaccctgc gcgcggcacg tgaacggcca cgggcaccga    13860
tcctcaacct gacgccgaac ctgaacaccg cgcgccgcct gagcgtggct ggggtgtgc     13920 attcggtggt caacgaccgc ctgcgtcagg tcgacgaggt ggtttccacc gccctggaga    13980
ttgcccaggc gcaaggcatg gccagccgtg gcgacacgct gctgatcacc gctggcgtgc    14040
ctttcggcaa gccgggtacg actaacacgc tgcggatcga actttgatc tgaactagt     14099
```

<210> SEQ ID NO 5
<211> LENGTH: 7236
<212> TYPE: DNA
<213> ORGANISM: Artificial Sequence
<220> FEATURE:
<223> OTHER INFORMATION: engineered plasmid pSEVA_gcl_glx

<400> SEQUENCE: 5

```
ttaattaatt gacaccatcg aatggtgcaa aacctttcgc ggtatggcat gatagcgccc      60
ggaagagagt caattcaggg tggtgaatgt gaaaccagta acgttatacg atgtcgcaga    120
gtatgccggt gtctcttatc agaccgtttc ccgcgtggtg aaccaggcca gccacgtttc    180
tgcgaaaacg cgggaaaaag tggaagcggc gatggcggag ctgaattaca ttcccaaccg    240
cgtggcacaa caactggcgg gcaaacagtc gttgctgatt ggcgttgcca cctccagtct    300
ggccctgcac gcgccgtcgc aaattgtcgc ggcgattaaa tctcgcgccg atcaactggg    360
tgccagcgtg gtggtgtcga tggtagaacg aagcggcgtc gaagcctgta aagcggcggt    420
gcacaatctt ctcgcgcaac gcgtcagtgg gctgatcatt aactatccgc tggatgacca    480
ggatgccatt gctgtggaag ctgcctgcac taatgttccg gcgttatttc ttgatgtctc    540
tgaccagaca cccatcaaca gtattatttt ctcccatgaa gacggtacgc gactgggcgt    600
ggagcatctg gtcgcattgg gtcaccagca atcgcgctg ttagcgggcc cattaagttc     660
tgtctcggcg cgtctgcgtc tggctggctg gcataaatat ctcactcgca atcaaattca    720
gccgatagcg gaacgggaag gcgactggag tgccatgtcc ggttttcaac aaaccatgca    780
aatgctgaat gagggcatcg ttcccactgc gatgctggtt gccaacgatc agatggcgct    840
gggcgcaatg cgcgccatta ccgagtccgg gctgcgcgtt ggtgcggata tctcggtagt    900
gggatacgac gataccgaag acagctcatg ttatatcccg ccgttaacca ccatcaaaca    960
ggattttcgc ctgctgggc aaaccagcgt ggaccgcttg ctgcaactct ctcagggcca    1020
ggcggtgaag gcaatcagc tgttgcccgt ctcactggtg aaaagaaaaa ccaccctggc    1080
gcccaatacg caaaccgcct ctccccgcgc gttggccgat tcattaatgc agctggcacg    1140
acaggtttcc cgactggaaa gcgggcagtg agcgcaacgc aattaatgtg agttagcgcg    1200
aattgatctg gtttgacagc ttatcatcga ctgcacggtg caccaatgct tctggcgtca    1260
ggcagccatc ggaagctgtg gtatggctgt gcaggtcgta atcactgca taattcgtgt    1320 cgctcaaggc gcactcccgt tctggataat gtttttttgcg ccgacatcat aacggttctg    1380
```

| | |
|---|---|
| gcaaatattc tgaaatgagc tgttgacaat taatcatccg gctcgtataa tgtgtggaat | 1440 |
| tgtgagcgga taacaatttc acaccctagg ccgcggccgc gcgaattcga gctcgctagg | 1500 |
| aggtcaaacc atgagcaaaa tgagagcaat cgatgcagcc gttctggtca tgcgccgtga | 1560 |
| aggtgtagat accgcgttcg gcatcccggg ggctgccatc aacccgttgt attcggccct | 1620 |
| gaaaaaagtc ggtggcatcg atcacgtcct cgctcgtcac gtcgaaggtg cctcgcacat | 1680 |
| ggccgagggc tacacccgcg ccaacccggg caacatcggt gtgtgcatcg gcacttccgg | 1740 |
| ccctgccggc accgacatgg tcaccggcct gtacagtgcc tcggccgact ccatcccgat | 1800 |
| tctgtgcatc actggccagg cgccacgtgc ccgtctgcac aaggaagact tccaggctgt | 1860 |
| cgacatcacc aacatcgtca agccagtgac caagtgggcg accaccgttc tggagccagg | 1920 |
| ccaggtgcct tacgccttcc agaaggcctt ctatgaaatg cgtaccgcc gcccaggccc | 1980 |
| ggtgctgatc gacctgccgt tcgacgtgca gatggccgaa atcgaattcg acatcgacgc | 2040 |
| ctacgaaccg ctgcccgtgc acaaccgtc cgccacacgc gtacaggccg aaaaagccct | 2100 |
| ggccctgctc aatgacgccg agcgcccact gctggtagcc ggtggcggca tcatcaacgc | 2160 |
| cgacgccagt gacaagctgg tcgaattcgc cgaactgacc ggcgtacccg tgatcccgac | 2220 |
| cctgatgggc tggggcacca tcccggacga ccacgcacag atggtcggca tggtcggcct | 2280 |
| gcagacctcg caccgctatg caacgcaac cctgctgaaa tccgacctgg tgttcggtat | 2340 |
| cggtaaccgc tgggccaacc gccacaccgg ttccgtcgat gtctacaccg aaggccgcaa | 2400 |
| gttcgtgcac gtcgacatcg aaccgaccca gatcggccgc gtgttcaccc cggacctggg | 2460 |
| catcgtttcc gatgctggta aggcactgga cgtgttcctg gaagtggccc gcgagtggaa | 2520 |
| agccgccggc aagctcaaat gccgcaaggc ctggctggaa gagtgccagg agcgcaagtc | 2580 |
| gagcctgcag cgcaagaccc acttcgacaa cgtgccggtc aagccgcagc gcgtctacga | 2640 |
| agaaatgaac caagtgttcg gcaaggacac ctgctacgtc agcaccatcg gcctgtcgca | 2700 |
| gattgccggc gcgcagttcc tgcatgtgta caagcctcgc cactggatca actgcggcca | 2760 |
| ggccggcccg ctgggctgga ccatccctgc tgcgctgggc gtggtcaaag ccgatccgaa | 2820 |
| gcgcaaggtt gtgcgctgt cgggtgacta cgacttccag ttcatgatcg aagaactggc | 2880 |
| ggtaggcgcc cagttcaacc tgccgtacgt ccacgtactg gtgaacaacg cctacctggg | 2940 |
| cctgatccgc caggcgcagc gtggcttcga catggattac tgtgtacaac tggcgttcga | 3000 |
| gaacatcaac tcgaccgacg ctgccaccta cggtgtcgac cacgtcgctg tggtcgaagg | 3060 |
| cctgggttgc aaggccatcc gtgtgttcga gccagcagaa atcgcccctg ccctgatcaa | 3120 |
| ggcacagaag atggccgaag agttccgcgt gccggtggtg gttgaagtga ttctcgagcg | 3180 |
| tgtgaccaac atttccatgg gcaccgagat caacgcggtc aacgaattcg aagacctggc | 3240 |
| cctggtcggc aacgacgcgc caaccgccat ctcgctgctg gactgatcgc ctgacgtcta | 3300 |
| gaataggagg tcaccagcta tggctaaaat cggtttcatc ggcaccggca tcatgggcaa | 3360 |
| gcccatggct cagaacctgc aaaaggcagg tcacagcctg ttcattcca cccaccacga | 3420 |
| cgccgcgcca gccgacctga tcgctgccgg tgccgtggcc ctggccaacc gaaagaggt | 3480 |
| tgcccaggaa gccgaattca tcatcgtcat ggtccccgac accccgcagg tcgaaagcgt | 3540 |
| cctgttcggt gaaaacggcg tggccgaggg cgttggcccg aacaaggtgg tgatcgacat | 3600 |
| gagctcgatc tcgccaaccg ccaccaaagc cttcgccgag aagatcaagg ctaccggtgc | 3660 |
| cgcctacctg gacgccccgg tgtccggtgg tgaagtcggc gccaaggcgg cgaccctgag | 3720 |
| catcatggtt ggtggctgcc cgaacgcctt cgagcgcacc ctgccgctgt tcgaagccat | 3780 |

```
gggcaagaac atcacccgcg tcggtggcaa cggtgacggc cagaccgcca aggtcgccaa    3840
ccagatcatt gtcgccctga acatccaggc cgtggccgaa gccctgctgt tcgccgccaa    3900
gaacggcgcc gaccctgcca aggtgcgcga agcactgatg gcggctttg cttcgtcgaa     3960 aatcctcgaa gtgcacgccg agcgcatgat caagggcacc ttcgacccag gcttccgcat    4020
caacctgcac cagaaggacc tgaacctggc cctgcaaggc gccaaggaac tgggcatcaa    4080
cctgcccaac acctccaatg cccagcaagt gttcaacacc tgccaggccc tgggcggcgg    4140
caactgggac cactcggcgc tgatcaaagg cctggagcac atggccaact tctcgatccg    4200
cgacgacaaa taagcatgca agcttgcggc cgcgtcgtga ctgggaaaac cctggcgact    4260
agtcttggac tcctgttgat agatccagta atgacctcag aactccatct ggatttgttc    4320
agaacgctcg gttgccgccg ggcgtttttt attggtgaga atccaggggt ccccaataat    4380
tacgatttaa atttgtgtct caaaatctct gatgttacat tgcacaagat aaaaatatat    4440
catcatgaac aataaaactg tctgcttaca taaacagtaa tacaaggggt gttatgagcc    4500
atattcagcg tgaaacgagc tgtagccgtc cgcgtctgaa cagcaacatg gatgcggatc    4560
tgtatggcta taaatgggcg cgtgataacg tgggtcagag cggcgcgacc atttatcgtc    4620
tgtatggcaa accggatgcg ccggaactgt ttctgaaaca tggcaaaggc agcgtggcga    4680
acgatgtgac cgatgaaatg gtgcgtctga actggctgac cgaatttatg ccgctgccga    4740
ccattaaaca tttttattcgc accccggatg atgcgtggct gctgaccacc gcgattccgg    4800
gcaaaaccgc gtttcaggtg ctggaagaat atccggatag cggcgaaaac attgtggatg    4860
cgctggccgt gtttctgcgt cgtctgcata gcattccggt gtgcaactgc ccgtttaaca    4920
gcgatcgtgt gtttcgtctg gcccaggcgc agagccgtat gaacaacggc ctggtggatg    4980
cgagcgattt tgatgatgaa cgtaacggct ggccggtgga acaggtgtgg aaagaaatgc    5040
ataaactgct gccgtttagc ccggatagcg tggtgaccca cggcgatttt agcctggata    5100
acctgatttt cgatgaaggc aaactgattg gctgcattga tgtgggccgt gtgggcattg    5160
cggatcgtta tcaggatctg gccattctgt ggaactgcct gggcgaattt agcccgagcc    5220
tgcaaaaacg tctgtttcag aaatatggca ttgataatcc ggatatgaac aaactgcaat    5280 tcatctgat gctggatgaa ttttttctaat aattaattgg accgcggtcc gcgcgttgtc     5340
cttttccgct gcataaccct gcttcggggt cattatagcg atttttcgg tatatccatc      5400 cttttcgca cgatatacag gattttgcca aagggttcgt gtagactttc cttggtgtat      5460
ccaacggcgt cagccgggca ggataggtga agtaggccca cccgcgagcg ggtgttcctt     5520
cttcactgtc ccttattcgc acctggcggt gctcaacggg aatcctgctc tgcgaggctg     5580
gccgtaggcc ggcctaccg gcgcggcagc gttaccgtg tcggcggctc caacggctcg        5640
ccatcgtcca gaaaacacgg ctcatcgggc atcggcaggc gctgctgccc gcgccgttcc     5700
cattcctccg tttcggtcaa ggctggcagg tctggttcca tgcccggaat gccgggctgg     5760
ctgggcggct cctcgccggg gccggtcggt agttgctgct cgcccggata cagggtcggg     5820
atgcggcgca ggtcgccatg ccccaacagc gattcgtcct ggtcgtcgtg atcaaccacc     5880
acggcggcac tgaacaccga caggcgcaac tggtcgcggg gctggccca cgccacgcgg      5940 tcattgacca cgtaggccga cacggtgccg gggccgttga gcttcacgac ggagatccag     6000
cgctcggcca ccaagtcctt gactgcgtat tggaccgtcc gcaaagaacg tccgatgagc     6060
ttggaaagtg tcttctggct gaccaccacg gcgttctggt ggcccatctg cgccacgagg     6120
```

-continued

```
tgatgcagca gcattgccgc cgtgggtttc ctcgcaataa gcccggccca cgcctcatgc      6180
gctttgcgtt ccgtttgcac ccagtgaccg ggcttgttct tggcttgaat gccgatttct      6240
ctggactgcg tggccatgct tatctccatg cggtaggggt gccgcacggt tgcggcacca      6300
tgcgcaatca gctgcaactt ttcggcagcg cgacaacaat tatgcgttgc gtaaaagtgg      6360
cagtcaatta cagattttct ttaacctacg caatgagcta ttgcgggggg tgccgcaatg      6420
agctgttgcg tacccccctt ttttaagttg ttgatttttta agtctttcgc atttcgccct     6480
atatctagtt ctttggtgcc caagaaggg caccctgcg gggttcccc acgccttcgg         6540 cgcggctccc cctccggcaa aaagtggccc ctccggggct tgttgatcga ctgcgcggcc      6600
ttcggccttg cccaaggtgg cgctgccccc ttggaacccc cgcactcgcc gccgtgaggc      6660 tcgggggggca ggcgggcggg cttcgcccctt cgactgcccc cactcgcata ggcttgggtc    6720
gttccaggcg cgtcaaggcc aagccgctgc gcggtcgctg cgcgagcctt gacccgcctt     6780
ccacttggtg tccaaccggc aagcgaagcg cgcaggccgc aggccggagg cttttcccca     6840
gagaaaatta aaaaaattga tggggcaagg ccgcaggccg cgcagttgga gccggtgggt    6900
atgtggtcga aggctgggta gccggtgggc aatccctgtg gtcaagctcg tgggcaggcg     6960
cagcctgtcc atcagcttgt ccagcagggt tgtccacggg ccgagcgaag cgagccagcc     7020
ggtggccgct cgcggccatc gtccacatat ccacgggctg gcaagggagc gcagcgaccg     7080
cgcagggcga agcccggaga gcaagcccgt agggggggcg cgcccagctg tctagggcgg     7140
cggatttgtc ctactcagga gagcgttcac cgacaaacaa cagataaaac gaaaggccca     7200
gtctttcgac tgagcctttc gttttatttg atgcct                               7236
```

<210> SEQ ID NO 6
<211> LENGTH: 591
<212> TYPE: PRT
<213> ORGANISM: Pseudomonas putida

<400> SEQUENCE: 6

```
Met Ser Lys Met Arg Ala Ile Asp Ala Ala Val Leu Val Met Arg Arg
1               5                   10                  15

Glu Gly Val Asp Thr Ala Phe Gly Ile Pro Gly Ala Ala Ile Asn Pro
            20                  25                  30

Leu Tyr Ser Ala Leu Lys Lys Val Gly Gly Ile Asp His Val Leu Ala
        35                  40                  45

Arg His Val Glu Gly Ala Ser His Met Ala Glu Gly Tyr Thr Arg Ala
    50                  55                  60

Asn Pro Gly Asn Ile Gly Val Cys Ile Gly Thr Ser Gly Pro Ala Gly
65                  70                  75                  80

Thr Asp Met Val Thr Gly Leu Tyr Ser Ala Ser Ala Asp Ser Ile Pro
                85                  90                  95

Ile Leu Cys Ile Thr Gly Gln Ala Pro Arg Ala Arg Leu His Lys Glu
            100                 105                 110

Asp Phe Gln Ala Val Asp Ile Thr Asn Ile Val Lys Pro Val Thr Lys
        115                 120                 125

Trp Ala Thr Thr Val Leu Glu Pro Gly Gln Val Pro Tyr Ala Phe Gln
    130                 135                 140

Lys Ala Phe Tyr Glu Met Arg Thr Gly Arg Pro Gly Pro Val Leu Ile
145                 150                 155                 160

Asp Leu Pro Phe Asp Val Gln Met Ala Glu Ile Glu Phe Asp Ile Asp
                165                 170                 175
```

-continued

Ala Tyr Glu Pro Leu Pro Val His Lys Pro Ser Ala Thr Arg Val Gln
            180                 185                 190

Ala Glu Lys Ala Leu Ala Leu Leu Asn Asp Ala Glu Arg Pro Leu Leu
        195                 200                 205

Val Ala Gly Gly Gly Ile Ile Asn Ala Asp Ala Ser Asp Lys Leu Val
    210                 215                 220

Glu Phe Ala Glu Leu Thr Gly Val Pro Val Ile Pro Thr Leu Met Gly
225                 230                 235                 240

Trp Gly Thr Ile Pro Asp Asp His Ala Gln Met Val Gly Met Val Gly
                245                 250                 255

Leu Gln Thr Ser His Arg Tyr Gly Asn Ala Thr Leu Leu Lys Ser Asp
            260                 265                 270

Leu Val Phe Gly Ile Gly Asn Arg Trp Ala Asn Arg His Thr Gly Ser
        275                 280                 285

Val Asp Val Tyr Thr Glu Gly Arg Lys Phe Val His Val Asp Ile Glu
    290                 295                 300

Pro Thr Gln Ile Gly Arg Val Phe Thr Pro Asp Leu Gly Ile Val Ser
305                 310                 315                 320

Asp Ala Gly Lys Ala Leu Asp Val Phe Leu Glu Val Ala Arg Glu Trp
                325                 330                 335

Lys Ala Ala Gly Lys Leu Lys Cys Arg Lys Ala Trp Leu Glu Glu Cys
            340                 345                 350

Gln Glu Arg Lys Ser Ser Leu Gln Arg Lys Thr His Phe Asp Asn Val
        355                 360                 365

Pro Val Lys Pro Gln Arg Val Tyr Glu Glu Met Asn Gln Val Phe Gly
    370                 375                 380

Lys Asp Thr Cys Tyr Val Ser Thr Ile Gly Leu Ser Gln Ile Ala Gly
385                 390                 395                 400

Ala Gln Phe Leu His Val Tyr Lys Pro Arg His Trp Ile Asn Cys Gly
                405                 410                 415

Gln Ala Gly Pro Leu Gly Trp Thr Ile Pro Ala Ala Leu Gly Val Val
            420                 425                 430

Lys Ala Asp Pro Lys Arg Lys Val Val Ala Leu Ser Gly Asp Tyr Asp
        435                 440                 445

Phe Gln Phe Met Ile Glu Glu Leu Ala Val Gly Ala Gln Phe Asn Leu
    450                 455                 460

Pro Tyr Val His Val Leu Val Asn Asn Ala Tyr Leu Gly Leu Ile Arg
465                 470                 475                 480

Gln Ala Gln Arg Gly Phe Asp Met Asp Tyr Cys Val Gln Leu Ala Phe
                485                 490                 495

Glu Asn Ile Asn Ser Thr Asp Ala Ala Thr Tyr Gly Val Asp His Val
            500                 505                 510

Ala Val Val Glu Gly Leu Gly Cys Lys Ala Ile Arg Val Phe Glu Pro
        515                 520                 525

Ala Glu Ile Ala Pro Ala Leu Ile Lys Ala Gln Lys Met Ala Glu Glu
    530                 535                 540

Phe Arg Val Pro Val Val Val Glu Val Ile Leu Glu Arg Val Thr Asn
545                 550                 555                 560

Ile Ser Met Gly Thr Glu Ile Asn Ala Val Asn Glu Phe Glu Asp Leu
                565                 570                 575

Ala Leu Val Gly Asn Asp Ala Pro Thr Ala Ile Ser Leu Leu Asp
            580                 585                 590

```
<210> SEQ ID NO 7
<211> LENGTH: 297
<212> TYPE: PRT
<213> ORGANISM: Pseudomonas putida

<400> SEQUENCE: 7
```

Met Ala Lys Ile Gly Phe Ile Gly Thr Gly Ile Met Gly Lys Pro Met
1               5                   10                  15

Ala Gln Asn Leu Gln Lys Ala Gly His Ser Leu Phe Ile Ser Thr His
            20                  25                  30

His Asp Ala Ala Pro Ala Asp Leu Ile Ala Gly Ala Val Ala Leu
        35                  40                  45

Ala Asn Pro Lys Glu Val Ala Gln Glu Ala Glu Phe Ile Ile Val Met
    50                  55                  60

Val Pro Asp Thr Pro Gln Val Glu Ser Val Leu Phe Gly Glu Asn Gly
65                  70                  75                  80

Val Ala Glu Gly Val Gly Pro Asn Lys Val Val Ile Asp Met Ser Ser
                85                  90                  95

Ile Ser Pro Thr Ala Thr Lys Ala Phe Ala Glu Lys Ile Lys Ala Thr
            100                 105                 110

Gly Ala Ala Tyr Leu Asp Ala Pro Val Ser Gly Gly Glu Val Gly Ala
        115                 120                 125

Lys Ala Ala Thr Leu Ser Ile Met Val Gly Gly Cys Pro Asn Ala Phe
130                 135                 140

Glu Arg Thr Leu Pro Leu Phe Glu Ala Met Gly Lys Asn Ile Thr Arg
145                 150                 155                 160

Val Gly Gly Asn Gly Asp Gly Gln Thr Ala Lys Val Ala Asn Gln Ile
                165                 170                 175

Ile Val Ala Leu Asn Ile Gln Ala Val Ala Glu Ala Leu Leu Phe Ala
            180                 185                 190

Ala Lys Asn Gly Ala Asp Pro Ala Lys Val Arg Glu Ala Leu Met Gly
        195                 200                 205

Gly Phe Ala Ser Ser Lys Ile Leu Glu Val His Ala Glu Arg Met Ile
210                 215                 220

Lys Gly Thr Phe Asp Pro Gly Phe Arg Ile Asn Leu His Gln Lys Asp
225                 230                 235                 240

Leu Asn Leu Ala Leu Gln Gly Ala Lys Glu Leu Gly Ile Asn Leu Pro
                245                 250                 255

Asn Thr Ser Asn Ala Gln Gln Val Phe Asn Thr Cys Gln Ala Leu Gly
            260                 265                 270

Gly Gly Asn Trp Asp His Ser Ala Leu Ile Lys Gly Leu Glu His Met
        275                 280                 285

Ala Asn Phe Ser Ile Arg Asp Asp Lys
290                 295

```
<210> SEQ ID NO 8
<211> LENGTH: 39
<212> TYPE: DNA
<213> ORGANISM: Artificial Sequence
<220> FEATURE:
<223> OTHER INFORMATION: Primer MFL158

<400> SEQUENCE: 8
gagagcggcc gcgaattcaa gcttgatatc attcaggac                          39

<210> SEQ ID NO 9
<211> LENGTH: 42
```

```
<212> TYPE: DNA
<213> ORGANISM: Artificial Sequence
<220> FEATURE:
<223> OTHER INFORMATION: Primer MFL159

<400> SEQUENCE: 9
gagacctgca gggaattctc tagagtgtga aattgttatc cg                        42

<210> SEQ ID NO 10
<211> LENGTH: 62
<212> TYPE: DNA
<213> ORGANISM: Artificial Sequence
<220> FEATURE:
<223> OTHER INFORMATION: Primer MFL160

<400> SEQUENCE: 10
gagacctgca gggggcctag atataggagg aataaccatg agcaaaatga gagcaatcga    60
tg                                                                   62

<210> SEQ ID NO 11
<211> LENGTH: 44
<212> TYPE: DNA
<213> ORGANISM: Artificial Sequence
<220> FEATURE:
<223> OTHER INFORMATION: Primer MFL161

<400> SEQUENCE: 11
gagattaatt aaattcgcgg ccgctcagtc cagcagcgag atgg                      44

<210> SEQ ID NO 12
<211> LENGTH: 62
<212> TYPE: DNA
<213> ORGANISM: Artificial Sequence
<220> FEATURE:
<223> OTHER INFORMATION: Primer MFL162

<400> SEQUENCE: 12
gagagcggcc gcgattagtc aggtaaggag cctaattatg actggatacg ttcaagtcgg    60
tg                                                                   62

<210> SEQ ID NO 13
<211> LENGTH: 32
<212> TYPE: DNA
<213> ORGANISM: Artificial Sequence
<220> FEATURE:
<223> OTHER INFORMATION: Primer MFL163

<400> SEQUENCE: 13
gagattaatt aattacaacc cgttacgcgc ct                                  32

<210> SEQ ID NO 14
<211> LENGTH: 48
<212> TYPE: DNA
<213> ORGANISM: Artificial Sequence
<220> FEATURE:
<223> OTHER INFORMATION: Primer MFL164

<400> SEQUENCE: 14
gagattaatt aaattcgcgg ccgctcagat caaagtctcg atccgcag                 48

<210> SEQ ID NO 15
<211> LENGTH: 39
<212> TYPE: DNA
<213> ORGANISM: Artificial Sequence
<220> FEATURE:
```

<223> OTHER INFORMATION: Primer MFL165

<400> SEQUENCE: 15
gagattaatt aagaattcaa gcttgatatc attcaggac                          39

<210> SEQ ID NO 16
<211> LENGTH: 62
<212> TYPE: DNA
<213> ORGANISM: Artificial Sequence
<220> FEATURE:
<223> OTHER INFORMATION: Primer MFL166

<400> SEQUENCE: 16
gagacctgca gggattagtc aggtaaggag cctaattatg actggatacg ttcaagtcgg   60
tg                                                                 62

<210> SEQ ID NO 17
<211> LENGTH: 32
<212> TYPE: DNA
<213> ORGANISM: Artificial Sequence
<220> FEATURE:
<223> OTHER INFORMATION: Primer MFL167

<400> SEQUENCE: 17
gagagcggcc gcttacaacc cgttacgcgc ct                                32

<210> SEQ ID NO 18
<211> LENGTH: 21
<212> TYPE: DNA
<213> ORGANISM: Artificial Sequence
<220> FEATURE:
<223> OTHER INFORMATION: Primer CJ288

<400> SEQUENCE: 18
ctagcttcac gctgccgcaa g                                            21

<210> SEQ ID NO 19
<211> LENGTH: 31
<212> TYPE: DNA
<213> ORGANISM: Artificial Sequence
<220> FEATURE:
<223> OTHER INFORMATION: Primer CJ289

<400> SEQUENCE: 19
ctaactcaca ttaattgcgt tgcgctcact g                                 31

<210> SEQ ID NO 20
<211> LENGTH: 62
<212> TYPE: DNA
<213> ORGANISM: Artificial Sequence
<220> FEATURE:
<223> OTHER INFORMATION: Primer CJ301

<400> SEQUENCE: 20
agtgagcgca acgcaattaa tgtgagttag aagccgaatg tcgatgatat ctacaacctg   60
ag                                                                 62

<210> SEQ ID NO 21
<211> LENGTH: 107
<212> TYPE: DNA
<213> ORGANISM: Artificial Sequence
<220> FEATURE:
<223> OTHER INFORMATION: Primer CJ302X

<400> SEQUENCE: 21

```
cctcctctct agagtgtgaa attgttatcc gctcacaatt ccacacatta tacgagccga    60
tgattaattg tcaacagctc gaattcaaaa aaccgcacct gggtgcg                 107
```

<210> SEQ ID NO 22
<211> LENGTH: 70
<212> TYPE: DNA
<213> ORGANISM: Artificial Sequence
<220> FEATURE:
<223> OTHER INFORMATION: Primer CJ306X

<400> SEQUENCE: 22

```
attcagacta gtagtcaaaa gcctccgacc ggaggctttt gactcatgga tgcctgaaag    60
gctcccttac                                                          70
```

<210> SEQ ID NO 23
<211> LENGTH: 54
<212> TYPE: DNA
<213> ORGANISM: Artificial Sequence
<220> FEATURE:
<223> OTHER INFORMATION: Primer CJ307

<400> SEQUENCE: 23

```
ccctgagtgc ttgcggcagc gtgaagctag gcccctctgg agaatcgaac gatg          54
```

<210> SEQ ID NO 24
<211> LENGTH: 48
<212> TYPE: DNA
<213> ORGANISM: Artificial Sequence
<220> FEATURE:
<223> OTHER INFORMATION: Primer MFL276

<400> SEQUENCE: 24

```
cacactctag aggaggac agctatgagc aaaatgagag caatcgat                   48
```

<210> SEQ ID NO 25
<211> LENGTH: 34
<212> TYPE: DNA
<213> ORGANISM: Artificial Sequence
<220> FEATURE:
<223> OTHER INFORMATION: Primer MFL279

<400> SEQUENCE: 25

```
actactagtt tatttgtcgt cgcggatcga gaag                                34
```

<210> SEQ ID NO 26
<211> LENGTH: 31
<212> TYPE: DNA
<213> ORGANISM: Artificial Sequence
<220> FEATURE:
<223> OTHER INFORMATION: Primer MFL280

<400> SEQUENCE: 26

```
actactagtt cagatcaaag tctcgatccg c                                   31
```

<210> SEQ ID NO 27
<211> LENGTH: 48
<212> TYPE: DNA
<213> ORGANISM: Artificial Sequence
<220> FEATURE:
<223> OTHER INFORMATION: Primer LJ100

<400> SEQUENCE: 27

```
gacatgatta cgaattcgag ctcggtaccc ttcgcggcgg ttcgacgc                 48
```

<210> SEQ ID NO 28
<211> LENGTH: 39
<212> TYPE: DNA
<213> ORGANISM: Artificial Sequence
<220> FEATURE:
<223> OTHER INFORMATION: Primer LJ101

<400> SEQUENCE: 28
ggtgcggttt tttgcgcggc tcactcgcaa cggttttg                        39

<210> SEQ ID NO 29
<211> LENGTH: 146
<212> TYPE: DNA
<213> ORGANISM: Artificial Sequence
<220> FEATURE:
<223> OTHER INFORMATION: Primer LJ102

<400> SEQUENCE: 29
gttgcgagtg agccgcgcaa aaaccgcac ccaggtgcgg ttttttgaat tcgagctgtt    60
gacaattaat catcggctcg tataatgtgt cagactcaat aataataata aggaggtatc   120
gaatgaatat cctgtacgac gaacgc                                      146

<210> SEQ ID NO 30
<211> LENGTH: 48
<212> TYPE: DNA
<213> ORGANISM: Artificial Sequence
<220> FEATURE:
<223> OTHER INFORMATION: Primer LJ103

<400> SEQUENCE: 30
cggccagtgc caagcttgca tgcctgcagg aggtgcacct cgcgggcc               48

<210> SEQ ID NO 31
<211> LENGTH: 65
<212> TYPE: DNA
<213> ORGANISM: Artificial Sequence
<220> FEATURE:
<223> OTHER INFORMATION: Primer LJ110

<400> SEQUENCE: 31
gcggataaca atttcacact aaagttaata ttaaggaggt aaacatgagc aaaatgagag    60
caatc                                                              65

<210> SEQ ID NO 32
<211> LENGTH: 38
<212> TYPE: DNA
<213> ORGANISM: Artificial Sequence
<220> FEATURE:
<223> OTHER INFORMATION: Primer LJ111

<400> SEQUENCE: 32
gttagttgtc gttttgatat cagtccagca gcgagatg                         38

<210> SEQ ID NO 33
<211> LENGTH: 64
<212> TYPE: DNA
<213> ORGANISM: Artificial Sequence
<220> FEATURE:
<223> OTHER INFORMATION: Primer LJ112

<400> SEQUENCE: 33
gctggactga tatcaaaacg acaactaact aaggaggtac actatggcta aaatcggttt    60
catc                                                               64

<210> SEQ ID NO 34
<211> LENGTH: 39
<212> TYPE: DNA
<213> ORGANISM: Artificial Sequence
<220> FEATURE:
<223> OTHER INFORMATION: Primer LJ113

<400> SEQUENCE: 34
cggtcggagg cttttgacta ttatttgtcg tcgcggatc                                      39

<210> SEQ ID NO 35
<211> LENGTH: 20
<212> TYPE: DNA
<213> ORGANISM: Artificial Sequence
<220> FEATURE:
<223> OTHER INFORMATION: Primer MFL299

<400> SEQUENCE: 35
aggcattcgt gaagtcatgg                                                           20

<210> SEQ ID NO 36
<211> LENGTH: 20
<212> TYPE: DNA
<213> ORGANISM: Artificial Sequence
<220> FEATURE:
<223> OTHER INFORMATION: Primer MFL300

<400> SEQUENCE: 36
atgtaaccgc tgagaacgtc                                                           20

<210> SEQ ID NO 37
<211> LENGTH: 19
<212> TYPE: DNA
<213> ORGANISM: Artificial Sequence
<220> FEATURE:
<223> OTHER INFORMATION: Primer MFL301

<400> SEQUENCE: 37
ctcgccactg gatcaactg                                                            19

<210> SEQ ID NO 38
<211> LENGTH: 21
<212> TYPE: DNA
<213> ORGANISM: Artificial Sequence
<220> FEATURE:
<223> OTHER INFORMATION: Primer MFL302

<400> SEQUENCE: 38
gaactggaag tcgtagtcac c                                                         21

<210> SEQ ID NO 39
<211> LENGTH: 20
<212> TYPE: DNA
<213> ORGANISM: Artificial Sequence
<220> FEATURE:
<223> OTHER INFORMATION: Primer MFL303

<400> SEQUENCE: 39
tgcagatcat ggaaggtgac                                                           20

<210> SEQ ID NO 40
<211> LENGTH: 21
<212> TYPE: DNA
<213> ORGANISM: Artificial Sequence
<220> FEATURE:

```
<223> OTHER INFORMATION: Primer MFL304

<400> SEQUENCE: 40
caggaagcgg tagttgatct c                                        21

<210> SEQ ID NO 41
<211> LENGTH: 19
<212> TYPE: DNA
<213> ORGANISM: Artificial Sequence
<220> FEATURE:
<223> OTHER INFORMATION: Primer MFL305

<400> SEQUENCE: 41
aaagaggttg cccaggaag                                           19

<210> SEQ ID NO 42
<211> LENGTH: 19
<212> TYPE: DNA
<213> ORGANISM: Artificial Sequence
<220> FEATURE:
<223> OTHER INFORMATION: Primer MFL306

<400> SEQUENCE: 42
cgagctcatg tcgatcacc                                           19

<210> SEQ ID NO 43
<211> LENGTH: 20
<212> TYPE: DNA
<213> ORGANISM: Artificial Sequence
<220> FEATURE:
<223> OTHER INFORMATION: Primer MFL307

<400> SEQUENCE: 43
ccatcctcaa acgctacaac                                          20

<210> SEQ ID NO 44
<211> LENGTH: 19
<212> TYPE: DNA
<213> ORGANISM: Artificial Sequence
<220> FEATURE:
<223> OTHER INFORMATION: Primer MFL308

<400> SEQUENCE: 44
tggcgatcaa ctggaagtg                                           19

<210> SEQ ID NO 45
<211> LENGTH: 20
<212> TYPE: DNA
<213> ORGANISM: Artificial Sequence
<220> FEATURE:
<223> OTHER INFORMATION: Primer MFL309

<400> SEQUENCE: 45
acatcttccg cctcaacttc                                          20

<210> SEQ ID NO 46
<211> LENGTH: 19
<212> TYPE: DNA
<213> ORGANISM: Artificial Sequence
<220> FEATURE:
<223> OTHER INFORMATION: Primer MFL310

<400> SEQUENCE: 46
ttgcaggtcc atgaggatg                                           19
```

```
<210> SEQ ID NO 47
<211> LENGTH: 20
<212> TYPE: DNA
<213> ORGANISM: Artificial Sequence
<220> FEATURE:
<223> OTHER INFORMATION: Primer MFL325

<400> SEQUENCE: 47
aactgaagct gatcctggtg                                              20

<210> SEQ ID NO 48
<211> LENGTH: 18
<212> TYPE: DNA
<213> ORGANISM: Artificial Sequence
<220> FEATURE:
<223> OTHER INFORMATION: Primer MFL326

<400> SEQUENCE: 48
agggtatgct gggctaca                                                18
```

US 11,021,721 B2

GENETICALLY ENGINEERED PSEUDOMONAS STRAINS CAPABLE OF METABOLIZING ETHYLENE GLYCOL AND ITS METABOLIC INTERMEDIATES

CROSS-REFERENCE TO RELATED APPLICATIONS

This application claims priority under 35 U.S.C. § 119 to U.S. Provisional Patent Application Nos. 62/535,074 filed on Jul. 20, 2017, and 62/650,925 filed on Mar. 30, 2018, the contents of which are hereby incorporated by reference in their entirety.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory. The United States Government has rights in this invention pursuant to contract no. DE-AC05-00OR22725 between the United States Department of Energy and UT-Battelle, LLC.

REFERENCE TO SEQUENCE LISTING

This application contains a Sequence Listing submitted as an electronic text file entitled "NREL 17-26_ST25.txt" having a size in bytes of 84 kb and created on 18 Feb. 2021. Pursuant to 37 CFR § 1.52(e)(5), the information contained in the above electronic file is hereby incorporated by reference in its entirety.

DEPOSIT OF MICROORGANISMS UNDER THE BUDAPEST TREATY

During the pendency of this application, access to the invention will be afforded to the Commission upon request. Upon granting of the patent the strain will be available to the public under the conditions specified in 37 CFR 1.808. The deposit will be maintained in a public repository for a period of 30 years or 5 years after the last request or for the effective life of the patent, whichever is longer. The deposit will be replaced if it should ever become unavailable.

BACKGROUND

Polyethylene terephthalate (PET) based plastics are widely used as containers for liquids and foods and in fibers for clothing. PET plastics are largely non-biodegradable. Breakdown products of PET plastic, occurring from recycling and other degradation processes, include ethylene glycol and terephthalic acid. These breakdown products are often not fully recovered and reused during the recycling process and end up as waste.

*Pseudomonas putida* KT2440 demonstrates broad substrate specificity for compounds of interest to bioremediation and has high toxicity tolerance. *P. putida* KT2440 is often used for industrial biotechnological applications. Naturally occurring strains of *P. putida* KT2440 are not able to efficiently metabolize ethylene glycol or use it as a sole carbon source.

SUMMARY

Disclosed herein are genetically engineered *Pseudomonas* strains capable of using ethylene glycol as a sole carbon source. In an embodiment, these *Pseudomonas* strains are capable of using ethylene glycol for the metabolism of compounds of interest.

In an aspect, disclosed is a genetically engineered *Pseudomonas* capable of growth on ethylene glycol as a sole carbon source. In an embodiment, the genetically engineered *Pseudomonas* has exogenous genes gcl, hyi, glxR, PP_4300, pykF, and glcDEF. In an embodiment, the genetically engineered *Pseudomonas* is capable of expressing an exogenous gcl (glyoxylate carboligase) operon. In another embodiment, the genetically engineered *Pseudomonas* is capable of expressing an exogenous glycolate oxidase. In an embodiment, the genetically engineered *Pseudomonas* is capable of expressing an exogenous gcl operon and expressing an exogenous glycolate oxidase operon (glcDEF). In yet another embodiment, the genetically engineered *Pseudomonas* is capable of expressing exogenous genes selected from the group consisting of gcl, hyi, glxR, PP_4300 and pykF. In an embodiment, the genetically engineered *Pseudomonas* is capable of expressing exogenous genes selected from the group consisting of gcl, hyi, glxR, PP_4300, pykF, and glcDEF. In an embodiment, the genetically engineered *Pseudomonas* is selected from strains MFL185, and MFL168. In an embodiment, the genetically engineered *Pseudomonas* is capable of growth in media containing up to about 2 M ethylene glycol. In another embodiment, the genetically engineered *Pseudomonas* has exogenous genes that are inserted into the genome of the *Pseudomonas*. In an embodiment, the genetically engineered *Pseudomonas* has exogenous genes that are inserted into the genome of the *Pseudomonas* between hpyA and PP_4218. In another embodiment, the genetically engineered *Pseudomonas* has exogenous genes that are under the control of an exogenous promoter. In an embodiment, the genetically engineered *Pseudomonas* is capable of consuming up to 0.16 g/L/h of ethylene glycol. In another embodiment, the genetically engineered *Pseudomonas* is capable of consuming 500 mM ethylene glycol within 120 hours. In an embodiment, the genetically engineered *Pseudomonas* has exogenous copies of gcl, hyi, glxR, PP_4300, and pykF, having greater than 90% identity with gcl, hyi, glxR, PP_4300, and pykF in SEQ ID NO: 4. In another embodiment, the genetically engineered *Pseudomonas* has exogenous copies of glcDEF having greater than 90% sequence identity with glcDEF from SEQ ID NO: 1. In an embodiment, the genetically engineered *Pseudomonas* has exogenous copies of gcl, hyi, glxR, PP_4300, and pykF having greater than 90% identity with gcl, hyi, glxR, PP_4300, and pykF in SEQ ID NO: 4, and has glcDEF genes having greater than 90% sequence identity with glcDEF from SEQ ID NO: 1.

In an aspect, disclosed is a genetically engineered *Pseudomonas* capable of growth on ethylene glycol as a sole carbon source wherein the *Pseudomonas* comprises exogenous genes gcl, hyi, glxR, PP_4300, pykF, and glcDEF and is capable of making polyhydroxyalkanoates. In an embodiment, the genetically engineered *Pseudomonas* is capable of producing polyhydroxyalkanoates at up to 0.06 grams per gram of dried cellular weight (DCW). In another embodiment, the genetically engineered *Pseudomonas* produces polyhydroxyalkanoates that are derived from the metabolism of ethylene glycol.

Other objects, advantages, and novel features of the present invention will become apparent from the following detailed description of the invention when considered in conjunction with the accompanying drawings.

*putida* KT2440. Identified key enzymes in the metabolism of ethylene glycol are shown; a question mark represents an unidentified enzyme or putative chemical reaction responsible for conversion of a particular metabolite. Green arrows indicate the proposed ethylene glycol metabolic route of the engineered strain; the corresponding overexpressed enzymes are denoted in blue. Alternative shuttling of glyoxylate into the glyoxylate shunt is shown in grey arrows. Steps in which redox equivalents are generated are indicated in red.

Figures 2A, 2B:
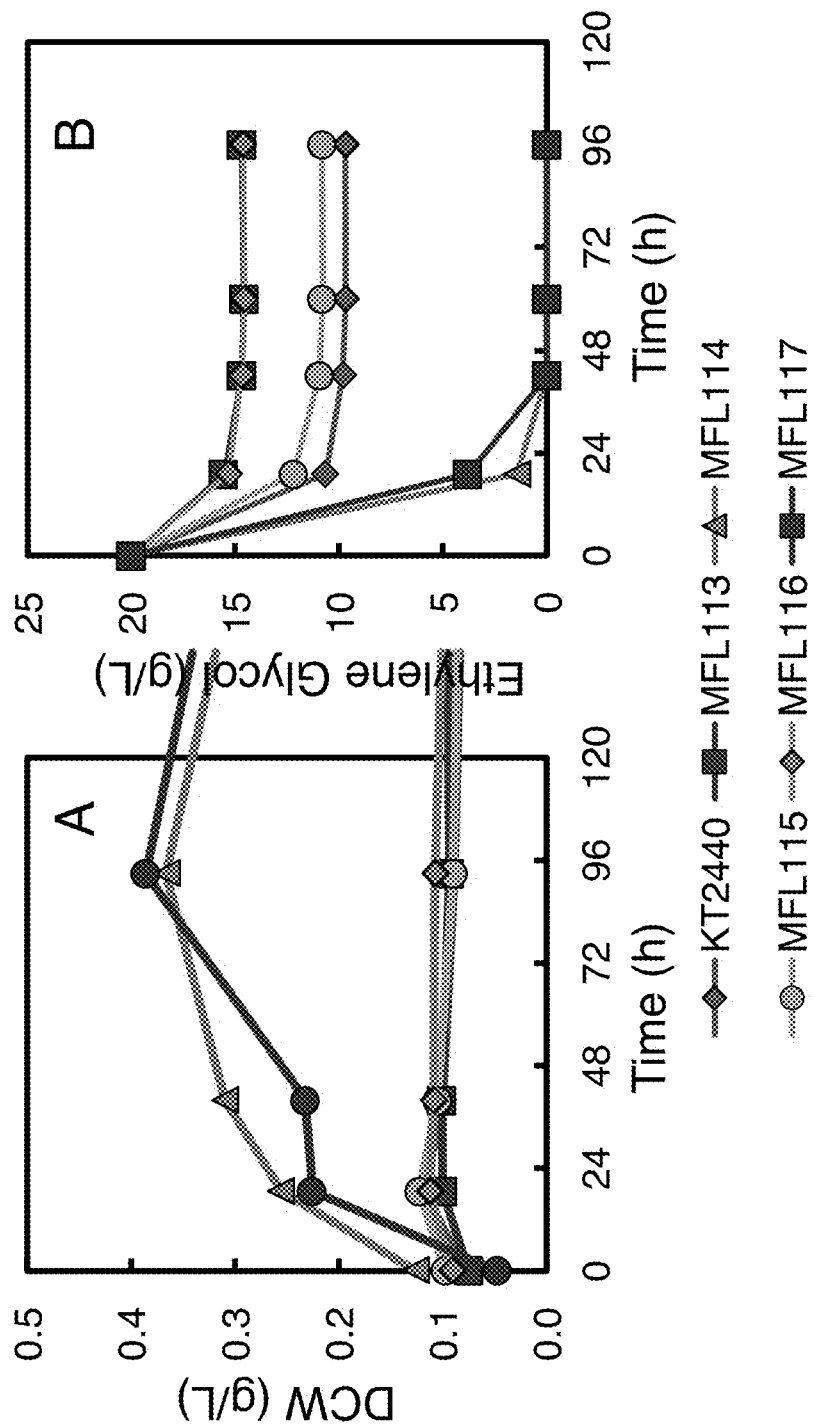

FIG. 2 depicts growth and ethylene glycol utilization of engineered strains. FIG. 2A depicts growth and FIG. 2B depicts ethylene glycol utilization of plasmid bearing strains: KT2440 (pBTL2), MFL113 (pBTL2-gcl), MFL114 (pBTL2-gcl-operon), MFL115 (pBTL2-glcB), MFL116 (pBTL2-gcl-glcB) and MFL117 (pBTL2-gcl-operon-glcB). Results are given as the average of n=2 with the corresponding SEM.

Figure 3:
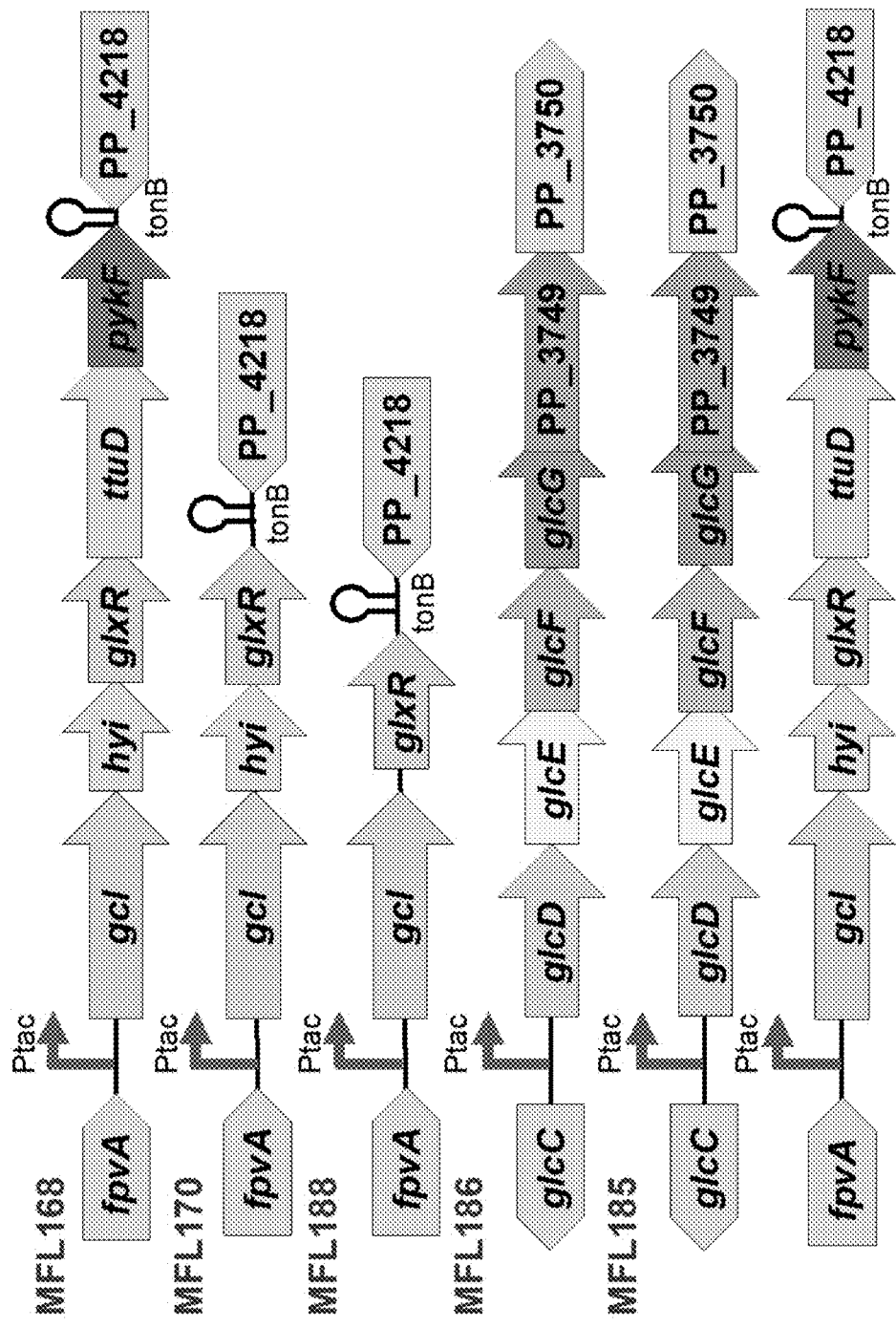

FIG. 3 depicts a drawing of the overexpression constructs used: MFL168, MFL170, and MFL188 harbor the overexpression constructs integrated in the intergenic region between fpvA and PP_4218 with the constitutive tac promoter driving gene transcription. MFL168 and MFL185 contain all native genes of the gcl cluster ($P_{tac}$::gcl-hyi-glxR-ttuD-pykF), whereas MFL170 ($P_{tac}$::gcl-hyi-glxR) and MFL188 ($P_{tac}$::gcl-glxR) expresses only three or two genes of the cluster. MFL185 and MFL186 both have the tac promoter inserted before the native glycolate oxidase operon (glcDEF) and differs in that MFL185 additionally harbors the same overexpression five genes as MFL168.

Figure 4:
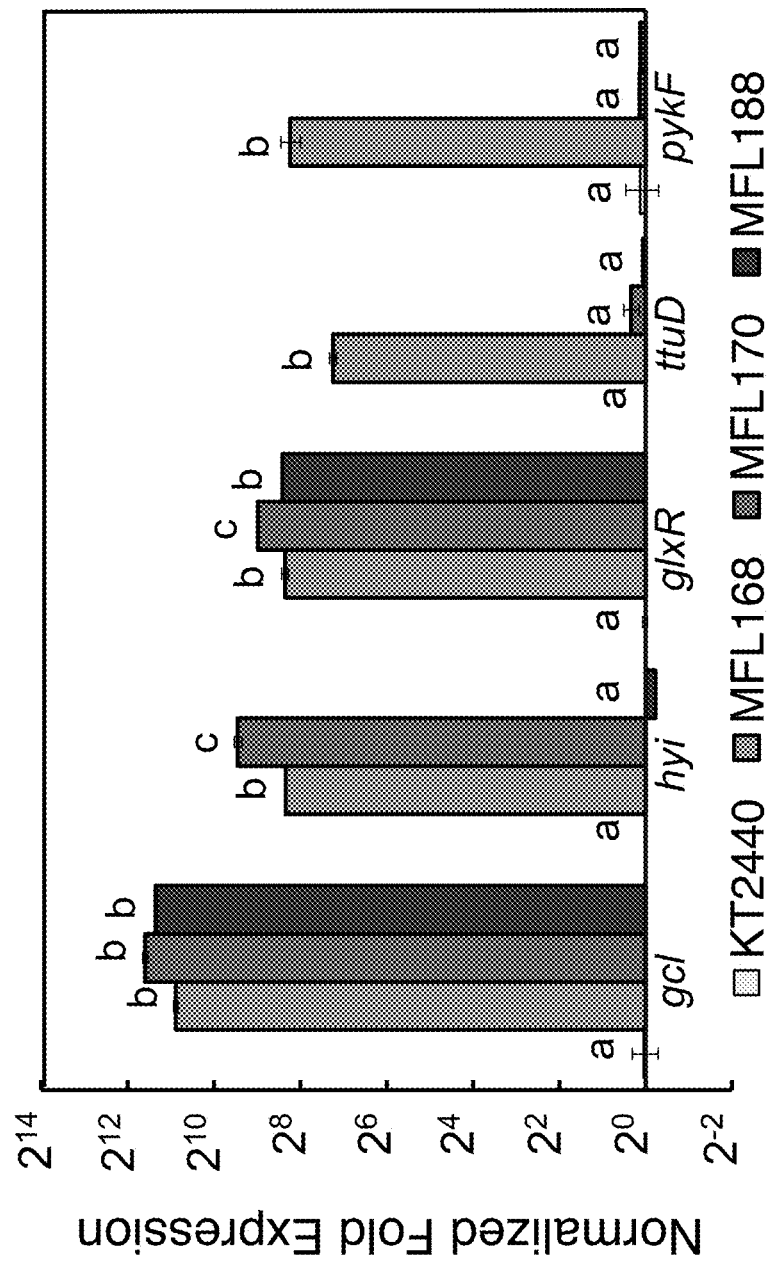

FIG. 4 depicts a qRT-PCR relative gene expression compared to wild type *P. putida* KT2440 ($2^{-\Delta\Delta Ct}$): Expression of gene targets from the gcl cluster (gcl, hyi, glxR, ttuD and pykF) are shown on log scale. Results are given as the average of n=2 with the corresponding SEM. Bars labeled with different letters indicate statistical significance of expression of a particular gene among the different strains ($p<0.05$; one-way ANOVA followed by Tukey's post hoc honest significance difference test).

Figure 5:
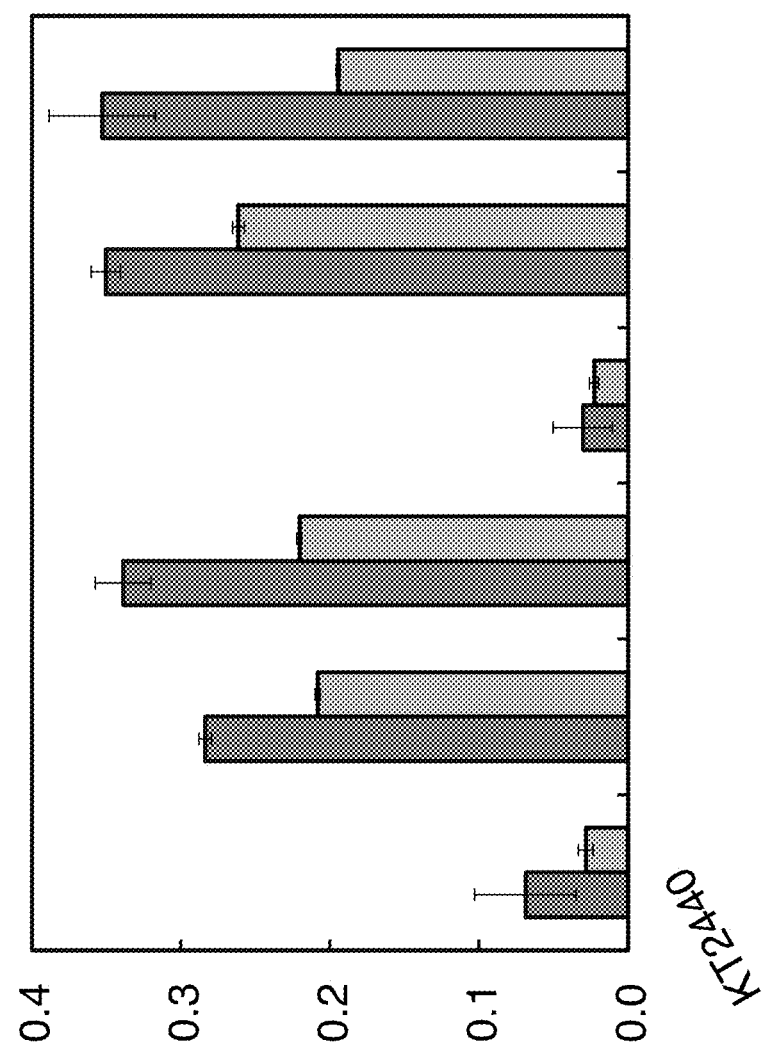

FIG. 5 depicts NAD(P)H-dependent hydroxypyruvate reduction activity of whole-cell lysates derived from engineered strains using NADH-dependent and NADPH-dependent hydroxypyruvate. Results are given as the average of n=3 with the corresponding SEM. Bars labeled with different letters indicate statistical significance ($p<0.05$; one-way ANOVA followed by Tukey's post hoc honest significance difference test). One unit (U/mg) is defined as the amount of enzyme required to convert 1 μmol of NAD(P)H to NAD(P)$^+$ per minute.

Figures 6A, 6B, 6C, 6D, 6E, 6F, 6G, 6H, 6I, 6J:
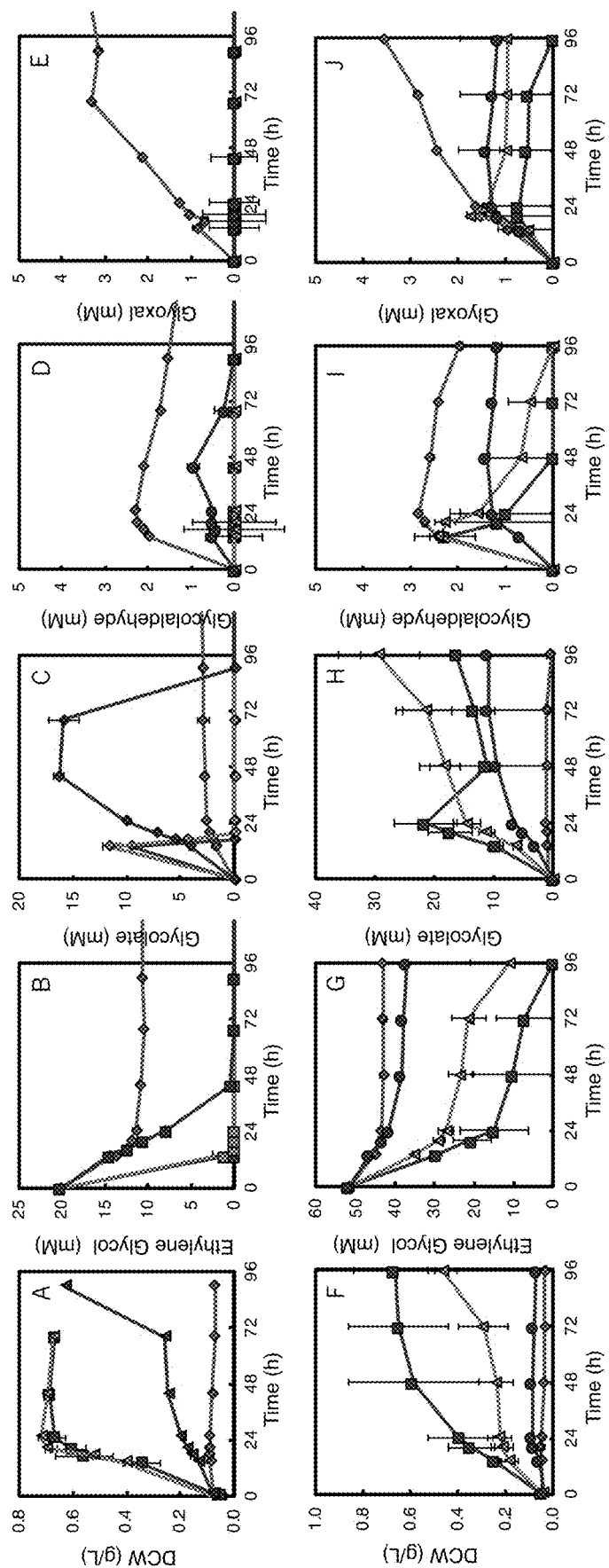

FIG. 6 depicts growth and metabolite concentrations of the corresponding engineered strains. FIGS. 6A-6E depict the growth of and resulting concentrations of various metabolites in solutions starting with 20 mM ethylene glycol over 96 hours. FIG. 6A depicts growth (DCW g/L), FIG. 6B depicts the concentration of ethylene glycol, FIG. 6C depicts the concentration of glycolate, FIG. 6D depicts the concentration of glycolaldehyde and FIG. 6E depicts the concentration of glyoxal. FIGS. 6F-6J depict the growth of and resulting concentrations of various metabolites in solutions starting with 50 mM ethylene glycol over 96 hours. FIG. 6F depicts growth (DCW g/L), FIG. 6G depicts the concentration of ethylene glycol, FIG. 6H depicts the concentration of glycolate, FIG. 6I depicts the concentration of glycolaldehyde and FIG. 6J depicts the concentration of glyoxal. Results are given as the average of n=2 with the corresponding SEM.

Figures 7A, 7B, 7C, 7D, 7E, 7F:
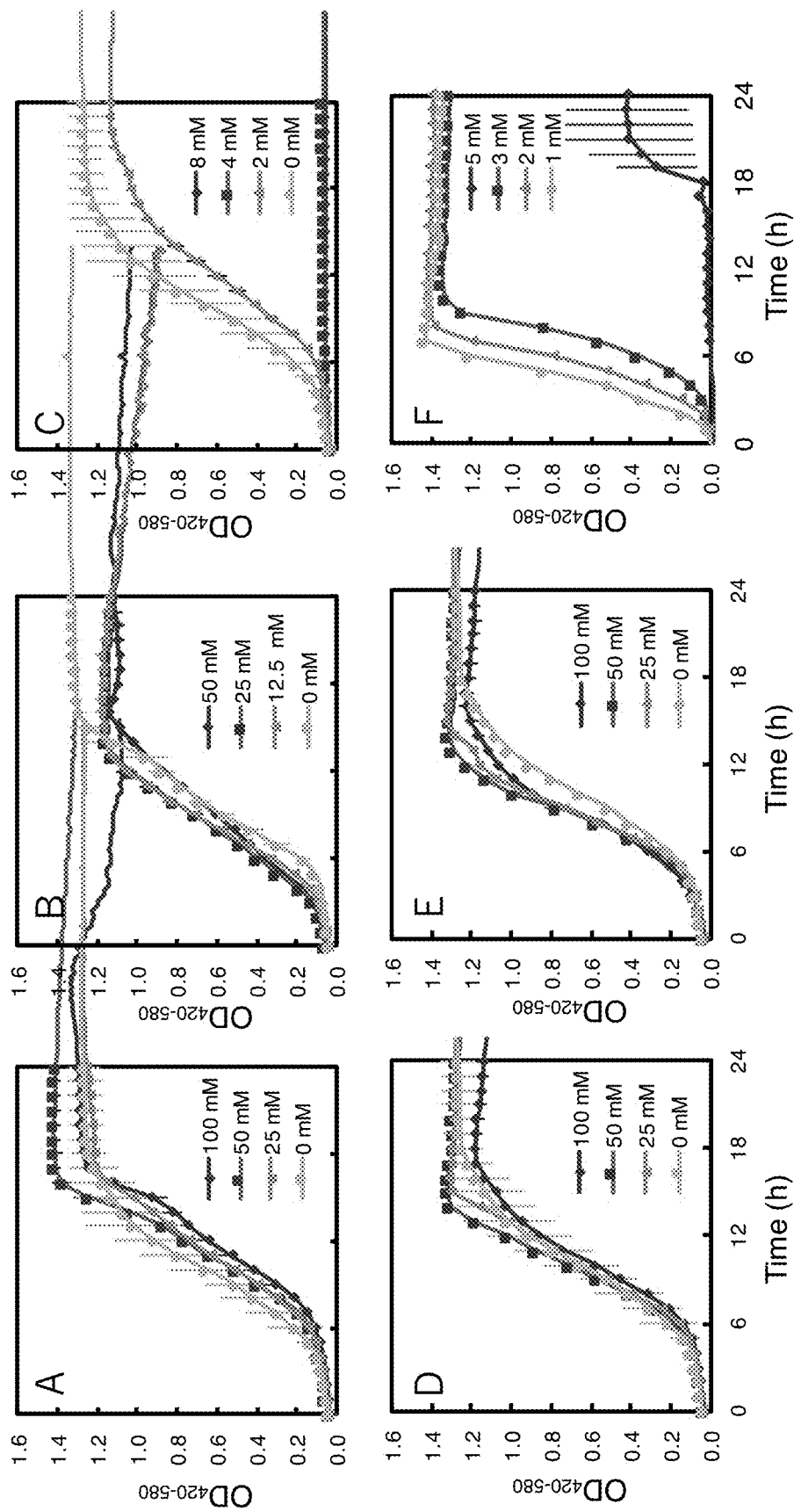

FIG. 7 depicts growth toxicity studies of *P. putida* KT2440 in the presence of 20 mM glucose in M9 minimal medium supplemented with various concentrations of metabolites. FIG. 7A depicts the growth of *P. putida* KT2440 in the presence of 0, 25, 50, and 100 mM ethylene glycol, FIG. 7B depicts the growth of *P. putida* KT2440 in the presence of 0, 12.5, 25 and 50 mM sodium oxalate, FIG. 7C depicts the growth of *P. putida* KT2440 in the presence of 0, 2, 4, and 8 mM glycolaldehyde, FIG. 7D depicts the growth of *P. putida* KT2440 in the presence of 0, 25, 50, and 100 mM sodium glycolate, FIG. 7E depicts the growth of *P. putida* KT2440 in the presence of 0, 25, 50, and 100 mM sodium glyoxylate, and FIG. 7F depicts the growth of *P. putida* KT2440 in the presence of 1, 2, 3, and 5 mM glyoxal. Results are given as the average of n=3 with the corresponding SEM.

Figures 8A, 8B, 8C, 8D, 8E:
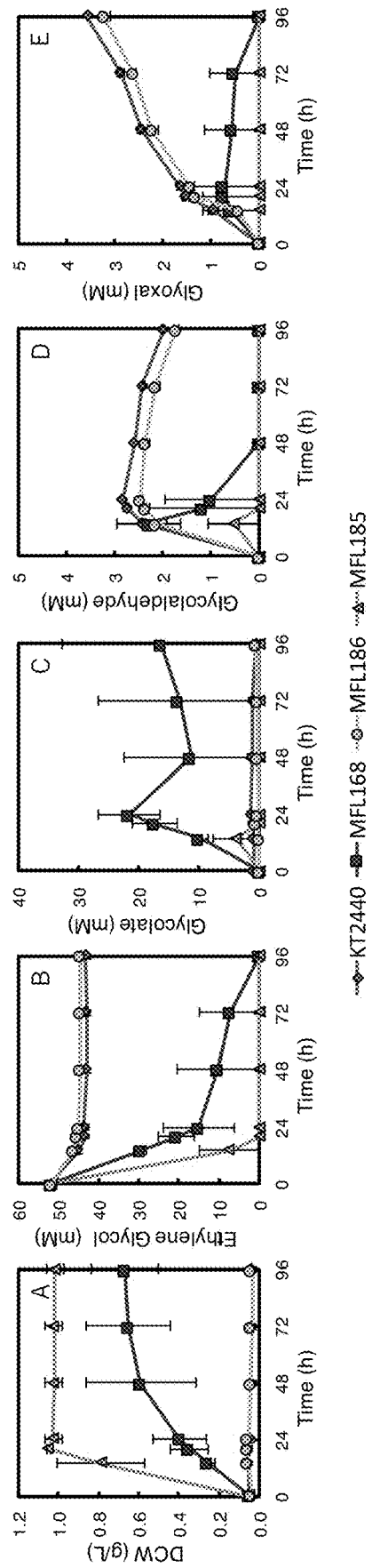

FIG. 8 depicts the growth of *P. putida* KT2440, MFL168, MFL186 and MFL185 and various metabolite concentrations in the media starting with 50 mM ethylene glycol over 96 hours. FIG. 8A depicts growth in DCW g/L, FIG. 8B depicts the concentration of ethylene glycol, FIG. 8C depicts the concentration of glycolate, FIG. 8D depicts the concentration of glycolaldehyde, and FIG. 8E depicts the concentration of glyoxal. Results are given as the average of n=2 with the corresponding SEM.

Figures 9A, 9B, 9C, 9D:
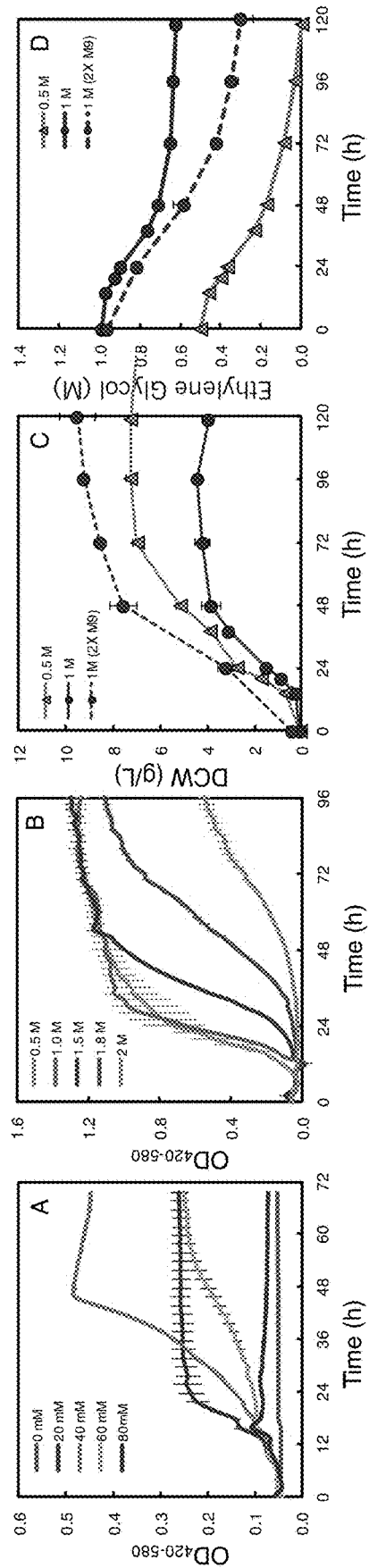

FIG. 9 depicts growth of engineered strains under various conditions. FIG. 9A depicts growth of MFL168 in M9 minimal medium containing 0, 20, 40, 60, and 80 mM concentrations of ethylene glycol. FIG. 9B depicts growth of MFL185 in M9 minimal medium containing concentrations of ethylene glycol of 0.5, 1.0, 1.5, 1.8, and 2 M as a sole carbon source as measured in the Bioscreen C. FIG. 9C depicts growth of MFL185 in M9 minimal medium containing concentrations of 0.5 M and 1 M ethylene glycol in shake flasks measuring DCW (g/L) over time. FIG. 9D depicts ethylene glycol utilization over time of MFL185 in M9 minimal medium containing concentrations of 0.5 M and 1 M ethylene glycol in shake flasks. In FIGS. 9C and 9D, data from cultures grown in 1 M ethylene glycol with twice M9 salts and a higher cell inoculum are designated by dashed lines. Results are given as the average of n=2 with the corresponding SEM.

Figures 10A, 10B, 10C:
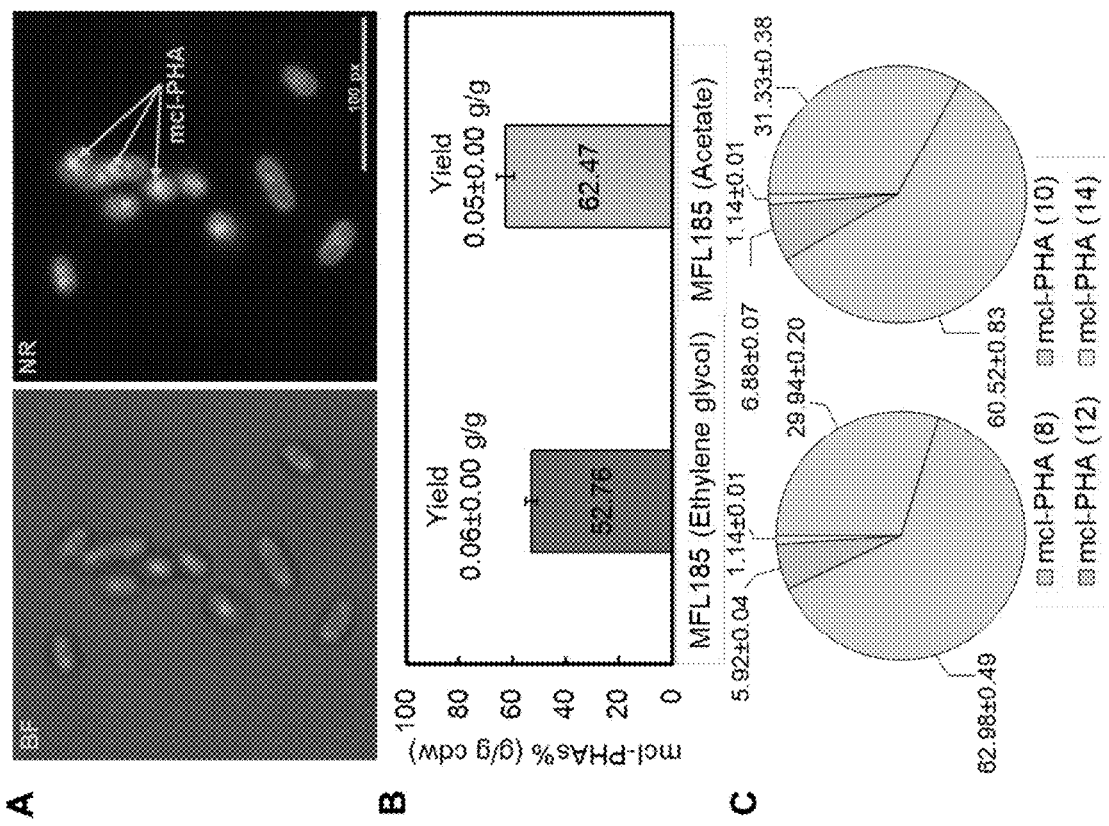

FIG. 10 depicts images of engineered strains, as well as quantity and type of mcl-PHAs produced. FIG. 10A depicts bright field (BF) microscopy of MFL185 cells after growth in ethylene glycol and fluorescent microscopic observation of mcl-PHAs via Nile Red (NR) staining of same cells. FIG. 10B depicts mcl-PHAs production on a dry cell weight basis. FIG. 10C depicts the composition of various chain length mcl-PHAs produced from ethylene glycol and acetate. Results are given as the average of n=3 with the corresponding SEM.

Figures 11A, 11B, 11C:
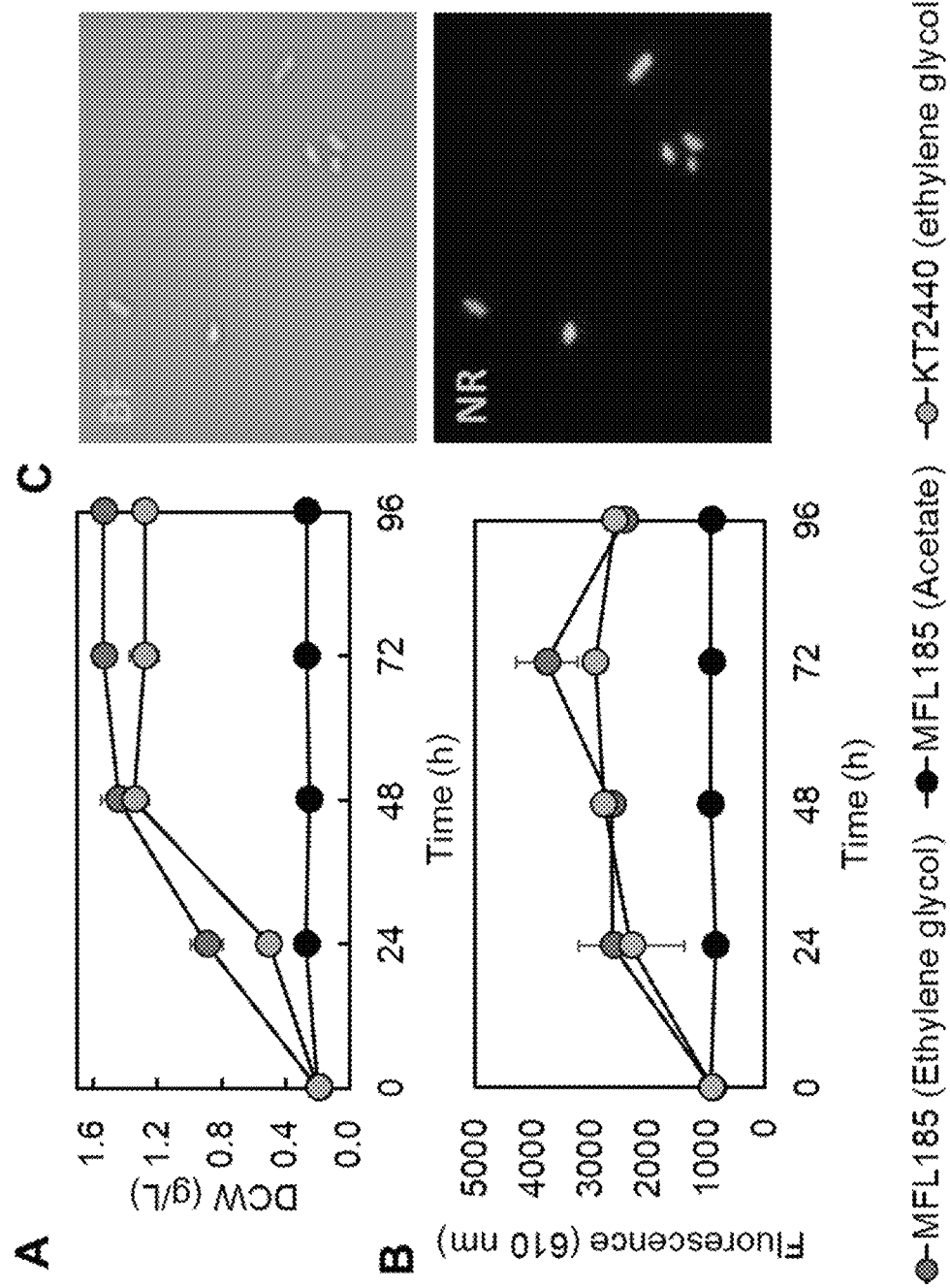

FIG. 11 depicts a comparison of mcl-PHAs production by MFL185 grown in 100 mM acetate or ethylene glycol. FIG. 11A depicts curves of strains over time. FIG. 11B depicts time-course of mean fluorescence of Nile Red stained cells. FIG. 11C depicts fluorescent microscopic observation of Nile Red stained MFL185 cells after 72 hours cultured in ethylene glycol. Results are presented as means±SEM (n=3).

Figure 12:
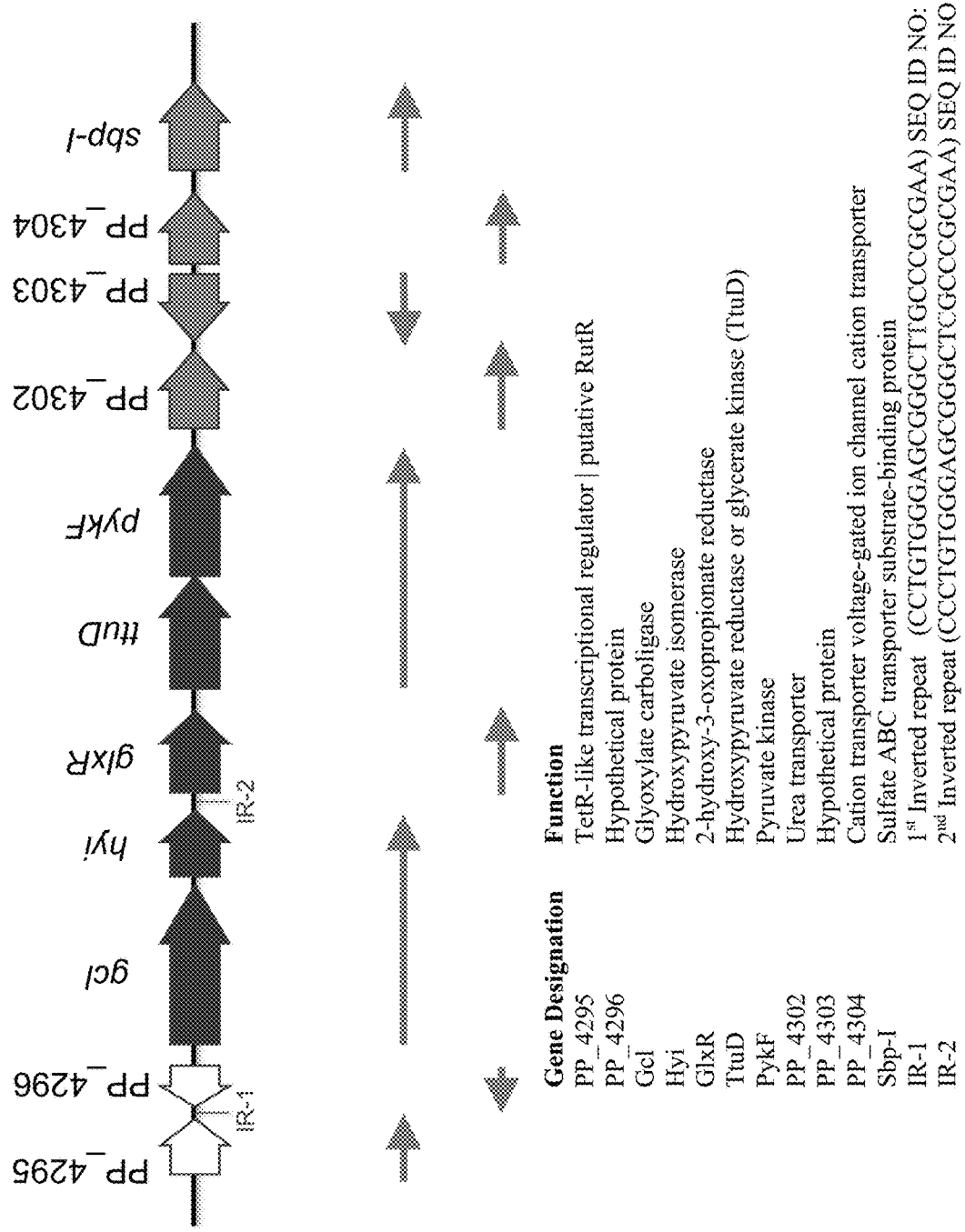

FIG. 12 depicts a prediction of transcriptional units (Database of PrOkaryotic OpeRons (DOOR)) is depicted here for genes in the proximity of the gcl operon. Predicted transcripts are indicated by grey arrows. In FIG. 12, the prediction or known function of the corresponding ORF are indicated below the predicted transcripts. The presence of two inverted repeats are shown as IR-1 (SEQ ID NO: 49) or IR-2 (SEQ ID NO: 50).

Figure 13:
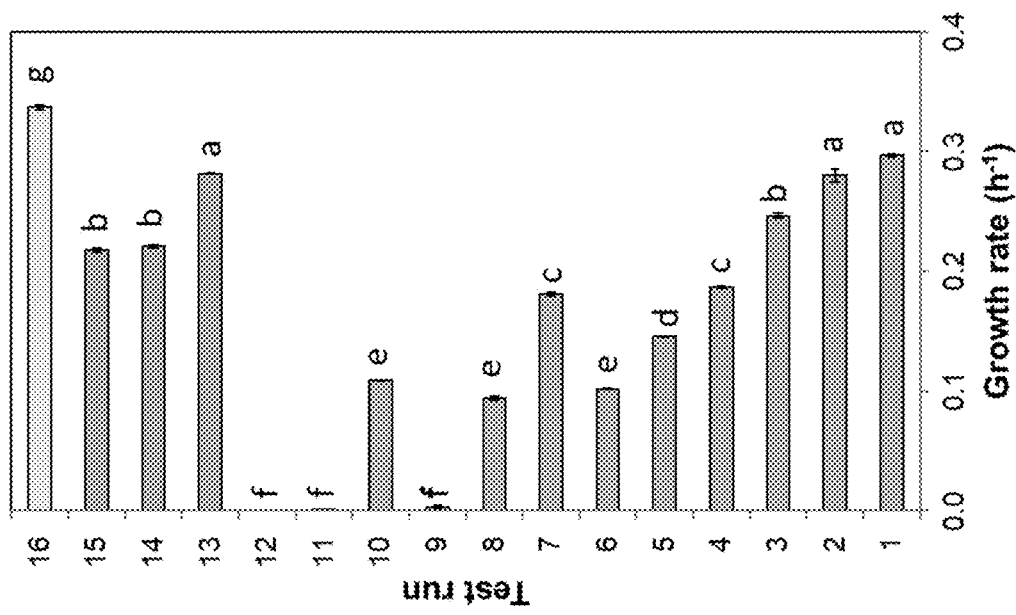

FIG. 13 depicts synergistic inhibitory effect of glycolaldehyde and glyoxal. Growth assays were conducted in 100 well plates in the Bioscreen C MBR analyzer. Individual wells of the plate were filled with 200 µL of M9 medium-containing 20 mM glucose and the respective concentration of glycolaldehyde and glyoxal according to a 3-level full-factorial design (Table 3), growth rates expressed as means±SEM (n=3). Bars labeled with different letters indicate statistical significance of different runs (p<0.05; one-way ANOVA followed by Tukey's post hoc honest significance difference test).

Figure 14:
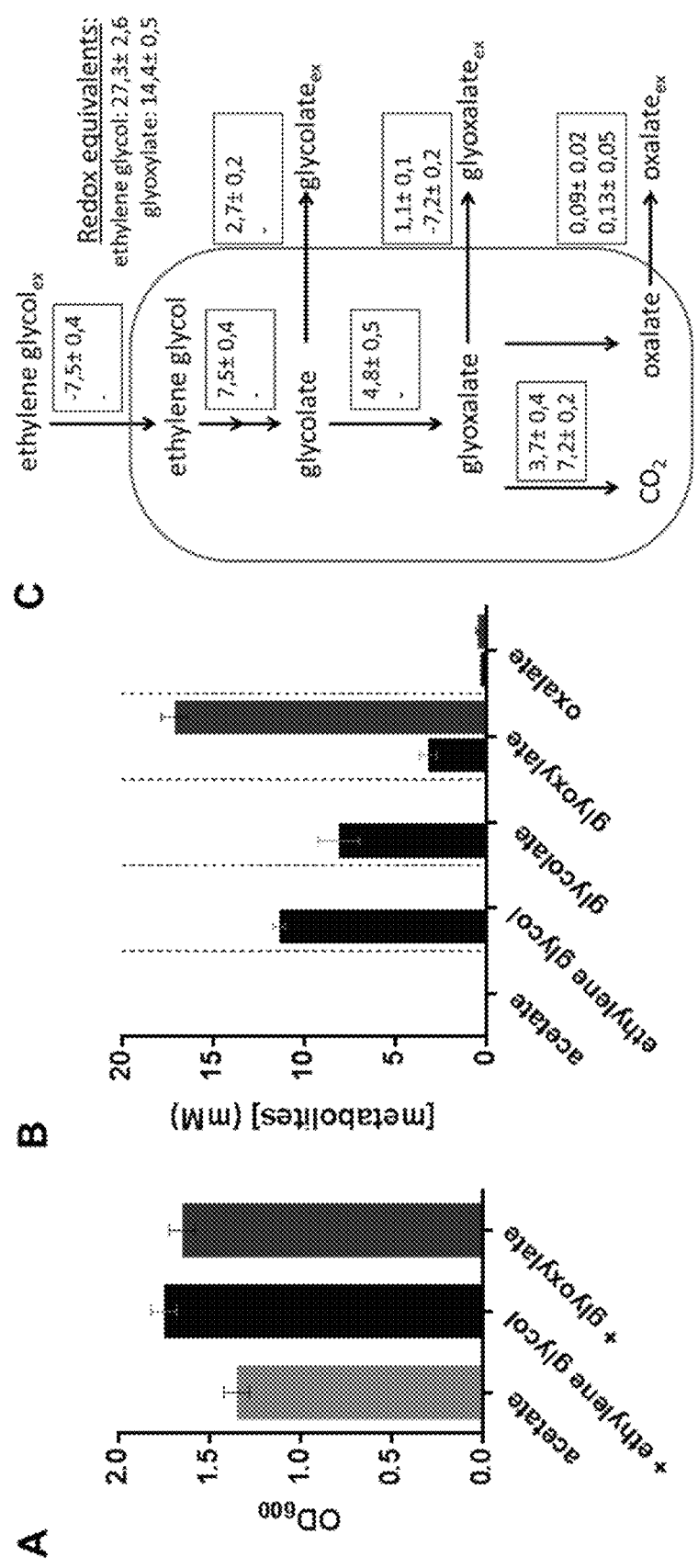

FIG. 14 depicts co-feeding of *P. putida* KT2440 in C-limited chemostat cultivations on mineral medium with 30 mM acetate supplemented with 30 mM ethylene glycol (black), 30 mM glyoxylate (green), or no co-feed (grey). FIG. 14A depicts a comparison of biomass ($OD_{600}$) at steady state. FIG. 14B depicts extracellular metabolites at steady state. The metabolites profile of the acetate control is not shown since none were detected. FIG. 14C depicts flux analysis of redox equivalent-yielding metabolism of ethylene glycol (upper value) or glyoxylate (lower value) in mM $gCDW^{-1}$ $h^{-1}$. Cells were grown at a dilution rate of 0.2. Error bars indicate the deviation from the mean (n=2).

Figure 15:
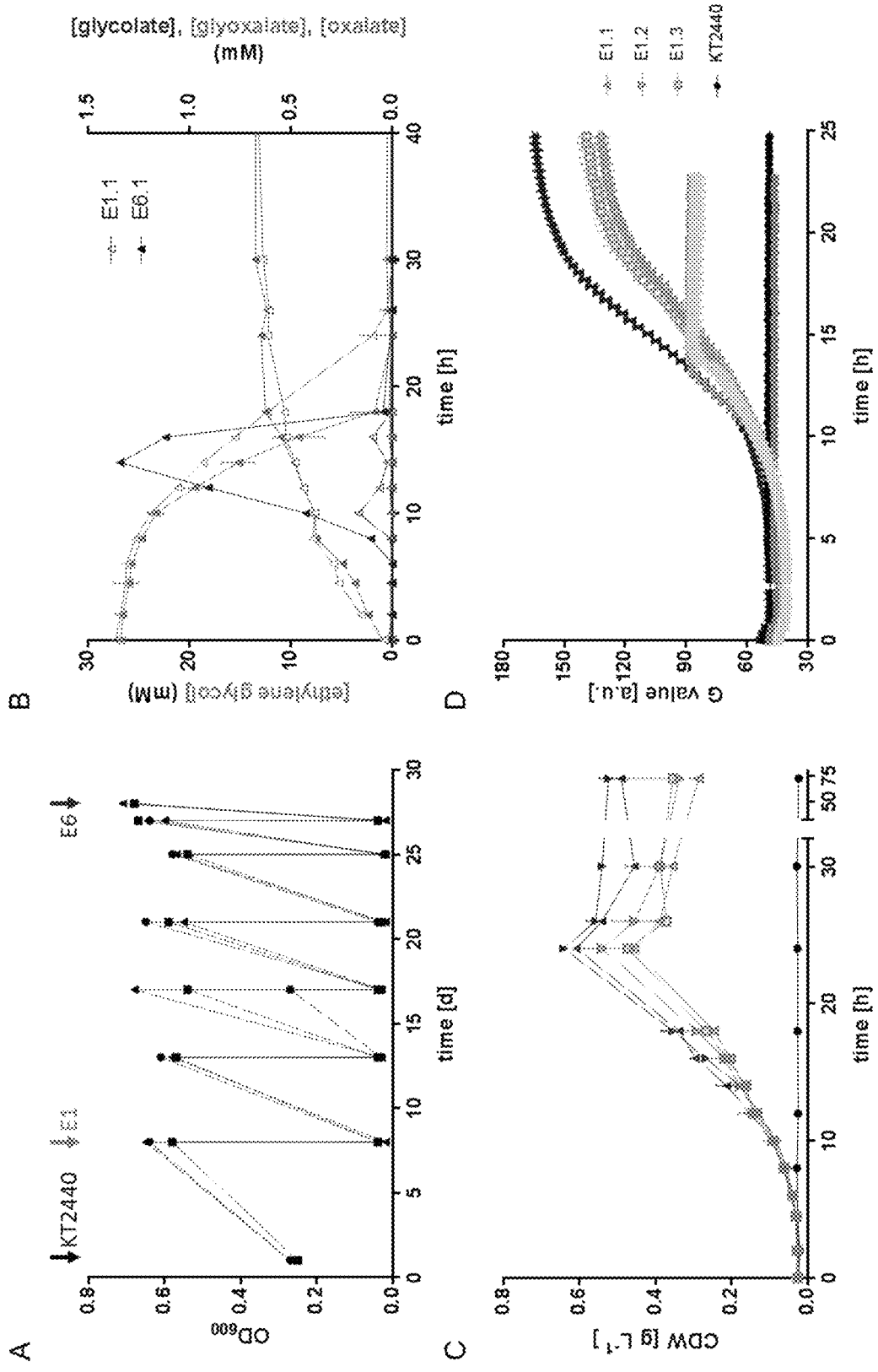

FIG. 15 depicts adaptive laboratory evolution of *P. putida* KT2440 on ethylene glycol and characterization of adapted strains. FIG. 15A depicts sequential batch cultivation on mineral medium with 15 mM ethylene glycol. Arrows indicate the time points where strains were isolated. FIG. 15B depicts extracellular metabolic products and FIG. 15C depicts biomass growth of the isolated ALE strains E1.1 and E6.1 growing on 30 mM ethylene glycol. FIG. 15C also depicts of *P. putida* KT2440 and all adapted strains in a shake flask cultivation on mineral medium with 30 mM ethylene glycol. FIG. 15D depicts growth comparison of *P. putida* KT2440 and all adapted strains in minimal medium containing 30 mM ethylene glycol (in light colors) and 120 mM ethylene glycol (in darker colors). Growth was detected via a growth profiler in 96-square-well plates. Error bars indicate the deviation from the mean (n=2).

Figure 16:
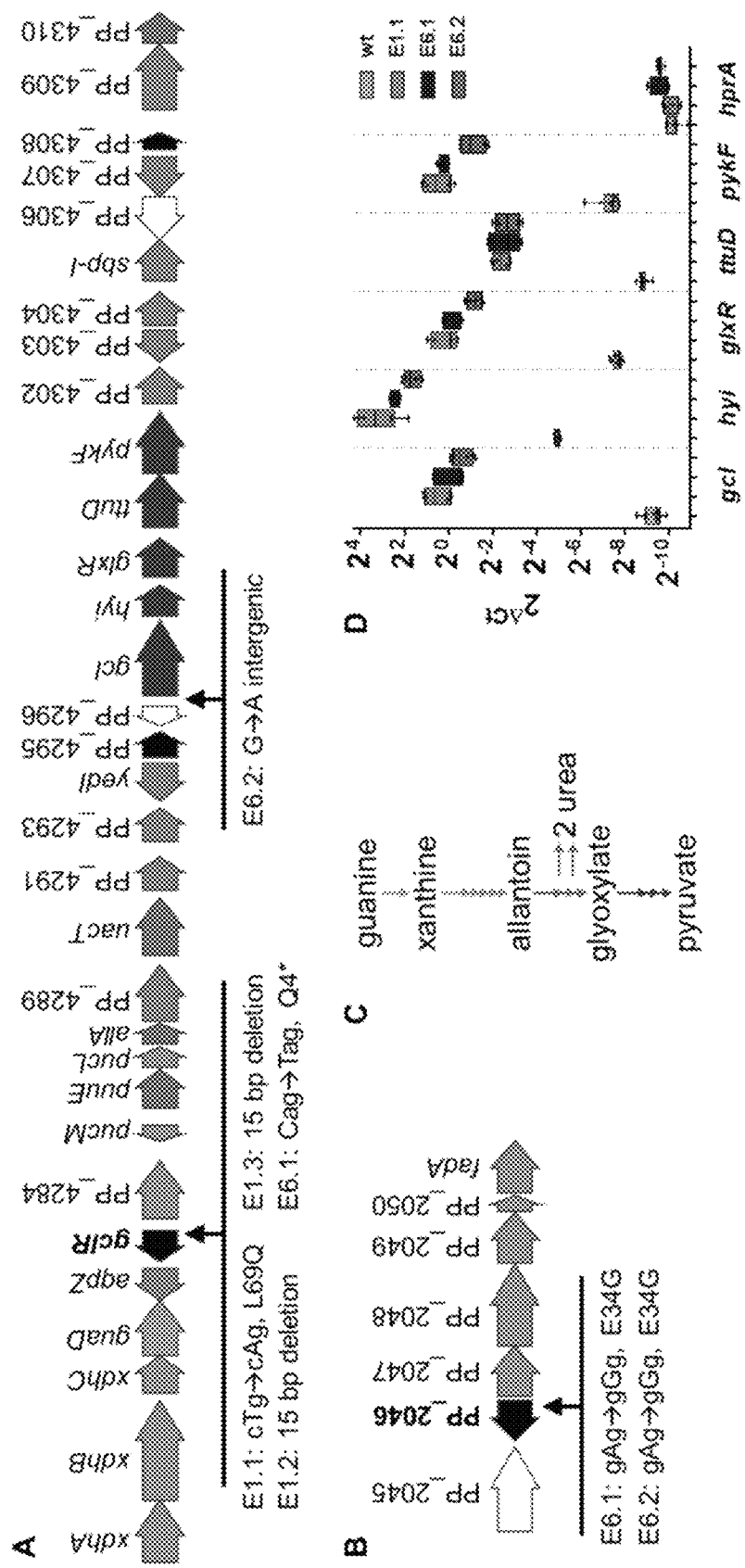

FIG. 16 depicts genomic and transcriptomic analysis of ethylene glycol adaptive mutations in *P. putida* KT2440. FIG. 16A depicts genomic context of mutations involved in the activation of the gcl pathway (coordinates: 4866804-4902814, 36 kb), and FIG. 16B depicts a beta-oxidation operon (coordinates: 2325342-2334253, 9 kb). Mutations and their effects are indicted below the affected site. Black arrows indicate transcriptional regulators, grey arrow indicate putative transporters, ochre arrows indicate functions related to beta-oxidation, and white arrows indicate miscellaneous unrelated functions. Other arrow colors correspond to metabolic functions shown in FIG. 16C depict a simplified representation of purine metabolism via allantoin and glyoxylate. FIG. 16D depicts a box-and-whisker plot of relative expression levels of genes implicated in ethylene glycol metabolism in *P. putida* KT2440 wt and evolved mutants determined by qRT-PCR. The 2ΔCt values were normalized to rpoD. Individual data points are plotted onto the graph, whiskers indicate minimum to maximum values.

Figure 17:
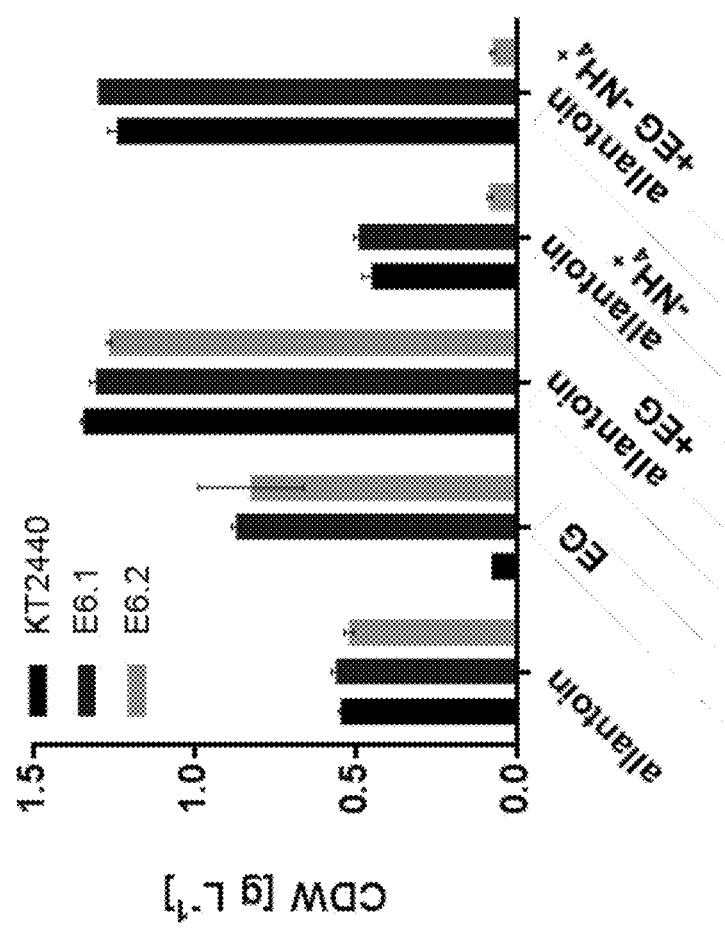

FIG. 17 depicts growth of *P. putida* KT2440 and ALE strains E6.1 and E6.2 after 25 h in mineral medium containing 20 mM allantoin and/or 20 mM ethylene glycol (EG). The label '—$NH_4^+$' indicates that ammonium was omitted from the medium, leaving allantoin as sole nitrogen source. Error bars indicate the deviation from the mean (n=2).

Figure 18:
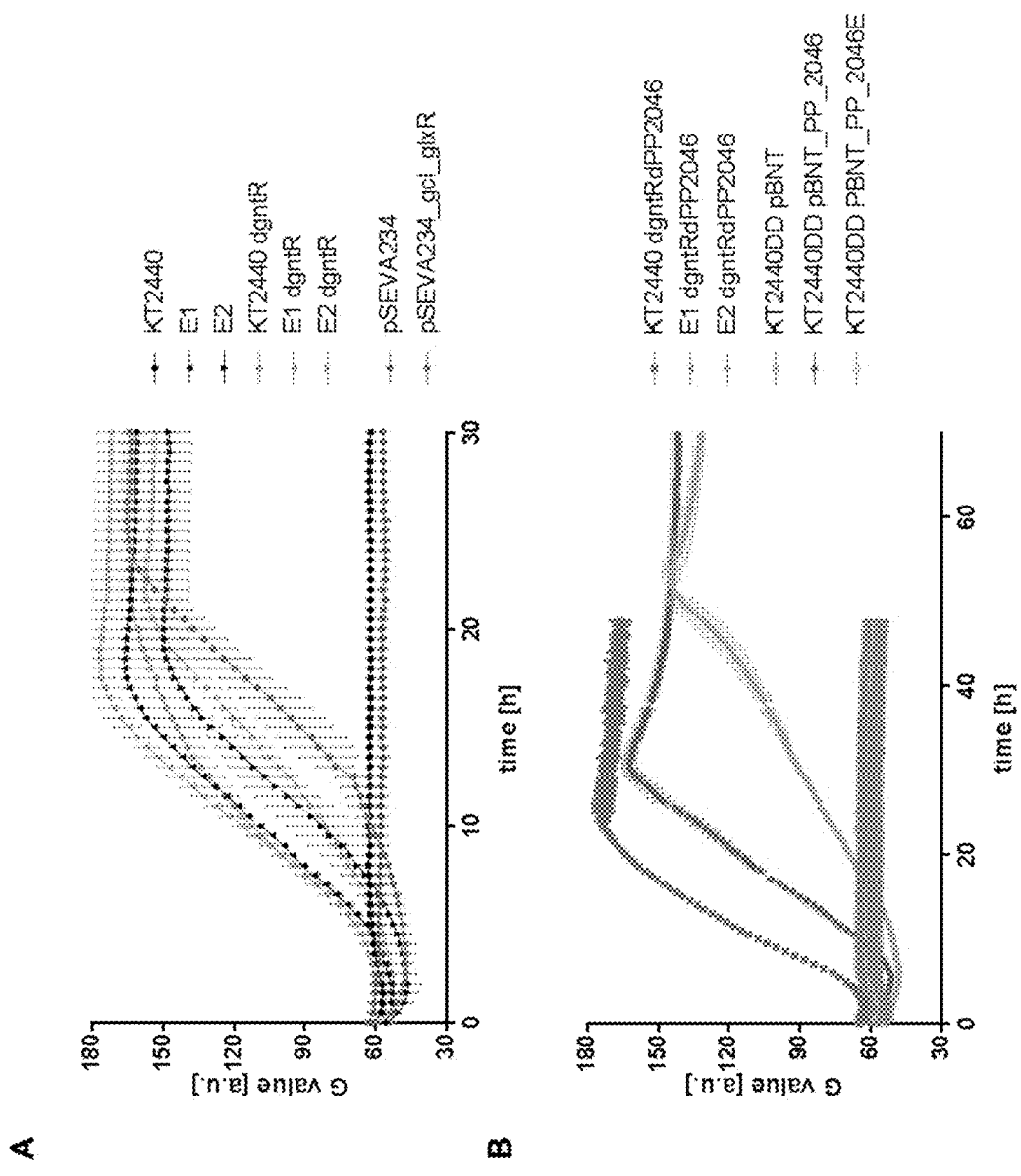

FIG. 18 depicts comparative growth of strains. FIG. 18A depicts a comparison of strains made by reverse engineering over a 30 minute period of time. FIG. 18B depicts a comparison of strains made by reverse engineering over a 60 minute period of time.

Figures 19A, 19B, 19C, 19D, 19E:
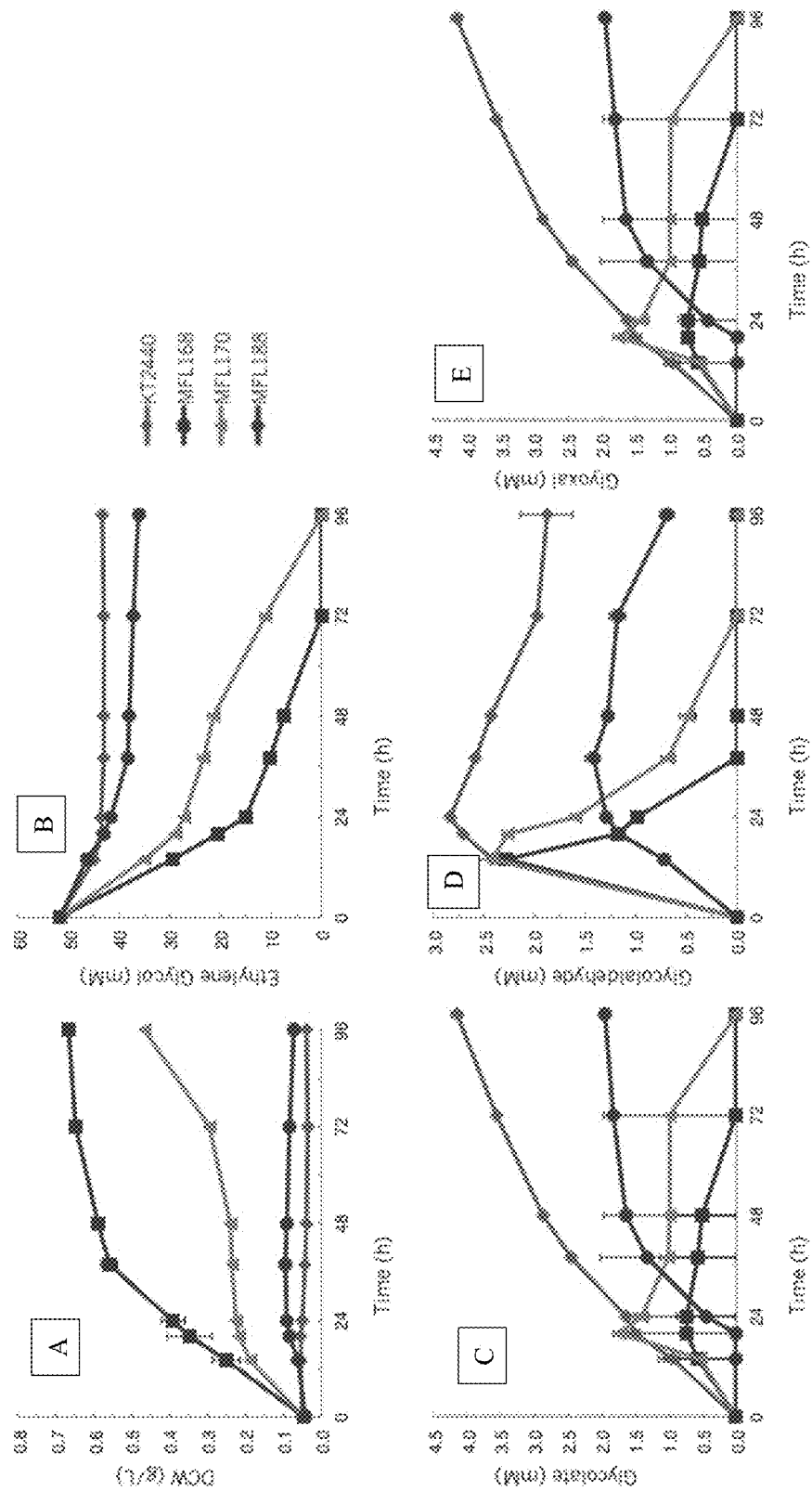

FIG. 19 depicts performance of integrated strains in M9 minimal medium containing 50 mM ethylene glycol. FIG. 19A depicts growth of integrated strains in M9 minimal medium containing 50 mM ethylene glycol in DCW (g/L). FIG. 19B depicts ethylene glycol utilization. FIG. 19C depicts the concentration of glycolate. FIG. 19D depicts the concentration of glycolaldehyde. FIG. 19E depicts the concentration of glyoxal.

Figures 20A, 20B, 20C, 20D, 20E, 20F:
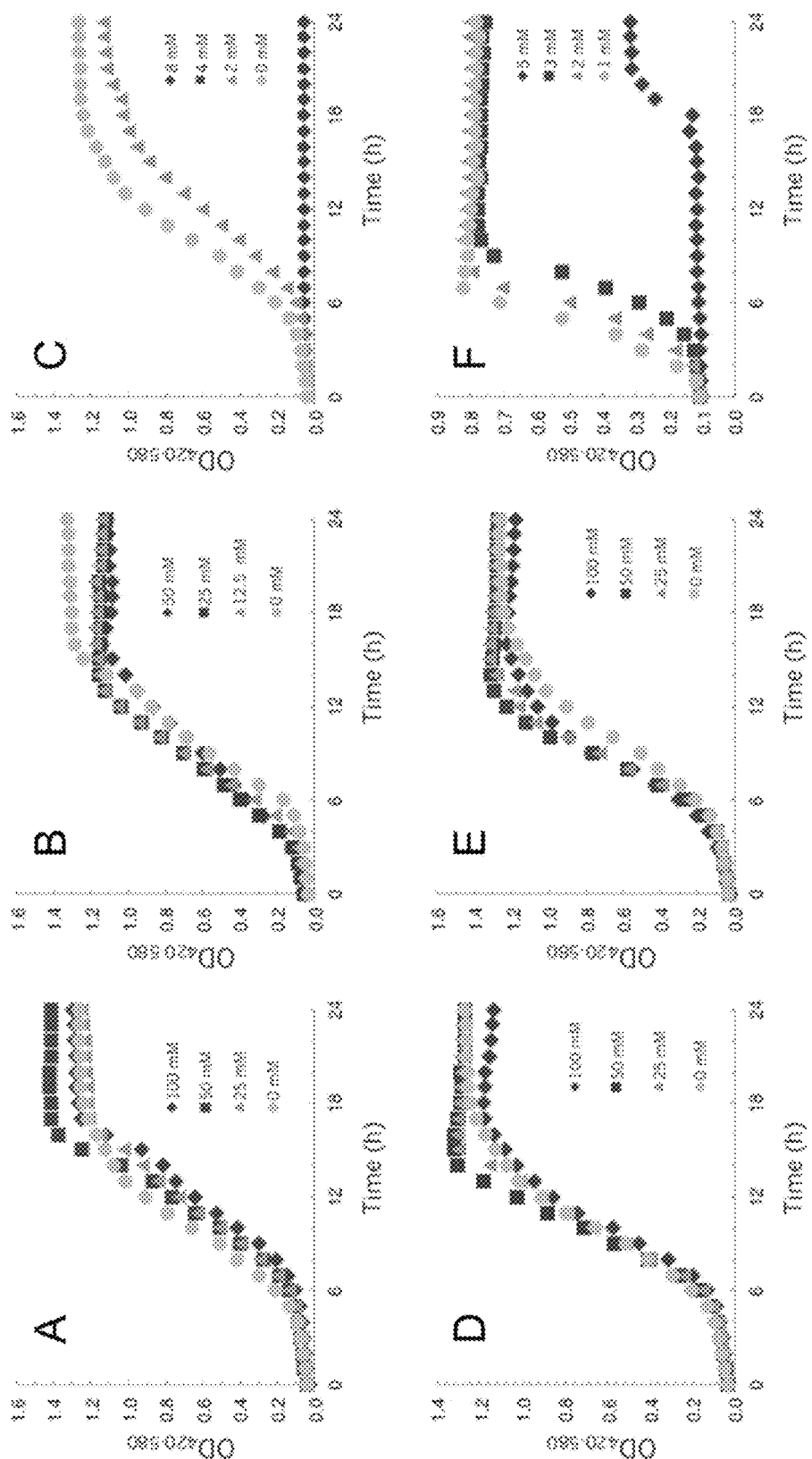

FIG. 20 depicts toxicity assays using the Bioscreen C with *P. putida* KT2440 performed in minimal medium containing 20 mM glucose and the following substrates or metabolites: FIG. 20A depicts growth with 0, 25, 50 and 100 mM ethylene glycol; FIG. 20B depicts growth with 0, 12.5, 25, and 50 mM sodium oxalate; FIG. 20C depicts growth with 0, 2, 4 and 8 mM of glycolaldehyde; FIG. 20D depicts growth with 0, 25, 50 and 100 mM glycolate; FIG. 20E depicts growth with 0, 25, 50 and 100 mM sodium glyoxylate; and 20 F depicts growth with 1, 2, 3, and 5 mM glyoxal.

Figures 21A, 21B, 21C, 21D:
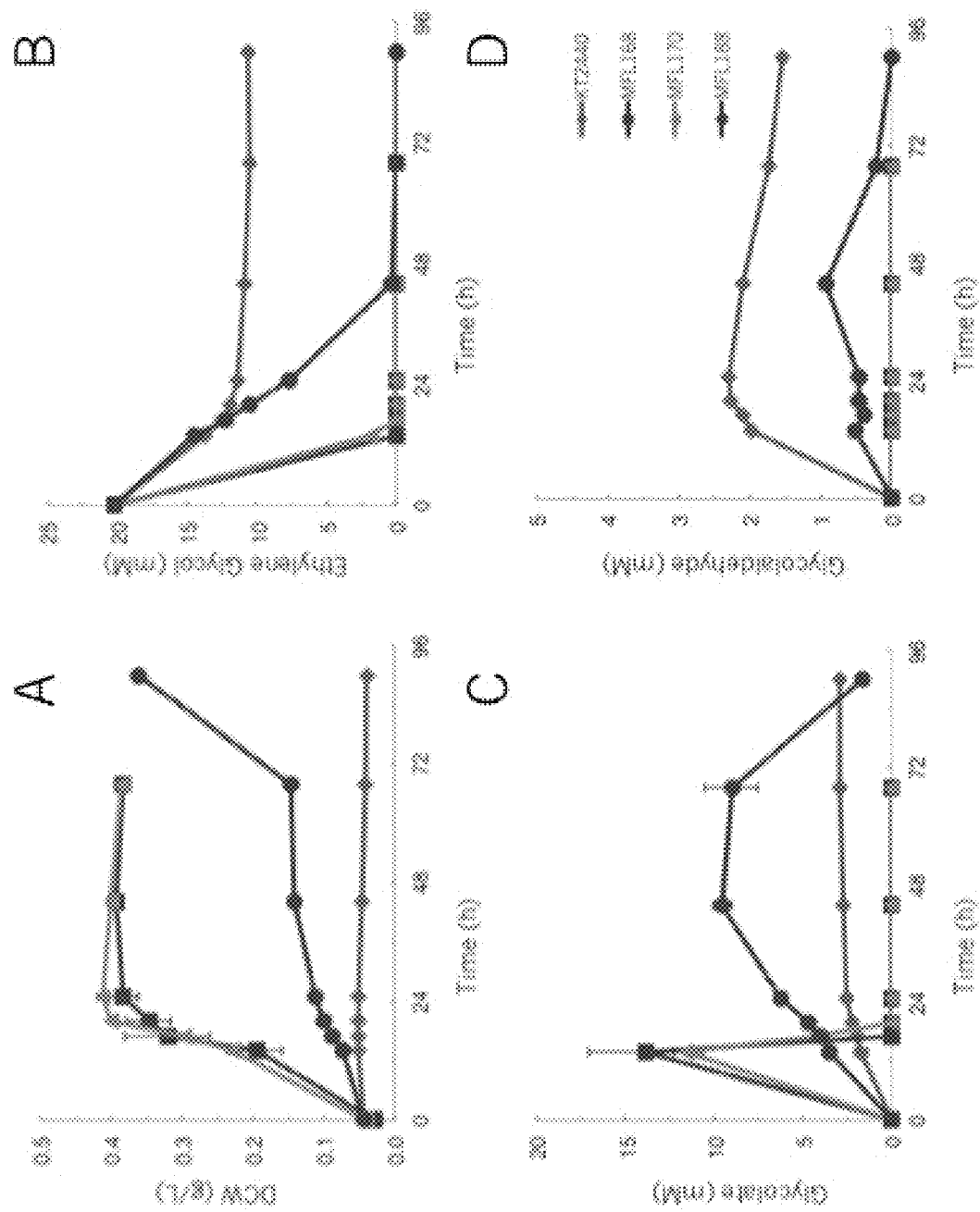

FIG. 21 depicts growth and metabolite concentrations of the corresponding overexpression strains with 20 mM ethylene glycol. FIG. 21A depicts growth in DCW (g/L). FIG. 21B depicts ethylene glycol concentration. FIG. 21C depicts glycolate concentration. FIG. 12D depicts glycolaldehyde concentration.

Figures 22A, 22B, 22C, 22D:
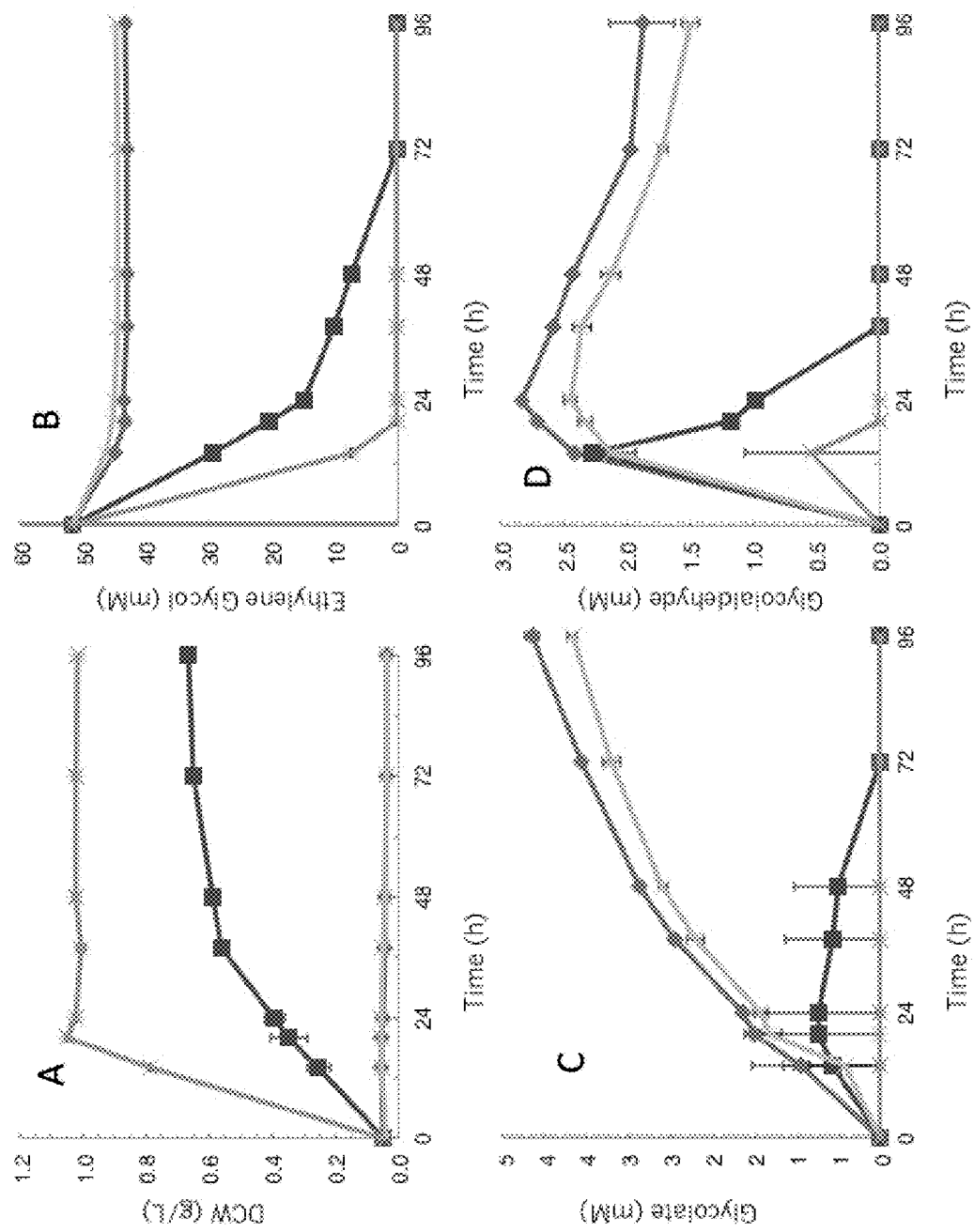

FIG. 22 depicts characterization of a glycolate oxidase overexpression strain that is also overexpressing the gcl operon. FIG. 22A depicts growth of *P. putida* KT2440, MFL168, MFL186 and MFL185 in 50 mM ethylene glycol. FIG. 22B depicts the concentration of ethylene glycol. FIG. 22C depicts the concentration of glycolate. FIG. 22D depicts the concentration of glycoaldehyde.

Figures 23A, 23B, 23C, 23D:
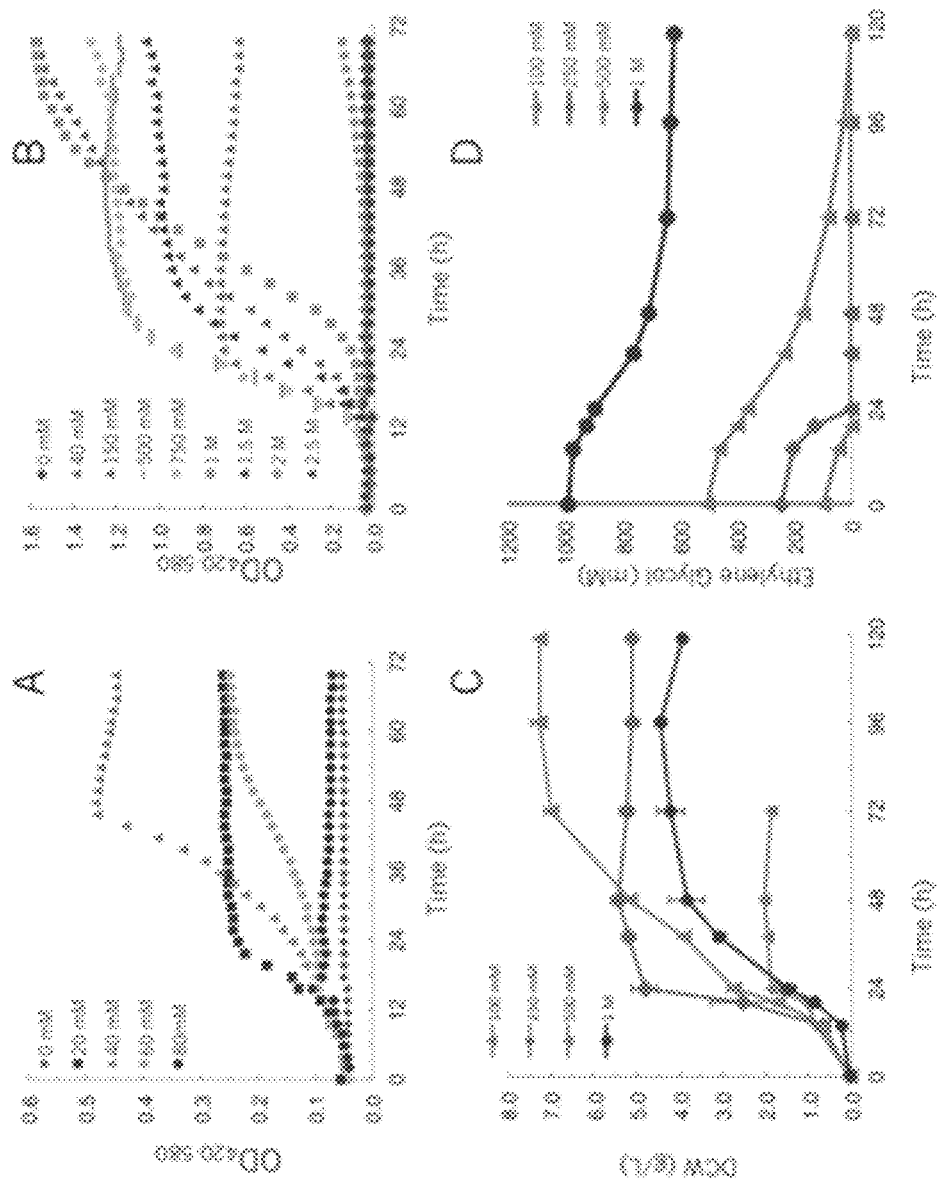

FIG. 23 depicts growth of engineered strains under various growth conditions. FIG. 23A depicts the growth of MFL168 in M9 minimal medium containing varying concentrations of ethylene glycol only as measured in the Bioscreen C. FIG. 23B depicts the growth of MFL 185 in M9 minimal medium containing varying concentrations of ethylene glycol only as measured in the Bioscreen C. FIG. 23C depicts growth of MFL185 in M9 minimal medium containing varying concentrations of ethylene glycol shake flasks measuring DCW (g/L) over time. FIG. 23D depicts ethylene glycol utilization over time.

Figure 24:
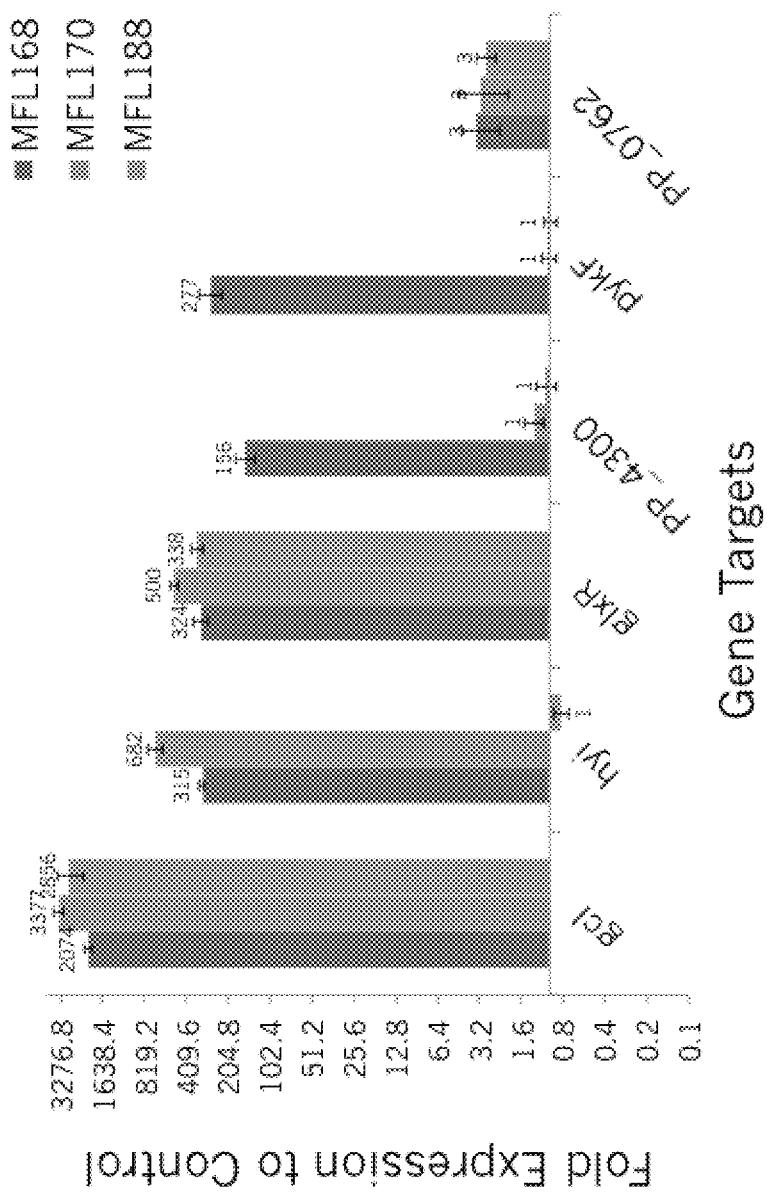

FIG. 24 depicts fold change in gene expression of various gene targets by qRT-RT experiments compared to the control *P. putida* KT2440. Expression of gene targets from the gcl operon (gcl, hyi, glxR, PP_4300 and pykF) in addition to the native hydroxypyruvate reductase (PP_0762). Expression levels were normalized to the housekeeping gene, rpoD and then normalized to expression levels present in the wild-type strain *P. putida* KT2440.

Figure 25:
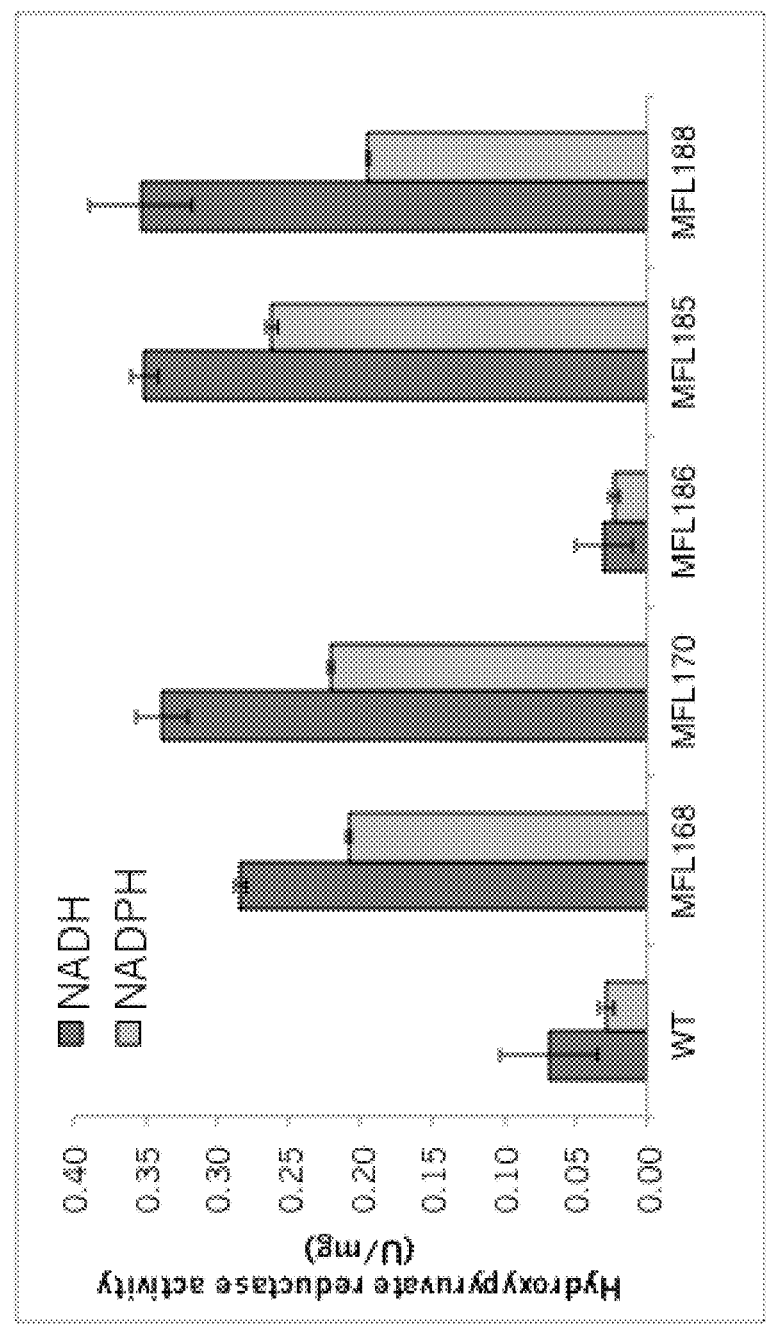

FIG. 25 depicts NAD(P)H-dependent hydroxypyruvate reduction activity of whole lysate protein of engineered strains using NADH-dependent and NADPH-dependent hydroxypyruvate reduction activity of whole cell lysates. Results are the average of n=3, bars labelled with different letters indicate statistical significance (p<0.05; one-way ANOVA followed by Tukey's post hoc honest significance difference test). One unit (U/mg) was defined as the amount of enzyme required to convert 1 µmol of NAD(P)H to NAD(P)+ per minute.

DETAILED DESCRIPTION

Wildtype *P. putida* KT2440 cannot grow on ethylene glycol as a sole carbon source. As disclosed herein, adaptive laboratory evolution experiments performed on wildtype strains of *P. putida* resulted in non-naturally occurring *P. putida* KT2440 mutants that can use ethylene glycol as their sole carbon source. The metabolism of ethylene glycol and its derivatives plays a pivotal role in the biotechnological utilization of plastic waste and lignin, and its oxidation products glycolic and glyoxylic acid are valued commodity chemicals. The characterization of the metabolic pathways in these mutants is useful for engineering *Pseudomonas* strains for the production of compounds of interest, and for using ethylene glycol as a redox energy yielding co-substrate. In an embodiment, the genetically engineered *Pseudomonas* strains disclosed herein can be used for the metabolism of glycoaldehyde.

A metabolic engineering approach to convert ethylene glycol into cellular biomass is disclosed herein. Although, *P. putida* KT2440 has all the genes necessary for growth in ethylene glycol, it is prevented from doing so, by its own regulation. By overexpressing the gcl operon, ethylene glycol can be used for cell growth. An exogenous gene or genes have been introduced into a genetically engineered organism and/or integrated into the genome of a genetically engineered organism resulting in a non-naturally occurring, genetically engineered organism. In an embodiment the engineered organisms disclosed herein express and/or overexpress glc operon and/or gcl operons that are exogenous.

In an embodiment, the genes introduced into the genetically engineered *Putida* organisms disclosed herein are exogenous. The exogenous genes may be additional copies of native genes in the genetically engineered organism. In an embodiment the genes introduced into engineered *Putida* strains disclosed herein are additional copies of native genes. In an embodiment, the genes introduced into engineered *Putida* strains disclosed herein are additional copies of native genes and are under the control of exogenous promoters.

As depicted herein, the quantitative physiological characterization of ethylene glycol co-metabolism by *P. putida* KT2440 provides valuable insights for the production of the latter value-added chemicals, and also identifies opportunities and bottlenecks for the use of ethylene glycol as a redox energy yielding co-substrate.

Experiments were performed to expand the ability of *P. putida* to both use and produce substrates of industrial interest by enhancing its metabolism of ethylene glycol via metabolic engineering through the overexpression of existing regulated pathways that include the glyoxylate carboligase (gcl) operon. Growth in concentrations of ethylene glycol above 50 mM was inhibited by the accumulation of toxic intermediates, glycolaldehyde and glyoxal. The additional overexpression of glycolate oxidase (glcDEF) operon removes the glycolate bottleneck and minimizes the production of these toxic intermediates, permitting the growth in up to 2 M (120 g/L) and consumption of greater than about 0.5 M (30 g/L) of ethylene glycol.

Ethylene glycol is used as a raw material in the production of polyethylene terephthalate, in antifreeze, as a gas hydrate inhibitor in pipelines, and for many other industrial applications. It is metabolized by aerobic microbial processes via the highly toxic intermediates glycolaldehyde and glycolate through C2 metabolic pathways. *Pseudomonas putida* KT2440, which has been engineered for environmental remediation applications given its high toxicity tolerance and broad substrate specificity, is not able to efficiently metabolize ethylene glycol, despite harboring putative genes for this purpose. To further expand the metabolic portfolio of *P. putida*, we elucidated the metabolic pathway to enable ethylene glycol via systematic overexpression of glyoxylate carboligase (gcl) in combination with other genes. Quantitative reverse transcription polymerase chain reaction demonstrated that all of the four genes in genomic proximity to gcl (hyi, glxR, ttuD, and pykF) are transcribed as an operon. Where the expression of only two genes (gcl and glxR) resulted in growth in ethylene glycol, improved growth and ethylene glycol utilization were observed when the entire gcl operon was expressed. Both glycolaldehyde and glyoxal inhibit growth in concentrations of ethylene glycol above 50 mM. To overcome this bottleneck, the additional overexpression of the glycolate oxidase (glcDEF) operon removes the glycolate bottleneck and minimizes the production of these toxic intermediates, permitting growth in up to 2 M (~124 g/L) and complete consumption of 0.5 M (31 g/L) ethylene glycol in shake flask experiments. In addition, the engineered strain enables conversion of ethylene glycol to medium-chain-length polyhydroxyalkanoates (mcl-PHAs). Overall, the methods and non-naturally occurring genetically modified organisms disclosed herein result in *P. putida* KT2440 strains that are now useful for ethylene glycol consumption, and can serve as a biocatalyst for applications in the remediation of waste polyester plastics and biomass-derived wastewater streams.

Ethylene glycol is a large-volume industrial chemical used for myriad applications including for the production of polyester plastics such as polyethylene terephthalate (PET), as a coolant in antifreeze, as a deicing fluid for aircraft, and as an inhibitor of clathrate hydrate formation in natural gas pipelines. Because of its widespread use, it is a common pollutant in the environment, where it is broken down either chemically or biologically. Plastic wastes, including ethylene glycol and terephthalic acid, offer novel substrates for industrial biotechnology to convert into value-added products, especially given the worldwide concern over plastic accumulation in the biosphere.

Aerobic ethylene glycol metabolism also generates the highly toxic intermediate glycolaldehyde. Besides being a metabolic intermediate in ethylene glycol metabolism, this compound is also often a significant component of lignocellulose-derived streams, and can also be present in pyrolysis wastewater in concentrations as high as 50 g/kg. Currently, wastewater streams containing significant amounts of glycolaldehyde from biomass pyrolysis are sent to thermal wastewater treatment processes, but converting this carbon to a value-added co-product stream would improve biorefinery economics.

Figure 1:
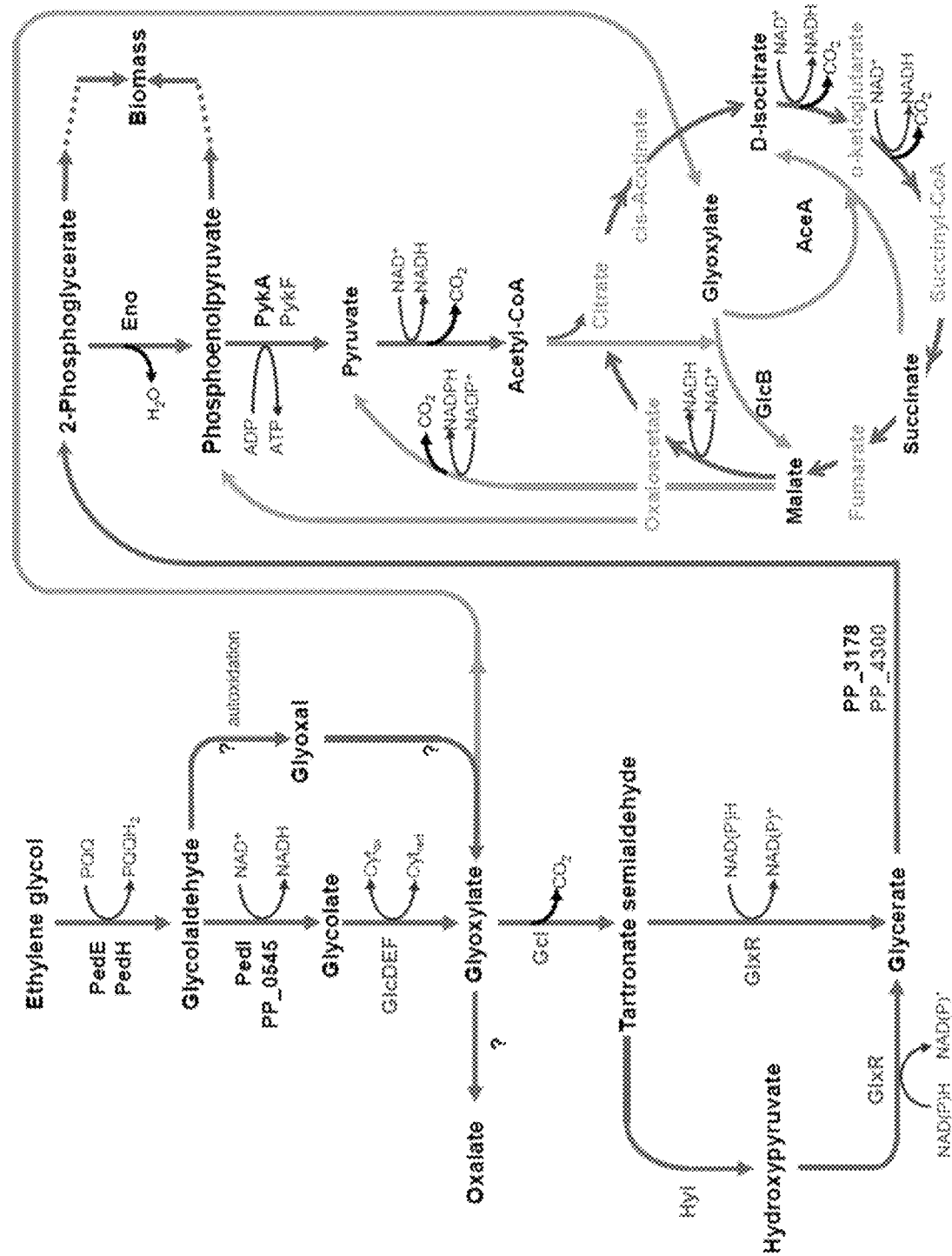
FIG. 1 depicts a schematic of ethylene glycol metabolism and strain modifications implemented in this study in *P.*

From an environmental perspective, disposal of ethylene glycol or its intermediate, glycolaldehyde, poses serious environmental problems. Soil bacteria, such as pseudomonads, are likely responsible for a substantial extent of ethylene glycol catabolism in the environment. The obligate aerobic organism *P. putida* KT2440 uses ethylene glycol only as a source for the production of reducing equivalents and energy, whereas ethylene glycol enables biomass formation in other *P. putida* strains, such as JM37. Through comparative proteomics of these two *P. putida* strains, the catabolism of ethylene glycol in *P. putida* KT2440 was proposed to proceed via two functionally redundant, periplasmic quinoproteins PedE and PedH and the subsequent activity of the two cytoplasmic aldehyde dehydrogenases PP_0545 and PedI, together with the membrane anchored oxidase GlcDEF, yielding glyoxylic acid (FIG. 1). Glyoxylic acid was then proposed to be further metabolized either through the dicarboxylic acid pathway initiated by ligation to acetyl-CoA catalyzed by malate synthase (GlcB) or through the partial use of TCA-cycle reactions initiated by the AceA-dependent ligation of glyoxylate and succinate to yield isocitrate (glyoxylate cycle). However, the metabolic regeneration of either of these adducts yields two molecules of $CO_2$, and thus the metabolism of glyoxylate through this cycle will not enable growth. In contrast, the catabolic pathway that allows biomass formation in strain JM37 proceeds through the glyoxylate carboligase, (Gcl) pathway, and energy generation through the glyoxylate shunt through malate synthase (GlcB) and isocitrate lyase (AceA).

In contrast to the productive use of ethylene glycol by other strains of *P. putida*, the lack of growth of *P. putida* KT2440 on ethylene glycol is puzzling, as the organism exhibits the genomic inventory to use ethylene glycol as a carbon source through the initial ligation of two glyoxylate molecules to tartronate semialdehyde by the glyoxylate carboligase (Gcl) enzyme. According to the *Pseudomonas* Genome Database predictions, the enzymes adjacent to gcl encode hydroxypyruvate isomerase (hyi), tartronate semialdehyde reductase (glxR), hydroxypyruvate reductase (ttuD), and pyruvate kinase (pykF), which could, together with glycerate kinase (garK) encoded on a different locus of the genome, allow conversion of glyoxylic acid into biomass. The lack of growth with ethylene glycol in native, naturally occurring *P. putida* KT2440 is caused by an unknown regulatory mechanism, which prevents the functional production of the aforementioned enzymes necessary to use ethylene glycol for growth. As disclosed herein, by using adaptive laboratory evolution techniques, it was discovered that the observed lack of growth with ethylene glycol is caused by an unknown regulatory mechanism wherein repression of gcl-operon genes is overcome by a mutation in a specific transcriptional regulator.

In the present disclosure, we demonstrate that efficient glyoxylate and ethylene glycol conversion into biomass involves the constitutive expression of gcl in addition to genes in proximity of gcl. Contrary to operon prediction software, transcriptomic analysis reveals that the operon consists of four other genes contiguous to gcl (hyi, glxR, ttuD, and pykF), permitting a different and more effective path from glyoxylate to glycerate, via hydroxypyruvate. An additional bottleneck was discovered at the metabolite glycolate as concentrations of substrate increased, resulting in the accumulation of a toxic intermediate (glycolaldehyde). The overproduction of the native glycolate oxidase operon (glcDEF) resolves this bottleneck, which leads to increased metabolic flux, and decreases the accumulation of toxic intermediates, transforming *P. putida* KT2440 into an efficient ethylene glycol-metabolizing strain. Also, disclosed herein are engineered strains that enable efficient conversion of ethylene glycol into medium-chain-length polyhydroxyalkanoates (mcl-PHAs), a high value chemical building block. Engineered *P. putida* strains disclosed herein can serve as a foundation for conversion of both ethylene glycol from plastic waste and glycolaldehyde in biomass-derived wastewater streams.

In an embodiment, disclosed herein are engineered *P. putida* strains that are capable of the expression of two exogenous genes (gcl and glxR) that confer the ability of engineered *P. putida* to grown on ethylene glycol. In an embodiment, engineered *P. putida* strains are disclosed that comprise a gcl operon that contains the genes gcl, hyi, glxR, ttuD, and pykF that allows for growth and/or improved growth in ethylene glycol. In another embodiment, *P. putida* strains are disclosed herein that are capable of overexpression of glycolate oxidase which removes a glycolate metabolic bottleneck. In an embodiment, disclosed herein are engineered *P. putida* KT2440 strains that consume up to about 31 g/L of ethylene glycol. In another embodiment, disclosed herein are engineered *P. putida* KT2440 strains capable of producing mcl-PHAs from ethylene glycol.

Plasmid Construction

Q5 Hot Start High-Fidelity 2X Master Mix (New England Biolabs) and primers synthesized by Integrated DNA Technologies (IDT) were used in all PCR amplification. Plasmids were constructed using Gibson Assembly Master Mix (New England Biolabs) according to the manufacturer's instructions. Primers used for PCR amplification and Gibson assembly are listed in Table 1.

Table 1 contains primers used for creating plasmid and integration constructs. Underlined nucleotides denote homology to a target gene. Nucleotides in bold font are restriction sites.

TABLE 1

| Primer ID | Primer Sequence | Template Used for PCR (region) | For Construction of |
|---|---|---|---|
| oMFL158 (SEQ ID NO: 8) | gagaGCGGCCGCGAATTCAAGCTT GATATCATTCAGGAC | pBTL-2 (NotI upstream from soxR term) | pMFL115 |
| oMFL159 (SEQ ID NO: 9) | gagaCCTGCAGGGAATTCTCTAGA GTGTGAAATTGTTATCCG | pBTL-2 (SbfI downstream from lac promoter) | pMFL115 |
| oMFL160 (SEQ ID NO: 10) | gagaCCTGCAGGGGGCCTAGATAT AGGAGGAATAACCATGAGCAAAA TGAGAGCAATCGATG | KT2440 (upstream targeting 5' of gcl with SbfI site and RBS) | pMFL113, pMFL114, pMFL116, pMFL117 |
| oMFL161 (SEQ ID NO: 11) | gagaTTAATTAAATTCGCGGCCGC TCAGTCCAGCAGCGAGATGG | KT2440 (downstream targeting 3' of gcl with NotI PacI sites) | pMFL113, pMFL116 |

TABLE 1-continued

| Primer ID | Primer Sequence | Template Used for PCR (region) | For Construction of |
|---|---|---|---|
| oMFL162 (SEQ ID NO: 12) | gagaGCGGCCGCGATTAGTCAGGT AAGGAGCCTAATT<u>ATGACTGGAT ACGTTCAAGTCGGTG</u> | KT2440 (upstream targeting 5' of glcB with NotI site and RBS) | pMFL115, pMFL117 |
| oMFL163 (SEQ ID NO: 13) | gagaTTAATTAA<u>TTACAACCCGTTA CGCGCCT</u> | KT2440 (downstream targeting 3' of glcB with PacI sites) | pMFL115, pMFL117 |
| oMFL164 (SEQ ID NO: 14) | gagaTTAATTAAATTCGCGGCCGC <u>TCAGATCAAAGTCTCGATCCGCAG</u> | KT2440 (downstream targeting 3' of gcl operon with PacI site) | pMFL114, pMFL117 |
| oMFL165 (SEQ ID NO: 15) | gagaTTAATTAA<u>GAATTCAAGCTTG ATATCATTCAGGAC</u> | pBTL-2 (PacI upstream from soxR term) | pMFL113, pMFL114, pMFL116, pMFL117 |
| oMFL166 (SEQ ID NO: 16) | gagaCCTGCAGGGATTAGTCAGGT AAGGAGCCTAATT<u>ATGACTGGAT ACGTTCAAGTCGGTG</u> | KT2440 (upstream targeting 5' of glcB with SbfI site and RBS) | pMFL115 |
| oMFL167 (SEQ ID NO: 17) | gagaGCGGCCGC<u>TTACAACCCGTT ACGCGCCT</u> | KT2440 (downstream targeting 3' of glcB with NotI sites) | pMFL115 |
| oCJ288 (SEQ ID NO: 18) | <u>CTAGCTTCACGCTGCCGCAAG</u> | pK18mobsacB around the world F | pMFL161 pMFL160 |
| oCJ289 (SEQ ID NO: 19) | <u>CTAACTCACATTAATTGCGTTGCG CTCACTG</u> | pK18mobsacB around the world R | pMFL161 pMFL160 |
| oCJ301 (SEQ ID NO: 20) | AGTGAGCGCAACGCAATTAATGT GAGTTAGAAGCCGAATGTCGATG ATATCTACAACCTGAG | Upstream targeting 3' of fpvA F with pK18mobsacB overlap in italics | pMFL161 pMFL160 |
| oCJ302X (SEQ ID NO: 21) | CCTCCTCTCTAGAGTGTGAAATTG TTATCCGCTCACAATTCCACACAT TATACGAGCCGATGATTAATTGTC AACAGCTCGAATTC<u>AAAAAACCG CACCTGGGTGCG</u> | Upstream targeting 3' of fpvA R with native terminator, Ptac, and XbaI | pMFL161 pMFL160 |
| oCJ306X (SEQ ID NO: 22) | ATTCAGACTAGTAGTCAAAAGCC TCCGACCGGAGGCTTTTGACT<u>CAT GGATGCCTGAAAGGCTCCCTTAC</u> | Downstream targeting 3' of fpvA F with tonB terminator and SpeI site | pMFL161 pMFL160 |
| oCJ307 (SEQ ID NO: 23) | CCCTGAGTGCTTGCGGCAGCGTG AAGCTAGG<u>CCCCTCTGGAGAATC GAACGATG</u> | Downstream targeting 3' of fpvA R with pK18mobsacB overlap in italics | pMFL161 pMFL160 |
| oMFL276 (SEQ ID NO: 24) | CACACTCTAGAGAGGAGGACAGC <u>TATGAGCAAAATGAGAGCAATCG AT</u> | Targeting 5' of KT2440 gcl operon F (underlined) with overlap to | pMFL161 pMFL160 |

TABLE 1-continued

| Primer ID | Primer Sequence | Template Used for PCR (region) | For Construction of |
|---|---|---|---|
| | | Ptac and RBS (oCJ302*) with XbaI site | |
| oMFL279 (SEQ ID NO: 25) | ACTACTAGTTTATTTGTCGTCGCG GATCGAGAAG | Targeting 3' of KT2440 glxR R (underlined) and SpeI site | pMFL160 |
| oMFL280 (SEQ ID NO: 26) | ACTACTAGTTCAGATCAAAGTCT CGATCCGC | Targeting 3' of KT2440 gcl operon (pykF) R (underlined) and SpeI site | pMFL161 |
| oLJ100 (SEQ ID NO: 27) | GACATGATTACGAATTCGAGCTCG GTACCCTTCGCGGCGGTTCGACGC | Upstream targeting of region 5' of glcC with overlap to pK18mobsacB (italics) | pLJ030 |
| oLJ101 (SEQ ID NO: 28) | GGTGCGGTTTTTTGCGCGGCTCAC TCGCAACGGTTTTTG | Downstream targeting region immediately 5' of glcD with overlap to soxR terminator (italics) | pLJ030 |
| oLJ102 (SEQ ID NO: 29) | GTTGCGAGTGAGCCGCGCAAAAA ACCGCACCCAGGTGCGGTTTTTTG AATTCGAGCTGTTGACAATTAATC ATCGGCTCGTATAATGTGTCAGAC TCAATAATAATAATAAGGAGGTA TCGAATGAATATCCTGTACGACG AACGC | Upstream targeting 5' of glcD including soxR terminator and tac promoter and RBS with overlap to 3' end of glcC (italics) and oLJ101 | pLJ030 |
| oLJ103 (SEQ ID NO: 30) | CGGCCAGTGCCAAGCTTGCATGC CTGCAGGAGGTGCACCTCGCGGG CC | Downstream targeting region immediately 3' of glcD with overlap to pK18mobsacB (italics) | pLJ030 |
| oLJ110 (SEQ ID NO: 31) | GCGGATAACAATTTCACACTAAA GTTAATATTAAGGAGGTAAACAT GAGCAAAATGAGAGCAATC | Targeting 5' of KT2440 gcl F (underlined) with overlap to pMFL160 (italics) and RBS | pJL032 |
| oLJ111 (SEQ ID NO: 32) | GTTAGTTGTCGTTTTGATATCAGT CCAGCAGCGAGATG | Targeting 3' of KT2440 gcl R (underlined) with overlap to 5' of glxR with RBS | pJL032 |
| oLJ112 (SEQ ID NO: 33) | GCTGGACTGATATCAAAACGACA ACTAACTAAGGAGGTACACTATG GCTAAAATCGGTTTCATC | Targeting 5' of KT2440 glxR (underlined) with overlap to 3' of gcl with RBS | pJL032 |
| oLJ113 (SEQ ID NO: 34) | CGGTCGGAGGCTTTTGACTATTAT TTGTCGTCGCGGATC | Targeting 3' of KT2440 gcl R (underlined) | pJL032 |

TABLE 1-continued

| Primer ID | Primer Sequence | Template Used for PCR (region) | For Construction of |
|---|---|---|---|
| | | with overlap to pMFL161 (italics) | |

The plasmid, pBTL2 was used as the backbone of all plasmid-based overexpression constructs in engineered *P. putida* KT2440 strains whose dried cellular weight (DCW) and use of ethylene glycol is depicted in FIG. 2. In an embodiment, features of the plasmids used include the lac promoter and a soxR terminator. Plasmids were constructed by amplifying the plasmid (pBTL2) or gene(s) of interest from *P. putida* KT2440, digesting with appropriate restriction enzymes then ligating vector and inserts to produce plasmids pBTL2-gcl, pBTL2-gcl-operon, pBTL2-glcB, pBTL2-gcl-glcB, pBTL2-gcl-operon-glcB (pMFL113-117, respectively); strain name designations are listed in Table 2.

They contain the 1 kb homology region on either side of the intergenic region immediately after the fpvA (outer membrane ferripyoverdine receptor) terminator and PP_4218 (lipase/esterase) of *P. putida* KT2440 (see Table 1 for primers used for construction).

Features include the tac promoter to drive gene expression and a tonB terminator situated behind the fragments cloned into the plasmid backbone, which are depicted in FIG. 3. The ribosomal binding site (RBS) (GAGGAGGA) in front of gcl was predicted to have a translation initiation rate (TIR) of 2700 using an online RBS calculator and was the same for MFL168, MFL170, and MFL185. We used the optimal RBS

TABLE 2

| Strain ID | Plasmid used for Integration | Strain genotype | Strain description |
|---|---|---|---|
| MFL1 | | *P. putida* KT2440 (KT2440) | Wild-type (WT) strain also designated as KT2440 |
| MFL142 | | KT2440 pBTL-2 | WT strain with control plasmid (pBTL2) |
| MFL113 | | KT2440 pBTL2-gcl | WT strain with plasmid expressing only gcl |
| MFL114 | | KT2440 pBTL2-gcl operon | WT strain with plasmid expressing gcl operon |
| MFL115 | | KT2440 pBTL2-glcB | WT strain with plasmid expressing only glcB |
| MFL116 | | KT2440 pBTL2-gcl-glcB | WT strain with plasmid expressing gcl and glcB |
| MFL117 | | KT2440 pBTL2-gcl-operon-glcB | WT strain with plasmid expressing gcl operon and glcB |
| MFL168 | pMFL161 | KT2440 fpvA::P$_{tac}$::gcl-hyi-glxR-ttuD-pykF | Strain expressing gcl operon integrated between fpvA and PP 4218 |
| MFL170 | pMFL160 | KT2440 fpvA::P$_{tac}$::gcl-hyi-glxR | Strain expressing gcl-hyi-glxR integrated between fpvA and PP_4218 |
| mFL185 | pMFL161 and pLJ030 | KT2440 fpvA::P$_{tac}$::gcl-hyi-glxR-ttuD-pykF, andP$_{tac}$::glcDEF | Strain expressing gcl operon integrated between fpvA and PP_4218 and with tac promoter integrated in front of glcDEF:PP 3748:PP3749 operon |
| MFL186 | pLJ030 | KT2440 Ptac::glcDEF | Strain with tad promoter integrated in front of glcDEF:PP_3748:PP3749 operon |
| MFL188 | pLJ032 | KT2440 fpvA::P$_{tac}$::gcl-glxR | Strain expressing gcl-glxR integrated between fpvA and PP_4218 |

Plasmids for gene integration were constructed in plasmid pK18mobsacB from ATCC (American Type Culture Collection, Manassas, Va.), which is unable to replicate in *P. putida* KT2440, and contains the kanamycin-resistant marker to select for integration of the plasmid into the genome by homologous recombination and sacB to counterselect for a second recombination event to subsequently remove the plasmid backbone from the genome.

The plasmids, pMFL160 and pMFL161, used for of integration of operons containing the gene gcl in strains MFL168, MFL170, MFL185, and MFL188 were constructed based on the integration vector pK18mobsacB.

(AAGGAGGT) for expression of gcl and glxR in MFL188. The sequences of all other promoter regions, genes, or operons remained unchanged, and thus represent the native chromosomal sequence. The overexpression of glycolate oxidase genes (glcDEF) in plasmid pLJ030, which was used to construct strains MFL185 and MFL186, was achieved by integrating the tac promoter upstream of the glycolate oxidase operon (glcDEFG_PP_3749) and behind the native promoter, while additionally optimizing the RBS for glcD (AAGGAGGT). The nucleotide plasmid sequences are SEQ ID NO: 1 for pLJ030, SEQ ID NO: 2 for pLJ032, SEQ ID NO: 3 for pMFL160, and SEQ ID NO: 4 for pMFL161.

Plasmids were transformed into competent NEB 5-alpha F'I$^q$ E. coli (New England Biolabs) according to the manufacturer's instructions. Transformants were selected on LB plates containing 10 g/L tryptone, 5 g/L yeast extract, 5 g/L NaCl, and 15 g/L agar, supplemented with 50 µg/mL kanamycin grown at 37° C. The sequences of all plasmid inserts were confirmed using Sanger sequencing.

Strain Construction

P. putida KT2440 (ATCC 47054) was used as the strain for engineering and gene replacements that were made using the antibiotic/sacB system of selection and counter-selection. To prepare electrocompetent cells of different P. putida KT2440 strains, we used a modified protocol. Briefly, cultures were grown overnight in LB broth and incubated at 30° C., shaking at 225 rpm. The next day, cells were centrifuged 21,130×g in an Eppendorf centrifuge for 1 minute at room temperature, washed three times in 0.3 M sucrose in half the original volume. Finally, the cells were resuspended in $\frac{1}{50}^{th}$ of the culture's original volume in 0.3 M sucrose. Cells were immediately used for electroporation by introducing 5 µL (200 ng-2 µg) of plasmid DNA to 50 µL of the electrocompetent cells, transferred to a chilled 0.1 cm electroporation cuvette, and electroporated at 1.6 kV, 25 µF, 200Ω. Subsequently, 950 µL SOC (NEB) was added and the cells were incubated shaking at 225 rpm, 30° C., for 2 h. The entire transformation was plated on an LB agar plate containing appropriate antibiotics and incubated at 30° C. overnight. Initial colonies from the transformation plates were re-streaked on selective LB agar plates and grown at 30° C. overnight to obtain clonal transformants. For sucrose counter-selection, clonal transformants were streaked on YT plates containing 25% (YT+25%; w/v) sucrose (10 g/L yeast extract, 20 g/L tryptone, 250 g/L sucrose, 18 g/L agar), and incubated at 30° C. overnight. P. putida KT2440 containing the sacB gene can grow on YT+25% sucrose media. Therefore, single colonies presumed to have lost the sacB gene via homologous recombination, indicated by larger colonies, were picked and re-streaked on fresh YT+25% sucrose plates and incubated at 30° C. overnight to finally obtain clonal sucrose resistant and antibiotic sensitive strains. All strains were analyzed for the correct gene replacement by performing a colony PCR at the site of integration. Table 2 lists the specific strains produced in this work and the plasmids used for the integration.

Culture Growth and Metabolite Analysis

Shake flask experiments were performed using M9 minimal media (Sigma-Aldrich) containing 6.78 g/L disodium phosphate, 3 g/L monopotassium phosphate, 0.5 g/L NaCl, 1 g/L $NH_4Cl$, 2 mM $MgSO_4$, 100 µM $CaCl_2$), and 40 µM $FeSO_4.7H_2O$ supplemented with 20 mM glucose (Fisher Scientific), ethylene glycol, or sodium acetate (Sigma-Aldrich). For analysis of mcl-PHA production, nitrogen-limiting M9 medium was prepared by substituting 1 g/L of $NH_4Cl$ with 0.132 g/L of $(NH_4)_2SO_4$ (Sigma-Aldrich). For growth experiments with ethylene glycol, glyoxylate, or glycolaldehyde, overnight cultures were harvested, washed in M9 minimal media without a carbon source, and used for inoculation of fresh medium to an $OD_{600}$ of 0.1 and at $OD_{600}$ of 0.5 for cultures grown in 2×M9 salts. Cultures were grown with a volume of 25 mL in 125 mL baffled shake flasks, incubated at 30° C. with shaking at 225 rpm. Growth of the cultures was followed by periodic measurement of the optical density at 600 nm ($OD_{600}$) using a Beckman DU640 spectrophotometer (Beckman Coulter, Brea Calif.). The dry cell weight of samples (DCW) was calculated by using the conversion factor y=0.5746x, where y is DCW in g/L and x=$OD_{600}$, supported by experimental data that included $OD_{600}$ measurement values <3.3. Except for experiments conducted with plasmid-bearing strains, all shake flask cultures were performed in duplicate. Concentrations of glucose, ethylene glycol, glycolaldehyde, glyoxal, glycolate, glyoxylate, and oxalate in sterile-filtered culture supernatants were measured with high performance liquid chromatography (HPLC) on an Agilent1100 series system (Agilent USA, Santa Clara, Calif.) utilizing a Phenomenex Rezex RFQ-Fast Fruit H+ column (Phenomenex, Torrance, Calif.) and cation H+ guard cartridge (Bio-Rad Laboratories, Hercules, Calif.) at 85° C. A mobile phase of 0.1 N sulfuric acid was used at a flow rate of 1.0 mL/min and a diode array detector was utilized for compound detection. Products were identified by comparing the retention times and spectral profiles with pure compounds and were calculated based on a calibration curve generated for each compound. To quantify yield and composition of mcl-PHAs as a percent of the dry cell weight in cultures growth in media containing ethylene glycol or acetate, shake-flask experiments were performed in 250-mL Erlenmeyer flask filled with 50 mL of nitrogen-limiting M9 medium-containing 100 mM of ethylene glycol. The detailed descriptions of microscopic observations and analytical quantification of mcl-PHA are described below.

mcl-PHA Observation, Quantification, and Characterization

Medium chain length PHA formation in P. putida KT2440 was observed by using an epifluorescence Nikon Eclipse 80i microscope. One mL samples were taken from ethylene glycol-containing shake flask cultures. Cells were pelleted by centrifugation at 13,000 rpm for 1 min, washed twice with 1× phosphate buffer saline (PBS), resuspended in 1 mL PBS-containing 10 µg/mL Nile Red (Molecular probes, Invitrogen Cooperation, USA), and incubated at room temperature in the dark for 30 min. Cells were pelleted again, washed twice with 1×PBS, and resuspended in 1 mL PBS. 5 µL of resuspended cells were mixed with 5 µL of 1% (w/v) low-melting-temperature agarose to immobilize the cells and placed on a microscopic slide with coverslip. Nile Red fluorescence was observed with band-pass filtering between 560-590 nm.

Fluorescence-activated cell sorting (FACS) analysis of mcl-PHAs: Time course of mcl-PHA production of P. putida was monitored using a BD FACSAria (BD Biosciences, USA) instrument equipped with BD FACSDiva data acquisition and analytical software. After cells were stained with Nile Red as previously described, cell pellets were washed twice with PBS solution and resuspended in BD FACSFlow sheath fluid (BD Biosciences, USA) for analysis. Samples were loaded into FACS, mcl-PHA content of cells were monitored using the 488 nm (exited) laser coupled with B610-20A (610 nm) detection channels, and 20,000 events were recorded to generate the histograms for obtaining mean fluorescents.

Analysis of mcl-PHA quantity and composition: Extraction and quantification of mcl-PHAs in P. putida was performed. Samples were prepared for derivatization by adding about 30 mg of biomass to a gas chromatography glass (GC) vial. To track derivatization, 25 µL of benzoic acid (Sigma Aldrich) dissolved in dichloromethane (8 mg/mL) was added as an internal surrogate. Samples were derivatized by adding about 1 mL of 20% $BF_3$/MeOH to the GC vial, which was sealed, vortexed, and placed in a heating block at 80° C. for about 16 hrs. Vials were then removed from the heating block and allowed to cool to room temperature. Vial contents were pipetted into a 10 mL volumetric flask and the vial residual was rinsed twice with dichloromethane (DCM)

(Sigma Aldrich) before filling the flask to 10 mL total with additional DCM. The 10 mL solution was transferred to a (polytetrafluoroethylene) PTFE capped vial and about 3 mL of water was added to form a bi-phase and vortexed to wash out residual $BF_3$ to the aqueous layer. The DCM layer (2 mL) was then transferred into another gram vial containing $Na_2SO_4$ and $Na_2CO_3$ to dry and neutralize any remaining $BF_3$. The dried and neutralized solutions were syringe filtered (0.2 μm PTFE) into fresh GC vials for analysis. To track recovery of PHAs during sample derivatization and analysis, triplicate biomass samples of P. putida KT2440 grown at NREL were processed in parallel. Recovery yields during sample workup were calculated based on a cell dry weight PHA content of 24% determined by bulk sample solvent extraction. Hydroxyacid methyl esters were identified and the distribution quantified by gas chromatography mass spectroscopy (GC-MS) using an Agilent 6890N GC equipped with a 5973 MSD (Agilent Technologies). Agilent MSD Productivity Chemstation G1701 software was used to collect and quantitate analytes. 8-Hydroxyoctanoic acid methyl ester, 10-hydroxydecanoic acid methyl ester, 12-hydroxydodecanoic acid methyl ester, and 14-hydroxytetradecanoic acid methyl ester were obtained from Matreya (98+ percent purity, Matreya, State College, Pa., USA), and used to determine the GC-MS instrument response. Samples were injected at a volume of 1 μL onto a Stabilwax-DA (Restek, Bellefonte, Pa.) column (30 m×0.25-mm id, 0.25-μm film) in splitless mode, with helium at 1 mL/min constant flow used as the carrier gas. The GC/MS method consisted of a front inlet temperature of 250° C., and an auxiliary transfer line temperature of 260° C. The separation used had a starting temperature of 35° C. and this was held for 5 min, then ramped at 15° C./min to a temperature of 225° C. and held for 2.0 minutes, then ramped at 15° C./min to a temperature of 250° C. and held for 5.67 minutes with a solvent delay time of 6 minutes, for a total run time of 27 min. Sample total ion counts were collected on the mass spectrometer at scan range from 30 to 450 m/z. Calibration curves where made by using target ions and diluting the derivatized standards between a concentration of 10-1000 μg/L. A minimum of seven calibration levels was used resulting in an $r^2$ coefficient of 0.995 or better for each analyte and a check calibration standard (CCS) was analyzed every ten samples to insure the integrity of the initial calibration. An internal standard of 1,2-diphenylbenzene (99.9+ percent purity, AccuStandard, New Haven, Conn.) was added to all standards and samples at a concentration of 20 ug/L to adjust for any detector response changes.

Toxicity Tests and Competitive Inhibition Assays

Toxicity tests and competitive inhibition assays were performed using Bioscreen C MBR analyzers (Growth Curves US, Piscataway, N.J.). For toxicity tests, overnight cultures of P. putida KT2440 were grown in M9 medium containing 20 mM glucose starting at an $OD_{600}$ of 0.05-0.1 at 30° C. with shaking at 225 rpm in baffled shake flasks until the $OD_{600}$ reached about 1.0-1.5. Cells were subsequently concentrated by centrifugation and inoculated into wells of Bioscreen C microplates at an initial $OD_{600}$=0.05. Each well contained a total volume of 300 M9 medium, 20 mM glucose, and inhibitors at various concentrations. Incubations were performed at 30° C. with maximum shaking. Absorbance readings were taken every 15 min. For competitive inhibition assays, individual wells of the plate were filled with 200 μL of M9 medium containing 20 mM glucose and a respective concentration of glycolaldehyde and glyoxal according to full-factorial test run results of which are presented in Table 3 and depicted in graphical form in FIG. 13. Initial $OD_{600}$ was set at 0.1 by using an overnight culture of wild type P. putida KT2440. Samples were incubated as described above. Operation of the Bioscreen C MBR and collection of turbidity measurements ($OD_{420-580}$) were computer automated with EZ Experiment.

TABLE 3

Inhibitory effects of glycolaldehyde and glyoxal on P. putida KT2440 growth

| Test (Run#) | Glycolaldehyde (mM) | Glyoxal (mM) | Growth Rate(1/h) | SEM |
|---|---|---|---|---|
| 1 | 0 | 1.0 | 0.297 | 0.001 |
| 2 | 0 | 1.5 | 0.280 | 0.006 |
| 3 | 0 | 2.0 | 0.246 | 0.002 |
| 4 | 1.0 | 1.0 | 0.187 | 0.001 |
| 5 | 1.0 | 1.5 | 0.145 | 0.001 |
| 6 | 1.0 | 2.0 | 0.102 | 0.000 |
| 7 | 1.5 | 1.0 | 0.181 | 0.002 |
| 8 | 1.5 | 1.5 | 0.094 | 0.001 |
| 9 | 1.5 | 2.0 | 0.003 | 0.000 |
| 10 | 2.0 | 1.0 | 0.010 | 0.001 |
| 11 | 2.0 | 1.5 | 0.001 | 0.000 |
| 12 | 2.0 | 2.0 | 0.001 | 0.001 |
| 13 | 1.0 | 0 | 0.281 | 0.001 |
| 14 | 1.5 | 0 | 0.221 | 0.001 |
| 15 | 2 | 0 | 0.218 | 0.002 |
| 16 | 0 | 0 | 0.337 | 0.002 |

RNA Extraction, cDNA Synthesis and Quantitative Reverse Transcription Polymerase Chain Reaction (qRT-PCR)

To prepare P. putida cultures for RNA extraction, cells were grown overnight in M9 minimal medium containing 20 mM glucose in baffled shake flasks at 30° C., 225 rpm. Cells were then diluted and used to inoculate fresh cultures containing 20 mM ethylene glycol and 40 mM sodium acetate to an initial $OD_{600}$ of 0.1. After incubation at 30° C. with shaking at 225 rpm to mid-exponential growth phase ($OD_{600}$ 0.8-1), 2× volume of Qiagen RNAprotect Bacteria Reagent was added to the cultures and allowed to mix for 5 minutes. Subsequently, cells were harvested by centrifugation at 5,000×g for 15 min at 4° C. Supernatant was removed and cells were frozen and stored at −80° C. until further analysis. Supernatants of cultures prior to addition of RNA-protect reagent was analyzed for acetate and ethylene glycol by HPLC that showed that substrate was still available. RNA was extracted from cells using Qiagen's RNeasy mini kit following manufacturer's instructions including a DNAse (Qiagen RNase-Free DNase) in column digestion for one hour at room temperature following manufacturer's instructions. After one round of RNA isolation, a DNase digestion was performed (TURBO DNase; Ambion, Austin, Tex., USA). After two hours incubation at 37° C., the DNase was removed from the RNA sample with an additional purification step using the Qiagen's RNeasy mini kit. cDNA was prepared from the purified RNA using an iScript Reverse Transcription supermix kit for RT-qPCR (Bio-Rad). The expression levels of seven genes were analyzed using primers designed by the Realtime PCR tool for RT-qPCR and is listed in Table 4.

TABLE 4

Forward and reverse primers used for qRT-PCR.

| Primer ID | | Primer Sequence | Gene Target |
|---|---|---|---|
| oMFL299 (SEQ ID NO: 35) | (Fw) | AGGCATTCGTGAAGTCATGG | rpoD |
| oMFL300 (SEQ ID NO: 36) | (Rw) | ATGTAACCGCTGAGAACGTC | rpoD |
| oMFL301 (SEQ ID NO: 37) | (Fw) | CTCGCCACTGGATCAACTG | gcl |
| oMFL302 (SEQ ID NO: 38) | (Rw) | GAACTGGAAGTCGTAGTCACC | gcl |
| oMFL303 (SEQ ID NO: 39) | (Fw) | TGCAGATCATGGAAGGTGAC | hyi |
| oMFL304 (SEQ ID NO: 40) | (Rw) | CAGGAAGCGGTAGTTGATCTC | hyi |
| oMFL305 (SEQ ID NO: 41) | (Fw) | AAAGAGGTTGCCCAGGAAG | glxR |
| oMFL306 (SEQ ID NO: 42) | (Rw) | CGAGCTCATGTCGATCACC | glxR |
| oMFL307 (SEQ ID NO: 43) | (Fw) | CCATCCTCAAACGCTACAAC | ttuD |
| oMFL308 (SEQ ID NO: 44) | (Rw) | TGGCGATCAACTGGAAGTG | ttuD |
| oMFL309 (SEQ ID NO: 45) | (Fw) | ACATCTTCCGCCTCAACTTC | pykF |
| oMFL310 (SEQ ID NO: 46) | (Rw) | TTGCAGGTCCATGAGGATG | pykF |
| oMFL325 (SEQ ID NO: 47) | (Fw) | AACTGAAGCTGATCCTGGTG | PP_0762 |
| oMFL326 (SEQ ID NO: 48) | (Rw) | AGGGTATGCTGGGCTACA | PP_0762 |

Quantitative RT-PCR was performed using iQ SYBR Green Supermix (Bio-Rad) on a Bio-Rad CFX96 Touch Real-Time PCR Detection System (Bio-Rad Lab, Hercules, Calif., USA). The reaction conditions were 10 min at 95° C., 39×(15 s at 95° C., 45 s at 55° C., followed by melting curve analysis: 1 min at 95° C., 81×(30 s starting at 55° C., increasing 0.5° C. per cycle, ending at 95° C.). Experiments were performed in triplicate with biological duplicates. The gene expression levels were assessed by comparing the Ct value of the house keeping gene rpoD to the Ct value of the target gene using the following formula:

$$\text{Gene expression level} = 2^{Ct(rpoD) - Ct(target)}$$

Ct values represent the first cycle at which the instrument can distinguish the fluorescence of nucleic acid amplification generated as being above the background signal. Final expression levels were averaged for each target gene and normalized to the expression level of the control (*P. putida* KT2440) strain.

Cell Preparation, Extraction, and NAD(P)H Oxidizing Activity Assays

For extracting whole lysate protein for enzyme assays, strains were grown in LB medium and harvested by centrifugation at 3,828×g for 5 min at 4° C. during exponential growth phase. After washing with water twice, cells were finally re-suspended in B-PER (Thermo Fisher Scientific, Waltham, Mass., USA) solution supplemented with protease inhibitor cocktail (Thermo Fisher Scientific). Whole cell lysates were obtained by following the manufacturer recommended protocol (Thermo Fisher Scientific). The protein concentration of samples was assessed using a NanoDrop 2000/c Spectrophotometer (Thermo Fisher Scientific) by following the manufacturer protocol. Hydroxypyruvate reduction activity of samples was measured by monitoring oxidation of NAD(P)H at 340 nm with FLUOstar Omega micro plate reader (BMG Labtech, Ortenberg, Germany). For this, two hundred µL of a reaction mixture-containing 150 µL of 50 mM potassium phosphate buffer (pH 7), 20 µL of 0.5 M lithium (3-hydroxypyruvate hydrate (Sigma-Aldrich, St. Louis, Mo., USA), 20 µL of 0.7 mM NAD(P)H, and 10 µL of the cell extracts were used for the enzyme activity assay. One unit (1 U) of enzyme was defined by the conversion of 1 µM of NAD(P)H into NAD(P)$^+$ per minute. The units were normalized to the total protein content of the corresponding sample (mg).

Statistical Analysis

All experiments, except the initial plasmid-bearing strains, were performed in duplicate or triplicates as mentioned in figure legends. The results are expressed in mean values and standard errors of the means (SEM). A one-way analysis of variance (ANOVA) followed by Tukey's post hoc honest significance difference test was adopted for multiple comparisons. Data analysis was performed using KaleidaGraph statistical program (Synergy Software, PA, USA). For a pair-wise comparison of the differences between the sample averages of two groups, a one-tailed Student's t-test without known deviations was employed.

Growth of *P. putida* KT2440 Plasmid-Bearing Strains in Ethylene Glycol

Given that the gene cluster containing gcl, hyi, glxR, ttuD, and pykF together with glcB are needed for glyoxylic acid catabolism in *P. putida* KT2440, experiments were performed to identify the minimal enzymatic setup which would allow growth of the organism. As such, various combinations of gcl or the gcl cluster and glcB were cloned into the plasmid pBTL2 under the control of a lac promoter and transformed into *P. putida* KT2440. Based on the Database of Prokaryotic Operons (DOOR), the gene glcB is predicted to represent a single transcriptional unit (FIG. 12). In contrast, gcl is predicted to be co-transcribed along with hyi, the gene that encodes hydroxypyruvate isomerase. In proximity and predicted to be in two additional transcripts are three additional genes, namely glxR, ttuD, and pykF, which are annotated by the Biocyc database as tartronate semialdehyde reductase, a hydroxypyruvate reductase, and a pyruvate kinase, respectively. As a consequence, Hyi, which catalyzes the isomerization between hydroxypyruvate and tartronate semialdehyde and ttuD could catalyze a reduction reaction from hydroxypyruvate to glycerate that would provide an alternative route from tartronate semialdehyde to glycerate via hydroxypyruvate, see FIG. 1. The GlxR protein is also likely important as it enables the conversion of tartronate semialdehyde directly to glycerate.

Strains constitutively expressing gcl (MFL113), glcB (MFL115), or both (MFL116), do not exhibit any growth in a minimal medium supplemented with 20 mM ethylene glycol (FIG. 2A). However, when the entire gcl cluster (gcl, hyi glxR, ttuD and pykF) is expressed as in strains MFL114 and MFL117, growth is observed. This reveals that expression of gcl alone is insufficient to support growth with ethylene glycol. Concomitant with growth, a rapid reduction of ethylene glycol concentrations is observed (FIG. 2B).

Despite the fact that growth is not observed for KT2440, or the plasmid bearing variants MFL113, MFL115, and MFL116, partial metabolism of ethylene glycol in the first 24 h of incubation is observed for these cultures, although with varying efficiencies.

Construction of Genomically Engineered *P. putida* KT2440

To ascertain which genes are critical for ethylene glycol metabolism and to provide a base strain for further improvements, different combinations of genes from the gcl cluster were overexpressed in an intergenic region between fpvA and PP_4218 (FIG. 3). The tac promoter was used for driving expression of the genes and the RBS in front of gcl was modified for optimal ribosome binding using an RBS calculator. Strain MFL168 includes all five genes (gcl, hyi, glxR, ttuD, and pykF), MFL170 includes three genes (gcl, hyi, glxR), MFL188 includes only two genes (gcl, glxR), representing the minimal requirement for a glyoxylate metabolizing unit. The genes behind gcl and the intergenic regions on the clusters were not genetically modified from that on the chromosome, except for the RBS of glxR in MFL188, which was again optimized using a RBS calculator.

Expression Analysis of Gcl Gene Cluster by qRT-PCR

As mentioned, the genes engineered into MFL168 were predicted to be transcribed in three different transcriptional units, namely gcl-hyi, glxR, and ttuD pykF. To resolve the question of whether genes located together in this gene cluster are co-expressed, we conducted quantitative real-time PCR experiments to measure transcript levels of gcl, hyi, glxR, ttuD, and pykF. We employed the housekeeping gene, rpoD, to quantify transcript levels between each of our samples using the $2^{-\Delta\Delta Ct}$ method.

As shown below, Ct values obtained for each sample and gene are provided in Table 5 and summarized as fold expression to transcript levels obtained from the control (*P. putida* KT2440) after normalizing gene expression to rpoD (FIG. 4).

TABLE 5

| | $Ct_{Control}$ | | | | | | |
|---|---|---|---|---|---|---|---|
| | Biological Sample | | | | | | |
| | KT2440-A | | | KT2440-B | | | |
| | Technical Replicate | | | | | | |
| | 1 | 2 | 3 | 1 | 2 | 3 | Avg |
| rpoD | 19.75 | 19.89 | 19.82 | 20.65 | 20.29 | 20.29 | 20.12 |
| gcl | 29.2 | 29.32 | 29.11 | 29.18 | 29.22 | 29.23 | 29.21 |
| hyi | 24.75 | 24.82 | 24.86 | 25.43 | 25.37 | 25.26 | 25.08 |
| glxR | 27.67 | 27.46 | 27.43 | 27.95 | 28.09 | 28 | 27.77 |
| PP_4300 | 28.54 | 28.59 | 28.55 | 29.16 | 29.32 | 29.05 | 28.87 |
| pykF | 27.45 | 27.48 | 27.52 | 26.82 | 27.56 | 28.02 | 27.48 |
| PP_0762 | 30.12 | 30.06 | 30.13 | | 35.43 | 37.16 | 32.58 |
| rpoD (neg)* | 35.22 | 34.45 | 35.25 | 33.68 | 34.76 | 35.12 | 34.75 |

| | $\Delta Ct_{Control}$ | | | | | | |
|---|---|---|---|---|---|---|---|
| | Biological Sample | | | | | | |
| | KT2440-A | | | KT2440-B | | | |
| | Technical Replicate | | | | | | |
| | 1 | 2 | 3 | 1 | 2 | 3 | Avg |
| rpoD | 0 | 0 | 0 | 0 | 0 | 0 | 0.00 |
| gcl | 9.45 | 9.43 | 9.29 | 8.53 | 8.93 | 8.94 | 9.10 |
| hyi | 5 | 4.93 | 5.04 | 4.78 | 5.08 | 4.97 | 4.97 |
| glxR | 7.92 | 7.57 | 7.61 | 7.3 | 7.8 | 7.71 | 7.65 |

TABLE 5-continued

| PP_4300 | 8.79 | 8.7 | 8.73 | 8.51 | 9.03 | 8.76 | 8.75 |
|---|---|---|---|---|---|---|---|
| pykF | 7.7 | 7.59 | 7.7 | 6.17 | 7.27 | 7.73 | 7.36 |
| PP_0762 | 10.37 | 10.17 | 10.31 | | 15.14 | 16.87 | 12.57 |
| rpoD (neg)* | 15.47 | 14.56 | 15.43 | 13.03 | 14.47 | 14.83 | 14.63 |

| | $2^{-\Delta Ct}_{Control}$ | | | | | | |
|---|---|---|---|---|---|---|---|
| | Biological Sample | | | | | | |
| | KT2440-A | | | KT2440-B | | | |
| | Technical Replicate | | | | | | |
| | 1 | 2 | 3 | 1 | 2 | 3 | Avg |
| rpoD | 1.00 | 1.00 | 1.00 | 1.00 | 1.00 | 1.00 | 1.00 |
| gcl | 0.00 | 0.00 | 0.00 | 0.00 | 0.00 | 0.00 | 0.00 |
| hyi | 0.03 | 0.03 | 0.03 | 0.04 | 0.03 | 0.03 | 0.03 |
| glxR | 0.00 | 0.01 | 0.01 | 0.01 | 0.00 | 0.00 | 0.01 |
| PP_4300 | 0.00 | 0.00 | 0.00 | 0.00 | 0.00 | 0.00 | 0.00 |
| pykF | 0.00 | 0.01 | 0.00 | 0.01 | 0.01 | 0.00 | 0.01 |
| PP_0762 | 0.00 | 0.00 | 0.00 | | 0.00 | 0.00 | 0.00 |
| rpoD (neg)* | 0.00 | 0.00 | 0.00 | 0.00 | 0.00 | 0.00 | 0.00 |

| | $2^{-\Delta\Delta Ct}_{Control}$ | | | | | | |
|---|---|---|---|---|---|---|---|
| | Biological Sample | | | | | | |
| | KT2440-A | | | KT2440-B | | | |
| | Technical Replicate | | | | | | |
| | 1 | 2 | 3 | 1 | 2 | 3 | Avg |
| rpoD | | | | | | | |
| gcl | 0.78 | 0.79 | 0.87 | 1.48 | 1.12 | 1.11 | 1.03 |
| hyi | 0.98 | 1.03 | 0.95 | 1.14 | 0.92 | 1.00 | 1.00 |
| glxR | 0.83 | 1.06 | 1.03 | 1.28 | 0.90 | 0.96 | 1.01 |
| PP_4300 | 0.97 | 1.04 | 1.02 | 1.18 | 0.83 | 1.00 | 1.01 |
| pykF | 0.79 | 0.85 | 0.79 | 2.28 | 1.06 | 0.77 | 1.09 |
| PP_0762 | 4.60 | 5.29 | 4.80 | | 0.17 | 0.05 | 2.98 |

| | $Ct_{MFL168}$ | | | | | |
|---|---|---|---|---|---|---|
| | Biological Sample | | | | | |
| | MFL168-A | | | MFL168-B | | |
| | Technical Replicate | | | | | |
| | 1 | 2 | 3 | 1 | 2 | 3 |
| rpoD | 20.63 | 20.79 | 20.68 | 21.03 | 21.03 | 21.09 |
| gcl | 19 | 19.1 | 18.81 | 19.23 | 19.22 | 19.20 |
| hyi | 17.37 | 17.4 | 17.3 | 17.69 | 17.65 | 17.69 |
| glxR | 19.85 | 20.04 | 19.88 | 20.72 | 20.37 | 20.25 |
| PP_4300 | 22.16 | 22.13 | 22.66 | 22.7 | 22.43 | 22.36 |
| pykF | 20.12 | 20.1 | 19.99 | 20.06 | 19.93 | 19.91 |
| PP_0762 | 30.04 | 30.44 | 29.59 | 29.56 | 29.56 | 29.57 |
| rpoD (neg)* | 35.44 | 35.86 | 36.66 | 40 | 40 | 35.12 |

| | $\Delta Ct_{MFL168}$ | | | | | |
|---|---|---|---|---|---|---|
| | Biological Sample | | | | | |
| | MFL168-A | | | MFL168-B | | |
| | Technical Replicate | | | | | |
| | 1 | 2 | 3 | 1 | 2 | 3 |
| rpoD | 0 | 0 | 0 | 0 | 0 | 0 |
| gcl | −1.63 | −1.69 | −1.87 | −1.8 | −1.81 | −1.89 |
| hyi | −3.26 | −3.39 | −3.38 | −3.34 | −3.38 | −3.4 |
| glxR | −0.78 | −0.75 | −0.8 | −0.31 | −0.66 | −0.84 |
| PP_4300 | 1.53 | 1.34 | 1.98 | 1.67 | 1.4 | 1.27 |
| pykF | −0.51 | −0.69 | −0.69 | −0.97 | −1.1 | −1.18 |
| PP_0762 | 9.41 | 9.65 | 8.91 | 8.53 | 8.53 | 8.48 |
| rpoD (neg)* | 14.81 | 15.07 | 15.98 | 18.97 | 18.97 | 14.03 |

TABLE 5-continued $2^{-\Delta Ct}{}_{MFL168}$
Biological Sample

| | MFL168-A | | | MFL168-B | | |
|---|---|---|---|---|---|---|
| | Technical Replicate | | | | | |
| | 1 | 2 | 3 | 1 | 2 | 3 |
| rpoD | 1.00 | 1.00 | 1.00 | 1.00 | 1.00 | 1.00 |
| gcl | 3.10 | 3.23 | 3.66 | 3.48 | 3.51 | 3.71 |
| hyi | 9.58 | 10.48 | 10.41 | 10.13 | 10.41 | 10.56 |
| glxR | 1.72 | 1.68 | 1.74 | 1.24 | 1.58 | 1.79 |
| PP_4300 | 0.35 | 0.40 | 0.25 | 0.31 | 0.38 | 0.41 |
| pykF | 1.42 | 1.61 | 1.61 | 1.96 | 2.14 | 2.27 |
| PP_0762 | 0.00 | 0.00 | 0.00 | | 0.00 | 0.00 |
| rpoD (neg)* | 0.00 | 0.00 | 0.00 | 0.00 | 0.00 | 0.00 |

$2^{-\Delta\Delta Ct}{}_{MFL168}$
Biological Sample

| | MFL168-A | | | MFL168-B | | | |
|---|---|---|---|---|---|---|---|
| | Technical Replicate | | | | | | |
| | 1 | 2 | 3 | 1 | 2 | 3 | Avg |
| rpoD | | | | | | | |
| gcl | 1693 | 1764 | 1999 | 1904 | 1917 | 2027 | 1884 |
| hyi | 300 | 328 | 326 | 317 | 326 | 330 | 321 |
| glxR | 345 | 338 | 350 | 249 | 318 | 360 | 327 |
| PP_4300 | 149 | 170 | 109 | 136 | 164 | 179 | 151 |
| pykF | 234 | 265 | 265 | 322 | 352 | 372 | 302 |
| PP_0762 | 9 | 8 | 13 | 16 | 16 | 17 | 13 |

$Ct_{MFL170}$
Biological Sample

| | MFL170-A | | | MFL170-B | | |
|---|---|---|---|---|---|---|
| | Technical Replicate | | | | | |
| | 1 | 2 | 3 | 1 | 2 | 3 |
| rpoD | 20.27 | 20.24 | 20.32 | 22.62 | 22.6 | 22.76 |
| gcl | 17.64 | 17.85 | 17.7 | 20.21 | 20.27 | 20.24 |
| hyi | 15.93 | 15.74 | 15.53 | 18.15 | 18.21 | 18.45 |
| glxR | 18.94 | 18.86 | 19.04 | 21.26 | 21.15 | 21.62 |
| PP_4300 | 28.84 | 28.98 | 28.84 | 30.75 | 30.8 | 31.2 |
| pykF | 27.58 | 27.69 | 27.32 | 29.85 | 29.66 | 30.05 |
| PP_0762 | 29.34 | 29.98 | 29.99 | 31.31 | 30.99 | 31.2 |
| rpoD (neg)* | 34.21 | 34.46 | 34.4 | 33.5 | 33.64 | 32.06 |

$\Delta Ct_{MFL170}$
Biological Sample

| | MFL170-A | | | MFL170-B | | |
|---|---|---|---|---|---|---|
| | Technical Replicate | | | | | |
| | 1 | 2 | 3 | 1 | 2 | 3 |
| rpoD | 0 | 0 | 0 | 0 | 0 | 0 |
| gcl | −2.63 | −2.39 | −2.62 | −2.41 | −2.33 | −2.52 |
| hyi | −4.34 | −4.5 | −4.79 | −4.47 | −4.39 | −4.31 |
| glxR | −1.33 | −1.38 | −1.28 | −1.36 | −1.45 | −1.14 |
| PP_4300 | 8.57 | 8.74 | 8.52 | 8.13 | 8.2 | 8.44 |
| pykF | 7.31 | 7.45 | 7 | 7.23 | 7.06 | 7.29 |
| PP_0762 | 9.07 | 9.74 | 9.67 | 8.69 | 8.39 | 8.44 |
| rpoD (neg)* | 13.94 | 14.22 | 14.08 | 10.88 | 11.04 | 9.3 |

$2^{-\Delta Ct}{}_{MFL170}$
Biological Sample

| | MFL170-A | | | MFL170-B | | |
|---|---|---|---|---|---|---|
| | Technical Replicate | | | | | |
| | 1 | 2 | 3 | 1 | 2 | 3 |
| rpoD | 1.00 | 1.00 | 1.00 | 1.00 | 1.00 | 1.00 |
| gcl | 6.19 | 5.24 | 6.15 | 5.31 | 5.03 | 5.74 |
| hyi | 20.25 | 22.63 | 27.67 | 22.16 | 20.97 | 19.84 |
| glxR | 2.51 | 2.60 | 2.43 | 2.57 | 2.73 | 2.20 |
| PP_4300 | 0.00 | 0.00 | 0.00 | 0.00 | 0.00 | 0.00 |
| pykF | 0.01 | 0.01 | 0.01 | 0.01 | 0.01 | 0.01 |
| PP_0762 | 0.00 | 0.00 | 0.00 | | 0.00 | 0.00 |
| rpoD (neg)* | 0.00 | 0.00 | 0.00 | 0.00 | 0.00 | 0.00 |

$2^{-\Delta\Delta Ct}{}_{MFL170}$
Biological Sample

| | MFL170-A | | | MFL170-B | | | |
|---|---|---|---|---|---|---|---|
| | Technical Replicate | | | | | | |
| | 1 | 2 | 3 | 1 | 2 | 3 | Avg |
| rpoD | | | | | | | |
| gcl | 3385 | 2866 | 3362 | 2906 | 2750 | 3137 | 3068 |
| hyi | 633 | 708 | 865 | 693 | 656 | 620 | 696 |
| glxR | 506 | 523 | 488 | 516 | 549 | 443 | 504 |
| PP_4300 | 1 | 1 | 1 | 2 | 1 | 1 | 1 |
| pykF | 1 | 1 | 1 | 1 | 1 | 1 | 1 |
| PP_0762 | 11 | 7 | 7 | 15 | 18 | 18 | 12 |

$Ct_{MFL188}$
Biological Sample

| | MFL188-A | | | MFL188-B | | |
|---|---|---|---|---|---|---|
| | Technical Replicate | | | | | |
| | 1 | 2 | 3 | 1 | 2 | 3 |
| rpoD | 21.11 | 21.32 | 21.3 | 20.98 | 21.01 | 21 |
| gcl | 19.38 | 19.16 | 19.3 | 18.4 | 18.48 | 18.7 |
| hyi | 26.59 | 26.25 | 26.39 | 26.12 | 26.21 | 26.37 |
| glxR | 20.57 | 20.63 | 20.62 | 20.1 | 20.16 | 20.11 |
| PP_4300 | 30.15 | 29.78 | 29.73 | 29.79 | 29.67 | 29.88 |
| pykF | 28.55 | 28.33 | 28.43 | 28.21 | 28.2 | 28.42 |
| PP_0762 | 29.92 | 30.26 | 30.15 | 30.23 | 30.21 | 30.36 |
| rpoD (neg)* | 34.87 | 36.3 | 36.12 | 32.86 | 32.3 | 32.26 |

$\Delta Ct_{MFL188}$
Biological Sample

| | MFL188-A | | | MFL188-B | | |
|---|---|---|---|---|---|---|
| | Technical Replicate | | | | | |
| | 1 | 2 | 3 | 1 | 2 | 3 |
| rpoD | 0 | 0 | 0 | 0 | 0 | 0 |
| gcl | −1.73 | −2.16 | −2 | −2.58 | −2.53 | −2.3 |
| hyi | 5.48 | 4.93 | 5.09 | 5.14 | 5.2 | 5.37 |
| glxR | −0.54 | −0.69 | −0.68 | −0.88 | −0.85 | −0.89 |
| PP_4300 | 9.04 | 8.46 | 8.43 | 8.81 | 8.66 | 8.88 |
| pykF | 7.44 | 7.01 | 7.13 | 7.23 | 7.19 | 7.42 |
| PP_0762 | 8.81 | 8.94 | 8.85 | 9.25 | 9.2 | 9.36 |
| rpoD (neg)* | 13.76 | 14.98 | 14.82 | 11.88 | 11.29 | 11.26 |

$2^{-\Delta Ct}{}_{MFL188}$
Biological Sample

| | MFL188-A | | | MFL188-B | | |
|---|---|---|---|---|---|---|
| | Technical Replicate | | | | | |
| | 1 | 2 | 3 | 1 | 2 | 3 |
| rpoD | 1.00 | 1.00 | 1.00 | 1.00 | 1.00 | 1.00 |
| gcl | 3.32 | 4.47 | 4.00 | 5.98 | 5.78 | 4.92 |
| hyi | 0.02 | 0.03 | 0.03 | 0.03 | 0.03 | 0.02 |
| glxR | 1.45 | 1.61 | 1.60 | 1.84 | 1.80 | 1.85 |
| PP_4300 | 0.00 | 0.00 | 0.00 | 0.00 | 0.00 | 0.00 |
| pykF | 0.01 | 0.01 | 0.01 | 0.01 | 0.01 | 0.01 |
| PP_0762 | 0.00 | 0.00 | 0.00 | | 0.00 | 0.00 |
| rpoD (neg)* | 0.00 | 0.00 | 0.00 | 0.00 | 0.00 | 0.00 |

TABLE 5-continued

| | $2^{-\Delta\Delta Ct}{}_{MFL188}$ | | | | | | |
|---|---|---|---|---|---|---|---|
| | Biological Sample | | | | | | |
| | MFL188-A | | | MFL188-B | | | |
| | Technical Replicate | | | | | | |
| | 1 | 2 | 3 | 1 | 2 | 3 | Avg |
| rpoD | | | | | | | |
| gcl | 1814 | 2444 | 2187 | 3270 | 3158 | 2693 | 2594 |
| hyi | 1 | 1 | 1 | 1 | 1 | 1 | 1 |
| glxR | 292 | 324 | 322 | 370 | 362 | 373 | 341 |
| PP_4300 | 1 | 1 | 1 | 1 | 1 | 1 | 1 |
| pykF | 1 | 1 | 1 | 1 | 1 | 1 | 1 |
| PP_0762 | 14 | 12 | 13 | 10 | 10 | 9 | 12 |

*Negative control - no reverse transcriptase

Transcript levels of all gcl cluster genes in the wild type were very low. Values of 2–ΔCt of gcl, hyi, glxR, ttuD and pykF are 31-532 fold lower than for the control, rpoD (Table 5), confirming that this strain fails to induce this pathway on ethylene glycol. Transcript levels for gcl were approximately 2,000-fold higher in the engineered strains compared to the wild type, since it is driven by the strong tac promoter. For MFL168, transcript levels of the following genes in the cluster (hyi, glxR, ttuD, and pykF) are approximately the same, but 6-12 fold lower than gcl.

This was unexpected since a 27-base pair region (CCCTGTGGGAGCGGGCTCGCCCGCGAA (SEQ ID NO: 51)) which is present downstream from hyi is repeated as inverse complement further downstream, forming a 91 bp inverted repeat. Interestingly, a similar repeat region is present in the vicinity of gcl, downstream from PP_4296 (hypothetical protein) that differs by 1 nucleotide from the repeat downstream of hyi and forms an 81 bp inverted repeat. The presence of the inverted repeat did obviously not diminish the expression of downstream genes, since transcript levels for gcl, hyi, and glxR in MFL170 and MFL188 are similar to those in MFL168, for genes that were overexpressed. These results indicate that under the conditions tested, the putative terminators in the gcl gene cluster do not affect transcription of downstream genes, and that all of the genes in the cluster are transcribed as a single transcriptional unit and will thus be referred to as an operon.

Hydroxypyruvate Reductase Activity Assays

If a secondary pathway from tartronate semialdehyde to glycerate exists as shown in FIG. 1, then a question remains as to which enzyme is responsible for directing hydroxypyruvate conversion to glycerate and back to the central metabolic pathway. From growth experiments and our qRT-PCR analysis, neither ttuD nor PP_0762 (hprA), a gene annotated as a hydroxypyruvate reductase in the BioCYC Database collection, are required for ethylene glycol assimilation (FIG. 4 and Table 5). To identify the corresponding gene that is responsible for this catalytic step, we tested cell extracts from different strains for activity on the substrate hydroxypyruvate by monitoring NADH and NADPH oxidation (FIG. 5). From these experiments, we found that cell extracts from *P. putida* KT2440 exhibit very little activity towards hydroxypyruvate, whereas, cell extracts from MFL168, MFL170, and MFL188 were all much more active for NADH oxidation in the presence of hydroxypyruvate. MFL188 only expresses two genes in addition to the control strains: gcl and glxR. Since Gcl does not have cofactor reducing capabilities, GlxR must be responsible for the activity.

Characterization of Engineered *P. putida* KT2440

To characterize the relative contribution of single genes of the gcl operon, the engineered strains were compared in minimal medium containing 20 and 50 mM ethylene glycol (FIG. 6). On 20 mM ethylene glycol, both MFL168 (full operon) and MFL170 (gcl, hyi, glxR) grew sufficiently well consuming all substrate within 14 h (FIG. 6B). MFL188 (gcl, glxR) grew much more slowly and exhibited a long intermittent lag phase after an initial period of growth, although ethylene glycol was metabolized completely by MFL188 within 48 h. Growth was resumed at 72-92 h, after glycolate was consumed. There was transient accumulation of glycolaldehyde with very little production of glyoxal (FIGS. 6C, D and E) while glycolate levels were elevated. MFL168 tended to perform better than the other strains when cultured in 50 mM ethylene glycol (FIG. 6F-J), however, there was some discrepancy between the duplicate flasks, whereby one culture consumed ethylene glycol sooner. MFL170 exhibited a two-staged growth associated with the accumulation of intermediates growing in 50 mM ethylene glycol (FIG. 6F-J), whereas MFL188 hardly grew in this higher substrate concentration, and the accumulated glycolate and glycolaldehyde were not metabolized. Intermediate glycolate levels (FIG. 6H) were higher in cultures with 50 mM, compared to 20 mM ethylene glycol, as expected. Glycolaldehyde levels rose to nearly 2.5 mM for both MFL168 and MFL170, but then fell as glycolate was consumed. Glyoxal was also present in culture samples and is derived from the oxidation of glycolaldehyde. In general, after an initial growth phase, further growth seems to be inhibited by the accumulation of ethylene glycol oxidation products. The engineered strains differ mostly in their metabolism of these intermediates, thereby recovering growth, especially at higher substrate concentrations. In particular, the aldehydes are highly toxic to microorganisms.

Therefore, an investigation of the intermediate metabolites (glycolaldehyde, glyoxylate, glycolate, oxalate, and glyoxal) and the substrate, ethylene glycol, was conducted to understand their impact on ethylene glycol metabolism.

Substrate, Metabolite, and Toxicity Assays

The toxicity of ethylene glycol, glyoxylate, glycolaldehyde, glyoxal, and oxalate to *P. putida* KT2440 were examined by monitoring growth in the Bioscreen C instrument (a microplate reader that monitors turbidity over time) in the presence of M9 minimal medium containing 20 mM glucose and the potential inhibitor. The average of at least five wells is shown in FIG. 7. Ethylene glycol, sodium glyoxylate, and sodium glycolate at concentrations up to 100 mM are not significantly inhibitory, nor is sodium oxalate up to 50 mM. However, glycolaldehyde is toxic and completely inhibited growth at 4 mM. Glyoxal is also inhibitory to *P. putida* KT2440 at 5 mM, leading to a long lag phase before some growth can be observed. At 7.5 mM, glyoxal is lethal. Collectively, these data reveal that glycolaldehyde and glyoxal are the key intermediate metabolites that likely inhibit growth of *P. putida* on ethylene glycol. It has been reported that glycolaldehyde exerts a combinational inhibitory effect with other aldehydes. Thus, we investigated combinational effects of glycolaldehyde and glyoxal (Table 3 and FIG. 13). Growth rates in the presence of 2 mM glycolaldehyde or glyoxal are 0.22 $h^{-1}$ and 0.25 $h^{-1}$, respectively. When combining 1 mM glycolaldehyde and 1 mM glyoxal, the growth rate is only 0.19 $h^{-1}$, demonstrating a minor synergistic effect on inhibition of the two compounds.

Characterization of a Glycolate Oxidase Overexpressing Strain

We observed that all three engineered strains transiently accumulated large amounts of glycolate in 20 mM ethylene glycol cultures (FIG. 8). Therefore, glycolate oxidase was overexpressed in *P. putida* KT2440 by introducing glcDEF under control of the tac promoter (see FIG. 3 for details). The new strain (MFL185) was compared to MFL168 and the wild type on several different concentrations of ethylene glycol. Overexpression of the glycolate oxidase alone (MFL186) does not permit growth on ethylene glycol (FIG. 8). However, the combined overexpression of glycolate oxidase and the gcl operon increased the growth rate and biomass yield on ethylene glycol with very little glycolate accumulation and no discernible glycolaldehyde present.

Growth rates, maximum dry cell weights, and consumed substrate are shown in Table 6 for cultures grown in the presence of 50 mM ethylene glycol which demonstrates a trend in ethylene glycol metabolic efficiencies for the engineered strains (MFL185>>MFL168>MFL170>MFL188).

TABLE 6

Comparison of metabolism of engineered strains grown in 50 mM ethylene glycol

| Strain | Maximum DCW (g/L) | Growth Rate (1/h) | Ethylene glycol consumed (g/L/h) |
|---|---|---|---|
| KT2440 | 0.04 ± 0.00 | 0.00 ± 0.00 | 0.01 ± 0.00 |
| MFL168 | 0.67 ± 0.17 | 0.12 ± 0.01 | 0.05 ± 0.00 |
| MFL170 | 0.48 ± 0.02 | 0.08 ± 0.02 | 0.03 ± 0.00 |
| MFL185 | 1.02 ± 0.04 | 0.19 ± 0.02 | 0.16 ± 0.00 |
| MFL186 | 0.10 ± 0.00 | 0.04 ± 0.00 | 0.01 ± 0.00 |

We also compared growth on ethylene glycol at concentrations much higher than 50 mM, first in the Bioscreen C and then for MFL185 in shake flasks (FIG. 9). Growth of MFL168 was optimal at 40 mM, reduced at 60 mM, and inhibited at 80 mM after a short initial growth. In contrast, MFL185, overexpressing the additional glycolate oxidase, grew in concentrations up to 2 M, the equivalent of 124 g/L. In shake flasks containing M9 minimal medium with 0.5 and 1.0 M ethylene glycol (FIG. 9C-D), MFL185 was able to completely consume 500 mM ethylene glycol within 120 h, although its growth lags compared to the culture with 250 mM. MFL185 consumed about 40% of the ethylene glycol at 1 M in shake flasks. There was some accumulation of glycolate (8-18 mM) between 14 and 24 h from samples grown in 100 to 500 mM samples; however, there was very little glycolaldehyde or glyoxal present. Due to high cell densities, we considered that perhaps nutrients might be limiting. To test this hypothesis, we added twice the M9 salts, which includes additional magnesium, nitrogen, calcium and iron and increased the inoculum from $OD_{600}$=0.1 To 0.5. Ethylene glycol consumption was improved at 1 M (dashed line in FIG. 9C) implying nutrients were indeed limited.

Production of mcl-PHAs from Ethylene Glycol

As a proof-of-concept for converting ethylene glycol to value-added products, we evaluated the ability of MFL185 to convert ethylene glycol into native carbon storage products, mcl-PHAs. Given that *P. putida* induces mcl-PHA production under nitrogen-limiting conditions, we grew cells in nitrogen-limiting M9 medium supplemented with 100 mM of ethylene glycol as the sole carbon source (FIG. 11A). We observed formation of mcl-PHAs from ethylene glycol by MFL185 using Nile Red staining (FIG. 10A), and monitored mcl-PHA production via flow cytometry over time. Cells reached maximum mcl-PHA production after 72 hours (FIG. 11 B-C). MFL185 produced 52.8±2.2% of its dry cell weight as mcl-PHA at a product yield of 0.06 g of mcl-PHA produced per g of ethylene glycol consumed (FIG. 10B). Compositional analysis revealed that MFL185 produced the expected mcl-PHA chain length distribution in *P. putida* KT2440 which includes carbon chain lengths of C8, C10, C12, and C14, with greater than 93% of product belonging to C8 and C10 mcl-PHAs (FIG. 10C). Of note, the wild-type *P. putida* KT2440 strain is unable to grow or produce mcl-PHAs in nitrogen-limiting M9 medium containing 100 mM ethylene glycol (FIG. 11A-C). Comparison of mcl-PHAs production parameters of MFL185 revealed that mcl-PHA production from acetate and ethylene glycol are similar (yields: 0.05 per g of acetate vs 0.06 per g of ethylene glycol, 0.05>p) (FIG. 10B-C). This finding highlights that ethylene glycol is a suitable substrate for the production of PHAs using engineered *P. putida* strains as disclosed herein, compared to other C2 molecules. Collectively, these results demonstrate that MFL185 efficiently diverts ethylene glycol into an exemplary high-value product.

Although *P. putida* KT2440 has the genes necessary to convert ethylene glycol into cellular biomass, previous studies demonstrated that the organism is not capable of growing with ethylene glycol as the sole source of carbon and energy. We initially hypothesized that growth on ethylene glycol should depend on the functional expression of the gcl operon with glyoxylate carboligase (gcl) and tartronate semialdehyde reductase (glxR) as key enzymes. A prediction of the exact composition of a gcl operon from the genomic context was however, not straightforward. From a functional perspective, the co-transcription of gcl, hyi (hydroxypyruvate isomerase), glxR, ttuD, and pykF (pyruvate kinase) would make sense since those enzymes would allow two different routes for the conversion of glyoxylate to glycerate (FIG. 1). However, from computational analysis, according to DOOR prediction (FIG. 12), these genes are predicted to be transcribed in three different transcriptional units, namely gcl-hyi, glxR, and ttuD-pykF. As such, we conducted different qRT-PCR experiments and demonstrated, contradictory to the bioinformatics prediction, that all five genes are expressed as a single transcript representing one functional operon.

Without being limited by theory, the minimal requirement for glyoxylate metabolism from the gcl operon (FIG. 1) is the expression of two genes (gcl, glxR). Notably, the expression of these genes in MFL188 enabled ethylene glycol metabolism, but at slower uptake rates than MFL170 that contains hydroxypyruvate isomerase (hyi) as an additional gene. Our results indicate that the gene ttuD is not necessary for growth in ethylene glycol since growth is achieved with the expression of gcl-glxR. However, its expression along with PykF, in MFL168, improved metabolic performance in shake flasks, compared to MFL170. Our biochemical data found no increased hydroxypyruvate reductase activity in strain MFL168 compared to MFL170, lacking ttuD, which was annotated as hydroxypyruvate reductase (BioCYC Database collection). However, in the KEGG (Kyoto Encyclopedia of Genes and Genomes) pathway database, TtuD is identified as a glycerate kinase. Our results suggest the latter is more likely. As such, we propose that TtuD represents a functional glycerate kinase and adjusted the pathway map accordingly (FIG. 1). With activity assays using cell free extracts of MFL188, we demonstrated that GlxR could also function as a hydroxypyruvate reductase, in addition to its ability to convert tartronate semialdehyde to glycerate linking hydroxypyruvate to the central metabolic pathway (FIG. 1). These results support that the activity of GlxR from *P. putida* using the substrates, tartronate semialdehyde and hydroxypyruvate, is in the presence of reduced pyridine nucleotide cofactors. Hydroxypyruvate functioned as a substrate at a 10-fold lower maximal velocity than tartronate semialdehyde. Also noted, was that glycolate inhibits this enzyme with a $K_i$=3 mM. Therefore, an accumulation of glycolate could impede glyoxylate metabolism, which explains our observation that concentrations of glycolate were higher in strain MFL188 when grown in 20 mM ethylene glycol (FIG. 6C).

At elevated levels of ethylene glycol (>50 mM), glycolate and more importantly, glycolaldehyde and glyoxal levels increased to inhibitory levels, except in strain MFL185. The biomass yield for MFL168 in 20 mM ethylene glycol is high at 0.54 g DCW/g of ethylene glycol consumed and dropped to 0.16-0.27 g DCW per g of ethylene glycol consumed, when the substrate concentration was raised to 50 mM. The loss in biomass yield could be the result of the accumulation of intermediates, such as glycolaldehyde and glyoxal, which was not observed in 20 mM ethylene glycol (FIG. 6), that might be diverted to other pathways that do not result in biomass formation. In strain MFL 185, the biomass yield in 50 mM ethylene glycol is 0.35 g/g, which is higher than from MFL168, but still lower at about 50% less than when grown in 20 mM ethylene glycol. It is also possible that the detoxification of glycolaldehyde and glyoxal requires ATP and NAD(P)H, in which carbon might be diverted towards ATP and redox cofactor generation rather than to biomass formation. In addition, higher glyoxylate concentrations result in some of it being redirected towards the glyoxylate shunt, which would result loss of carbon.

To improve the ethylene glycol conversion at higher substrate concentrations, we used the overexpression of glycolate oxidase to increase its conversion and thus to minimize the accumulation of the toxic intermediates glycolaldehyde and glyoxal. By combining glycolate oxidase with the gcl operon overexpression we generated a strain (MFL185) that can efficiently consume 0.5 M ethylene glycol (32 g/L) under shake flask conditions. Furthermore, we show that MFL185 can tolerate growth in up to 2 M (124 g/L) ethylene glycol. Moreover, with the addition of twice the M9 medium salt composition, we observed further consumption of ethylene glycol in the presence of 1 M (62 g/L) ethylene glycol (up to 37 g/L). Thus, with proper bioreactor control and the addition of limiting nutrients (i.e. nitrogen, iron) even higher substrate utilization might be possible.

Dynamic branching of intracellular metabolites is crucial for eliminating imbalance of cellular metabolism in microorganisms. For instance, in trehalose cycling, a side-pathway pushes glycolysis toward the trehalose metabolism for establishing steady state of the upper and lower pathway of glycolysis, thus eliminating the accumulation of intermediate metabolites. The failure to do so results in metabolic malfunctioning and growth arrest in high glucose containing medium. Similarly, Hyi siphons the ethylene glycol metabolite intermediate tartronate semialdehyde into hydroxypyruvate. Overexpression of hyi may facilitate a synthetic steady-state of ethylene glycol metabolism and relieve the bottleneck at tartronate semialdehyde, allowing for more efficient utilization of ethylene glycol. Otherwise cells exhibit metabolic and growth arrest. This might explain why the strains MFL168 and MFL170 perform better than strain MFL188. In addition, as described in the "push-and-pull" concept, the amplification of upstream, metabolite-forming pathways combined with a similar increase in the flux of downstream, metabolite utilization pathways could overcome feedback inhibition, and steer *P. putida* to achieve large flux of ethylene glycol at high rate.

Beyond the superior growth characteristics of MFL185 in ethylene glycol, we demonstrated that ethylene glycol could be converted to high-value products such as mcl-PHAs. Together with the conversion of terephthalate, this now enables the complete biotransformation of depolymerized PET into mcl-PHAs with *P. putida*. mcl-PHAs can be upgraded into chemical precursors and fuels via straightforward catalytic process. Several metabolic engineering strategies have been developed to enhance mcl-PHAs production in *P. putida*, and these approaches could be used to increased mcl-PHA production in the MFL185 strain. As disclosed herein, metabolic modeling coupled with techno-economic analysis are useful tools for identifying ideal product(s) from ethylene glycol. The source of ethylene glycol should be considered for tailoring MFL185 as a biocatalyst to valorize ethylene glycol containing streams. For instance, in PET-degraded streams, ethylene glycol could be used for growth, energy, and/or PHA production.

Thus, presented herein is an engineered strain (MFL185) for ethylene glycol consumption, and a foundation strain for further development as a biocatalyst for the conversion of ethylene glycol in waste plastics streams, and for the conversion of glycolaldehyde in thermochemical wastewater streams, and generally for additional environmental bioremediation applications.

TABLE 7

Primers, genes, vectors, and restriction enzymes targeted/used for construction.

| Construct# | Primer 1 | Primer 2 | Vector or Gene Target | RE Digests | Plasmid ID |
|---|---|---|---|---|---|
| 1 | oMFL165 | oMFL159 | pBTL2 | SbfI/PacI | pMFL113 |
|  | oMFL160 | oMFL161 | gcl | SbfI/NotI |  |
|  | oMFL162 | oMFL163 | glcB | NotI/PacI |  |
| 2 | oMFL165 | oMFL159 | pBTL2 | SbfI/PacI | pMFL114 |
|  | oMFL160 | oMFL164 | gcl operon | SbfI/NotI |  |
|  | oMFL162 | oMFL163 | glcB | NotI/PacI |  |
| 3 | oMFL158 | oMFL159 | pBTL2 | SbfI/NotI | pMFL115 |
|  | oMFL166 | oMFL167 | glcB | SbfI/NotI |  |
| 4 | oMFL165 | oMFL159 | pBTL2 | SbfI/PacI | pMFL116 |
|  | oMFL160 | oMFL161 | gcl | SbfI/NotI |  |
|  | oMFL162 | oMFL163 | glcB | NotI/PacI |  |
| 5 | oMFL165 | oMFL159 | pBTL2 | SbfI/PacI | pMFL117 |
|  | oMFL160 | oMFL164 | gcl operon | SbfI/NotI |  |
|  | oMFL162 | oMFL163 | glcB | NotI/PacI |  |

Plasmid Construction of pMFL113-pMFL117

The plasmid, pBTL2 was amplified with primers as designated above to introduce NotI and SbfI sites or PacI and SbfI sites to the plasmid. PCR products obtained from amplification from KT2440 genomic DNA using primers above and the vector were purified and digested with restriction enzymes noted above, purified again and ligated together, then transformed into NEB 5-alpha F'Iq *E. coli*. After confirmation of sequence, DNA was transformed into *P. putida* KT2440 and the strains designated as MFL113 to MFL117.

Plasmid construction details of pMFL160, pMFL161, pLJ030, pLJ031 and pLJ032 (Integration constructs for MFL168, MFL170, MFL185, MFL186 and MFL188) are depicted in Table 8.

TABLE 8

| Assembly | Primer 1 | Primer 2 | Vector or Gene Target | Plasmid ID |
|---|---|---|---|---|
| #1 | oCJ288 | oCJ289 | pK18mobsacB | pMFL160 |
| (XbaI/SpeI) | oCJ301 | oCJ302X | Upstream fpvA | pMFL161 |
|  | oCJ306XX | oCJ307 | Downstream fpvA |  |
| XbaI/SpeI | oMFL276 | oMFL279 | gcl-glxR | pMFL160 |
| XbaI/SpeI | oMFL276 | oMFL280 | gcl operon | pMFL161 |
| #2 | oLJ110 | oLJ113 | pMFL160 | pLJ032 |
|  | oLJ110 | oLJ111 | gcl |  |
|  | oLJ112 | oLJ113 | glxR |  |
| #3 | oLJ100 | oLJ103 | pK18mobsacb | pLJ1030 |
|  | oLJ100 | oLJ101 | glcC (upstream glcD) |  |
|  | oLJ102 | oLJ103 | glcD |  |

In order to construct the integration plasmids, pMFL160 and MFL161, 3 PCR fragments for assembly #1 (Table 8) were assembled using NEBuilder® HiFi DNA Assembly Master Mix following manufacturer's instructions. The fragment was digested with XbaI and SpeI along with PCR fragments generated from oMFL276 and oMFL279 (gcl-hyi-glxR) or oMFL276 with oMFL280 (gcl operon), which were also cut with XbaI, and SpeI. Fragments were PCR purified, ligated and transformed into *E. coli* as described above to generate either pMFL160 (integration overexpression construct for MFL170 (gcl-hyi-glxR)) or to generate pMFL161 (integration construct for MFL168 and MFL185 expressing the entire gcl operon), both of which are contain the pK18mobsacb backbone. The integration plasmid, pMFL160 was used as a template for the construction of pJL032 for integration of gcl-glxR. Briefly, three fragments were assembled as shown in the table above, then assembled (assembly #2) and transformed into NEB 5-alpha F'Iq *E. coli*. For assembly of the integration construction to insert the tac promoter in front of the glcDEF operon, three PCR fragments were generated (assembly #3 above), assembled and transformed into NEB 5-alpha F'Iq *E. coli*. All plasmids were confirmed by sequencing prior to integration into *P. putida* KT2440.

Redox Equivalent Homeostasis in the Utilization of Ethylene Glycol as Co-Substrate An analysis of the *P. putida* genome reveals that it possesses open reading frames that putatively encode enzymes that if expressed might be useful in metabolic pathways that could potentially enable ethylene glycol metabolism. In one such ethylene glycol metabolic pathway, referred to herein as the "energy yielding pathway", the diol (ethylene glycol) is converted into glyoxylate in a series of oxidation reactions catalyzed by a set of redundant dehydrogenases, PQQ-dependent PedI, PedE and PedH (see FIG. 1). Further oxidation from glyoxylate to oxalate can occur, but only very small traces of this metabolically dead-end product have been observed.

The complete conversion of ethylene glycol to glyoxylate yields three reducing equivalents, either in the form of NADH, $PQQH_2$, or a direct coupling to the electron transport chain. Glyoxylate can be further metabolized by the AceA or GlcB enzymes involved in the glyoxylate shunt. Although this shunt is usually a carbon conservation pathway for growth on C2 substrates that enter primary metabolism at the level of acetyl-CoA, the overall stoichiometry of glyoxylate metabolism via either of the reactions catalyzed by the AceA or GlcB enzymes can only yield 2 $CO_2$ and 2 reducing equivalents (see FIG. 1). Thus, the overall conversion of ethylene glycol to 2 $CO_2$ can yield a total of five reducing equivalents, making it a promising energy-yielding co-substrate. In comparison, typical redox energy co-substrates such as formate can only yield one reducing equivalents per C mole of substrate, and even the complete oxidation of glucose through primary metabolism only yields approximately 1.66 reducing equivalents per C mole of substrate.

To investigate the applicability of ethylene glycol as a co-substrate, *P. putida* KT2440 was cultured in carbon-limited chemostat cultivations with acetate as carbon source, and either ethylene glycol or glyoxylate as an energy source. Acetate was chosen because it induces the glyoxylate shunt enzymes. Compared to the control with only acetate, a co-feed of ethylene glycol or glyoxylate significantly increased the biomass yield on acetate by 29.6±1.1% or 22.2±8.2%, respectively. This increase can likely be attributed to the additional reducing equivalents generated through the co-substrate metabolism, enabling a more efficient carbon metabolism of the primary substrate. However, the fed ethylene glycol was only partly metabolized, and several intermediate oxidation products were secreted. A limitation in the upstream oxidation reactions can be excluded, since glyoxylate was also not completely metabolized under these conditions.

Energy and redox equivalent homeostasis is essential for efficient growth of a bacterial cell. As such, the observed inefficiency in metabolism of ethylene glycol could result from a potential imbalance in the pool of redox equivalents. Assuming that all glyoxylate is metabolized through the glyoxylate shunt, 27.3±2.6 mmol (g CDW)$^{-1}$ h$^{-1}$ of reducing equivalents were generated through the co-metabolism of ethylene glycol. In contrast, under similar conditions reached the maximal achievable biomass yield on glucose already with 7.6±0.9 mmol (g CDW)$^{-1}$ h$^{-1}$ using a co-feed of formate. Thus, under these conditions, the generated flux of reducing equivalents from an ethylene glycol co-feed likely constitute a strong surplus in energy. This is further supported by the fact that a glyoxylate co-feed, yielding only 14.4±0.5 mmol (g CDW)$^{-1}$ h$^{-1}$ of reducing equivalents, enabled almost the same biomass yield increase as the ethylene glycol co-feed. This surplus of reducing equivalents leads to an imbalance of redox cofactors, inhibiting the further conversion of ethylene glycol under these conditions.

Isolation of Mutants Able to Utilize Ethylene Glycol as Sole Carbon Source

In an alternative to the energy yielding pathway, the genome of *P. putida* KT2440 contains open reading frames (PP_4297-PP_4301) that if expressed might encode for enzymes useful in a pathway to metabolize glyoxylate through a glyoxylate carboligase which converts two glyoxylate into tartronate semialdehyde and $CO_2$. In this pathway, glyoxylate is converted to glycerate, either directly or via hydroxypyruvate, and subsequently to 2-phosphoglycerate (see FIG. 1B). Thus, this pathway is referred to herein as the 'gcl pathway'. If operative, the gcl pathway could allow for the utilization of ethylene glycol as a sole carbon source.

Adaptive laboratory evolution (ALE) techniques were applied to *P. putida* KT2440 and lead to the emergence of adaptive mutations allowing for growth on ethylene glycol as a sole carbon source. Two independent ALE experiments were performed in two different laboratory *P. putida* KT2440 wildtype strains using different minimal media recipes supplemented with ethylene glycol as a sole carbon source. As depicted in FIG. 19, as a result of the ALE experiments, adaptive mutants emerged, leading to observable growth after a lag phase of 4-6 days.

Three isolates were obtained from independently evolved cultures directly after this initial growth. The best growing clones from each culture were selected from nine individual clones and subcultured three times on LB-agar plates to obtain strains E1.1, E1.2 and E1.3.

A series of three parallel ALE cultivations was performed where batches were sequentially re-inoculated into fresh medium with ethylene glycol after growth became apparent by visual inspection, see FIG. 17. After six serial transfers, 36 individual strains were isolated on LB-agar plates and grown in liquid cultures. The best growing strains were selected to obtain strains E6.1 and E6.2.

All five resulting strains (E1.1, E1.2, E1.3, E6.1, and E6.2) demonstrated a stable ethylene glycol-growing phenotype. No major differences could be observed within the E1 and E6 groups. When grown in minimal medium with 26.7±0.4 mM ethylene glycol as a sole carbon source, both groups grew at approximately the same initial rate (0.19±0.02 $h^{-1}$). However, the maximum biomass concentration of the E6 cultures (0.63±0.02 $g_{cdw}$ $L^{-1}$) was significantly higher than that of the E1 cultures (0.49±0.07 $g_{cdw}$ $L^{-1}$) (FIGS. 15A, 15C). The differences between the E1 and E6 strains becomes more apparent upon cultivation in 120 mM ethylene glycol (FIG. 15D). In this case, the E6 strains grew 1.4-fold faster than the E1 strains (E1: 0.08±0.004 $h^{-1}$, E6: 0.12±0.004 $h^{-1}$), also reaching a higher final biomass concentration. The difference between E1 and E6 groups was also reflected in the metabolism of ethylene glycol and the formation of intermediate oxidation products. As depicted in FIG. 15B, the ethylene glycol uptake rate of E6.1 is about 1.8-fold higher than that of E1.1. E6.1 also produces up to 7.9-fold more glycolate than E1.1.

Genomic and Metabolic Context of Adaptive Mutations

Whole genome resequencing was performed on the E1 and E6 strains in order to discover the mutations responsible for the stable phenotypic switch in the E1 and E6 ALE strains. In comparison to publicly available sequence of *P. putida* KT2440 (AE015451.2) (see FIG. 12), the sequences of E1 and E6 had 92-99 Single Nucleotide Polymorphisms (SNP) and Insertion-Deletion polymorphisms (InDel). However, the vast majority of these were already present in the two wildtype strains from which E1 and E6 were derived. The mutations were mainly in non-coding regions, due to transposon effects, or errors due to low coverage, read quality, or silent mutations having no major effect.

The mutations identified in strains E1 and E6 were very similar to each other, even though they were derived from different wildtype *P. putida* KT2440 strains. After subtracting parental, silent, and intergenic mutations, two additional mutated regions were identified in the E1 and E6 strains. One region (coordinates 4866804 to 4902814, of *P. putida* KT2440) was mutated in all the evolved strains (E1.1, E1.2, E1.3, E6.1, and E6.2), while the other region (coordinates 2325342 to 2334253) was only mutated in the E6 group (E6.1, and E6.2), see FIG. 16.

In the first region, E1.1, E1.2, E1.3, and E6.1 contained mutations in the gene with locus tag PP_4283 encoding a putative GntR-type transcriptional regulator gclR. Using RegPrecise, GclR is predicted to be a regulator of xanthine metabolism, with two predicted binding sites upstream of the gcl gene. The mutations in the first region included one nonsense mutation in E6.1 giving rise to a stop codon in the 4th triplet, indicating that the gene function is disrupted. Strain E6.2 did not contain a mutation in gclR, instead it has a SNP 12.5 kb downstream in the promotor region of the gcl gene, which is the first gene in the PP_4297-PP_4301 cluster that encodes the enzymes of the gcl pathway.

Transcript levels of all five genes (PP_4297-PP_4301) in this cluster are very low in the wildtype *P. putida* KT2440 strain. In contrast, all five genes (PP_4297-PP_4301) in the cluster were strongly upregulated in strains E1.1, E6.1 and E6.2 having 2ΔΔCt values between 71 and 842 vs. wildtype, see FIG. 4D. The distally located hprA gene (PP_0762), which encodes a second possible glyoxylate/hydroxypyruvate reductase, is not expressed under these conditions, see FIG. 16D. Thus, GclR is a repressor of the PP_4297-PP_4301 gene cluster. Through the disruption of gclR, or the disruption of the GclR binding site in the case of strain E6.2, the repression of the transcription and expression of all five genes (PP_4297-PP_4301) in the cluster was substantially eliminated, thereby enabling growth on ethylene glycol as a sole carbon source.

In *P. putida*, ethylene glycol and/or glyoxylate are not the effectors which bind GclR to relieve repression of the PP_4297-PP_4301 gene cluster. The genomic context of the gclR gene in *P. putida* KT2440 which, similarly to other organisms such as *E. coli, Streptomyces coelicolor*, and *Bacillus subtilis*, encode multiple genes known or predicted to be involved in the metabolism of purines via allantoin and glyoxylate, see FIG. 10. In aerobically growing *E. coli*, the genes encoding the gcl pathway are repressed in the presence of allantoin through the action of the AllR regulator. This repression is alleviated by glyoxylate, which concomitantly induces an alternative allantoin metabolic pathway which ultimately yields ammonia, $CO_2$ and ATP, predominantly active under anaerobic conditions. This alternative pathway seems to be absent in *P. putida* KT2440, befitting its obligate aerobic lifestyle. The genomic context of gclR suggests that the failure of wildtype *P. putida* KT2440 to activate the gcl pathway on ethylene glycol or glyoxylate is because it is part of a larger metabolic context, governed by inducers that lie upstream of their metabolism.

Both wildtype *P. putida* KT2440 and strain E6.1 are able to grow on allantoin as a sole carbon and nitrogen source (see FIG. 17), showing that allantoin, and not glyoxylate, is the inducer of the genes encoding the gcl pathway. A co-feed of allantoin and ethylene glycol resulted in a higher biomass concentration through the activation of the gcl pathway. Similar results were obtained with xanthine, which also enabled growth on ethylene glycol.

E6.2 was not able to utilize allantoin as sole nitrogen source, although it retained the ability to utilize it as a carbon source, either with or without the addition of ethylene glycol. This indicates that there is regulatory cross-talk between allantoin and ethylene glycol metabolism, possibly involving the PP_4296 gene whose expression is likely affected by its mutation in E6.2. The product of the PP_4296 gene shows sequence similarity to the *E. coli* GlcG protein which is implicated in glycolate metabolism.

In addition to the mutations involving gclR, an additional mutation was found in both of the strains E6.1 and E6.2. Both strains contained the same missense mutation (E34G) in the gene with locus tag PP_2046, a LysR-type transcriptional regulator. This regulator controls the adjacent operon which encodes a beta-oxidation pathway including a CoA-transferase, an acyl-CoA thioase, and several (enoyl-CoA-) dehydrogenases, see FIG. 16B. Although the C2 compound ethylene glycol cannot be metabolized through beta-oxidation, the dehydrogenases could accelerate its oxidation as exemplified in that E6.1 transiently accumulates much more glycolate than E1.1, see FIG. 3B. However, initial ethylene glycol oxidations are mostly performed in the periplasm by PedE and/or PedH since a knockout of the pedE-pedI cluster (PP_2673-PP_2780) in the E6 strains eliminates the ability to grow on ethylene glycol. CoA activation may be involved and enzymatic activities in the operon suggest that glycolyl-CoA is formed and converted to glyoxyl-CoA and subsequently to glyoxylate. An additional pathway would help to accelerate the apparent rate-limiting step in the E6 mutants, and possibly also alleviate the toxicity of glyoxylate by CoA activation (see FIG. 20).

Reversed Engineering of Ethylene Glycol Metabolism

Mutations in the gclR and PP_2046 genes contribute to the efficient growth of P. putida KT2440 on ethylene glycol as a sole carbon source. To determine how these mutations assert their effect, we replicated the phenotype of the mutant strains through reverse engineering.

Growth on ethylene glycol was assessed in gclR knockouts of the wildtype, E6.1, and E6.2 strains, see FIG. 17. P. putida KT2440 ΔgclR grows readily on minimal medium with ethylene glycol as the sole carbon source, while the growth of strain E6.1 ΔgclR is not significantly changed compared to its progenitor E6.1. Thus, the gclR mutations in the ALE strains were disruptive in nature, and GclR is a repressor of the genes encoding the gcl pathway.

Strain E6.2 ΔgclR grows slower than its parental strain. This, together with the fact that E6.2 can't use allantoin as sole nitrogen source, is indicative of a more complex regulatory mechanism, perhaps one analogous to that of E. coli's A11R, which can bind both allantoin and glyoxylate leading to either the repression or the activation of genes. To verify that it is only the activation of the gcl pathway, excluding any polar regulatory effects, the gcl and glxR genes were expressed episomally in wildtype P. putida KT2440 under the control of the LacIq-Ptrc promoter on plasmid pSEVA234 (SEQ ID NO: 5). Indeed, the resulting strain KT2440 pSEVA234_gcl-glxR grows on ethylene glycol. Although qRT-PCR experiments determined that in the ALE strains, the five genes were upregulated, two of these are redundant, and P. putida KT2440 contains another gene encoding a glycerate kinase (PP_3178). In an embodiment, only gcl and glxR need to be expressed to enable growth on ethylene glycol. A significant contribution of the redundant pathway via hydroxypyruvate is indicated by strain KT2440 pSEVA234 gcl-glxR growing slower than KT2440 ΔgclR or the ALE strains.

In contrast to the ALE mutations in gclR, the E6 strains both contained the same SNP in the PP_2046 gene leading to an E34G substitution. It is unclear whether this mutation simply disrupts activity, or whether it changes the functionality of the encoded regulator. To distinguish between these effects, PP_2046 was knocked out and the mutant variant of the gene was episomally re-introduced into this knockout under the control of the NagR-P¬nagAa promoter on plasmid pBNTmcs. These modifications were made in P. putida KT2440 ΔgclR, because modification of PP_2046 alone didn't enable growth on ethylene glycol. Both strains P. putida KT2440 ΔgclRΔPP_2046 pBNT_PP_2046E34G and the empty vector control KT2440 ΔgclRΔPP_2046 pBNTmcs still grow on ethylene glycol, but the latter much slower than the former.

Engineering P. putida KT2440 for Efficient Ethylene Glycol Utilization

To further expand the ability of P. putida for substrates of industrial interest, the metabolism of ethylene glycol was enhanced via metabolic engineering through the overexpression of existing regulated pathways that include the glyoxylate carboligase operon. Growth in concentrations of ethylene glycol above 50 mM was inhibited by the accumulation of toxic intermediates, glycolaldehyde and glyoxal. The additional overexpression of glycolate oxidase (glcDEF) operon removed the glycolate bottleneck and minimized the production of these toxic intermediates, permitting the growth in up to 2M (120 g/L) and consumption of greater than about 0.5M (30 g/L) of ethylene glycol.

Construction and Characterization of Integrated Engineered P. putida KT2440

In order to ascertain which genes were important for ethylene glycol metabolism and to provide a base strain for further improvements, genes of interest were integrated into an intergenic region between fpvA and PP_4218. This region was chosen because we have successfully integrated other genes in this location, in addition to having native terminators present in both directions. The tac promoter was used for driving expression of the operon and the RBS in front of gcl modified for optimal ribosome binding, see FIG. 3. MFL168 included all 5 genes (gcl, hyi, glxR, PP_4300 and pykF) behind the tac promoter, MFL170 included 3 genes (gcl, hyi, glxR) MFL188 expressed only 2 genes (gcl, glxR), the minimal requirement for a glyoxylate metabolizing unit. The genes behind gcl and the intergenic regions on the operons were not genetically modified from that on the chromosome, except for the RBS of glxR in MFL188 that was optimized with the use of an RBS calculator.

Cultures were compared for growth in the presence of 20 mM ethylene glycol in minimal medium, see FIG. 21. Both MFL168 (gcl, hyi, glxR, PP_4300 and pykF) and MFL170 (gcl, hyi, glxR) grew sufficiently well and were able to consume ethylene glycol within 14 hours, see FIG. 21B). MFL188 expressing only gcl and glxR grew much more slowly and exhibited a long lag phase until growth was nearly complete at 90 hours, although ethylene glycol was metabolized completely within 48 hours, due to the incomplete utilization of glycolate and some glycolaldehyde that eventually dissipated until nearly gone at 90 hours, see FIGS. 21C and D).

Integrated strains were tested for growth in 50 mM ethylene glycol and it was discovered that strains had more difficulty in consuming the higher concentration of ethylene glycol, see FIG. 19. MFL168 required 72 hours for total substrate utilization, and for MFL170, 96 hours, whereas MFL188 barely grew. Glycolate levels were much lower than that observed for 20 mM ethylene glycol, but glycolaldehyde measurements rose to nearly 2.5 mM for both MFL168 and MFL170. Glyoxal was also present in culture samples. Glyoxal is derived from the oxidation of glycolaldehyde. Glycolaldehyde is toxic and has been shown to be more inhibitory than 5-hydroxymethyl furfural (5-HMF) and furfural for Saccharomyces cerevesiae. Therefore, an investigation of glycolaldehyde toxicity as well as other intermediate metabolites (glyxoylate, glycolate, oxalate, and glyoxal) and the substrate, ethylene glycol, was conducted to better understand their impact on ethylene glycol metabolism.

Substrate, Metabolite, and Competitive Inhibition Toxicity Assays

The toxicity effects of ethylene glycol, glyoxylate, glycolaldehyde, glyoxal and oxalate on P. putida KT2440 were examined by monitoring growth in the Bioscreen C instrument (a microplate reader which monitors turbidity over time) in the presence of M9 minimal medium containing 20 mM glucose and the inhibitor, see FIG. 20. The average OD of at least 5 wells was plotted in FIG. 9. Ethylene glycol, sodium glyoxylate, and sodium glycolate at concentrations up to 100 mM were not significantly inhibitory; nor was sodium oxalate up to 50 mM. However, glycolaldehyde was very toxic and completely inhibited growth at 4 mM and inhibits growth at 3 mM. Glyoxal, an oxidation product of glycolaldehyde, is also very inhibitory to P. putida KT2440 growth at a 5 mM concentration where a long lag phase is observed. At 7.5 mM, glyoxal is lethal to the cells. Therefore, glycolaldehyde and glyoxal are intermediate metabolites which result in ethylene glycol toxicity on *P. putida* KT2440. Glycolaldehyde exerts combinational inhibitory effect with other compounds, such as 5-HMF, furfural, and methylglyoxal. The combinational inhibitory effect of glycolaldehyde and glyoxal was determined by running three level full-factorial growth experiments, see FIG. 13 and Table 3.

Glycolaldehyde and glyoxal have a synergistic inhibitory effect where, the growth rates in the presence of 2 mM glycolaldehyde is 0.291±0.001 $h^{-1}$, 2 mM glyoxal is 0.297±0.001 $h^{-1}$, and 1 mM glycolaldehyde+1 mM glyoxal is 0.197±0.001 $h^{-1}$.

Characterization of an Overexpressing Glycolate Oxidase Strain

In 20 mM ethylene glycol cultures, all three engineered strains accumulated large amounts of glycolate (see FIG. 21), particularly within the first 14 hours for MFL168 and for MFL170 and for MFL188, between 48 and 72 hours. An overexpressing glycolate oxidase was constructed by introducing a tac promoter in front of the native glycolate oxidase operon that includes 5 genes, 3 of them necessary for glycolate oxidase activity (glcDEF), see FIG. 3. A comparison of the new strain (MFL185) with MFL168 and the wild-type strain, *P. putida* KT2440, was made in several different concentrations of ethylene glycol. FIG. 22 compares the strains when grown in 50 mM ethylene glycol. MFL185 grows much faster in ethylene glycol (top line in FIG. 22A), consumes ethylene glycol faster, with very little glycolate accumulation and no discernible glycolaldehyde present.

Growth at concentrations higher than 50 mM was compared between Bioscreen C and in shake flasks, see FIG. 23. FIG. 23A compares growth of MFL168 in up to 80 mM ethylene glycol. Growth was optimal at 40 mM, reduced at 60 mM and inhibited for growth at 80 mM. In contrast, MFL185, containing an additional overexpressing glycolate oxidase, grew in concentrations up to 1.5 M, the equivalent of 90 g/L. This is significantly higher than that achieved without the glycolate oxidase expression, approximately 25-fold higher.

A shake flask study in M9 minimal medium containing only ethylene glycol from 25 mM to 3 M was conducted to determine whether MFL185 can utilize this much extra ethylene glycol, see FIGS. 23C and D which depict concentrations of 100 mM to 1 M of ethylene glycol. There was some growth at 2 M in both the microplates and in the shake flasks but very little ethylene glycol used. MFL185 was able to completely consume 500 mM ethylene glycol within 120 hours, although its growth lagged behind growth in 250 mM ethylene glycol. MFL185 consumed about 40% of the ethylene glycol present in 1 M under these shake flask conditions. There was some accumulation of glycolate (from 8-18 mM) between 14 and 24 hours from samples grown in 100 to 500 mM samples, however, there was very little glycolaldehyde or glyoxal present.

qRT-PCR

The genes engineered into MFL168 were predicted to be transcribed in three different transcriptional units, namely gcl-hyi, glxR, and PP_4300-pykF. There is a strong inverted repeat located in the intergenic region between hyi and glxR, which indicates that glxR would be on a different transcript, however, no potential promoters were predicted to be present upstream of glxR using an online software prediction program, BPROM. Quantitative real-time PCR experiments were conducted to measure transcript levels of gcl, hyi, glxR, PP_4300 and pykF in addition to PP_0762 to determine whether genes located together on this operon are expressed. PP_0762 was annotated to function as a hydroxypyruvate reductase and could be involved in converting hydroxypyruvate to glycerate in ethylene glycol metabolism. A housekeeping gene, rpoD, was used to quantify transcript levels between each of our samples using the $2^{-\Delta\Delta Ct}$ method. Cultures were grown up in M9 minimal medium with 40 mM sodium acetate and 20 mM ethylene glycol. For ethylene glycol consuming cultures, acetate was utilized first, followed by ethylene glycol. All cultures were harvested at about an $OD_{600}$ of 1 at which point, the substrates acetate and ethylene glycol were still available for growth.

Ct values were obtained for each sample and gene and are summarized as fold expression to transcript levels obtained from the control (*P. putida* KT2440) after normalizing gene expression to rpoD, see FIG. 24. Transcript levels for gcl were expected to be much higher than in the control strain, since it is driven by the strong tac promoter and are about 2,000 times greater in MFL168 than in the wild-type strain. For MFL168, transcript levels of both hyi and glxR are approximately the same and about 300 times greater than the control. Transcript levels for both PP_4300 and pykF are slightly lower but still much higher than the control (about 150-300) fold greater. Transcript levels for gcl, hyi and glxR in MFL170 and MFL188 are similar to those in MFL168, for genes that were overexpressed. These results indicate that all of these genes are indeed located on the same operon and are being expressed together. The transcript levels for PP_0762 (hprA) were also measured and had a relatively low expression in the control strain and in the engineered strains under these conditions. Under these conditions, it is unlikely that this enzyme plays a role in conversion of hydroxypyruvate to glycerate.

Activity Assays

Experiments were performed to determine which enzyme is responsible for converting hydroxypyruvate to glycerate. PP_4300 and hprA (PP_0762) are not required for ethylene glycol assimilation, so assays were conducted to test cell extracts for activity on the substrate hydroxypyruvate by monitoring NADH and NADPH oxidation, see FIG. 25. Cell extracts from *P. putida* KT2440 exhibited very little activity towards hydroxypyruvate, whereas, cell extracts from MFL168, MFL170 and MFL188 were all positive for NADH oxidation in the presence of hydroxypyruvate. MFL188 expresses two genes above that of the control strains: gcl and glxR. Since Gcl does not have cofactor reducing capabilities, GlxR is likely responsible for the activity. Previous work purified and characterized tartronate semialdehyde reductase (GlxR) from *P. putida* and discovered that hydroxypyruvate also acts as a substrate, albeit at a 10-fold lower maximal velocity than when tartronate semialdehyde was used as a substrate. Furthermore, that work also noted that glycolate inhibits this enzyme with a $K_i$=3 mM, which may explain why MFL188 does not perform as well as MFL168 or MFL170.

A prediction of the exact composition of a gcl operon from the genomic context is not straightforward. From a functional perspective the co-transcription of gcl, hyi (hydroxypyruvate isomerase), glxR (tartronate semialdehyde reductase) and PP_4300 (hydroxypyruvate reductase) and pykF would make functional sense since they would allow two different routes for the conversion of glyoxylate to glycerate, see FIG. 1. However, from computational analysis, according to DOOR prediction, these genes are predicted to be transcribed in three different transcriptional units, namely gcl-hyi, glxR, and PP_4300-pykF. The qRT-PCR experiments performed herein indicate that they are expressed as one operon. In an embodiment, the minimal requirement for a glyoxylate-metabolizing unit is the expression of two genes (gcl, glxR), such as in MFL188, which does metabolize ethylene glycol, but at slower uptake rates than MFL170 that contains an additional gene (hyi). It was discovered with activity assays of cell extracts that GlxR could also function as a hydroxypyruvate reductase, converting hydroxypyruvate to glycerate which connects hydroxypyruvate to the central metabolic pathway, see FIG. 1. Hydroxypyruvate can act as a substrate for GlxR and glycolate can inhibit its activity. This might explain why strains MFL168 and MFL170 perform better than MFL188.

The two additional enzymes, PP_4300 (TtuD) and PykF, expressed in MFL168, compared to MFL170, showed improved performance under our conditions, but not to a lesser extent than the addition of Hyi. PP_4300 was predicted to function as a hydroxypyruvate reductase (BioCYC Database collection), but PP_4300 was identified as a glycerate kinase in the KEGG (Kyoto Encyclopedia of Genes and Genomes) pathway database, see FIG. 1.

At elevated levels of ethylene glycol (>50 mM), glycolate, glycolaldehyde and glyoxal levels increased. The accumulation of glycolate caused the concentration of glycolaldehyde to increase to inhibitory levels and is likely responsible for inhibition of GlxR activity. A strain (MFL185) was engineered to overexpress glycolate oxidase. MFL185 can metabolize 500 mM ethylene glycol (30 g/L) under shake flask conditions. MFL185 will tolerate growth in up to 1.5 M (90 g/L) ethylene glycol. Increased substrate utilization with proper fermentation control and the addition of limiting nutrients (i.e. nitrogen, iron) may be possible.

The deregulation of the gcl operon allows for growth of *P. putida* KT2440 in ethylene glycol. Furthermore, growth of engineered strains in higher concentrations of ethylene glycol can be inhibited by the accumulation of the toxic intermediates, glycolaldehyde and glyoxal. The addition of glycolate oxidase removes the glycolate bottleneck and minimizes the production of these toxic intermediates, allowing for the growth in up to 2 M (120 g/L) and consumption of 0.5M (30 g/L) or more of ethylene glycol under the shake flask growth conditions.

Plasmid Construction

Q5 Hot Start High-Fidelity 2X Master Mix (New England Biolabs) and primers synthesized by Integrated DNA Technologies (IDT) were used in all PCR amplification for plasmid construction. Plasmids were constructed using Gibson Assembly® Master Mix (New England Biolabs) according to the manufacturer's instructions. Plasmids for gene integration were constructed in pK18mobsacB from ATCC (American Type Culture Collection, Manassas, Va.), which is unable to replicate in *P. putida* KT2440, and contains the kanamycin resistant marker to select for integration of the plasmid into the genome by homologous recombination and sacB to counter select for recombination of the plasmid out of the genome. The plasmid, CJ0XX, used for of integration of operons containing the gene gcl (MFL168, MFL170, MFL185, and MFL188) contains the 1 kb homology region on either side of the intergenic region immediately after the fpvA (outer membrane ferripyoverdine receptor) terminator and PP_4218 (lipase/esterase) of *P. putida* KT2440. Features include the tac promoter to drive operon expression and a tonB terminator situated behind the operon (FIG. 3). The RBS for gcl was optimized for gcl expression and were the same for MFL168, MFL170 and MFL185. The RBS for glxR in MFL188 was also optimized. The remaining RBS and gene sequences remained the same as on the native chromosome. The overexpression of glycolate oxidase genes (glcDEF) in MFL185, MFL186 and MFL188 was achieved by integrating the tac promoter upstream of the glycolate oxidase operon (glcDEFG_PP_3749) and behind the native promoter, while additionally optimizing the RBS for glcD. Primers used for PCR amplification and Gibson assembly are listed in Table 4.

Plasmids were transformed into competent NEB 5-alpha F'Iq *E. coli* (New England Biolabs) according to the manufacturer's instructions. Transformants were selected on LB (Lennox) plates containing 10 g/L tryptone, 5 g/L yeast extract, 5 g/L NaCl, and 15 g/L agar, supplemented with either 10 µg/mL tetracycline or 50 µg/mL kanamycin grown at 37° C. The sequences of all plasmid inserts were confirmed using Sanger sequencing (GENEWIZ, Inc.). Specific plasmid construction details can be found in the supplementary materials and methods.

Strain Construction

*P. putida* KT2440 (ATCC 47054) was used as the basis of strain engineering and gene replacements were made using the antibiotic/sacB system of selection and counter-selection. To prepare cells of *P. putida* KT2440 and strains derived from it for transformation by electroporation, cultures were grown up overnight in LB broth and incubated at 30° C., shaking at 225 rpm. The next day, cells were centrifuged 15,000 rpm in an Eppendorf centrifuge for 1 minute at room temperature, washed three times in 0.3M sucrose in half the original volume, centrifuged again then resuspended then resuspended in ⅕₀th of the culture's original volume in 0.3M sucrose. Cells were immediately used for electroporation by introducing 5 µL (200 ng-2 µg) of plasmid DNA to 50 µL of the electrocompetent cells, transferred to a chilled 0.1 cm electroporation cuvette, and electroporated at 1.6 kV, 25 µF, 200 ohms. 950 µL SOC outgrowth medium (NEB) was added to the cells immediately after electroporation and the resuspended cells were incubated shaking at 225 rpm, 30° C., for two hours. The entire transformation was plated on an LB agar plate containing appropriate antibiotics (50 µg/mL kanamycin for pBTL2 and pK18mobsacB-based plasmids) and incubated at 30° C. overnight. Transformants were restreaked for single colonies on LB agar and incubated at 30° C. overnight to reduce the possibility of untransformed cells being transferred. For sucrose counter-selection, restreaked transformants were streaked for single colonies on YT+25% sucrose plates (10 g/L yeast extract, 20 g/L tryptone, 250 g/L sucrose, 18 g/L agar), and incubated at 30° C. overnight. *P. putida* KT2440 containing the sacB gene can grow, although very slowly, on YT+25% sucrose media. Therefore, colonies presumed to have recombined the sacB gene out of the genome—those colonies that were larger than most were restreaked on YT+25% sucrose plates and incubated at 30° C. overnight to reduce the possibility that cells that had not recombined would be carried along with sucrose resistant isolates. Colonies from the second YT+25% sucrose plates were subjected to colony PCR to check for gene replacement at both junctions. These isolates were also plated on LB plates containing appropriate antibiotics to ensure that they had lost antibiotic resistance and, thus, represented pure gene replacements. FIG. 3 depicts a schematic representation of the organization of the open reading frames of some of the engineered strains produced in this work. For overexpression, the tac promoter was used and ribosomal binding sites were optimized using an online RBS calculator.

Toxicity Tests in Bioscreen C

Growth curves were obtained from Bioscreen C analyzers (Growth Curves US, Piscataway, N.J.). Overnight cultures of *P. putida* KT2440 were grown in M9 medium containing 20 mM glucose starting at an $OD_{600}$ of 0.05-0.1, 30° C., 225 rpm (baffled shake flask) until the $OD_{600}$ reached ~1.0-1.5. Cells were concentrated by centrifugation and inoculated into wells of Bioscreen C microplates containing various inhibitors and concentrations in the presence of 20 mM glucose at and additional $OD_{600}$=0.05 in a total volume of 300 μL. Incubations were performed at 30° C. and absorbance readings were taken every 15 min. Operation of the Bioscreen C and collection of turbidity measurements ($OD_{420-580}$) were computer automated with EZ Experiment. Data was collected and exported to Microsoft Excel spreadsheets for analysis.

Culture Growth and Metabolite Analysis

Shake flask experiments were performed using M9 minimal media (Sigma-Aldrich) containing 6.78 g/L disodium phosphate, 3 g/L monopotassium phosphate, 0.5 g/L NaCl, 1 g/L $NH_4Cl$, 2 mM $MgSO_4$, 100 μM $CaCl_2$), and 40 μM $FeSO_4.7H_2O$ supplemented with 20 mM glucose (Fisher Scientific), ethylene glycol, or sodium acetate (Sigma-Aldrich). Cultures were grown in 225 mL baffled shake flasks, incubated at 30° C., 225 rpm. Culture growth was followed by periodic measurement of the optical density at 600 nm ($OD_{600}$) using a Beckman DU640 spectrophotometer (Beckman Coulter, Brea Calif.). When testing for growth on ethylene glycol, glyxoylate or glycolaldehyde, overnight cultures were spun down, washed in M9 minimal media lacking substrates and resuspended in same media prior to inoculating into shake flasks at OD600=0.1. Growth was conducted in shake flasks under the same conditions described above. Except for experiments conducted with plasmid-bearing strains, all cultures were performed in duplicate. Concentrations of glucose, ethylene glycol, glycolaldehyde, glyoxal, glycolate, glyxoylate, and oxalate in filtered culture supernatant samples were measured by high performance liquid chromatography (HPLC) on an Agilent1100 series system (Agilent USA, Santa Clara, Calif.) utilizing a Phenomenex Rezex RFQ-Fast Fruit $H^+$ column (Phenomenex, Torrance, Calif.) and cation H+ guard cartridge (Bio-Rad Laboratories, Hercules, Calif.) at 85° C. A mobile phase of 0.1 N sulfuric acid was used at a flow rate of 1.0 mL/min and a diode array detector was utilized for compound detection. Products were identified by comparing the retention times and spectral profiles with pure compounds.

RNA Extraction, cDNA Synthesis and Quantitative Real-Time PCR

To prepare *P. putida* cultures for RNA extraction, cells were grown up overnight in M9 minimal medium containing 20 mM glucose in baffled shake flasks at 30° C., 225 rpm. Cells were then diluted and transferred to fresh cultures containing 20 mM ethylene glycol and 40 mM sodium acetate @ OD600=0.1, 30° C., 225 rpm. Cells were harvested at mid-exponential growth phase when OD600 reached 0.8-1 by adding cells to 2× volume of Qiagen RNAprotect Bacteria Reagent, mixing well and resting for 5 minutes prior to centrifugation at 5,000×g for 15 min at 4° C. Supernatant was removed and cells were frozen and stored at −80° C. until use. RNA was extracted from cells using Qiagen's RNeasy mini kit following manufacturer's instructions including a DNAse (Qiagen RNase-Free DNase) in column digestion for 1 hour at room temperature following manufacturer's instructions. After isolation, and additional DNase digestion was performed with Ambion's TURBO DNase (Ambion, Austin, Tex., USA) for 2 hours at 37° C. that was followed by an additional RNA purification to remove DNase using the same kit. cDNA was prepared from RNA using an iScript Reverse Transcription supermix kit for RT-qPCR (Bio-Rad). The expression levels of seven genes were analyzed using primers designed by the Realtime PCR tool for RT-qPCR and is listed in Table 4. Quantitive real-time PCR was performed using iQ SYBR Green Supermix (Bio-Rad) on a Bio-Rad CFX96 Touch Real-Time PCR Detection System (Bio-Rad Lab, Hercules, Calif., USA). The reaction conditions were 10 min at 95° C., 39×(15 s at 95° C., 45 s at 55° C., followed by melting curve analysis: 1 min at 95° C., 81×(30 s starting at 55° C., increasing 0.5° C. per cycle, ending at 95° C.). Experiments were performed in triplicate with biological duplicates. The gene expression levels were assessed by the following formula:

$$\text{Gene expression level} = 2^{Ct(rpoD)-Ct(target)}$$

Ct values represent the first cycle at which the instrument can distinguish the fluorescence of nucleic acid amplification generated as being above the background signal. This method compares the Ct value of the house keeping gene rpoD to the Ct value of the target gene. Final expression levels were averaged for each target gene and normalized to the expression level of the control (*P. putida* KT2440) strain.

NAD(P)H oxidizing activity assays used for measuring hydroxypyruvate substrate conversion For extracting whole lysate protein for enzyme assays, strains were grown in LB medium and harvested during exponential growth phase. The cells were collected by centrifugation at 4,800 rpm for 5 min, washed with water twice, and re-suspended in B-PER solution supplemented with protease inhibitor cocktail (Thermo Fisher Scientific, Waltham, Mass., USA). Whole lysate proteins were obtained by following manufacture recommended protocol (Thermo Fisher Scientific, Waltham, Mass., USA). The protein concentration of samples was assessed using a NanoDrop 2000/c Spectrophotometers (Thermo Fisher Scientific, Waltham, Mass., USA) by following manufacturer protocol. Hydroxypyruvate reduction activity of samples was measured by monitoring oxidation of NAD(P)H at 340 nm with FLUOstar Omega micro plate reader (BMG Labtech, Ortenberg, Germany). Two hundred microliters of a reaction mixture-containing 150 μL of 50 mM potassium phosphate buffer (pH 7), 20 μL of 0.5 M lithium β-hydroxypyruvate hydrate (Sigma-Aldrich, St. Louis, Mo., USA), 20 μL of 0.7 mM NAD(P)H, and 10 μL of the cell extracts were used for the enzyme activity assay. One unit (1 U) of enzyme was defined by the conversion of 1 μM of NAD(P)H into $NAD(P)^+$ per minute. The units were normalized to the total protein (mg).

Sequences:

(SEQ ID NO: 1)
pLJ030 (P*tac*::glcDEF) 5'-3' sequence (SEQ ID NO: 1)

```
ttcgcggccgttcgacgcgagagggccgatacaaggccgcttcaacccccagccatccatacgcatggtcgcctgaccaggcgctgcttcctgctcgatcccc
gcaaactgtccgctatgccgttgatatgtcacgggccgcgtcggcccttgcgctcggcgaagttgttcatgactgccgagtcggagcatgtgccatgcgatcaatct
gggcttctcgcgccgcagttcaagtgttgaccgacgaaacaccgtgctcaactcagtcacgctggagcgattcaggtgtcaccggtatgcaccactggttatgc
gacgcctactgatgccggtgaaaggccgtgcacgtggtcaggagtggggcatgcggggccgactggttcacgggccatcgagcgcctcgtgcgcagccagtcttctgcgagcgc
ggcgattagcaggccggtgcgactggtgctacaaaggcgtagacaacaggtgcacccgctccccggtgagatcggcgacgactcggcggacagatgccgcgc
cacgcgaaacgaacctgcgcccccaagccgcaagccgcaagcttcaaccacgcgcccccttccccgcgccgattcgcgccactcgcctgggaccaccagccgc
ttcgacgataagccgctcaaccgtcggccacccggtcgcggcacctgcttcactcagtccaaccactcagaccacaccaagcgacgacctgactcactatc
gccaatctagcctgcagacagaaccctgaatgacaactactgcccgaggagaaactgtaggaccagtcaatctcactcgaccccaaacatcactagcacgcgacgctgc
atccggtcgaccgcttctgccaacaacaaaaccgtccagtggagcggctgagtgcgcttgatcatggtgcccgccgcgcaccacaatccactaatcatcg
gctcgtatatgtcagactcaatatataacgcacggtagtaacatcctgacgacgaaccgtccctgatctggcgccctccaaccgctgccgccccgcgcccc
tgttcagggcgctggcgatgccccccgatcttgaaacctcaccgcgatgcgaacctcaaaaccgcccgtccctgatagcggcgaagcgtcgatcgcaccgtgcc
actctggtggcgctgccggagcgctgccgcggcccaggcgcgacggacgctgttgaagcttgccctgagcagatcgcgcttgatgaggctagcccgtacgcgtgcgccgatgtt
ctgtgatgtcgaccctccccaggcctgccaaggccaaccgcaagtcttcatccatcgcgcagggccggaagattgctgacagtccgtgcggtagcagccactccaggt
gtgccttcaacgccctcgacgtgcgacccccgttccggagccgtgcagggcaaacaatcgcgccagcaagcatcgccggcaccattcggctcgcggcggtctgatcatcg
tgcagaacctgagactcgcgcgtccggcggcgcagctgaccaagtgcacagctcggagctcaatgcagctgcacctactgtagtcaaagcctcgaccctcgagcgcggca
cgacagcgcgcagcgtcccatagcagcgaatctgccccctcagcagctgcggtccgatgatattccgctcgctggtgtgtagctcggagcccctgttgaccgctcggcgga
tgcctgaaagctccctctggccccttacagatgctgcctcagtgctgccagcctcccgaccaatgtcgtcgccctcaagtgtcgccaagcatgccccaggtgacggagcccgga
gccggggtatactgcgtcatgcatggccgcatttcatacagtcaggcatttgggaaaagctcaatcgctgcggcaaaccgccgccgcatttcccgggcggctggagagatgatgg
acaacctggacctcgcgcgacgcttctgtcgcagcaactttcatccatcgcatggtcgcgcgcaaccgtgacagctgctcacctggcctcggcatatgctggagaaccactccaggt
ggccgccaatctgccgaccaagttgctcgcgacgtatgcacggcggccaccacctgccgccgccatggcagtgccgccacggcccgcatggctgagagggctcatggcgaacagctgcacggcgcccgga
cagtaggccgcgagagcctgcgagagactcttcgaactgcggccggcctgcgccgtccgtccgccccagggcactagctgccactccagggcctcccacctgaccacagtg
cgaatcgccagcagccgccgggacctcttcagggacctcgttcagtcgaccagaaaacgcaagtcttgagccgcctactggccctcgtcgtcgcgcaaagcaagctgcctaaagagaag
cagtaggccgcgcagagaaacgcagtccgcagaaagagcgaccaaagaacctgttcgctgccgcagagagctatctggaagcagtgaaacgcaagcgcagctacttggacacaaggagaaacgcaagcgcaagcgggtc
agtagcttcgcaaggtggcttcatgtgcgatagcagctcgatgctgatacgagcagcaggagcgaacgcggaattgccaggcgggccctcgtaagctaagtgggaa
ccctgcaagtaaactggatggctctcgcggccgcagttctccggcagatcctatggcggcaggatcatggcgcagggatcgatcaaagacgcgatgatccgcatcgattgaac
aagatgattgcaacgcagttgaactgcagttcagcgccggtctggtgagacagctgtatgcggcagggtctgacagacggtcaaagatctgacagacggctgcgtccgcgccgtctcggctg
ctagcagcgggccccggtctcttfigctcaagcgaccgtgctgcaggaccacgaccaccctgtcaagacggaggagacgaacggaattgccaagctggagcaggcccgatccgcgagctgccaccaaccggtattccgtgctgccgcgcctgccgctgctgaccggct
gtcctgcctgcgaccgctgaccgtcatgccacacaaggcgaagagcgtctactgatgcagctgtcaagggcaagggatgctatatggcgtacgaccagtcttcgcggctgacaatctactctctctacagtgctcactccctgcc
ctcgatgaagccggctcgtgcggtacctctgttgcgatcaggatgattgcggcagagtcggacgaaggagcatcatgttggggaaaatggcccagtcagtggtgtcggac
gtacgtcggaggcgatcagggccccgtgcgatgccgatatttggctgaaatggtggcgtacgctcttcacgatccgcctcgtgttcaccattagt
gcgtatcaggcaacatatgcttcatgccctccctgacgagtcttctgatgtcttgatagtctaccacctgcgaaggatcgatctttaaccatcatcacacagaagccgcaccactattttagt
gaaatgagatcatgtagactcttctgtcactgcacacaaaggcaacttatggccatgcaaacagaaaactacaacagagagaaatagaaggcgaaaagt
gtcctttaggcccgcagtgcccaaatccttgattgtgattgatgaatgcttgaatctcatcaaccaaaaggaaatagacagcagtcaaatgcgcagagctgcaaccgtgataggactttcttttgcgt
aaatgaattgcaagccggggtttgttactgatcaaggcaaggcagaagatgtaacttggccctattcctcatattcaccccttacataaattaggtctctctttattgcgt
aactaactgctaaccttaccccataaacaggaggcagaaaggcagaaacccgctccaatctccagggtgaactcaagcgttcgaaccatatagactgatgtagaacctgca
gaacagtattaaactttactgatatcgcgaaacctccgacaacagccagaaaaataaatgaaattgatcgtcccaacactgaaactgaaaagccatccca
tattacacgcgtctatcgcgaccaactcgtcgcaaactgcgacactgcattgcggacagctggcagctctcgtccaactacgaaatgccaggaactatcaatgcaaagaaacgaacgagcattcca
gacgtttgggacagtcggcattgacaagcctacgacgtcgacgacactgcattgcgatcgtctttgcattgcattgcattgcaaaaggcctg
gagcgtttgggacagtccgtcttgcttgcattgcgtcttcactggcacaactccgagatcctagcggtaccatcgacgagaatgcaaagcctg
```

-continued

Sequences:

acatgattacatgttctatcaaaagtggcgaaacttctattgacagctggaaaaacgctgccggctcttaaagacagcgacaaattcgatgcaaatgattctatc
ctaaaagaccaaaacaagaatggtcaggttcagcacattctgacggcacactgcgttcagtcagcatcagacagctcttgaacatcacgtgtgaggattataaatcaatcttgacggtgacggaaacgatcaaaatgta
cagcagttctcatcgatgaaggcaactacagctccaggcgacaaccatacgtgagagatcctcactcagtgaagataaaggccaaatactagtatttgaacgaa
cactggaactgaagatggctaccaaggccgaagaatcttctatttaacaaagcactacttcttccgtcaagaaagtcaaaaactctgcaaagc
gataaaaacgctgcagttgaacgcggagtagcaaacggcgactgctctcgtatgatttagctaacagacatgtacacactgaaaaagtgatgaaacgctgatcatctacaca
gtaacagatgaaattgaacgcgcgaacgctcttaaaatgaacggcaaatgtactcgtcactgactcccgcgatcaaaatggcccgatcaaaatggcgcattacgctaac
gatattcactgcttggttcgtcttcaattcttaactgcccatcaagccctgattctaacaagacaaatggtgtcaagtctatatgacaaaacaggagatcgtgttaacaagagaggatttgatcctatctacacgacacaaaatggcgatgacaactaacaaccaacggtttgcgccgagct
actccacttcgttgtaccaagaaaacaatgcgtgatcaagagcaagacatcctgtgatcaagaagcaataaacaagtaaaaataaaaagcaaaaagaaaatgccgatgg
gtaccagccagaaatgaccgaccaagcgacgcccaactcgtccatcacgagattcgattccaccgcgtccttcatgaagatgccaagggcttcggaatcgtttccggcaatgtttcggga
cgccctccgggacgtgctcatccctcgttcgctcgagcagaaggaggtacaccgtgatttggagccgtggtgctgcccttcatcagccatgtcggtggctcaccgt
ctccatcgctcttcgttcctctggaaggcagtacaccgtgagccgcgagcagcagtccgtcaaggaaagttctccacgagatcttcatcgcatcgtcgaaaaggtggatatccgtgaaaaggtgcctgatataccgaaaatcg
ctatcctgccgcctgacgcgtgatacaccaaggaaagcgtgcctcctgcgtttgcttgtgaataatcctcgtatatcgacactgaaacagcaatggatcaggaattactgaaact
gagggacaggcgagagatgcgaaagcctccgataactcgataatacgccggtagtgatcttcattatggtgaacctctt
agtgcctgatcaactcctcttcttcgcaaagttggccaacttcatcctcgaagttcatcctcaaacagagtcctccaaagtgcgtgatgcttcgggtgatgtcaaggtgcgtgcgtcaagctcaacttggtgcagtttagtgat
tattcggcgcaaagtgcggtcgggatgctctatttctgcgaagttcgccaacttcattatctgctgaaccttactgccgccaggctctcttgttctcatcagctcctgaaatcctgccgg
actcaaaatacccgcagttcgctttgcccaaaggttcccgcaagtgatttattcgcacagatcacgccttactgggccgcagcttgcgatctggatttgttctgcgttgcccactccaaaaggatcaaaggtagtgat
gatgtgttttgaggtgtccgggtgctccaggctgcttctcatcaggctggatgatctccaggcggatgatctcccgcggcggatctgctcgatcaagcatgctgagcgaacgcaatt
gaagatcatttgataatccatgaccaaaaatcccttaacgtgagttctcgtcctaacgcgtaccaggtgattgttcgtcaaggtaccaatcttttccgaaggtaactgcttcagcaga
gcgcgtaatctgcttgcaaataactgttctccttctagtgcgcgtagtagcgagggatagttaccgggttacccgtctaatcctgctaccagtggct
gctggggctgcgtgataagtgtctccttcaccggatccttgaaccaaccgctctagcaccgtcaggagtgaaacgcgaacgggggttcgtgcacacagcc
agctggaggcgaacgaccacaacccgaactagatccacagcggagctccaggagagaaagcgcacgttccgaaaaggcgatcggccagggtatccgtaag
cggaggtcgtcaggggggcggaaacaggagctcatgggcctatgaaaacgcagcaacccggcggcaaacgccggaacacgccggtttcctaagttcgccgcattgctcacatgttcttcctgcgttatc
gtgatgtcgtcagggcgtcgtattgcggtaccgctttcgagtgagccgttgggccgcggcgcctcatccggacacacacaaccagccgattcgccgagcgttccgacgggtgcgcagcggttcccgactgcgcgagtgagccagagcggaacgcaatt
ccctgattctgtggataaccgtattacccgctttgagtgagctgataccgctcgccgcagccgaacgaccgagcgcagcgagtcagtgagcgaggaagcggaaga
gcgccaatacgcaaaccgcctctccccgcgcgttggccgattcattaatgcagacacaaagtcggtgtacagacaagtcggtacagacgctcgtactcccgtgcagcaagt aacgcgctgatatccgtgcagcaatcaacagcgatacaagtcccctatacgttccgaactgcgaccccgtg
aagtcatccggagcggagtccggagtgcacgtgtacagcaagcgggaaatcaacagcacgctacacaaatctcatgccgcaatcgaacctgccgcctgaccggt
ccatcatccgcaccaaagcagaaaacacgatcgcaatccgtcaaggtcaaggtggcctcaaggtcaacaagaacctcagatcgaccag
gaaaaccgccgcagaagttcaaccaggaagttgcgcagctacacctgcgcatccgaaccaggtatccggcaatcggctaccaaggtacgcaccacccggtatcgcaccctggagttgatg
ggcgcactgccaccccactgcgcaagctcggcgcaccaagatgccgacaagatccgaagatggcgcgtggccgctaaccgtgatgccagaaccgcaccaagttcgaca
tcaacaaggccgcagcaccactgttccaagctgactgagcaaccaccctgatctcaaggtgcgcaaccctgtcaaggtcaacaagaaccctcgacatcc
gcctgaaccctcaacagttctgacgcgcatttgacaaagaagtactaccaggcattgcgcagcaacaccgcgtgtcctgagccgctacgacgcgtatgtgaccacgcaacttcaccatc
accgccaatcaaacagtttctgatctgcctgactgtgaacgcaaaaaaccgtgtcgggttttgaattgacaattaatcatcggctcgtataatgtg
gaatgtgagcggataacaatttcacacctctaga SEQ ID NO: 2
pLJ032 (fpvA::Ptac::gc1-g1xR) 5'-3' sequence (SEQ ID NO: 2)
tagtcaaagcctcgaccggagcttggactcatggatgcctccttacagatgcctgtgcctgcagtgcctgaccaccctgaccatcggcctcatggcc
tcctcgatgatcgaacccatacgtagtcattgcctccggatcctccgggagatcgcacgctcccgcgttcaccccgcctcccaagctgccgtcataagcgaca
ccctggtcatgcagcgggctattgcagctggtacatcagtgcgagtgcgccagcgtcgagtgcgcctccaaggaggcatcgtgaacgtgacgtct
gccggcaccgtggcgttgctgctgagaaccactccagggtctcgcttcaaggaggtaaccgctgcgcagcaggtaacgctgcgcagcaggtaaccgctgaccaaggtgaccgcaactgcggcatcg
gtcaccgggtagatcattactgaggcgatgcgcgaggtgccgagctgcgccagcaactggttggccagagctaccagggaatgtgaccgtctgcggcagtgctacaccgaccgcctgcctgcctgcagcagcatgtgccgacaactgcgccc
accaccgccgccagccgcgcctgcatgcccagccctcggctgcgtccgaccaaccagtgggttgaattgacattaatcatcggctcgtataatgtgtggaatgtgagcggataacaatttcacacctctaga -continued Sequences:

```
ggcgcagcggtagccaggcaatcaccggcaccccggcatctgcgccaggtccagcacacagcgtcatcgaatcgaggctgccaccacgtagccgcc
gccatcgcaggtacagcagcccgcgccaggtcggcctgccgcagtcgcgtcggcctgcgccggtcggccgcaaagcgcaccgcaaggtatggccatcgcggtcaacgaa
aagtcgctcagtcagtccggctcgttcggccttgccaccagtgcaggtaggcgcgccagttcaggtacatcgtcgattctccaagggcctagctcacgctgccg
acctgccggcggtcgtccggctcaaggcagcggaacacagtcgctaaaggaagcggaacacagtcgccagaaacgttgctgaccagactggtgctagactcactgactcagctgactgcagctcagctcacgggctatc
tggacaagggaaaacgcaagggctgctcggtaagaggagacagctgtcagctacttgactgatgtcatatcgcgatatacatgagactggcggtttatggacgcaagcaaccgg
aattgccagtcgggcgccctcgtaaggttgggaagcctgcagattgaacaagatgattgacacgcaggttctcccgccgcctggggtgagaggctatccgatgatgggcac
atcaagagacaggatgagggctgcgttctgatgcggtcgttctcggtgcagtcgaatgaagaggatgaatcttttttgcaagaccgacctgtccggtgcctgaatgaactccaa
aacagacaatcggctgctatcggtcgcgcgcacgagcgcgggctttccctgccgacgtgctcactgacgtgcacgttaccggtgtacggtgccgcctggggcgaa
gacgaggcagcgcgctatcggtggctggctccgacacggttctcctgccgagaagtatccatcatgctgatgcaatggcggtcatacgcgtgatccggtacctgccc
gtgccggggcaggattccctggtcatctcctgtcctccgagaaagtatccatcggaagtggaaagtgtcgttcggcgatgatatcaggcggggcaggattccctcaggtaagtgtcgttctgaaaccggtgtccgatctccgtgacccatggagctcgactgtcgaactttctcaaacaa
cagctgaccaccaaccaaccgaaactgcctccaagctgtccaagcctcggaagcgaggatcctgccgtgaccatggaatgatctccgatctgcgttgccgaatctcatggtggaaatggcc
gctttctcgatcatcgactgatgtggcggtgggtgggtgtgagctgtaccggtgcgattctgaaaagagctgcggcggaatgggct
gaccgctcctcgtcttctcgtgctttacgacgctcgcgcccgatcgcagtcgacatacggcgatgtctgacgttaaggcctggcagcaggcctactacaa
atcatccttctgctttaacccatcacatacaagaatgaaaagaatagttgaaatgaatatatctctctctgaatgtgattaaaaagcaacttatgcccatg
caacagaaactcttaaccggtcgcctgaaaaacgctgaaatcgcggatatctctacactttaaggcgctttatcttttaggtcttttattgcgtactactggcacactgtcaaacactggaac
gaggaaatagaccgttcagcccgaatccaaacagagctctaatagagaaggggctaatgaagctgcaaagtaaatcgcgaaagtgtcttgtatttcttatgatttcaaacaggcagcacgcacgctaataat
gtgtcaaggcaaagtgtatacttaaaaggagacatgaacatgaacaagcaacatttgcaaaaccaagttgcatctgtactgcgtaactgctaaccttactggctgctgcgcagtgcgcactgcactccga
agaccgctaacagtcaagcggtttgcgaagaagaacatgaacgaaccatgaaccaaacaagcattcccatatctccacatgatgcaagaatcctgaa
cagcaaaaaatgcaagctcgatttcgaattgattcgtcaaacatgaagcctaacaagcaataactctctccttctgcgggttggaacagcctggcctttacaa
acgcgaccggcactgcctgccaaactatcacgtcgcgccgtctcttgcattagccggaatccaaatgcggatcgcgatgacaactcggatgatcacatccttcatcaag
agtcggcgaaactctattgacagctcgaaaaacgctgccgcgtcttaaaggacagcggaccaaatccggttatctctactaccggtaaacactcgcgcaaactgaccacaagtt
aatgtccaggtcagctccatcttacatcgacggcagagaaaaatccggttattctccacactgcaaaacactaagacgatcttttgacgcgcaaacactgacactggac
acagtatcacgacattcagacagctcaggcgcaacatacgcgtgaagctagagacatacaaccaatcaatgcacccaaaatccggttgacacggaactatacgcgtgaagcaacactgaac
gatgaggcaactacagctcaggcgaagatctttatttaacagccctctccggtatgatcagcaactgcaaccctaacaatgatgagacgctgattgcgtcaactaacagt
aaacgcacggctggtagcaaggcgaagacttctaaattgaacggcaaatgtagaggattgataaatgaaggcgaaatgctgcactaccactactaagcgcaaccaaactgaaatgtgaaccgctgattgcgcatggcgcattacgttaa
tgaagatggctaccaaggcgaagatcttcatcagctcaggcgacaaactacgcgagagatcatatctctacaaagagcaaatggcacaaatggccctcaccctgaaccagctctaaggcgcattacgtaa
cgatattacacttcgctggtagcaaggcgaagatcttcatcaattccttaaccggcaacatacgtgattaacaggcaaatgccttgcaccctgaacctatactcggtagagatatcttgaacaaaatgtcggcagacaaacaaaacaaagatggttcaacgatgattaaccaccccgaaaatatacgccgtagtcagattccaagttg
tttacttcactcacacttcgctctgaacatcaaaggcaagaagaaacatcgtgtcaaagacagcgcctgaaccagcaatttaacgacaataaaaacgcaaaagctaaaactgacagctgaacaatttaaacagaatccaaaagaagttggcttcggcgct
aaatgcttttccggacagtggatacccgggcgaaaatgaacgacgccaagcgatttccaccgccgccgcttcaccgagatttcgattccacccgccgttcacgccgagattgcaccgcaccgccgccgcttgagccgcaccgccggcatctgagcctctatggtggttcggtgcaggcaggatccctctatgagaaagtctggtgcgccgcgccagcaccccgccttgccaccggtgccttgtgcaggcaggatctctatgagaaagtccatcagctccactggctcatcagccgctaaccttcggcagtccggttcatcagccgctcgcctgcctct
cccgcgccttttctcctccaatcgcctgcctggtcgctgaaaggcagtaccagctgaagaggcaggatcccgatcgcgagagagcacagtttcatgtccgcagtgcagccggttgcagcttggccagctcagccaagcgccagcaagccagctgcagcaatgccagcacgccagcaagcagcaggatccgatcgcctcgtttcatcagccgctaccaatttcacggcagtacagaccgatttacgatgatcagctttatcaatcaagggttgtttctgtaatatcaccgtcgatctgcgccc
catcgttacgccgcggcgaggacgagccgatctccagacagggacaggtctctgcagctgcgcatgctggaaaacgtgcagacagtgaccccgcagcctcgagcgctcagctgagcccatcagctgagcgcgcagtggtcttgtcaccgctggaatcctggcgaaaggatccctgtgcaggacaagcggcctgacgccggttcatgatgcaagtgctacaatttcttctcagcctcatcagccgctaccaatttcacggcagtgatcctcagccgcggagcgctctctgtcacgctggatgctgaatttctttcatcggtctgttcctcatcaggcctgatgatcctcagccgcggatcctcagccgcggtatttattcggcaaagat
gggtgggcctacttcactcgtcgaccgtggccgtgataccaggaaagtctacacaccaaggaaaccttggcacaccatcctgctacagcgtgcaatatcctgtacttggctgcaataatcctgtacttggctgcaaaaatccttgaaaaatcctgtactgcgaaaaagat
ggatatccagacgctatatggtcgatgtaatactcaaaaaaatactgtagttcattatgtgctgtgtctcttcattatgctaagtgaaccttcatttgaagctggccgaatctacccgactgaaacagc
ctccgtttctatcgctcgcaaactcttgaaggcttcgcgtatacttttcaaagatgatcaacgcagcgattccctccgcacaggatgatattatctcgcacaggtacttccgcacagttattccggcagttattccggcgcaaa
ctcattttcgccaaaagtggcctatcgtccccagcagaaccagatttatttattctcgaaggtgtctgttctcatcaggctcctgtttctgttcctcatcaggctgatgatcctcggaattattcggcgcgga
gtgtggcgggtgatgctgccaactactgatttagtgtgatgtgtttggagtgtttgaggctcctgatgtaatctcatgagctcatcatgaatggcgatatcctcggcagcagcgcgggga
tcctgcatccggaggtcttcgcccccaaagatggtgaaggatccctaggctgacttcactctctagctgtgtcaacatcctcaaccctcaaccgccccgtagcgagttgttgccg
gacccgtagaattgactcctcaataatcgctagagagctgctctgtcacaagcagataccaaacaaacatcggatcgccagacgcagcagctgcagagtcttgacgaactgctgaaaaactgtctagggttgcgtgattgggttgccctgagagtctgtcatcagctgatctaacgctcagcttttcgcc
gatcaagagctgccaacctccttcgccgaaagtaacggctcaaaaataactctctttcttctcagtgcgagttcaatatctgtcaccctatcgcactcatcagctgtgctcctatccaaggctgcctccctgagccaccctaaccaccgttgacaatcagcagcaggccaaaatacgcaatcagctcgtatccaccacactatgaggagcaccgagcctctgatgtatccacactgccaagatatccacttgcccagggattgcatctctgaccggcagcaaagacgatagttaaac
gaaagcgcccagcgcttcccccgaagggagaaaggcgcggaaggcggacggacaggatccggtaagcgggcaagcgcaggatcaccggaagcaccgagcagcaggagcgcgaagtcaagaa
```

-continued

Sequences:

ctggtatccttatagtcctcggttcgccacctctgactgagctgattttgtgatgctcgtcaggggggcggagcctatgaaaacgccagcaacgg
cctttacggttcctggccttctgcctactgtgaaatgtctcacatgttcttcctgcgttactctgttgataaccgtataaccgccttgagtgagcgataccgc
tcgcccagccgaccgacgaggagcgcagcagtcagtgacggcgaggagagcgcaacgcaaaccgctctcccgcgttgcgtgcgattcattaa
gcagctgcacgcagaggttccgactggagaagcgggcagtgaaagcgggacagggaggagcgcaattaatgtgaagcgaatgctgatctactaaccgagcga
gctacgtcgagcgaaatcaacgacaggctacacaccaccgccgttcaacagccgattctacacgacagtcacgccctgaagctgacgaccaagcaagtcgg
tgtactgcgaaatcaacgacgagctactacacagaccgattcttcatgcgaactcgaactcgaacatcgaacctggccgtggacgctccacctgaagcagacaagtcgg
tcgtctaaccggtactccgacggtcacgatatcttcatgcgaactggcgtgaccgtccaatcatccgccaatcgaaggcaagaactacgagatcggcatc
aaggcgagtacttcgacggcactcgacaagctcgggcatcccacctctcagatcgacgcgatcttccagatcgacaggaacaagcagcaaccgcgccagaagtcgacgattgcgtg
acatcacctgctaagaagtcttgggcactgagtctcgacgtatgacccaagtatgacgtcaagcccgaaccacctgtcaagctgagcaccaca
tactcgcaaacccgtacgcaaggatgcgaccgagtgcgaacaagaaggacaaccagtcgaccagacaactgacccgagtcgaccaactcctcgccgtcgactaccacgcaacc
cctgcgggcgagctgaaccagtggcgtggcgtgggtggtctacaagtgcagagcagcattcaacaaaggcagcaactcgacaacgttcggcaactgactcggtacca
caagtgcattgccagcaactcctgagccgtacgacggttgatgtgctatgtgacacgcaaacttcaccgccaagtgcttctgatcgctgacgttgaacgc
gggcattgccagcaaatccctgagccgtacgacggttgatgtgacacgcaaactctgcagtacattcacccctaaagt
aaaaaccgcacccaggtgaaacggtaaaacatgacaatcgatcttgacaattcatcatcggctcgtatataatgtgaattgagccgataacaattcacctaagt
taatattaaggaggtcaaaatgagacaatgatgagccgttcgtgtgatcagcagcacaacgtcgacgcaacgatacagtcgagcgcacaccgctga
catcaaccgttgattccgccctgaaaagtcggcacttccggctgtgtgacagtggacccgcatgtgctgactgtctggctgcagcgccgacctccccctgtgca
aacctgggccaatatggtcacttcggccaccgtcgcctgtcgcaccatccaaagcatcaacagcccagcagcagccaagtgcgaccaagccacagttcggg
aggcaggccagtcgactcgagcagcaagcagccacgagcagccaggctacgcgcctcccaacaacctggccgaacctggcgcatgcgtcgtcgagatggccag
aaatcgaattcgcgacatcgagcgcgtggctgggcgatatcaacgacgcagtgagacaaaaagccgtaattgcgaatcgacggtgcttaacaccctgaattcggaccgcagcccctgtcgaatcgacgctgt
ggccactgctcccgaccatatccagacgtcgatctcgcagacctgttcggcatgtcgcagaaaccctctgtacacacgcagccaatccgccagcctggaatccgacctggt
gtccggtgcttcaccgcggaccctgatggtcgtcggacccagcatgagcgcagcagttgatgtcacaactgacgccgttcctggggccaccagtcaaatg
ccgaagcctggccaagttggaagagcaacccccgggtggagagaccatctgctacgccagtctctgtacgctgcgtacgttccatgttgtacaagctcctggactca
actgccgtcatgatcgaaggaacatcgggagtcgacgccatcaactgctgagctcagaacaactcaatcgagcgacagaggagctgcaacacgcctactctgggctctgcaccagcggcagc
tccagtcagactatcgaatgtgtgatctgtgtacaactggtctcgacaactaacagcaggagatgcccgcgccctgatccgaccgacgtgtgatgcagtctcgaaggccagcctggg
gtggtttcgacaatgaacttcgacggtgtttcgaccagggtcgaggagttcgtcgccaggcgtggtcgtgctggtggtgaagatgat
tctcaaggcgtgaaccatgttcatcagcgaaccagatcaacgacagaattcgaagacctgaagaacgacgccgccaaccgccattctgct
gctgactgtatatcaaaagcagaaacaactcacagccaccaccaccaaagaggttacactatggtttcatcgtcgccagcatcactgggcttcagcgaagactgca
aaagcagccaccgcacagtctcattcccacccacgacgcccagtcaggtccgctgtatcgtcggtgcatcctgttggccctggtcaggagtcttgccca
ggaagccgaattcatcatgtccggaaccagatcttgcgtgtcgcgtcggaaacgctctggtcgccgagaacaaggtgg
tgatcgcaaccagctcgatccgaccagatcctcgcgagaagaatcaaggcaccgaaggtcctcgctggtgccctgtccggtgtgag
tgcgccaagcggccgggcgcgaccctgagcatcatgttggtctgcgcaaccgagcatcatgcgctagacggtctgaccctggctgtcgaagacatcaccgcg
tcggtggcaacggtcgacgcagcaggttgcgcaagtgcgaagctggggctcgcaccctgaacatgcgcaaggtgcctgttccgccaagaac
acggccaccgccgcagtgacgcgcagagagagccctgagcgtgggccaaggctctccgctgcgccagaccgtgcaggcagtcgcctcgccatcgacggttccggtcgtcgg
gaagttcgaccaactgcaacgagccaaggaccagaggactccaagaagctcgagctccgagagtgactccgcccacctcaacgagtcaagccaagaagaagctcccaccctggaccctt
gcctccgcacctcctcctgtcacccgcgatcctgccctgcggcaccggagcccagttccagccacacaactctcgatcctcgacgagttgtt
caacctcgccaaggccctgggcgggccgtcggaccactggaccactggccacatggccaacatggccacgacgaacctcggagacatggccacgaactag
t SEQ ID NO: 3
pMFL160 (fpvA::Ptac::gcl-hyi-glxR) 5'-3' sequence (SEQ ID NO: 3)
agtcaaaagcctccgaccgagggtttgactcatgatgctcagatgctgccagtgctgcagtgcctgcctgaccaccatgctgcctcatcggcct
cctgatgatccgaaccatgccaattgaagtcatggtcactccggatcaccgcaagtgcaccccggcttgctcaagtgcgtgcaaggcgacac
ccggtcatccagaggtcaccgaggtcgcaatcagcagtcaagcacctcagtaagatagccggagcgctcagcaggagttcccggtcatg
ccgcaccgggcggcgcattgctggtggtagaaccactccagggctgccttcaaggatcgcgcttcaagcaggcgctgcagcgcgccaactggcagccgatcgg
tcaccgggtagatcattacctcaagggctcgggtcagccagggtgccagcagcagatcgccgtctgctgccaccggcagcagcaccactgagtcgccca
gccgcagcgggcagccggagccgcggcaatccgccgcacccgcatccgcgccaggtccagttccagcacagcagttccagcagtcccatgcgccagctaccactgaggctgccggccgcaat aact
gccgccagccggagccggcaactcaaggcccggcgcaccgccagcaggtccagttccagcacagttccagcagtcccatgctgaatcgacagcgttccagaccaccagtggtcgccgcg -continued Sequences:

```
ccatcaggtacagcagcgcgcgccagtcaggtcgagcggctgcgcggcgggcagcaagcgcaccggcaaggtatggccatcgggtgtcaacgaaa
ggtcgctgatcgcagtccggctccgtcgtccgcctcacccagtgccaatccagcccgagactcttcgaactgcgcccgtccgtccgccaggcatgatggcagca
cctgcgcggctccggtcccgctccaccagttgcagtaggccgccaggttcaggacatgttcgattccagagggccctagttcagctgccgc
aagcactcagggcgcaagggctgtcaaaggaggaagcggaacaccagtccgcagaaacagctgctgaccccgatgatgtcagtcagctggtatct
ggcaagtcagggaaaacgcaaggacaaggagaaggcaggtagcttgcagtgggcttacagcgaacagcgccggcgtttcttgtgacagcaggcgg
aattgccagctgggcgcctctggtaaggttggaagtgggaagccctgcaaagtaaactggatggctgctcctgccgcaaggactgcccaggatctg
atcaagagacaggatgaggctgcttcgatggtcgatcgcgccgtgtccgccagcgtccagcgcaggagcgccggttctcttgcgacggccaggagt tgggagaggctattcggctatgactgggcac
gacaggcagcgggccgtatcgtgcttggctggtcgcacgggtgttcgcacgcagtctgtgctccgacgtctgtcactgaagtgcgcttggggctatt tgggcgaa
gtcgcggaggctcctccctccgactgtcctctccgagaaagatcatcgtcatcgtgacgctgcatcatggcatccggctgactcggctaccctg cc
atccgaccaccaagcgaaacatcgcatcgagcgacgtactcggagagccgttctgctgctgtgatcagggatagtctgacgagacatcgggcttcgc
cagccgaactgttcgccaggctcatcgactgtggccgctggtgtggtgcgaccgctatcagagacagctgttgtaccgttgctcgatatctgcgaatggct
gcctctcctcgcttcacgtctcgcgctccgatcgcgcacctacgctgacgccgcctctaagccgtctacgagtccttcggggtctcagtgcagagg
gaccgtcctccgcactgctacgttcgcttcgcctacgtcgaatttctgaatgtgataatattcaaaatgatgagatcctcgagcgcggtgttcgtccatcaaaaa
atcgatcctttaaccatcacatatatccgtccttcactattatgcgagaaacagatattttctgaatgtgattaaaaagcaactttatgccatg
caacagaaactataaaatacagagatgaaagaaacagatgattttatgtcgcgtacaaatagctttcaatcctttatgattttcatcaaacaa
gaggaaaatagaacgtcaatccaaacagagtctaaaacagagtctgaaatgaggctataagataattgcgcggggtttgtactgataaagcaggcaagacctaaaat
gtgtaaaggcaaagtgtatcttgccgctgaatttagtcttattgctgcatatcttgcatcctgccaacctgctaacctgctaacctgctgccaggcgggcggaagagc
agaccgctacacagtactacacaaaagggacactgaacgatgaacaatcatttgaagacatttactaacctcgatatcctagtgcactgcctgcag
gagcgcaactcaagcgttgcgaagagaaacgaaaccataaggaaacatgaaccctatacaaccgatgaacatccgatgcatcacgatatcgcaaatccctgaa
aacaaaatgaaaatgaaaaatcaagtttgattcgtccacacatatctctcgcaaaaggcctggacgtttgggacagtggccatacaaa
agctgaccattgcaaaatctgcaactttctttgcaatatcgcaaaatccgaatccatgcaggagagagatgcagcagatcttatcatcaaaa
atcgatcctttcattgacagtggaaaaactgtggcgcgctttaaagacagcgacaaatcgacgaatgattctatcctaaagaccaaacaag
agtgtcaggttcagtcagcacatttacatcgacgaaatccgttatctctacgattttctacggccaaccaaactgcaactgcaacagtt
aatgtcagcggacagctcttgaactcaacggtcgagaggattctaaatcaattcttgacggtgacgaaaaacgtacagccaatgccacaatgcttatgcacgt catcg
aacgatcagcactagacgacagctctgacactcttgaactcaacggtcgagaggatctaaatcaacggtgacgaaaaacgtacagccaatgccacaatgcttatgcacgt catcg
atgaaggccactaccaaggcgaagaatcttatttaacaagacatctatatgccaaagccagctagctaagcaacaactggaact
gaagattgcaccgaggctagcaaacggctgtctcgttagattgagctaaacgatgatttaacaactgtcacactgactccggctagcaagggtaactatgactctaac
aaacgacagcgctgaattgaacgcgaacgttctcttaaaatgaacgaactggtctctcatctgaactccggacgaaaatgatcaaaaagcgtagaggccttgatcctaactatgtaact ct
acattacatgcttggttatgttctaattcttaactgccaagacagatctgaaactgtctgttaaaaatggatctgttttgttaaaatgatcctgatcctacagtgaacct
ttactactcaccctgctacccaagccaagaggaacaatctcgtatacagaacagaagaccttcgtcagcgctaacacaactcaagcgttgc
gccagcttcctgctgaacatcaagcaagaacactcgttgcaagacagcatcctgaacaagacatcaaagtcaatgacaggcaaatataaaacgcaaaga
aaatgccgatgggctaccagcgagcaaatgaccgagcaaggtatcgacgaggcaggttatgcagggactatgaagaaaaagttggggcttcga
atcgttccggagcctcccggcgacgtgcacgactgtaaggctgctagcacctgaaggcgtcacgacgcctgagtcatcaagatgaagcatcatcatgccgc
gccgcgcccttccaatcgctctcgcttgcgcttgcgaagacagcaaggtcaatattggctcgcacccctcttgcttctacgtcagcgcctcgcctgccctc
atctgttcacggcggtgcagaagcctagcccgtcctaagagcaggccagggactggccctgaccttgcgaataggcgaaggactaaggtgggagcaaatatcttcaggaccaccgctcgcg
ggtggcctacttcacctcgcccgcgctatcctctgaacaaaggcgagaagagcagtccacgactccgctcaagccttgcaaatcgtatcgtgcgaaaaagatg
aaatgccgatgggctatcataatgaccctcgagcaggttatgccgagcaggttatgccgaggcagttatgccgaccaaggagaaggttcgcgacactgagcagcca
atcgtttccgagacctcggcgacgctccatgatgctggtgagcctgcctggcctgagccctgctgcctggcctgctgctgagttgtttcatgctggccatcgcccctgccggcctggccgaccgccgccgc gccgcgcccttcctcaatcgctcgtcgtgtcttcgaagccttgatacacaatgccctaggaccaatatacgccgtagtgatcttcattt gctgttctctacatcagcagtgcggcgaatactcgataactcaaaaatagatatgtagggagcgtagtttccgcaatatcactcttcatacccgatcaacgt
cattttcgccaaagtgttcggcaatctgcggacaggattattattccgcagcaggttactgcgccctcgccgaccaccaggtattatcggccaaag
tgcgtcggtgatgtgctacacgctgtagtgaagatcctttgagtgcgaagatctcatgaatctcatgacccctaaacttccagtgaggatgatcttctccaagcttt ctaggttcagc
ctcatcgtgagtgctttccgccacccccgaaaaggatcctttggatctccgcgctaatctcgtgctcatgccatgcacccaggattcctactgagctgcgg
gatcaggctaagctagcgggtttgattcgctgggatcccaagcagggtactcccttgaacttgcatagctccaggcaaaaacaccacacgcaactga aagaagc
gcgaggctgaaagtctaaaagtaaaaaacaaataaagacaaatcccttgataactatcaactagtaaaatcggaaacacttaggaggggcatca
aaaggccacgctcccgaggagaagcggaagggcgaaaggggcggacaggtatccggtaagggcgtaagcgcaggagcgcacgagggagcagtcctg tcaggagtctgccaggagcagccaggagcggcccacagttccggcctatctagcgcccgccggattcctgccggaaaaccggggttcaaacacaggaaacgcctatctgggagcttc gtcagctcgagagcaggcacgcaaccggctgggcgaaggcggatcccagcaaaaacgacagcgaggccagcacgatatga
tggtatctttatagtcctgtcgggtttcgccacccctgacgagcatcacaaaaatcgacgctcaagtcagaggtggcgaaacccgacaggactataaa
```

-continued

Sequences:

```
cttttacggttcctggcctttgtggctcttcctgcatgtcttcctgcgttatccctgattcgtgataacgtattaccgccttgagtgagcgatacogct
cgccgcagccgaaccgagccgacgagccgagtcagtgacgcgaggaaagcgacgaagccgcaattaacgcctcccccgcgttggccgatcattaat
gcagtggacgacaggttcccgactggaaagcgggcagtgagcgcaacgcaattaatgtgagttagagcgcaatcgatgtatctacaacctgagcgag
cacgtcgagcaggaggggcgtactgccaccacccgcctgaactgcgcaaagctcctggtgcacgctggactggtacgaccaacaagtcggt
gtacagccagtcaacgacggctactacaccagcgattactaccaagtcaccgcaaactaccacaaactaccggagtgatctacgacctgaccgaccactt
cggtctacgccagtccagcgatatcttcatgccgaactggccgcgttcatcatcggccaaacggccgcaggaagcttcaccggccaagatcgatcga
agggcgagtcacttcgacggtgccactcaaggctacggcagccgggcgatcttcagatgacggtatgggcgcagcgtatggcccaatgcccccaatgctta
atccctgtacgaacaagttacgccgacactgcaaggtacgcaccagcaaaccgaagcgaccaacaccaagtcgacgacctgcaagtcggcgcaggctaccactacaca
ctcgcaaaccaagttacccgaagtccaagggagaccttctgaaaatgcgtccagaacgtcacaccacaactcggccaactacccagaatgacgatcat
ttgccgggcagctcctatgacgctgatgtgcgtaaccgctatgtgcgggtaaccgctgcaagcacacctgaacactcgcctaaaactgaacacgatac
agtcgacatacgcggtagtgtcggtatggctccgacgcagcgtcggctacaccgatcgcaaccctgaacctcaaccgccgaagtactcacactctagaga
gcattgccagcagcaactcctggagccctgaatcgagctgtgcaattgacatatcatcgctcgtataatgtggaattgtgagcggataacactcagagaga
aaaacgcaccaccaacgtgctttttgaatctgagcttgaattcacagcgcaactcaccgcaagttcaaagtcagtctcaccgtgagcgg
ggaaggacagctatggacgccagcaaatgagagaactgagcgccttgcatgcggccaatgagtatcccggggctccgctcgatcaaacgtcctcgat
cgtgatcggccctgaaaaagcggttagcatcgtcgatcggtcgagctcacggcctcaaccccgtcagtgtcgaatggcctccgctaactgccaaccgg
gcaacatcgtgtggccgactccgcctgccagcaatgtgccactggaccacgcaccgacctgtcgaccaagctcccgactgtcggccactgcgcaagtc
cagggccacatgcctgccgcacagcccggctctccagacttcctcaagcccatgcgctcgatgatcgctcacccagcctggtgcaagctgacgtcagg
tgcgggccttacgcgtcatgcgtgcggcctctcagtgatcaggccggcactgcgtgatcaaggagaatctgaccaagctggcaccagcgcgcaagtcgaa
ccagtgcatcgacgctgaccgacccggctcacccgcccaggccctgaattcctgaagccggcgctgccccttcccgcgtacccgcgcaagtcgacaat
gcctagcgatacgactgagggcgcatcaaccgacgatcgtacaacctcaaccctagatgtggctcgacaaccgcccaactgtcagttggccactatttctc
caccatccgacgaccgcaccagcagatggctcggccaagtccctgatgtccccgaagtcatggtccgcgatccgcaaatccaagcggccagctacctctccgtccagtgtc
atgaagccagctctgcgtcaactgccgttgaaacatcaactgccctacgagctgccacctacgtgtgcgaccacgcatgacgtgcgcgtgcggctgagcgagaatcgc
gacatgattactgtgtacaactggcgttcgaaccatctgcctgcatctgtcgaaggtcgacacgctgtggtcggctgaagctcaagg
ccatcgtgttcgagccagcagaatgcccctgcatcaaggcacagaaggccagagctccagcctcccgtgcgtgccgcgtggtggtgaatgatctcgagc
gtgtgaccaacattccatggccaccgagatcggccacagattccaacgaattcaaccgaagacccttgccacatgggcctcatttcgtctgcgtgact
gatccgccgacccgcggccctggggcctcagcacgaaggacagcaaccatgccgccttgcctcatcgttcaaccgaccatcagccagcagtgaggccaac
cctgcccgcttcaaggctgccgcgatcgtgttcagggcgcgaatacctgttccgtcgacttcagcgtccaaccatcgaacaggttccgtgcggtgtc
ggcctgaccaaggtgctgttcaacctgcgccggccggctcaacatcaccaaggtacgcggtatacctccgcaccagacccggatcgccaccgtccggtaagacctt
caagccatcgaatgaccgcccaaggtcggccatggcatcagcctgcccaaaggccaccgcccgatgtgtcgcggggagcccctccacagg
cgtcgaacgccctggccctacgcgccgcacgagcctcgccgaggccggcggcagaccccgggatcgccggaaggccatggcctctcaacctgaactgaacac
accccagccaggccctgaaatcccggcgaagtggcgacaaacctgtccctgcaataccactaccacatccggttcatcggcatccggcaagcgtcgca
ccaaaagccaggccaccggtgagactacaaagaggtaactttctcatggccgacaccccaggcgtcctgtctggtgaaaacgcgtctgtgtggagaaacagg
gaacaactcggacccctcgatggctgccgcaaggccaacatcatcttcgccggaaagataagcttcgccgagaagatcaaggcctcacctgcccgagccggtg
ggcaagctttgctgagaactacagaaggtaatcttcatgcctaaaatcggttcatggcttcatcggccgcaagccatggccatggctcagaaggttg
tgcaaaagcagtcaaccctgcacacgttcattttcaccaccagcctgcgccaggcgtgcccatacggctgccacgccctccgcaacatggctcagaaggttg
ccccaggaagccagtcatcatcgtcatgtccgcaccgccaccaagagcctcgccgaagatcttcgccgcccttcgagcctggccaccgccgaaaacggctgcccgaacaag
gtgtgatcggccaagggccgccaccgggaccgagccatcatggttggtgcctgccacctcgacctgtcttcgagacctgagccatggccagaagatcac
gaagtcggccaaggcgccctggcgacctggccaagcctgatcagcggcatacgaacctgtccctggaaagcgccgagcgacgcatggcctcaaggcccttcg
ccgcgtgcggtgacgccaaggtgacgccaggatccggccaaggctgccaaccgagctgtgtccgtcaccgtgagcctgccgttcgaacagccgcgacgcaa
gaacaggctggcggcctgaccaaggctgccgaagcactgatggccctgaagctcgagaccaaccaaccgagcgtgtccaatgccctcagaa
acccagctcggcatcaacgtcaccagacgccagcctgaacctggcgcacactcccagagcctggagcctggagcctggccggagccgaacggaacatggccggagcacaactggaccgcgaacaactggaccgccagcaa
gtgttcaacacctgcgcaggcctggggcggcccctgggcgggccactcggacctgggagccctggagcctggagcgacacatggcgacactggccaact
aactagt
```

SEQ ID NO: 4
pMFL161 (fpvA::P<sub>tac</sub>::gcl-hyi-glxR-ttuD-pykF) 5'-3' sequence (SEQ ID NO: 4)

```
agtcaaaagcctccgaccggaggctttgactcatggatgcctgaaaggctccctacagatgtgctgcagtgcctcgcaccatgccaggcctcatcggctc
ctcgatgatgaacccatacgcatgaagtcacttccgggatcatggtcactccggagcctcaagtgcaccgcaccccgacgcttgctccagtgtcatggcgacacc
tggtcatgcagcggtcgcactcggcactcagtgcggcaatcagtcaggtcaggtgcactgttgtgtggcgacgcagtgcatcgcaagtgcactgctgcc
ggcaccgtggcgtattgctgtgtagaaccactccaggtgcggcttcaagcaggtctgcgctcgcgcagtcgccgcagcaactggttgctggcgcgatcgcatcgctc
acccggtagatcattacctcgaggcgcgtcgatcgaggcgcgcagtgccgcagttggctgcagaatggtggccactcatctactggtccagtcgtgcccac
caccgccagtcgtgctgcgcaattcctcaccatccgccaggtcaccaagtggtcatgcgaacggccagccaccctagcgcg
gccaccgtgggtacagcagccgcgcggcaacaagcgcggcctgcaagcaggcacaggtgcaccggtacaagccagtgcatgccggtggtcaacg
aaagtgcgtgatgcgtgctgctgcctccgcagttgagctaggccgccaggtgcaggactcttcgaacctgtcgattctccagaggggccccagctggggc
agcaccttgccgctgcctcgtgggtcagcgccttgctcaccggtccttgccgcagcagatctgtcgatctccaagtgaatcgcagtcagctggct
ccgcaagcactcaagggcaagctctaagaagaacagtagtcaagcgcagtaccagctgcaaagctagcgagaggccatagagattcagctactgggct
atctgacaagcaagggaaaacgcaagcgcaaagagaacaagcaagctgttcagtgaagcccctcttcgtgccaagatctgatgccgcaggcagaagat
ggaattgcagctgggcgcccctcggtaaggttggaagcgtccgatgtgcaagaaactggaatccgcaaaagtcgatgatcgtcctgccgcaggataccagcgcagatct
gatcaagagacaggagagatcgttcgcatgattgaacaaagatggattgcacgcaggttctcacagcagcaggtgtcgcgtctggactgatgactggcaca
acagacaatgcgtcttcatgccgcggccagccgcctccagcagccagccagcggcaccagctcgcagagacgtccgctgtcaaatgaactccaaga
cgaggcagccgctctcgcgggctggctcatcaacttgctcatgcgaaagtactccataggctggctatcggcgtatgcctttcagcaggcctatgggaagt
gcccgggcaggattcctctgcatcaatgctgagacagctgccgtactcggatggaaggcggccatcgatcaaggcacatcggcctacctgcccattc
acaccaagccagcaaacatgcgactttccttcaagaatcgcctatattatgcccatgtcccatgatgctgccaatatcatgtgaaaatgccgctttt
cgtccaattaaaaatactctcttgccaaaggcgcgaggttgggaccgcttgggacgtgtgacaactgtgaccatcacgcgtcaccactacgcgtt
ctttgcattagccggagatcctaaaaatggatgacaaactggaatcttcattggacagttgacaactggcgaaactcgttattctac
ttaaagacagcgacaaattcgataccgtaaacattacgacaacaacaagcaatcgcaaggatggccgtcaggtcaaggaaatctgacgggaaaatccgtttattctac
actgattcctccggtaacgacgtaaacacttacggcaaacaatcgcgggttcaatgctgccaaaaacctttgaacatcaacggtgaggtgagggtataaatc
aatctttgacgctgacgagaaaacgtcatcaaattaccgagtcatcgcatcagcatccagcagcagcaaccatgccgtgaaagactccactacgtag
aagataagccacaagccaaaatcaacgttgccggccgagttcctgctgaacaagctgaacttgcaaagcgcagagtatgccgaatgccctggaagtactagcaaagcacatc
attctccgcaaggagcgattgatgcatcaacaagcaagcccttgcaaaacgacgcctgccgatggtacccgttcgattcactgactccgc
accgaaaagcgctgaagcaatcctctaagaaagcgaggccgatgtacaagtggacacgaaactggaaaaatcgccaaatgcaaatgccctgtgtt
ggctcaaaatgacctcacgggatacgtactctcaaatcgacactgtcctcacggtttcagctcaactaacaaaactggccttggttgcacttctgtc
aaactttcccgtgacgatgacgaaaacgcaaaaaaacttcgcgcccaaaaccaagcaatgcatccagcaatcatgcaataaacaagacaaattaccagt
aagataaaggccacaagccttgcgcacaggtcctgctgaacaacagtcgaggtgggctaccgcatcaacgagatttcgattctcactgactccgc
ctatgaaaggttgggcttcggaatcgttcccggcccgcgcctctatgaccggacggtgcatagcggcacacagtcctatggcccgaccaacacctgat
gcggagcctcatcgcccgctgccctggtaccgcgggcctagcccgctcctctgcagacgcagattcgaagcaatgtgcctcaggaagaccgtaccggttgtggatcggcgtagagatctgattggtacagcacctgt
atcacgccattccgtgcagcaggtcgcgggcctactccatctccctggccagccttgcgaccgcgtcgaccgcagtaccaggggaaaaaaaatctggatatctgc
gaaggccaaccccgccgcctgggtgtgcctcatctcaccgtctacacccaaggtaaaggtgtaccgcgcacggtgcggtgcgcgaacctttgtgcaaaatccgtat
atcgtgcaaaaggatctaccaaatagtacaggtgaaattacgaactagaggaccagcggagaagcgatgcaaagcgtcccggtatatgcggagccaaacactcttggcg
gactggaagcgcaatgggaaattactaagcagggaaatcacctgccgatgccgctccttttgccaagatgccgcctccgtatcaacaggaccaagg
agtgatcattattcgtatgtgtgtgaagttgaactgctaccatcatcgccaaaagtggccgatctcatttcgccaagtcccggatcaacagcccatctggatttcgaggtctc
attattttatccggaagtgtatctcgcccagtggtatccggcggcgtcagtagtcttatcattatggtgaaagttggacctcttactgcgccgatcaccg
```

-continued

Sequences:

```
tctcattttcgccaaaagtggccaagggcttccggtatcaacaggacaccaggattttattctgcgaagtgatcttcgtcaggtattattcggcaaagtg
cgtcggtgatgctgccaactactgattagtgtatgatggtgttttgaggtgctccagtggctcttcttcatcaggctgatgatccccagcgcgggatctcat
gctggagttcttcgccaccccaaaagatctagttgaagatccttttgataatctcatgacaaaatccctaactgagtttcgttcctgaccgtcagacccgt
agaaagatcaaaggatcctcttgagatctctttttctgcggctaatgctgcttgcaacaaaaacaccgctaccagcggtggtttgtttgccggatcaagagct
accaactctttttcgaaggtaactggcttcagagagcgcagtaccaaatactgtctttcagtagccgtagttaggcaccacttcaagaacttcgtgcaccgc
ctacatccccgctctgcatgtcgtcacacagccagcttcgagcgaacactacaccgaactcgagataactcagagcgtgagctgaacgcggccacgcc
gtcggctgaacggggtcgtgcacacaggtatccggtaaggcaggtccgtaagcggcaggtgcgaagcgaggagttcaggggaaacgcctgtatcttatagttc
ccgaaggggagaaaggcggacaggtatccggtaaggcgagcaggtttgtgatgctgtcagggtccgcaggggccagtggtcctgtctataccgctcttttttacgttcctggcc
tgctgggtttcgcctttgccttgaccatgtcttcttcctgctgcttctggaatactcgcgtgtcaataccgtatacccgcttgagtgagcgagtacccgcgccgaacgaccga
gcgagcgagtcagtgagcgaggagcagtgagcgcaagcgccataatgagccaacgcaatttaatgagtagaagcggaagaagcggaagcccatacacactggcgacaggttc
ccgactgaaagcgggcagtgagcgcaacgcgctgaacactcgtgaaagtcatcctggtgcacgcctgatgatatcacaactggtgtacgcgacactcaaaggc
tactacaccagcagcagattacaagccggtatccaggccggatattacaccgatctgacaacaagtcgggtgactacaccgtgtacgcctgctaccaccgata
tcttcatgcgcaatcggaactggtgtgatccgtccatcatccgcccaatgcaagaccaaatacgagatcggcatcaaggcgagtactccaaggcgagtactcgacggcact
caacgccagcggcgatctccagatcgacaggaaaccgccccagaagttcaaccagaagtttgtcgacatcacctgtcgaaaccaagtacctcggca
agtacgcaccacgttatcgacttgagtgatggcgcagttacccctcaacctactggcaagtcggccaacttactcgaaaccaagtacctacgaaggatacgaaggat
gccgacaagaagcagaccgtatgccacaggctcagcaccacctaaaaggcagcgaacaagcgtcgacccagtgccaccatcagactcgatcaccagtgagtgccagcagctggcg
cgtgggcggtcaacgtatgtgcaggaacctggttgatgctgcaactcttcaacagccagcagcagcactagctcgacaaggccggcaatcaaggccgaggaccgt
gtcggctacaaggctatggtgaccaacgtcaacttctaccatgcacaaccgcttctgatccgctgaacctcgaggtgtgcacagatgagcagcgaacatcaaccgcgatgcagcgatacagagaccggcagcgtcgtgtccggtttttgaattc
agcgtcgtatggtgaccaacattaatcatcggctgtaattgtgaattgagcggataaccaattcacaacttcacctagaaggacagcttatgagaggacagcaatcga
tgcagccgttctgtctcggtcatgccgtgaaggtgtagatacgcgtcggcatgcgcgaggctgcacatgacacaggtgctatcggcctgaaaaagtcggtggcatcg
atcgctcctcgcgtcaccacgtatcagatgccctgtacagtgctccgagtctctgtcagtggcgtcgcctatacactggccagcgcgccggccagccacagtgtgcagcggcctccggcctg
ccgcacccggatcaggtgcaccaacatcagcacttcggcctgagcactatcctcaccttaccacagccgcatcggtggctcaggccgtaagtcggaggacagtctctgaagactt
ccagcgtctgaactgaacctcaagaagacccggtgctcgatcggagaagcagtcctgactgagcgccagccagctcaagggaccacggcctccggcaccgttctatgaa
atgcgtaccgcgccacaagccgtacaaggccgaaaacgcctgctccggcgcgagcgccaactgcgtatgacgctgcagtgagcccctactgacgtcacccacgtgacgtgccacagacacccgcaccacatcagcacacccgcgccacg
aaacgtccgccacaagctggcggaatccgcggaactgagcgcggccacctggaaggaccagcgccgccgccaccacgtatcccgcagcatcaccccgaccagcagattcggc
ccagtgacaagctgaattccgggactgcgcgaagcttccccgaccgcgtcaaacccgtgatcggcggagcaacatccgcggtgtggggcaaccacggctccggacctcgcggc
atggtcggctccacgactatggccaaggcggcaacctgcttcatgtcgtacaagctcggccactgctaacctgggcactcgtcggtaacctggccggcaacatccctgctgcct
ggcgtgtcaaagccgatcgcaaggcgaaggatggtcgcaggtgtggcgcctgatgacttcatgacgtacgaactccagtcgctcgaagctgaagcccagtcaacctg
gcactgggactgttcctgaagtgcctggaaagctccggagtgccgcgccggcaagtcaaggctgctgccaggctgcatggatgatgtacactggcgttcgagaacatcaa
tgcagcgcaagacccacctgacgaacgctcgacaagcgtgccggtcaagctcgtgttcgagccaggccacctgttctcggccaggccaggcagcggacacccgtctgcggcctg
ctcaccgacgcgactgcccaacctacggtcgcacctggcgtgtggcgccgttcgtgcccggtgggatttccgagcgtggaccaacattccatgggcaccggagtgtcaaccgcggtca
atcaaggccacagaagatggcccgaagagtccgcggtcgcgcgttcaagattccggcgagcttcgtgaccatcgaaaccgcagcgagatcaacggcggtca
acgaattcgaaacaccaccagtcgcccccacaaggccgtgaccgacgaccgcaactcatcgctgcgatgcgaaccgcatgcgcccctgcggcctcatcg
caaggagacaactcatgcctgggtacgcctcggccgtcaaggcctgcgacatcaagcagcaggttgggtgatttcaccgaacaggcaacgccccacggaacaggctgttcaagctgcgcctgatgcggttcagcggcg
tcgaataactgtccgtacggcgcctatcaccccgaccagcgaaggccgatctgacaaggccatgagtcgcttcaaggtgctgggcaatactcag
caaaggtgagcgcgtatcaccatcccaaggtcgacggtgtccgtcgtccggttccgtgacaggcgccatgaaggccgaatcgcaagggc
gtcaaggcccctgatcaagccggcggcaaccctccccaagcccggccaatccgaaggccgaacctgcgcgcacgcgctaagccgcaaggccccgccagcgacc
cgggatccgcctgcatgaaatcgaacagcgacccggctctactgaacatccccggcctctcactgaaccagcatccgcatccccagcaggccgaagtgggcagcg
acaacctgtcctgcaaatgatcgacatctaccaacatgagatcagcacacatcggaagctgatgcatcaacgcccgctgtaacgcccagaccatcagctggcc
gacacccggcgtgaaccaggacgccgatgaaccaacgcccccaaggccgtcgctggctgaacaccccaaggacgaactcggccgagaaccttgcccgagaagccatggccccccaag
gatccgccctgcatgaaatgatcgaacagcgacccggtgtcactgaccgcctcgtcggtcgtcggcgagcgccaaagcttctgctgagatatcacaattacaaagaggtaat
caccggccaaagccggcggcccatcggaccgacccggtgccaccacagccccagtctgaccgaccaaagctgaagctgcaaaggcccccaatcctgcaagccagtgggccagcg
ttctcatgctcgtaaatcggttcatcggccatcggccacgtgccgcgtgccttccgccaccgggctgcggccaccatggccggcccatcggccatgatcatccatcgttcatttccaccgacacg
ccgggccagccagccgaccttcgtcggcctggcctccgagcccgtcggccgacccgaaaccccaagcccggcttggcccggggagccccgagaaggcctgctgcccgcgaa
caggtcgaaagcgtcctgttcggtgaaacggccggggaaaacgggccgggtgtgccccaacaaggtggtgatcgacaaggtggtgatcgagtgatgatgagctgctcgatccgctcgattcgccaacgcccaccaaagc
```

-continued

Sequences:

```
cttcgccgagaagatcaaggctaccggtgccgctcacctggacgcgccgtgtcgcggtgtgaagtcggcgacctgagcatcatggttgtg
gctgccgccctccgacgccttcgctcgacgcgtttcgaagccatgggcgacgaacatcacccgtcgtggcaacgtgacggcgacctgccaaggtgc
caaccagatcattcgcctcgaaatcctcgaagtgcctgccgcccagcgtcacgcgcgctcgcgctggcaccttcgacccaggtccgtccaacctgcaccagaggaacctgaacct
gcgcctttgctcgtccgaaggaactggcatcaacctgccaaccactctccaatggcaacctgcccagcaatctgccccagccggcggcaactggac
cactcggcggctgatcaaaggcacatggcgagcactgcagagcaactcctccatccgcgacgacaactaaatcgttttagcctcactggctcttcgcgggtaaacccgtcct
accaaagaccaccgcacccctggttcggcctgcatgtaggaggcagttccagggggtttttgattctgcagaacaacataatggagcctgcatgtcggtcgatcgcaa
gagcaacaccgccccgaacgttcgacacagccgtcgaaccctacccgcaagctctcgaacctttgattctgcagaacaacataatggagcctgcatgtcggtcgatcgcaa
aacttctccgcgaactgcgccgacccggtaaacagcaaccctactgcccaacgccacacctgcgacctttccaaccctacgccacaggcgccaactg
gcgccgaaggccgcagccgcatggcgagtgtcgagaaaagcgccaagcgtctcacagtgctcaccggttacggcatgccacgggccaactg
cccagaagatcgaggtggtcgaagcgccgcaccccgtccggactccggctgggccgtgccctgcgccgaagcgtgctgaagtcggccacaaccaaaggctgtgaactgtgcagcagatcaacaaggctgtgctgacagaagatcaagaactgctgtgctcggcctggagctgcagcagatcaacaaggctgtgctgacactgctaca
aatccggccacatcgaagatgaatgctcggcgagatgcttcggtgcgcaaggcgggcgtccgtcgatcctcggcgcgatatctcgcagtggtcgagcaggcatgtcgagccggcgccatcttcgcct
ctatccattccgatgtaccgggcccgatggcgcgccagtaatcgacctgctgcgctcatcgactggtcatcgaagcgtcaagcctgaacaccgcccagatgaccgctcaagcgctgcgacctccaagcgtgcgctgcccggccactccagt
ctacaacatcgaagcgccaaagcggtcatcgactggtcatcgcgcggccaaatcgttcaacaacacgcccagccgtcaaagccgcgcagtaaacaccctggctgacctctgcggccgatgacccagatctcctcatgaccgcgccaagggctgaatcgcgaatcgcgaagcatcctcatgaccctgca
tgatgccaagtgtatcgcgcgatccggcaaatcgtcaacagtccggacccgagcgtccggtcgtcaaatcgttcaacaacacgcccagccgtcaaagccgtcaaagccgcgaagccgcgagccgcacctggtcgcgggggctacgagccggcgacgagcagccgcg
gcggcaatgccgtggggggcatcgcggtcgttttcatgaaaacgcggtgcttcatgaccgcctcatgcacgcagccgctgcgccaagcctgcaaccgcgaagcctcaccgaaggctgcgaaccgtcgccgtgaccgtgca
ccatgatggctcggaagaaaacgcgaccggtgccttcatgaccgcagtgatcctcgcctgatcgtgaacgacctcaaccgacgccatcaacaaagctcaccggctgccttcacggacgacctgctcggcctggagactcctgagactcctgaagactcctgaactcatt
aacggctacggcttcgcgcgactggtcgatgtgcaacagagcctcaacgacccgatatctcgcagtggtcgagcaggcctgcaaggccggggtaacaacatctttcgcct
atgagccgctgataaaaagttaagatcctgccctgcccagcttggcgctgctggatgtcgagctgcgcaaccgaggcgcctggtgactggcgacatgtcagcagcatgtcgcgccagtttgcgccagttcgagttgg
agaaccgcacccgaacggttcgccttggctggccaaatccagaacatcgagaaaatcgagacctgcgagactggcgacctgcgagactgcgcaaccatccgcagcaaccatctccgactggaggacccgatcatggcccgtgtggacc
cgaccgcgctaccgctgatgccaaatcagaagaacatcgagaagctgcatccgcagtggagcatcctcgcagcaaccatcctcgccgtgacgcagaacctcatggcgacctctacggagctgcatcctcgccgtgacgcagacctcatggcgacctgagctcatcggggcatcctcgccgcgacctacaggccgcagcagatgct
tgggcgtgaagctggtgcgcccgagagtgttctccgccaaccagcggtcgaagcgcccatgtgacaccgccaaggtcagcacggtgccaagccggtcagcagtgccctgcaaacaggtgcagcagatgct
cgagcgatgcgttctacccgctgaaggcgactggtgcgagagactccgagagactcatgcggccgccggtggcaaccaccggttcgagcgtggctgcaccacggctgcctcgatgcagccggcagcaaagagtcgaggctgccggcgccggcaccacggctgcaccacggctgcaccacgg
cctgggtgattccgctgtgcagccgagacgttgagaagccacgaggcgtgcagcagagcagactgcagcagatcatccgccaagctccagttgagaaccgccgagcggaaacggtgaaccggcctaccaggcgcaggggagttggggcctcg
aaggccgaaccgcacgtgcagccaccggcgacaaggccgtagcatcccagcagccgcatgcggccgaaccgaaccgcacccggagattgccccggcgcccgcatgccaagcatgccggcagccgctgaagcgtgcgacgtgctcaaccggctgccatcggt
acctgcgccgggcaacgtgcagcgaagcccaggcaactgcggtttcccaccgccgagattgccccggcgcccgcatgccaagcatgccggcagccgctgaagcgtgcgacgtgctcaaccggctgccatcggt
ggtcaacgaccgcctgcgtgcagccgggccgacaaggccgacgcagcggacgactaagcgctgcgagactttgatttgatctgaactagt
ctgccgcttcggcagccgggcacgtaacacgctgcgagactttgattctgaacctagaactagt
```

SEQ ID NO: 5
pSEVA234_gcl_glx (SEQ ID NO: 5)

```
  1 ttaattaatt gacaccatcg aatgtgcaa aaccttcgc ggtatgcat gatagcgcc
 61 ggaagagagt caattcaggg tgtgaatgt gaaaccagta acgttatacg atgtcgcaga
121 gtatgccggt gtctcttatc agaccgtttc cgcgtggtg aaccaggcca atgtcgtttc
181 tgcgaaaacg cgggaaaaag tggaagcggc gatgcggag ctgaattaca ttcccaaccg
241 cgtggcacaa caactggcgg gcaaacagtc gttgctgatt ggcgttgcca cctccagtct
301 ggccctgcac gcgccgtcgc aaattgtcgc ggcgattaaa tctcgcgccg atcaactggg
361 tgccagcgtg gtggtgtcga tggtagaacg aagcggcgtc gaagcctgta aagcggcggt
```

```
421   gcacaatctt ctcgcgcaac ggtcagtgg gctgatcatt aactatccgc tggatgacca
481   ggatgccatt gctgtggaag ctgcctgac taatgttccg gcgttatttc ttgatgtctc
541   tgaccagaca cccatcaaca gtattatttt ctcccatgaa gacggtacgc gactgggcgt
601   ggagcatctg gtcgcattgg gtcaccagca aatcgcctg ttagcgggcc cattaagttc
661   tgtctcggcg cgtctgcgtc tggctggctg gcataaatat ctcactcgca atcaaattca
721   gccgatagcg gaacgggaag gcgactggag tgccatgtcc ggtttcaac aaaccatgca
781   aatgctgaat gagggcatcg ttcccactgc gatgctggtt gccaacgatc agatgcgct
841   gggcgcaatg cgccattta ccgagtccgg gctgcgcgtt ggtgcggata tctcggtagt
901   gggatacgac gatcacgaag acagctcatg ttatatccg cgttaaccca ccatcaaaca
961   ggattttcgc ctgctgggc aaaccagcgt ggaccgcttg ctgcaactct ctcagggcca
1021  ggcggtgaag ggcaatcagc tgtgccgt ctcactgtg aaaagaaaaa ccaccctggc
1081  gcccaatacg caaaccgcct ctccccgcg gttggccgat tcattaatgc agctgcacg
1141  acaggtttcc cgactggaaa gcggcagtg agcgcaacgc aattaatgtg agttagcgcg
1201  aattgatctg gtttgacagc ttatcatcga ctgcacggtg caccaatgct tctggcgtca
1261  ggcagccatc ggaagctgtg gtatggctgt gcaggtcgta aatcattgca taatcgtgt
1321  cgctcaaggc gcactcccgt tctgataat gttttttgcg ccgacatcat aacggttctg
1381  gcaaatattc tgaaatgagc tgttgacaat taatcatccg gctcgtataa tgtgtggaat
1441  tgtgagcgga taacaatttc acaccctagg ccgtgccgc gcgaattcga gctcgctagg
1501  aggtcaaacc atgagcaat cgatgcagcc catgcagcc gttctgtca tgcgctgta
1561  aggtgtgat accggttcg gcatccggg ggctgccatc aaccgttgt attcggcct
1621  gaaaaagtc ggtggcatcg atcagtcct cgctcgtcac gtcgaagtg cctcgcacat
1681  ggccgaggc tacaccccg ccaaccggg caacatcgt gtgcatcg gcacttccgg
1741  ccctgccggc accggcgat tcaccggcc gtacagcc tcggccgact ccatcccgat
1801  tctgtcatc actgccagg cgccagtgc cgtctgcac aaggaagact tccagctgt
1861  cgacatcaac aacatcgtca agccagtgac caagtgggcg accaccgttc tggagccagg
1921  ccaggtgcct tacgccttcc agaaggcct ctatgaaatg cgtaccggcc gcccaggccc
```

-continued

Sequences:

```
1981  ggtgctgatc gacctgccgt tcgacgtgca gatggccgaa atcgaattcg acatcgacgc
2041  ctacgaaccg ctgcccgtgc acaaaccgtc cgccacacgt gtacaggccg aaaagccct
2101  ggccctgctc aatgacgccg agcgccact gctggtagcc ggtggcgca tcatcaacgc
2161  cgacgccagt gacaagctgg tcgaattcgc cgaactgacc ggcgtaccg tgatccgac
2221  cctgatggc tggggcacca tcccggacga ccacgcacag atggtcggca tggtcggct
2281  gcagacctcg caccgctatg gcaacgcaac cctgctgaaa tccgacctgg tgttcggtat
2341  cggtaaccgc tgggccaacc gccacaccgg ttccgtcgat gtctacaccg aaggccgcaa
2401  gttcgtcgac gtcacatcg aaccgaccca gatcggccgc gtgttcaccc cggacctggg
2461  catcgtttcc gatgctggta aggcacttga cgtgttcctg gaagtggccc gcgagtggaa
2521  agccgccggc aagtcaaat gccgcaaggc ctggctggaa gagtgccagg agcgcaagtc
2581  gagcctgcag cgcaagaccc acttcgacaa cgtgccgtc aagccgcagc gcgttcacga
2641  agaaatgaac caagtgttcg gcaaggacac ctgctacgtc agcaccatcg gcctgtcgca
2701  gattgcgcag gcgcagttcc tgcatgtgta caagcctgc cactgatca actgcggcca
2761  ggccggcccg ctgggctgga ccatccctgc tgcgctgggc gtggtcaaag ccgatccgaa
2821  gcgcaaggtt gtgcgctgt cgggtgacta cgacttccag gtgaacaacg ttcatgatcg aagaactggc
2881  ggtaggcgcc cagttcaacc tgccgtacgt cgacgtactg gtgaacaacg cctacctggg
2941  cctgatccgc caggcgcagc gtgcttcga catggattac tgtgtacaac tggcgttcga
3001  gaacattcaac tcgaccgacg ctgccaccta cgtgtcgac cacgtcgctg tggtcgaagg
3061  cctgggttgc aaggccatcc gtgttcga gccagcagaa atcgccctg ccctgatcaa
3121  ggcacagaag atgccgaag agttccgcgt gccggtggtg gttgaagtga ttctcgagcg
3181  tgtgaccaac atttccatgg gcaccgagat caacgcgtc aacgaattcg aagacctggc
3241  cctggtcggc aacgagcgc caacgccat ctgctgctg gactgatcgc ctgacgtcta
3301  gaataggagg tcaccagcta tggctaaaat cggtttcatc ggcaccggca ttcatgggcaa
3361  gcccatggct cagaacctgc aaaaggcagg tcacagcctg ttcatttcca cccaccacga
3421  cgccggccca gccgacctga tcgtgccgg tgccgcgccc ctggccaacc cgaaagaggt
```

| | Sequences: |
|---|---|
| 3481 | tgcccaggaa gccgaattca tcatcgtcat ggtccccgac accccgcagg tcgaaagcgt |
| 3541 | cctgttcggt gaaaacggcg tggccgaggg cgttggccca aacaaggtgg tgatcgacat |
| 3601 | gagctcgatc tcgccaaccg ccaccaaagc cttcgccgag aagatcaagg ctaccggtgc |
| 3661 | cgcctacctg gacgccccgg tgtccggtgg tgaagtcggc gccaaggcgg cgaccctgag |
| 3721 | catcatggtt ggtgctgcc cgaacgccct cgagcgcacc ctgcccgtgt tcgaagccat |
| 3781 | gggcaagaac atcacccgcg tcggtggcaa cggtgacggc cagaccgcca aggtcgccaa |
| 3841 | ccagatcatt gtcgccctga acatccaggc cgtggccgaa gccctgctgt tcgcgcccaa |
| 3901 | gaacggcgcc gacccctgcc agtgcgcga agcactgatg ggcggctttg cttcgtcgaa |
| 3961 | aatccctcgaa gtgcacgccg agcgcatgat caagggcacc ttcgacccag gcttccgcat |
| 4021 | caacctgcac cagaaggacc tgaacctggc cctgcaagt gccaaggcc tgggcatcaa |
| 4081 | cctgcccaac acctccaatg gtcaacacc cctggagcac tgccaggccc atggcaacct |
| 4141 | caactgggac cactggccgc tgatcaaagg cctggagcgc ccgtcctga ctggcgcact |
| 4201 | cgacgacaaa taagcatgca agcttgcggc cgcgataacg atgacctcag cggcgacc atttatcgtc |
| 4261 | agtcttggac tcctgttgat agatccagta atgacctcag aactcatct ggattgttc |
| 4321 | agaacgctcg gttgccgccg ggcgtttttt caaatctct atggtgaga cccatataat |
| 4381 | tacgattaa atttgtgtct caaaatctct gatgttacat tgcacaagat aaaatatat |
| 4441 | catcatgaac aataaaactg tctgcttaca taaacagtaa tacaaggggt gttatgagcc |
| 4501 | atattcagcg tgaaacgagc tgtagccgtc cgcgtctgaa cagcaacatg gatgcggatc |
| 4561 | tgtatggcta taaatgggcg cgtgataacg tgggtcagg cggcgcgacc atttatcgtc |
| 4621 | tgtatgccaa accggatgcg ccgaactgt ttctgaaaca tggcaaaggc agcgtggcga |
| 4681 | acgatgtgac cgatgaaatg gtgcgtctga actggcgtga cgaatttatg ccgcccga |
| 4741 | ccattaaaca tttattcgc accccggatg atgcgtggct gctgaccacc gcgattccgg |
| 4801 | gcaaaaccgc gtttcaggtg ctgaagaat cggcgatag atccggatac cggcgaaaac attggtgatg |
| 4861 | cgctgccgt gttctgcgt cgttctgcata gcattccgt gtgcaactgc ccgttaaca |
| 4921 | gcgatcgtgt gttcgtctg gcccaggcgc agagccgtat gaacgcggc ctggtggatg |
| 4981 | cgagcgattt tgatgatgaa cgtaacggct ggccggtgga acagtgtgg aaagaaatgc |

| | |
|---|---|
| 5041 | ataaactgct gccgttagc ccggatagcg tggtgaccca cggcgatttt agcctggata |
| 5101 | acctgatttt cgatgaaggc aaactgattg gctgcattga tgtggccgt gtgggcattg |
| 5161 | cggatcgtta tcaggatctg gccattctgt ggaactgcct gggcgaattt agcccgagcc |
| 5221 | tgcaaaaacg tctgtttcag aaatatggca ttgataatcc ggatatgaac aaaactgcaat |
| 5281 | ttcatctgat gctggatgaa tttttctaat aattaatgg accgcggtcc gcgcgttgtc |
| 5341 | cttttccgct gcataaccct gcttcggggt cattagcg attttttcgg tatatccatc |
| 5401 | cttttccgca cgatatacag gattttgcca aaggttcgt gtagacttttc cttggtgtat |
| 5461 | ccaaacgcgt cagccgggca ggataggtga agtaggccca cccgcgagcg ggtgttcctt |
| 5521 | cttcactgtc ccttattcgc acctggcggt gctcaacggg aatcctgctc tgcgaggctg |
| 5581 | gccgtaggcc ggccctaccg gcgcggcagc gttaccgtg tcgggctc caacggctcg |
| 5641 | ccatcgtcca gaaaacacgg ctcatcgggc atcggcaggc gctgctgccc gcgccgttcc |
| 5701 | cattcctccg tttggtcaa ggctggcagg tctggttcca tgccggaat gccgggctgg |
| 5761 | ctgggcggct cctcgcggg gccgtcggt agtgctgct cgcccggata cagggtcggg |
| 5821 | atgggcgcca ggtcgccatg ccccaacagc gattcgtcct ggtcgtcgtg atcaaccacc |
| 5881 | acggcgcac tgaacaccga caggcgcaac tgtgcgcggg gctgcccca cgccacgcgg |
| 5941 | tcattgacca cgtaggccga caggtcgcc gggccgttga gcttcacgac ggagatccag |
| 6001 | cgctcggcca ccaagtcctt gactgcgtat tgaccgtcc gcaaagaacg tccgatgagc |
| 6061 | ttggaaagtg tcttctggct gaccaccacg gcgttctggt ggccatctg cgccacgagg |
| 6121 | tgatgcagca gcattgccgc cgtgggtttc ctcgcaataa gcccgcccca cgccttcatgc |
| 6181 | gctttcggtt ccgttgcac ccagtgaccg ggcttgtcct tggcttgaat gccgatttct |

| | -continued |
|---|---|
| | Sequences: |
| 6241 | ctggactgcg tggccatgct tatctccatg cggtaggggt gccgcacggt tgcggcacca |
| 6301 | tgcgcaatca gctgcaactt ttcggcagcg cgacaacaat tatgcgttgc gtaaaagtgg |
| 6361 | cagtcaatta cagattttct ttaacctacg caatgagcta ttgcgggggg tgccgcaatg |
| 6421 | agctgttgcg taccccctt tttaagttg ttgattttta agtcttcgc atttcgccct |
| 6481 | atatctagtt ctttgtgcc caaagaaggg caccctgcg gggttccccc acgccttcgg |
| 6541 | cgcggtccc cctccggcaa aaagtggccc ctccggggct tgttgatcga ctgcggcc |
| 6601 | ttcggccttg cccaaggtgg cgctgccccc ttggaacccc cgcactcgcc gccgtgaggc |
| 6661 | tcgggggca ggcgggcggg cttcgccctt cgactgcccc cactcgcata ggcttggtc |
| 6721 | gttccaggcc cgtcaaggcc aagccgctgc gcggtgctg cgcgagcctt gacccgcctt |
| 6781 | ccacttggtg tccaaccggc aagcgaagcg cgcaggccgc aggccggagg ctttcccca |
| 6841 | gagaaaatta aaaaaattga tgggcaagg ccgcaggccg cgcagttgga gccgtgggt |
| 6901 | atgtggtcga aggtgggta gccgtgggc aatcccgtg gtcaagctcg tgggcaggcg |
| 6961 | cagcctgtcc atcagcttgt ccagcaggt tgtccacggg ccgagcgaag cgagccagcc |
| 7021 | ggtgccgct cgcggccatc gtccacatat ccacggctg gcaagggagc gcagcgaccg |
| 7081 | cgcagggcga agccggaga gccaagccc agggggggcg cgcccagctg tctagggcgg |
| 7141 | cggattgtc ctactcagga gagcgttcac cgacaaacaa cagataaaac gaaaggccca |
| 7201 | tttcgac tgagcctttc gttttattg atgcct |

Where nucleotides 1511 to 3286 of SEQ ID NO: 5 are gcl that encodes for glyoxylate carboligase PP4297.

Glyoxylate carboligase PP4297 has an amino acid sequence of SEQ ID NO: 6 as follows:

M S K M R A I D A A V L V M R R E G V D T A
F G I P G A A I N P L Y S A L K K V G G I D
H V L A R H V E G A S H M A E G Y T R A N P
G N I G V C I G T S G P A G T D M V T G L Y
S A S A D S I P I L C I T G Q A P R A R L H
K E D F Q A V D I T N I V K P V T K W A T T
V L E P G Q V P Y A F Q K A F Y E M R T G R
P G P V L I D L P F D V Q M A E I E F D I D
A Y E P L P V H K P S A T R V Q A E K A L A
L L N D A E R P L L V A G G G I I N A D A S
D K L V E F A E L T G V P V I P T L M G W G
T I P D D H A Q M V G M V G L Q T S H R Y G
N A T L L K S D L V F G I G N R W A N R H T
G S V D V Y T E G R K F V H V D I E P T Q I
G R V F T P D L G I V S D A G K A L D V F L
E V A R E W K A A G K L K C R K A W L E E C
Q E R K S S L Q R K T H F D N V P V K P Q R
V Y E E M N Q V F G K D T C Y V S T I G L S
Q I A G A Q F L H V Y K P R H W I N C G Q A
G P L G

Where nucleotides 3320 to 4213 of SEQ ID NO: 5 are glxR that encode for 2-Hydroxy-3 oxopropionate-reductase PP4299.

Hydroxy-3-oxopropionate-reductase PP4299 has an amino acid sequence of SEQ ID NO: 7 as follows:

M A K I G F I G T G I M G K P M A Q N L Q K
A G H S L F I S T H H D A A P A D L I A A G
A V A L A N P K E V A Q E A E F I I V M V P
D T P Q V E S V L F G E N G V A E G V G P N
K V V I D M S S I S P T A T K A F A E K I K
A T G A A Y L D A P V S G G E V G A K A A T
L S I M V G G C P N A F E R T L P L F E A M
G K N I T R V G G N G D G Q T A K V A N Q I
I V A L N I Q A V A E A L L F A A K N G A D
P A K V R E A L M G G F A S S K I L E V H A
E R M I K G T F D P G F R I N L H Q K D L N
L A L Q G A K E L G I N L P N T S N A Q Q V
F N T C Q A L G G G N W D H S A L I K G L E
H M A N F S I R D D K

In an embodiment, and as used herein, homologous nucleic acid sequences are about 60%, 65%, 68%, 70%, 75%, 80%, 85%, 90%, 91%, 92%, 93%, 94%, 95%, 96%, 97%, 98%, 99%, 99.5%, 99.9%, 99.95% or even higher identical to nucleic acids disclosed herein. In an embodiment, and as used herein, homologous amino acid sequences are about 60%, 65%, 68%, 70%, 75%, 80%, 85%, 90%, 91%, 92%, 93%, 94%, 95%, 96%, 97%, 98%, 99%, 99.5%, 99.9%, 99.95% or even higher identical to amino acids and proteins disclosed herein.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A genetically engineered *Pseudomonas* for growth on ethylene glycol as a sole carbon source comprising exogenous genes gcl (glyoxylate carboligase), hyi (hydroxypyruvate isomerase), glxR (tartronate semialdehyde reductase), PP_4300, pykF (pyruvate kinase), and glcDEF (glycolate oxidase operon).

2. The genetically engineered *Pseudomonas* of claim 1 expresses an exogenous gcl (glyoxylate carboligase) operon.

3. The genetically engineered *Pseudomonas* of claim 1 expresses an exogenous glycolate oxidase.

4. The genetically engineered *Pseudomonas* of claim 1 expresses an exogenous gcl operon and expressing an exogenous glycolate oxidase operon (glcDEF).

5. The genetically engineered *Pseudomonas* of claim 1 expresses exogenous genes selected from the group consisting of gcl, hyi, glxR, PP_4300 and pykF.

6. The genetically engineered *Pseudomonas* of claim 1 expresses exogenous genes selected from the group consisting of gcl, hyi, glxR, PP_4300, pykF, and glcDEF.

7. The genetically engineered *Pseudomonas* of claim 1 selected from the group consisting of MFL185, and MFL168.

8. The genetically engineered *Pseudomonas* of claim 1 grows in media containing up to 2 M ethylene glycol.

9. The genetically engineered *Pseudomonas* of claim 1 wherein said exogenous genes are inserted into the genome of the *Pseudomonas*.

10. The genetically engineered *Pseudomonas* of claim 1 wherein said exogenous genes are inserted into the genome of the *Pseudomonas* between fpyA and PP_4218.

11. The genetically engineered *Pseudomonas* of claim 9 wherein said exogenous genes are under the control of an exogenous promoter.

12. The genetically engineered *Pseudomonas* of claim 1 consumes up to 0.16 g/L/h of ethylene glycol.

13. The genetically engineered *Pseudomonas* of claim 1 consumes 500 mM ethylene glycol within 120 hours.

14. The genetically engineered *Pseudomonas* of claim 1 comprising exogenous copies of gcl, hyi, glxR, PP_4300, and pykF, having at least 90% identity with gcl, hyi, glxR, PP_4300, and pykF in SEQ ID NO: 4.

15. The genetically engineered *Pseudomonas* of claim 1 comprising exogenous copies of glcDEF having at least 90% sequence identity with glcDEF from SEQ ID NO: 1.

16. The genetically engineered *Pseudomonas* of claim 1 comprising exogenous copies of gcl, hyi, glxR, PP_4300, and pykF having 90% identity with gcl, hyi, glxR, PP_4300, and pykF in SEQ ID NO: 4 and glcDEF having at least 90% sequence identity with glcDEF of SEQ ID NO: 1.

17. A genetically engineered *Pseudomonas* that grows on ethylene glycol as a sole carbon source wherein the *Pseudomonas* comprises exogenous genes gcl, hyi, glxR, PP_4300, pykF, and glcDEF and that produces polyhydroxyalkanoates.

18. The genetically engineered *Pseudomonas* of claim 17 that produces polyhydroxyalkanoates at up to 0.06 grams per gram of dried cellular weight (DCW).

19. The genetically engineered *Pseudomonas* of claim 17 wherein said polyhydroxyalkanoates are derived from the metabolism of ethylene glycol.

* * * * *